(12) United States Patent
Ainley et al.

(10) Patent No.: US 11,198,883 B2
(45) Date of Patent: Dec. 14, 2021

(54) METHODS AND COMPOSITIONS FOR INTEGRATION OF AN EXOGENOUS SEQUENCE WITHIN THE GENOME OF PLANTS

(71) Applicants: Dow AgroSciences LLC, Indianapolis, IN (US); Sangamo Therapeutics, Inc., Richmond, CA (US)

(72) Inventors: W. Michael Ainley, Carmel, IN (US); Dmitry Y. Guschin, Richmond, CA (US); Matthew Hayden, Templestowe (AU); Daniel Isenegger, Ringwood (AU); John Mason, Preston (AU); Jeffrey C. Miller, Richmond, CA (US); Joseph F. Petolino, Zionsville, IN (US); Yidong Ran, Bundoora (AU); Tim Sawbridge, Coburg (AU); German Spangenberg, Bundoora (AU); Steven R. Webb, Westfield, CA (US)

(73) Assignees: Dow AgroSciences LLC, Indianapolis, IN (US); Sangamo Therapeutics, Inc., Brisbane, CA (US)

( * ) Notice: Subject to any disclaimer, the term of this patent is extended or adjusted under 35 U.S.C. 154(b) by 90 days.

(21) Appl. No.: 16/674,831

(22) Filed: Nov. 5, 2019

(65) Prior Publication Data
US 2020/0071712 A1    Mar. 5, 2020

Related U.S. Application Data

(62) Division of application No. 14/243,553, filed on Apr. 2, 2014, now Pat. No. 10,501,748.

(60) Provisional application No. 61/809,097, filed on Apr. 5, 2013, provisional application No. 61/820,461, filed on May 7, 2013.

(51) Int. Cl.
*C12N 15/82* (2006.01)
*C12N 15/90* (2006.01)

(52) U.S. Cl.
CPC ..... *C12N 15/8213* (2013.01); *C12N 15/8274* (2013.01); *C12N 15/8278* (2013.01); *C12N 15/90* (2013.01); *C12N 2800/80* (2013.01)

(58) Field of Classification Search
CPC ............ C12N 15/8274; C12N 15/8213; C12Y 202/01006
See application file for complete search history.

(56) References Cited

U.S. PATENT DOCUMENTS

| | | | |
|---|---|---|---|
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas et al. | |
| 6,200,759 B1 | 3/2001 | Dove et al. | |
| 6,242,568 B1 | 6/2001 | Barbas et al. | |
| 6,453,242 B1 | 9/2002 | Eisenberg et al. | |
| 6,453,261 B2 | 9/2002 | Boger et al. | |
| 6,479,626 B1 | 11/2002 | Kim et al. | |
| 6,534,261 B1 | 3/2003 | Cox et al. | |
| 6,784,626 B2 | 8/2004 | Otake et al. | |
| 6,794,136 B1 | 9/2004 | Eisenberg et al. | |
| 7,232,942 B2 | 6/2007 | Slinkard et al. | |
| 7,705,139 B2 | 4/2010 | Jamieson et al. | |
| 7,888,121 B2 | 2/2011 | Urnov et al. | |
| 7,914,796 B2 | 3/2011 | Miller et al. | |
| 8,034,598 B2 | 10/2011 | Miller | |
| 8,106,255 B2 | 1/2012 | Carroll et al. | |
| 8,329,986 B2 | 12/2012 | Butler et al. | |
| 8,399,218 B2 | 3/2013 | Gupta et al. | |
| 8,409,363 B2 | 4/2013 | Weber | |
| 8,409,861 B2 | 4/2013 | Guschin et al. | |
| 8,563,314 B2 | 10/2013 | Gregory et al. | |
| 8,586,323 B2 | 11/2013 | Okamoto et al. | |
| 8,586,363 B2 | 11/2013 | Voytas et al. | |
| 8,586,526 B2 | 11/2013 | Gregory et al. | |
| 8,592,645 B2 | 11/2013 | DeKelver et al. | |
| 2003/0232410 A1 | 12/2003 | Liljedahl et al. | |
| 2004/0158887 A1 | 2/2004 | Baltimore et al. | |
| 2004/0237134 A1 | 11/2004 | Pozniak et al. | |
| 2005/0026157 A1 | 2/2005 | Baltimore et al. | |
| 2005/0064474 A1 | 3/2005 | Holmes et al. | |
| 2005/0208489 A1 | 9/2005 | Carroll et al. | |
| 2006/0063231 A1 | 3/2006 | Yong-Li et al. | |
| 2006/0188987 A1 | 8/2006 | Guschin et al. | |
| 2007/0033670 A1 | 2/2007 | Konzak et al. | |
| 2007/0134796 A1 | 6/2007 | Holmes et al. | |

(Continued)

FOREIGN PATENT DOCUMENTS

| | | |
|---|---|---|
| GB | 2338237 | 8/1998 |
| WO | WO 95/19431 | 7/1995 |

(Continued)

OTHER PUBLICATIONS

Townsend, Jeffrey A., et al. "High-frequency modification of plant genes using engineered zinc-finger nucleases." Nature 459.7245 (2009): 442-445. (Year: 2009).*

Voytas, Daniel F. "Plant genome engineering with sequence-specific nucleases." Annual review of plant biology 64 (2013): 327-350 (Year: 2013).*

Bailey et al., "Tolerance of Imidazolinone-Resistant Corn (*Zea mays*) to Diclosulam," *Weed Technology* 17(1):60-64 (2003).

Beurdeley et al., "Compact Designer Talens for Efficient Genome Engineering," *Nature Communications* 4:1762 (2013) doi:10.10.38/ncomms2782.

(Continued)

*Primary Examiner* — Weihua Fan
(74) *Attorney, Agent, or Firm* — Foley & Lardner LLP

(57) ABSTRACT

Disclosed herein are methods and compositions for parallel or sequential transgene stacking in plants to produce plants with selected phenotypes.

16 Claims, 21 Drawing Sheets
Specification includes a Sequence Listing.

(56) References Cited

U.S. PATENT DOCUMENTS

| | | |
|---|---|---|
| 2008/0182332 A1 | 7/2008 | Cai |
| 2009/0029860 A1 | 1/2009 | Moffatt et al. |
| 2009/0068164 A1 | 3/2009 | Barbas et al. |
| 2009/0093366 A1 | 4/2009 | Wright |
| 2009/0098552 A1 | 4/2009 | Zhao et al. |
| 2009/0104700 A1 | 4/2009 | Samuel et al. |
| 2009/0117617 A1 | 5/2009 | Holmes et al. |
| 2009/0205083 A1 | 8/2009 | Gupta et al. |
| 2009/0263900 A1 | 10/2009 | DeKelver et al. |
| 2009/0305419 A1 | 12/2009 | Miller |
| 2010/0047805 A1 | 2/2010 | Wang |
| 2010/0199389 A1 | 8/2010 | Butler et al. |
| 2010/0257638 A1 | 10/2010 | Cai et al. |
| 2010/0287641 A1* | 11/2010 | McElver .............. A01N 43/50 800/260 |
| 2011/0041195 A1 | 2/2011 | Doyon |
| 2011/0145940 A1 | 6/2011 | Voytas et al. |
| 2011/0167521 A1 | 6/2011 | DeKelver et al. |
| 2011/0189775 A1 | 8/2011 | Ainley et al. |
| 2011/0201055 A1 | 8/2011 | Doyon et al. |
| 2011/0203012 A1 | 8/2011 | Dotson et al. |
| 2011/0207221 A1 | 8/2011 | Cost et al. |
| 2011/0239315 A1 | 9/2011 | Bonas et al. |
| 2011/0281361 A1 | 11/2011 | DeKelver et al. |
| 2011/0287512 A1 | 11/2011 | Paschon et al. |

FOREIGN PATENT DOCUMENTS

| | | |
|---|---|---|
| WO | WO 96/06166 | 7/1995 |
| WO | WO 98/37186 | 2/1996 |
| WO | WO 98/53057 | 8/1998 |
| WO | WO 98/53058 | 11/1998 |
| WO | WO 98/53059 | 11/1998 |
| WO | WO 98/53060 | 11/1998 |
| WO | WO 98/54311 | 11/1998 |
| WO | WO 00/27878 | 12/1998 |
| WO | WO 01/53480 | 7/2001 |
| WO | WO 01/60970 | 8/2001 |
| WO | WO 01/88197 | 11/2001 |
| WO | WO 02/016536 | 2/2002 |
| WO | WO 02/099084 | 12/2002 |
| WO | WO 03/014357 | 2/2003 |
| WO | WO 03/016496 | 2/2003 |
| WO | 2004/106529 A2 | 12/2004 |
| WO | WO 06/060634 | 6/2006 |
| WO | 2008/076290 A2 | 6/2008 |
| WO | WO 10/079430 | 7/2010 |
| WO | WO 2011/049627 | 4/2011 |
| WO | WO 2014/039684 | 3/2014 |

OTHER PUBLICATIONS

Bevan, et al., "Clearing a Path Through the Jungle: Progress in *Arabidopsis* Genomics," *Bioessays* 21:110-120 (1999).
Boch, et al., "Breaking the Code of DNA Binding Specificity of TAL-Type III Effectors," *Science* 326:1509-1512 (2009).
Boissel et al., "MEGATALS: a Rare-Cleaving Nuclease Architecture for Therapeutic Genome Engineering," *Nucl. Acid Res.* 42(4):2591-2601 (2014) doi:10.1093/nar/gkt1224.
Bonas et al., "Genetic and Structural Characterization of the Avirulence Gene AVRBS3 From Xanthomonas Campestris PV. Vesicatori," *Mol. Gen. Genet.* 218:127-136 (1989).
Cong, et al., "Multiplex Genome Engineering Using CRISPR/CAS Systems," 339:819 (2013) doi:Sciencexpress/10.1126/science.1231143.
Currie and Penner, "Magnitude of Imazethapyr Resistance of Corn (*Zea mays*) Hybrids With Altered Acetolactate Synthase," *Weed Sci.* 43:578-582 (1995).
D'Halluin et al., "Homologous Recombination: a Basis for Targeted Genome Optimization in Crop Species Such as *maize*," *Plant Biotechnology Journal* 6(1):93-102 (2008).
Doyon et al., "Heritable Targeted Gene Disruption in Zebrafish Using Designed Zinc-Finger Nucleases," *Nat. Biotechnology* 26:702-708 (2008).
Duke et al., "Potential Environmental Impacts of Herbicide-Resistant Crops," *Collect. Biosaf. Rev.* 2:66-143 (2005).
Durai et al., "Zinc Finger Nucleases: Custom-Designed Molecular Scissors for Genome Engineering of Plant and Mammalian Cells," *Nucleic Acids Research* 33(18):5978-5990 (2005).
Gautier et al., "Puroindoline Genes Are Highly Conserved in Diploid Ancestor Wheats and Related Species but Absent in *Tetraploid triticum* Species," *Plant Science* 153:81-91 (2000).
Gealy et al., "Gene Flow Between Red Rice (*Oryza sativa*) and Herbicide-Resist Antrice (*O. sativa*): Implications for Weed Management," *Weed Technology* 17:627-645 (2003).
Geurts et al., "Knockout Rats Produced Using Designed Zinc Finger Nucleases," *Science* 325(5939):433 (2009).
Guo et al., "Directed Evolution of an Enhanced and Highly Efficient FOKL Cleavage Domain for Zinc Finger Nucleases," *J. Mol. Biol.* 400(1):96-107 (2010).
Haft et al., "A Guild of 45 CRISPR-Associated (CAS) Protein Families and Multiple CRISPR/CAS Subtypes Exist in Prokaryotic Genomes," *PLoS Comput. Biol.* 1:e60 (2005) <http://www.jcvi.org/cms/nc/publications/listing/browse/3/article//Haft/#sthash.bXXP6pOi.dpuf>.
Halpin, "Gene Stacking in Transgenic Plants—The Challenge for $21^{st}$ Century Plant Biotechnology," *Plant Biotechnology Journal* 3:141-155 (2005).
Heuer et al., "Repeat Domain Diversity of AVRBS3-Like Genes in *Ralstonia solanacearum* Strains and Association With Host Preferences in the Field," *Appl. And Envir. Micro.* 73(13):4379-4384 (2007).
Jansen et al., "Identification of Genes That Are Associated With DNA Repeats in Prokaryotes," *Mol. Microbiol.* 43:1565-1575 (2002).
Jones, et al., "Regulatory Uncertainty Over Genome Editing," *Nature Plants* 1:14011 (2015).
Jones, et al. "Future of Breeding by Genome Editing is in the Hands of Regulators," *GM Crops & Food* 6:223-232 (2015).
Kay et al., "Analysis of Relative Gene Expression Data Using Real-Time Quantitative PCR and the 22DDCT Method," *Science* 318:648-651 (2007).
Kim, et al., "Effects of Deletions at the C-Terminus of Tobacco Acetohydroxy Acid Synthase on the Enzyme Activity and Cofactor Binding," *Biochemical Journal* 384(1):59-68 (2004).
Lee, et al., "Targeted Chromosomal Deletions in Human Cells Using Zinc Finger Nucleases," *Genome Res* 20:81-89 (2010).
Lee et al., "Single Nucleotide Mutation in the Barley Acetohydroxy Acid Synthase (AHAS) Gene Confers Resistance to Imidazolinone Herbicides," *PNAS USA* 108:8909-8913 (2011).
Li et al., A Mutation at the ALA122 Position of Acetohydroxy Acid Synthase (AHAS) Located on Chromosome 6D of Wheat: Improved Resistance to Imidazolinone and a Faster Assay for Marker Assisted Selection, *Molecular Breeding* 22:217-225 (2008).
Livak et al., "Analysis of Relative Gene Expression Data Using Real-Time Quantitative PCR and the 22DDCT Method." *Methods* 25(4):402-408 (2001).
Maddaloni et al., "The Sequence of the Zein Regulatory Gene Opaque-2 (O2) of *Zea mays*," *Nucleic Acids Res.* 17:7532 (1989).
Makarova et al., "A DNA Repair System Specific for the Thermophilic Archaea and Bacteria Predicted by Genomic Context Analysis," *Nucleic Acids Res.* 30:482-496 (2002).
Makarova et al., "A Putative RNA-Interference-Based Immune System Inprokaryotes: Computational Analysis of the Predicted Enzymatic Machinery, Functional Analogies With Eukaryotic RNAI, and Hypothetical Mechanisms of Action," *Biol. Direct.* 1:7 (2006).
Mali, et al., "RNA-Guided Human Genome Engineering via CAS9," *Science* 339(6121): 823-826 (2013).
Miller et al., "Repetitive Zinc-Binding Domains in the Protein Transcription Factor IIIA From Xenopus Oocytes," *EMBO J.* 4:1609-1614 (1985).
Mizutani, et al., "Unusual P450 Reactions in Plant Secondary Metabolism," *Archives of Biochemistry and Biophysics* 507:194-203 (2011).

(56) References Cited

OTHER PUBLICATIONS

Moehle et al., "Targeted Gene Addition Into a Specified Location in the Human Genome Using Designed Zinc Finger Nucleases," *Proc. Natl. Acad. Sci. USA* 104(9):3055-3060 (2007).
Moore et al., "Design of Polzinc Finger Peptides With Strutured Linkers," *PNAS USA* 98(4):1432-1436 (2001a).
Moore et al., "Improved DINA Binding Specificity From Polyzinc Finger Peptides by Using Strings of Two-Finger Units," *PNAS USA* 98(4):1437-1441 (2001b).
Moscou et al., "A Simple Cipher Governs DNA Recognition by TAL Effectors," *Science* 326:1501 (2009).
NCBI Reference Sequence: NC_002762.1 Apr. 15, 2009 (2009).
Newhouse et al., "Tolerance to Imidazolinone Herbicides in Wheat," *Plant Physiol.* 100:882-886 (1992).
Pattanayak, et al., "Revealing Off-Target Cleavage Specificities of Zinc-Finger Nucleases by in Vitro Selection," *Nature Methods* 8:765-770 (2011).
Pozniak et al.,, "Genetic Analysis of Imidazolinone Resistance in Mutation-Derived Lines of Common Wheat," *Crop Science* 44:23-30 (2004) doi:10.2135/cropsci2004.2300.
Rhodes, "Zinc Fingers," *Scientific American* 268(2):56-59, 62-65 (1993).
Schornack et al., "Gene-for-Gene-Mediated Recognition of Nuclear-Targeted AVRBS3-Like Bacterial Effector Proteins," *J. Plant Physiol.* 163(3):256-272 (2006).
Shimizu, et al., "Selectable Tolerance to Herbicides by Mutated Acetolactate Synthase Genes Integrated Into the Chloroplast Genome of Tobacco," *Plant Physiology* 147:1976-1983 (2008).
Shu, et al., "Plant Mutation Breeding and Biotechnology," FAO pp. 429-433 (2012).
Shukla et al., "Precise Genome Modification in the Crop Species *Zea mays* Using Zinc-Finger Nucleases," *Nature* 459:437-441 (2009).
Siehl et al. "Patterns of Crop-Tolerance to Herbicides Inhibiting Acetohydroxy Acid Synthase in Commercial Hybrids Designed for Tolerance to Imidazolinones," *Crop Sci.* 36:274-278 (1996).
Swanson et al., "Microspore Mutagenesis and Selection: Canola Plants With Field Tolerance to the Imidazolines," *Theor. Appl. Genet.* 78:525-530 (1989).
Szymczak et al., "Correction of Multi-Gene Deficiency in Vivo Using a Single 'Self-Cleaving' 2A Peptide-Based Retroviral Vector," *Nat. Biotechnol.* 22(5):589-594;760 (2004).
Tan et al., "Imidazoline-Tolerant Crops: History, Current Status and Future," *Pest Manag. Sci.* 61:246-257 (2005) doi: 10.1002/ps.993.
Terada et al., "Efficient Gene Targeting by Homologous Recombination in Rice," *Nat. Biotechnol.* 20(10):1030 (2002).
Terada et al., "Gene Targeting by Homologous Recombination as a Biotechnological Tool for Rice Functional Genomics," *Plant Physiol.* 144(2):846 (2007).
Toki et al., "Expression of a Maize Ubiquitin Gene Promoter-Bar Chimeric Gene in Transgenic Rice Plants," *Plant Physiology* 100:1503-1507 (1992).
Townsend et al., "High Frequency Modification of Plant Genes Using Engineered Zinc-Finger Nucleaes," *Nature* 459(7245):442-445 (2009).
Tzfira et al., "Genome Modifications in Plant Cells by Custom-Made Restriction Enzymes," *Plant Biotechnology Journal* 10(4):373-389 (2012) doi: 10.1111/j.1467-7652.2011.00672.x.
Urnov et al., "Genome Editing With Engineered Zinc Finger Nucleases," *Nature* 435(7042):646-651(2010).
Urnov et al., "Highly Efficient Endogenous Human Gene Correction Using Designed Zinc-Finger Nucleases," *Nature* 435:646-651 (2005).
Voytas, et al., "Plant Genome Engineering With Sequence-Specific Nucleases," *Annual Rev of Plant Biol* 64:327-350 (2013).
Wah et al., "Structure of FOKI Has Implications for DNA Cleavage," *PNAS USA* 95:10564-10569 (1998).
Wright et al., "Corn (*Zea mays*) Acetolactate Synthase Enzyme Sensitivity to Four Classes of ALS-Inhibiting Herbicides," *Weed Sci.* 46:8-12 (1998).
Yu, et al., "Resistance to AHAS Inhibitor Herbicides: Current Understanding," *Pest Management Science* 70:1340-1350 (2014).
Zhang, et al., "TALENs Enable Efficient Plant Genome Engineering," *Plant Physiology* 112 (2012).
Zhang, et al., "Transcription Activator-Like Effector Nucleases Enable Efficient Plant Genome Engineering," *Plant Physiology* 161(1):20-27 (2012).
Weinthal, et al., "Genome Editing in Plant Cells by Zinc Finger Nucleases," Trends in Plant Science 15 (6): 308-321 (2010).

\* cited by examiner

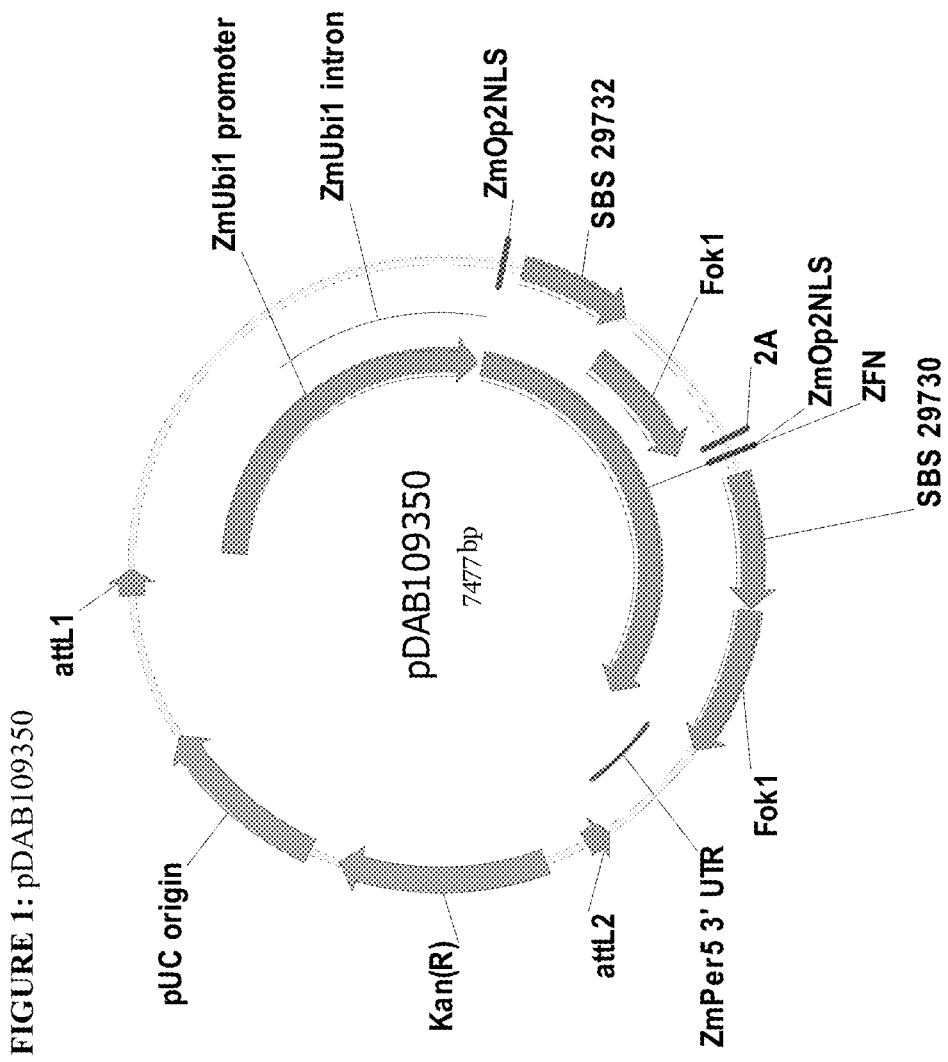
FIGURE 1: pDAB109350

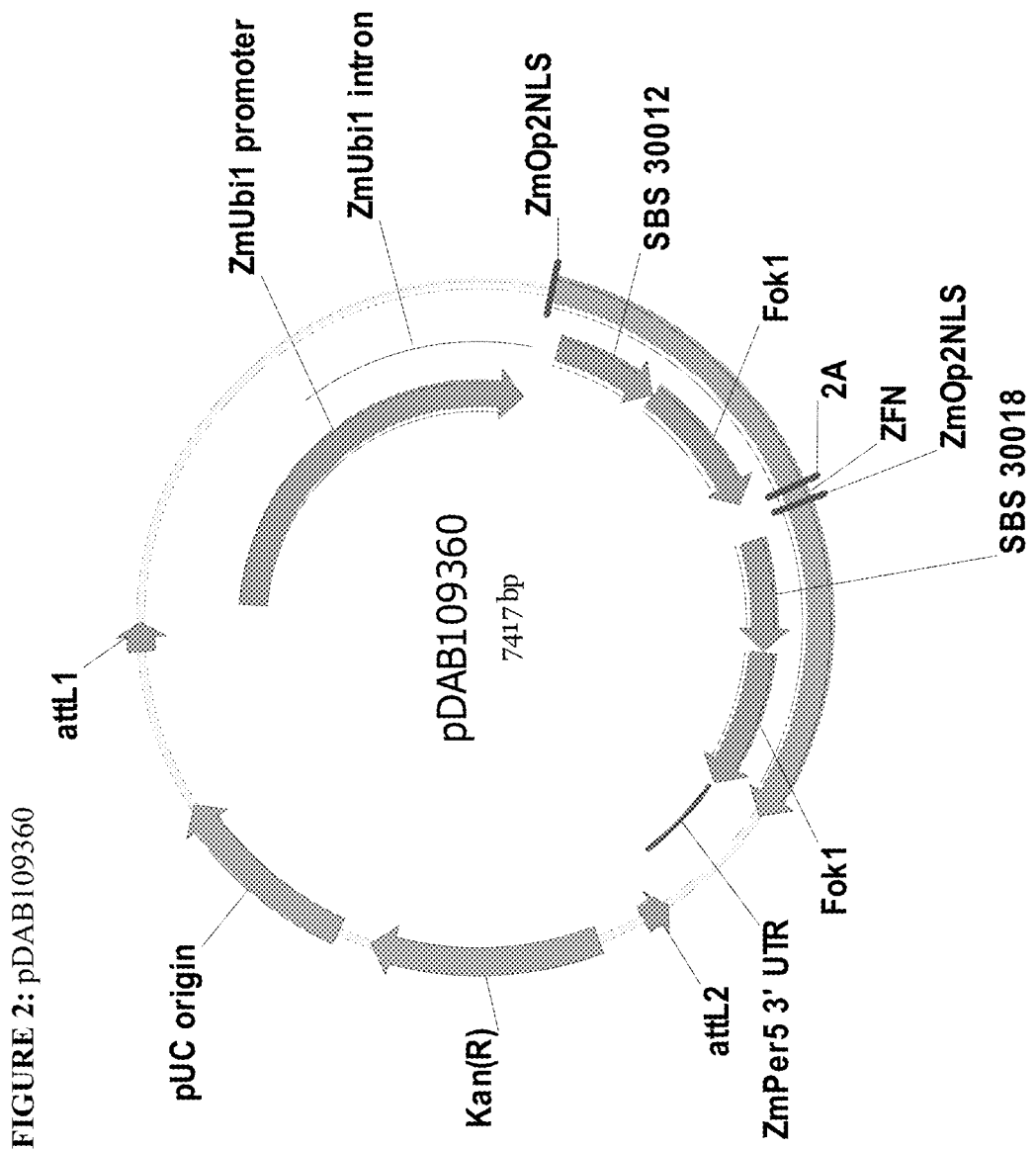
FIGURE 2: pDAB109360

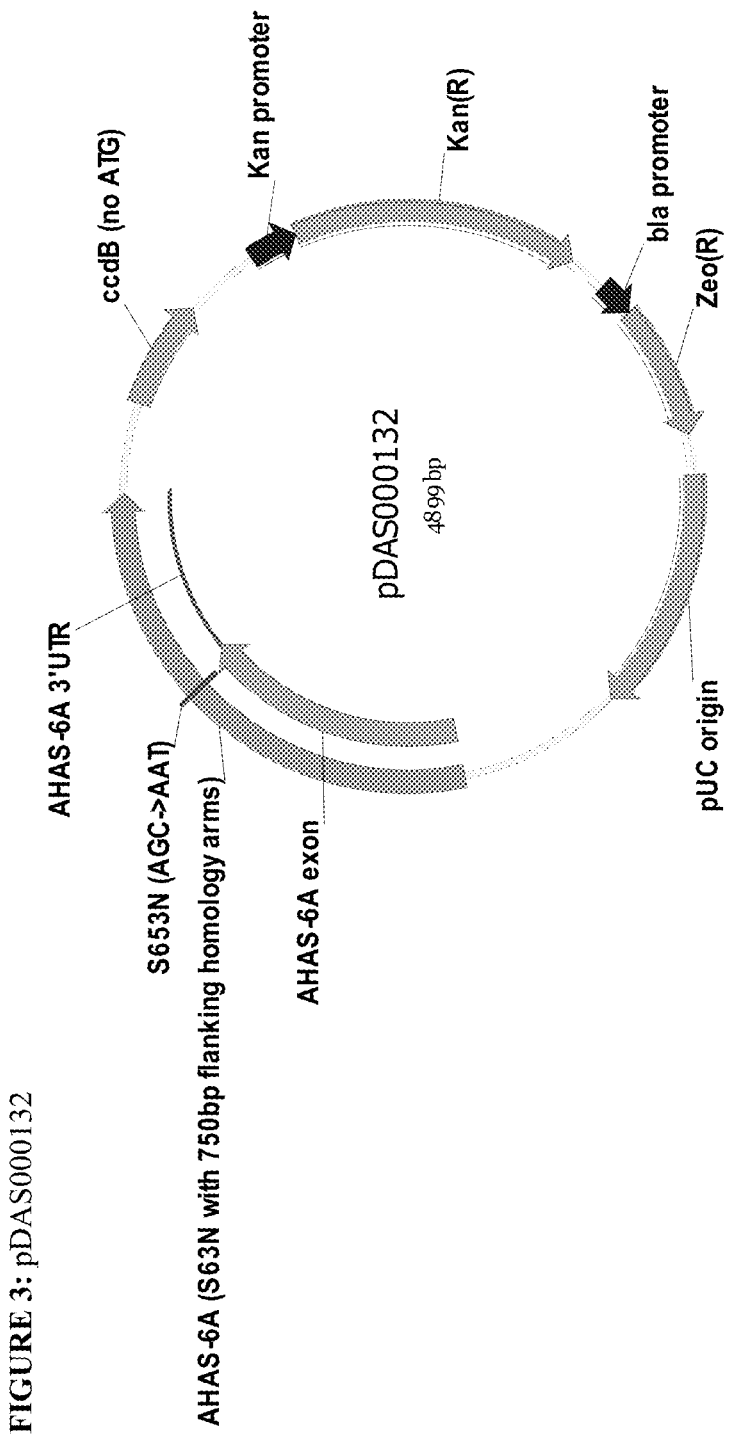
FIGURE 3: pDAS000132

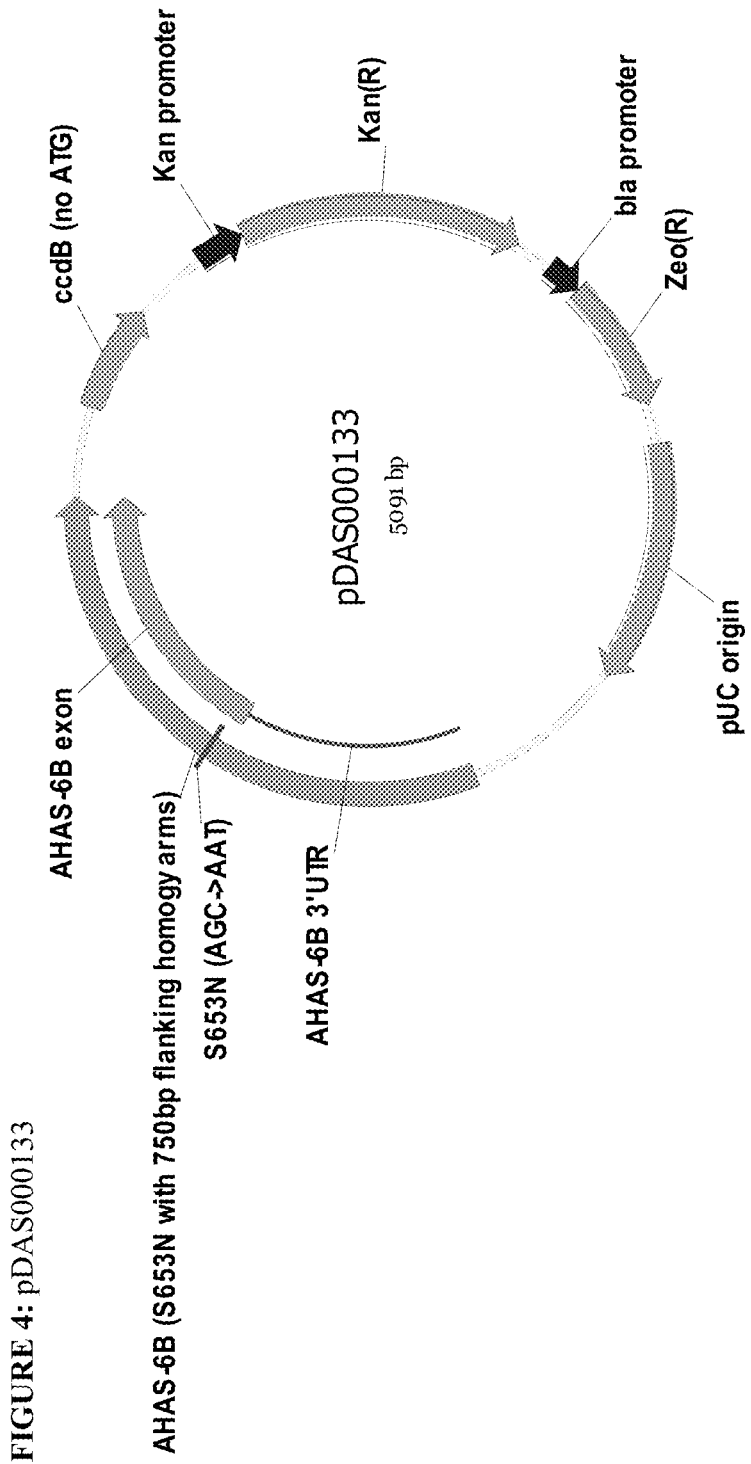
FIGURE 4: pDAS000133

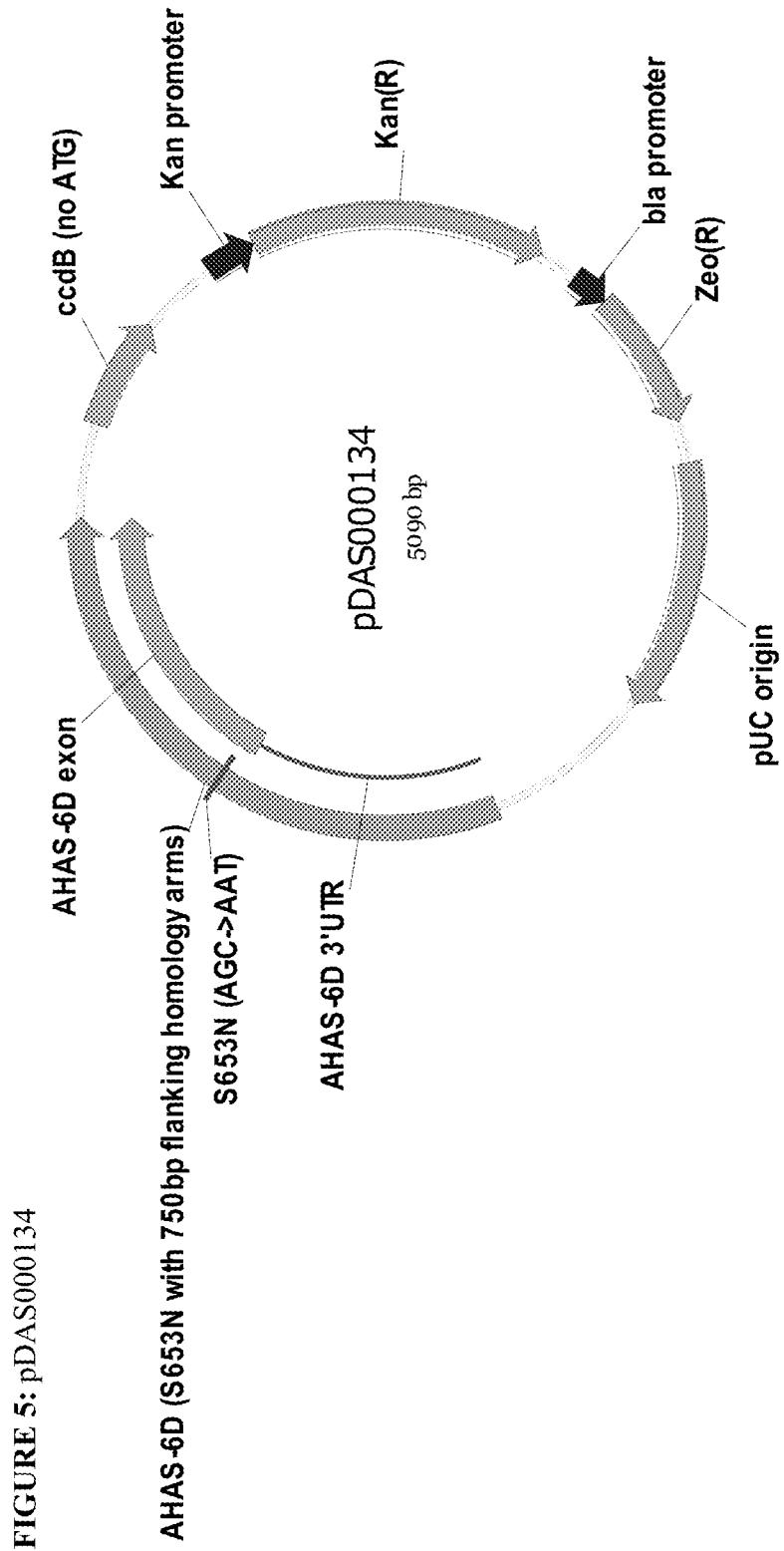
FIGURE 5: pDAS000134

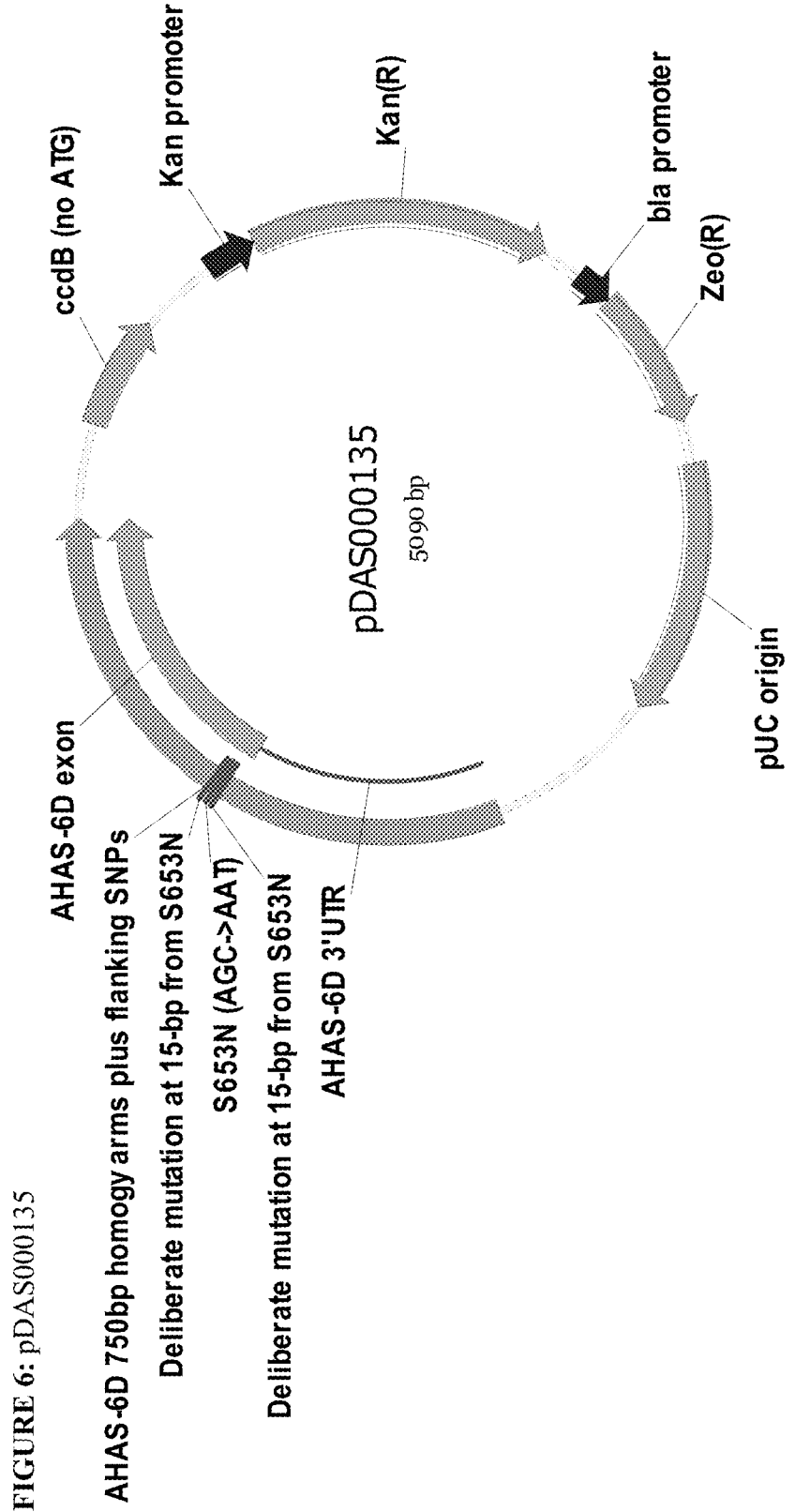
FIGURE 6: pDAS000135

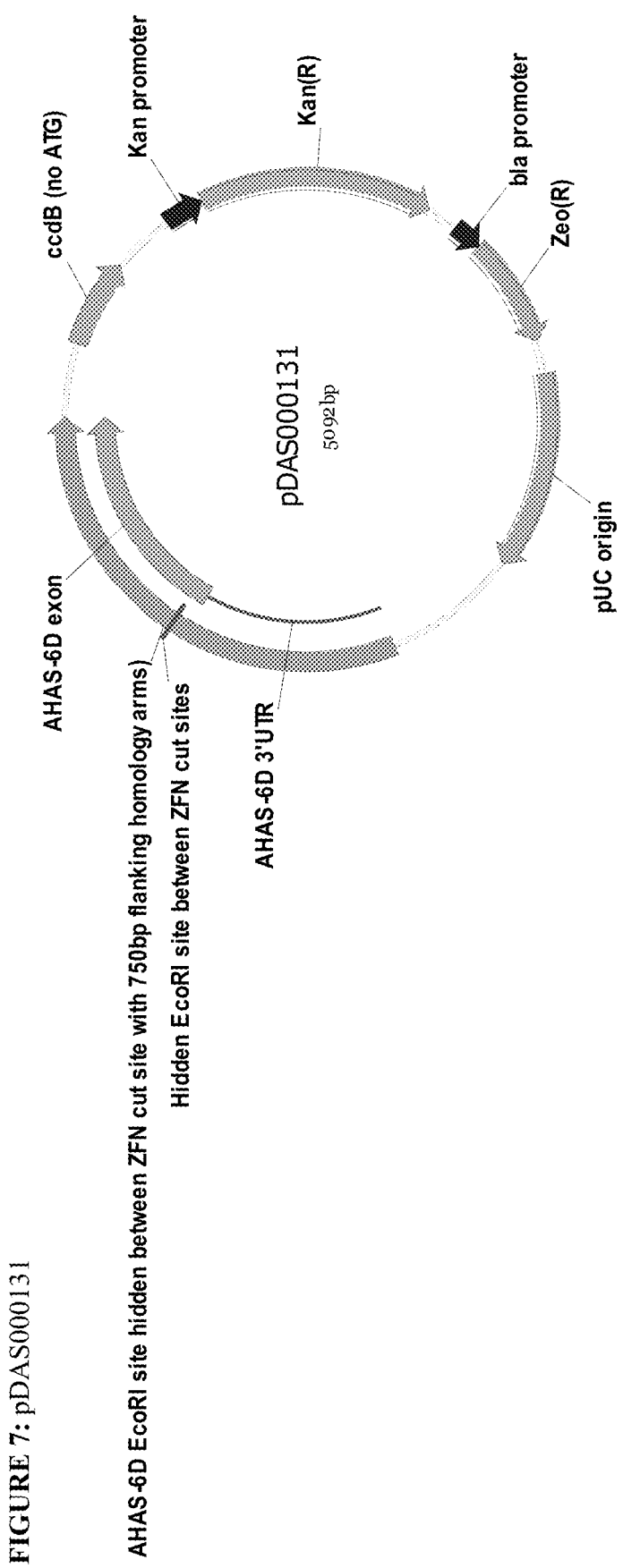
FIGURE 7: pDAS000131

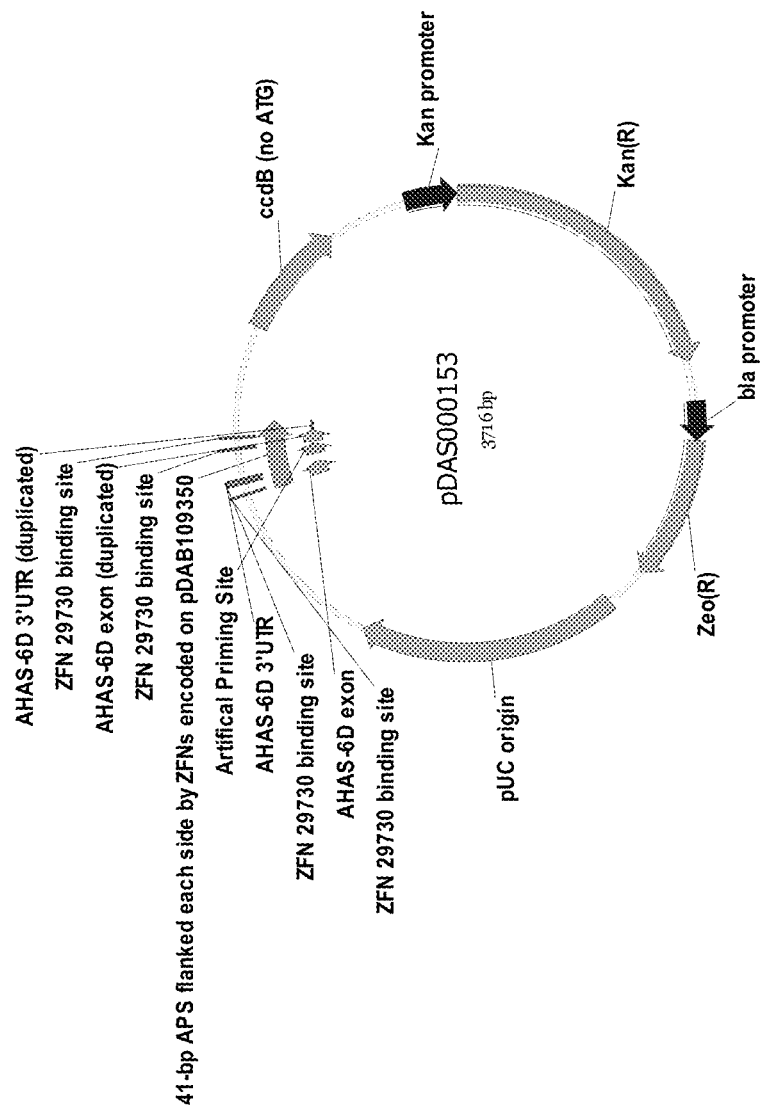
FIGURE 8: pDAS000153

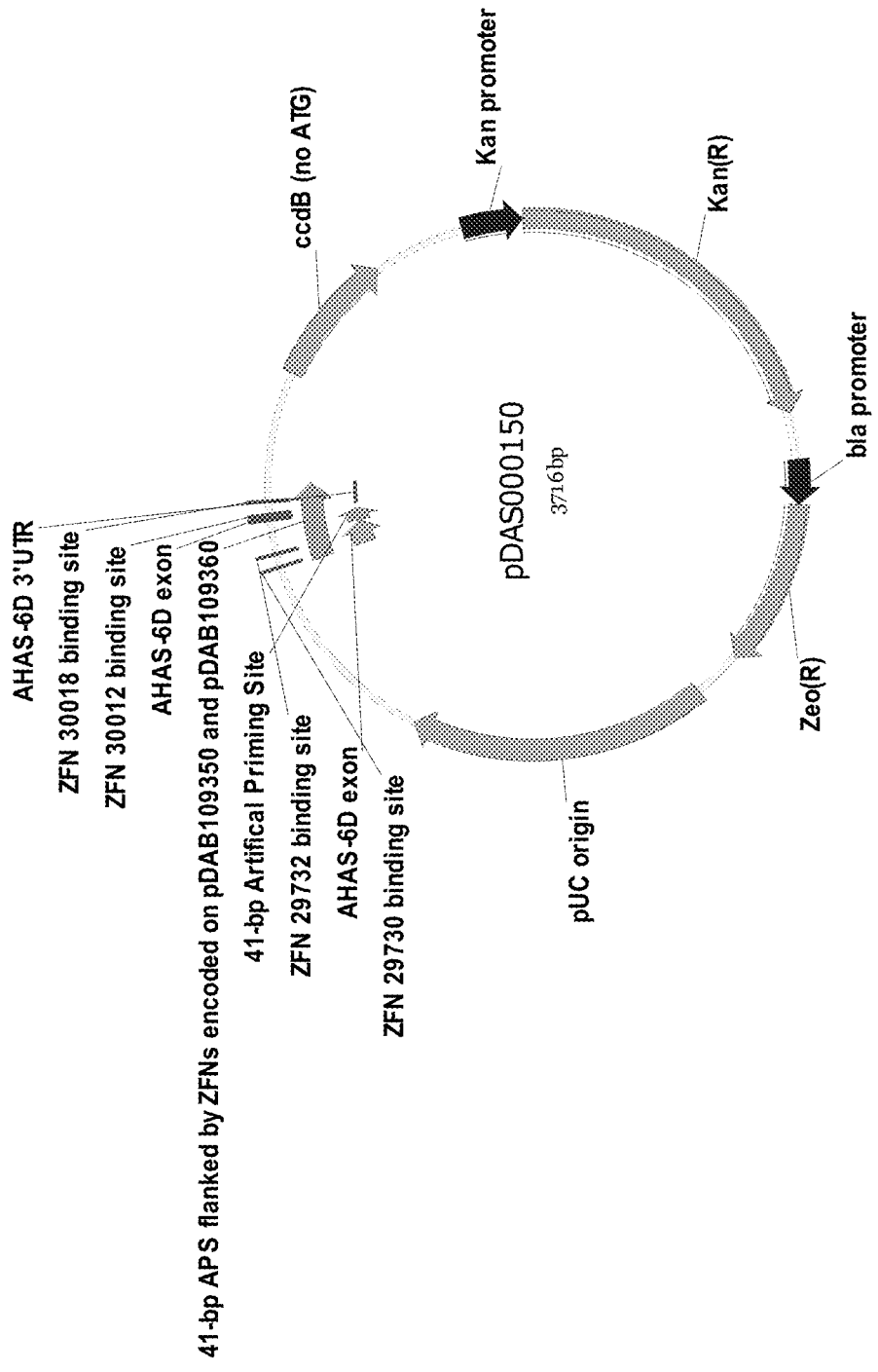
FIGURE 9: pDAS000150

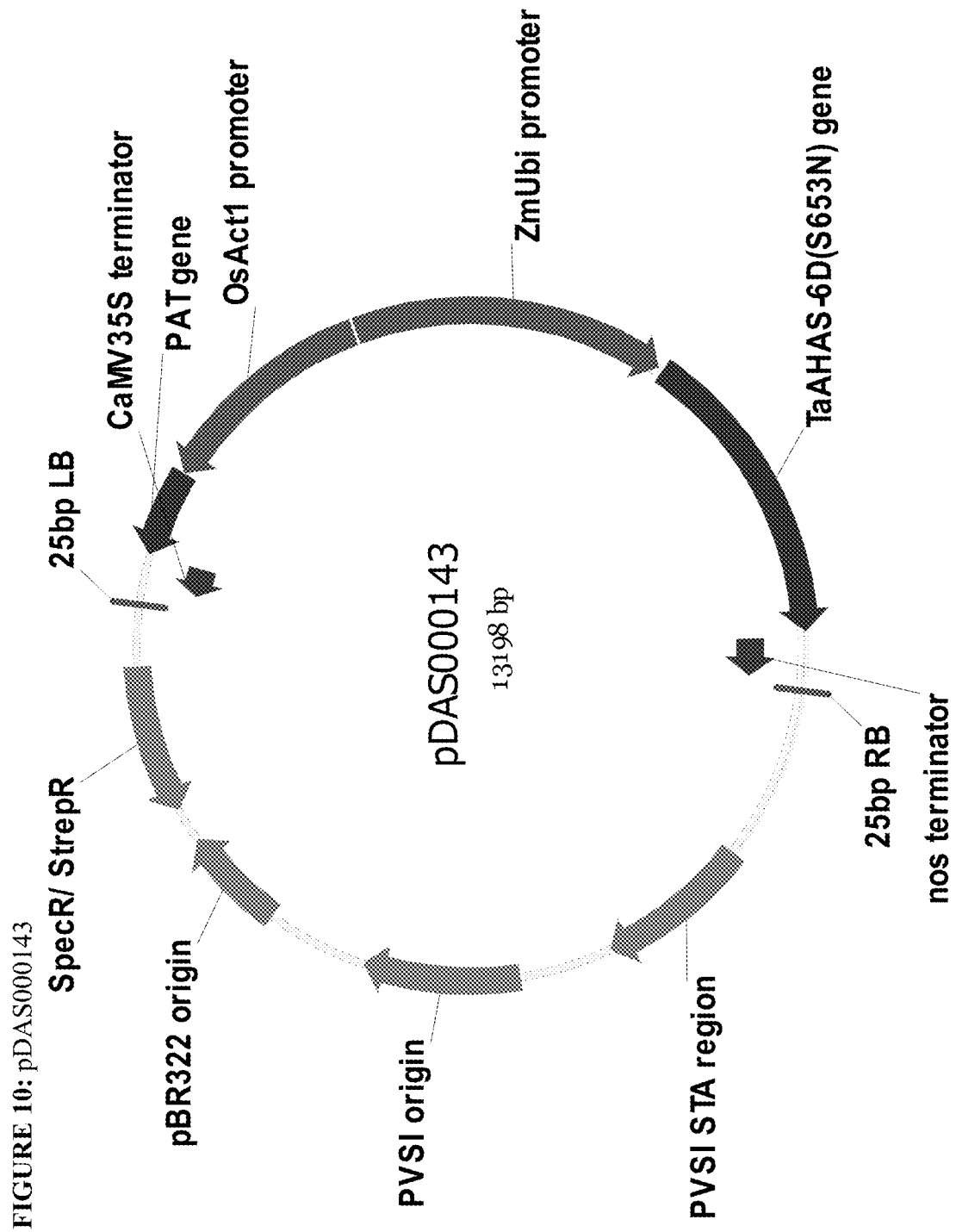
FIGURE 10: pDAS000143

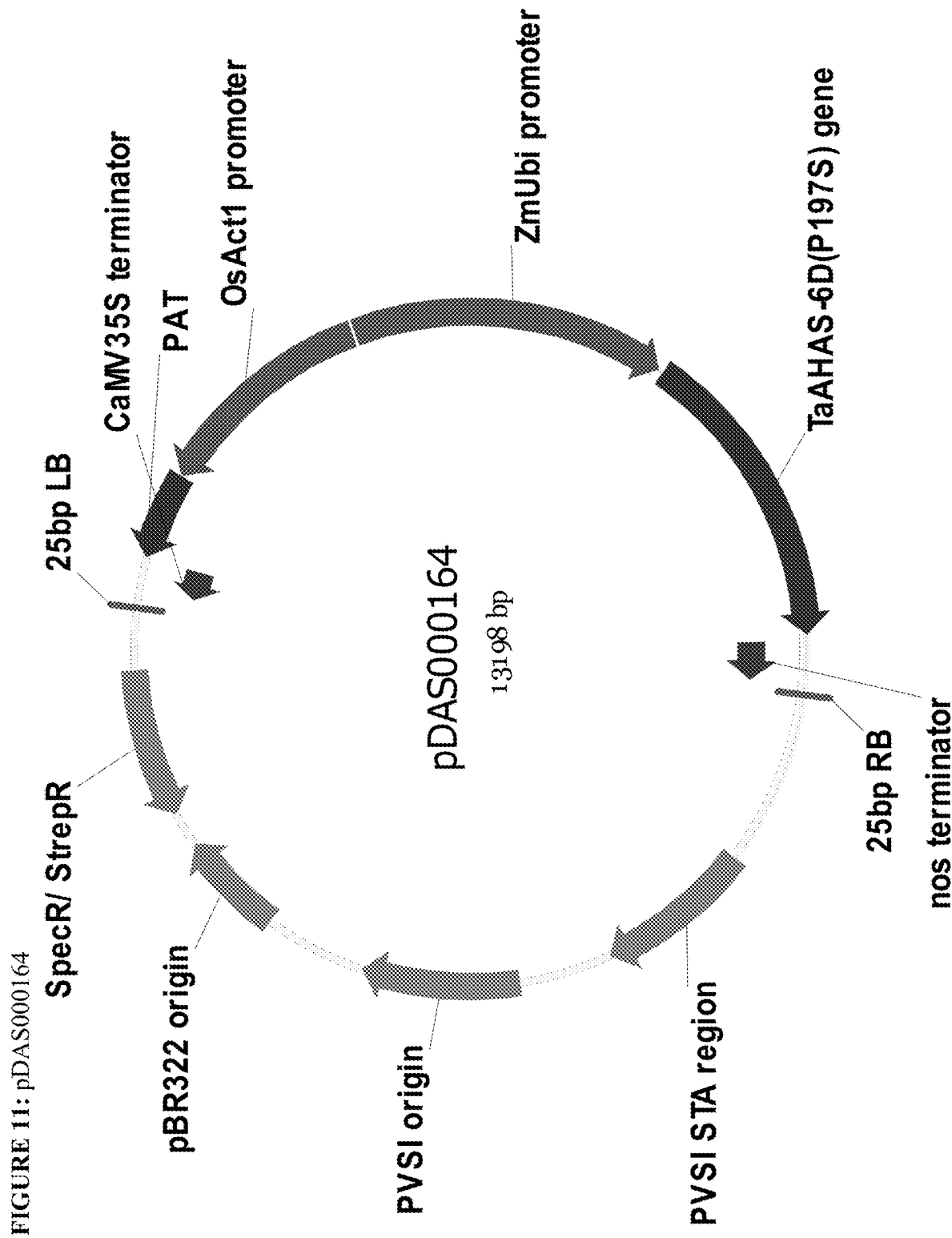
FIGURE 11: pDAS000164

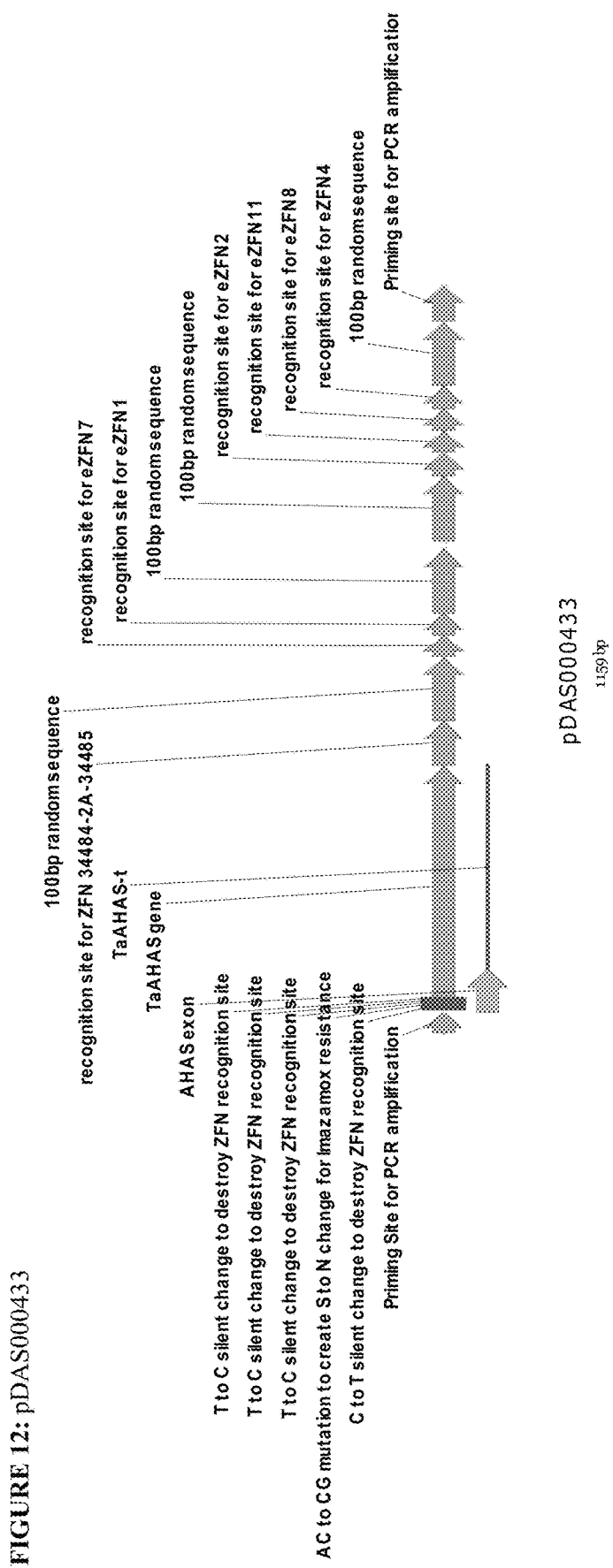
FIGURE 12: pDAS000433

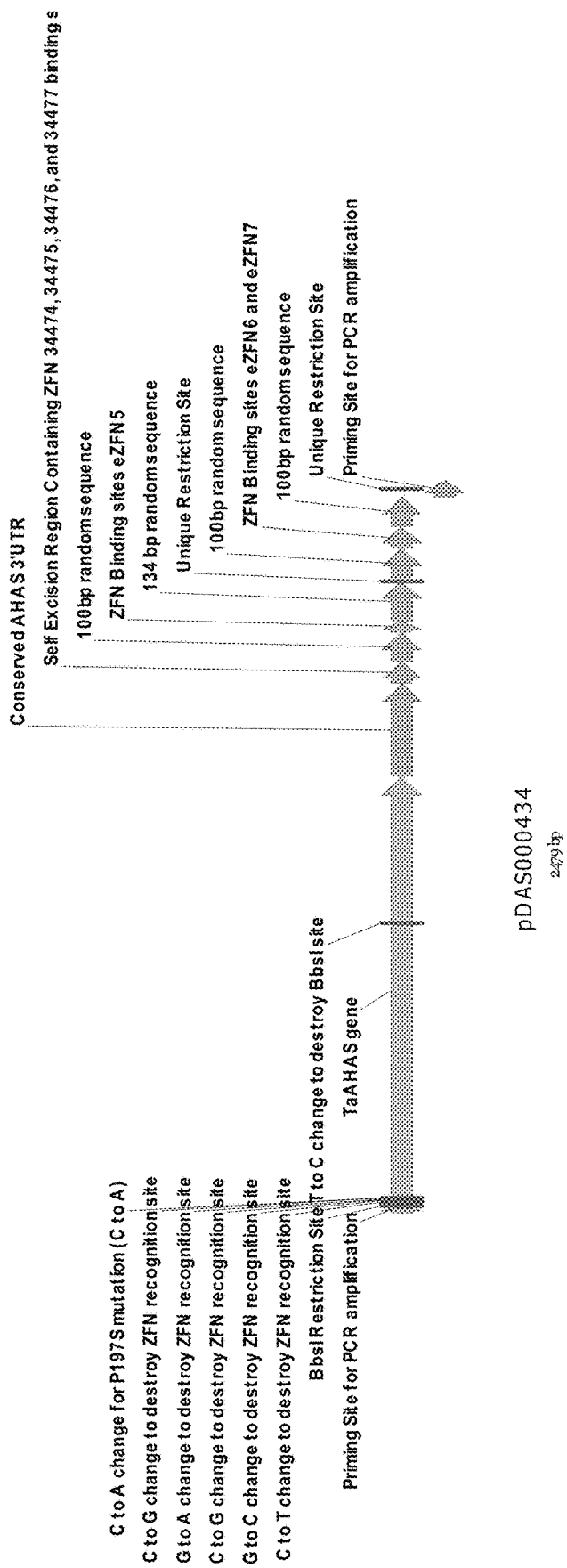
FIGURE 13: pDAS000434

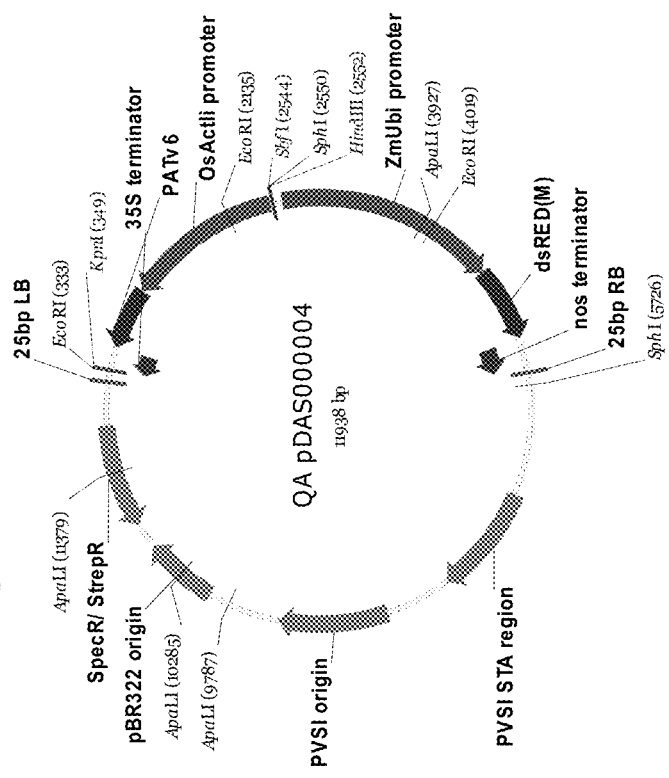
FIGURE 18: pDAS000004

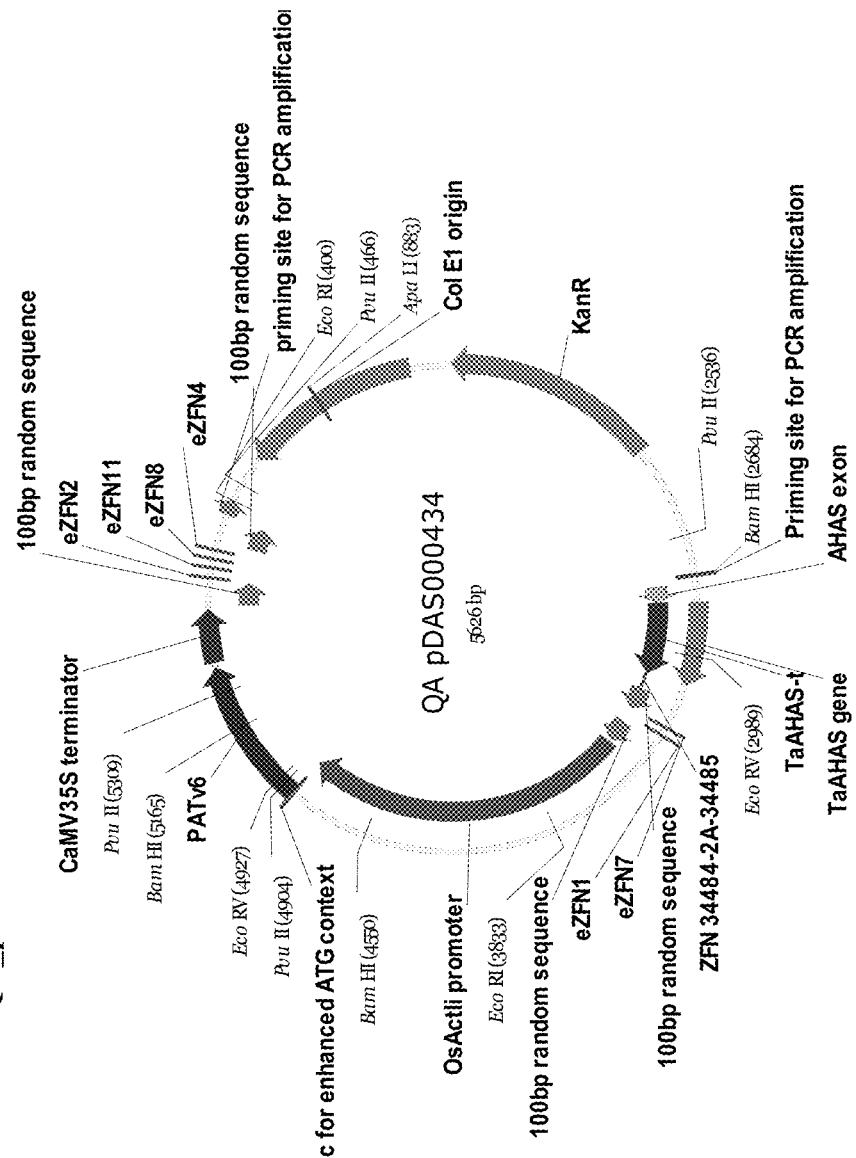
FIGURE 19: "QA_pDAS000434"

```
                              SEQUENCE LISTING

<160> NUMBER OF SEQ ID NOS: 314

<210> SEQ ID NO 1
<211> LENGTH: 2259
<212> TYPE: DNA
<213> ORGANISM: Artificial Sequence
<220> FEATURE:
<223> OTHER INFORMATION: AHAS homoeologous gene sequence
<220> FEATURE:
<221> NAME/KEY: misc_feature
<222> LOCATION: (2207)..(2207)
<223> OTHER INFORMATION: n is a, c, g, or t
<220> FEATURE:
<221> NAME/KEY: misc_feature
<222> LOCATION: (2210)..(2210)
<223> OTHER INFORMATION: n is a, c, g, or t

<400> SEQUENCE: 1
tcgcccaaac cctcgccgcc gccatggccg cagccacctc ccccgccgtc gcattctcgg      60
gcgccaccgc cgccgccatg cccaaacccg cccgccatcc tctcccgcgc caccagcccg     120
tctcgcgccg cgcgctcccc gcccgcgtcg tcaggtgttg cgccgcgtcc cccgccgcca     180
cctccgccgc gcctcccgca accgcgctcc ggccatgggg cccgtccgag ccccgcaagg     240
gcgccgacat cctcgtcgag gcgctcgagc gctgcggcat cgtcgacgtc ttcgcctacc     300
ccggcggcgc ctccatggag atccaccagg cgctgacgcg ctcgcccgtc atcaccaacc     360
acctcttccg ccacgagcag ggggaggcgt tcgcggcgtc cggctacgcc cgcgcgtccg     420
gccgcgtcgg cgtctgcgtc gccacctccg gcccggggc caccaacctc gtctccgcgc     480
tcgccgacgc cctcctcgac tccatcccca tggtcgccat cacgggccag gtcccccgcc     540
gcatgatcgg cacggacgcg ttccaggaga cgcccatagt ggaggtcacg cgctccatca     600
ccaagcacaa ctacctggtc cttgacgtgg aggatatccc ccgcgtcatc caggaagcct     660
tcttccttgc atcctctggc cgcccggggc cggtgctagt tgatatcccc aaggacatcc     720
agcagcagat ggctgtgccc gtctgggaca ctccaatgag tttgccaggg tacatcgccc     780
gcctgcccaa gccaccatct actgaatcgc ttgagcaggt cctgcgtctg gttggcgagt     840
cacggcgccc aattctgtat gttggtggtg gctgcgctgc gtctggcgag gagttgcgcc     900
gctttgttga gcttactggg attccagtta caactactct gatgggcctt ggcaacttcc     960
ccagcgacga cccactgtct ctgcgcatgc ttgggatgca tggcactgtg tatgcaaatt    1020
atgcagtaga taaggctgac ctgttgctcg catttggtgt gcggtttgat gatcgtgtga    1080
ctgggaaaat cgaggctttt gcaagcaggt ccaagattga gcacattgac attgacccag    1140
ctgagattgg cagaacaagc agccacatgt ctccatttgt gcagatgtta agcttgcttt    1200
acaggggttg aatgatctat taaatgggag caaagcacaa cagggtctgg attttggtcc    1260
atggcacaag gagttggatc agcagaagag ggagtttcct ctaggattca agactttgg     1320
```

```
cgaggccatc ccgccgcaat atgctatcca ggtactggat gagctgacaa aaggggaggc    1380
gatcattgcc actggtgttg ggcagcacca gatgtgggcg gctcagtatt acacttacaa    1440
gcggccacgg cagtggctgt cttcgtctgg tttggggca atgggatttg ggttaccagc     1500
tgcagctggc gctgctgtgg ccaacccagg tgttacagtt gttgacattg atggtgatgg    1560
tagtttcctc atgaacattc aggagttggc gttgatccgc attgagaacc tcccagtgaa    1620
ggtgatgata ttgaacaacc agcatctggg aatggtggtg cagtgggagg ataggtttta    1680
caaggccaat cgggcgcaca cataccttgg caacccagaa aatgagagtg agatatatcc    1740
agattttgtg acgattgcta aaggattcaa cgttccagca gttcgagtga cgaagaagag    1800
cgaagtcact gcagcaatca agaagatgct tgagacccca gggccatact tgttggatat    1860
catagtcccg catcaggagc acgtgctgcc tatgatccca agcggtggtg ctttcaagga    1920
catgatcatg gagggtgatg gcaggacctc gtactgaaat tcgacctac aagacctaca     1980 agtgtgacat gcgcaatcag catgatgccc gcgtgttgta tcaactacta ggggttcaac    2040
tgtgagccat gcgttttcta gtttgcttgt ttcattcata taagcttgta ttacttagtt    2100
ccgaaccctg tagttttgta gtctatgttc tcttttgtag ggatgtgctg tcataagatg    2160
tcatgcaagt ttcttgtcct acatatcaat aataagtact tccatgnaan aaaaaaaaa    2220 aaaaaaaaa aaaaaaaaa aaaaaaaaa aaaaaaaa                                2259

<210> SEQ ID NO 2
<211> LENGTH: 2265
<212> TYPE: DNA
<213> ORGANISM: Artificial Sequence
<220> FEATURE:
<223> OTHER INFORMATION: AHAS homoeologous gene sequence
<220> FEATURE:
<221> NAME/KEY: misc_feature
<222> LOCATION: (2213)..(2213)
<223> OTHER INFORMATION: n is a, c, g, or t
<220> FEATURE:
<221> NAME/KEY: misc_feature
<222> LOCATION: (2216)..(2216)
<223> OTHER INFORMATION: n is a, c, g, or t

<400> SEQUENCE: 2
tcgcccaaac cctcgccgcc gccatggccg cagccacctc ccccgccgtc gcattctcgg      60
gcgccgccgc cgccgccgcc gccatacccaa acccgcccg ccagcctctc ccgcgccacc     120
agcccgcctc gcgccgcgcg ctccccgccc gcatcgtcag gtgctgcgcc gcgtccccg     180 ccgccacctc cgtcgcgcct cccgccaccg cgctccggcc gtggggcccc tccgagcccc    240
gcaagggcgc cgacatcctc gtcgaggcgc tggagcgctg cggcatcgtc gacgtcttcg    300
cctaccctgg cggcgcgtcc atggagatcc accaggcgct gacgcgctcg ccagtcatca    360
ccaaccacct cttccgccac gagcaggggg aggcgttcgc ggcgtccggg tacgcccgcg    420
cgtccggccg cgtcggcgtc tgcgtcgcca cctccgccc gggggccacc aacctcgtct    480
ccgcgctcgc cgacgctctc ctcgactcca tccccatggt cgccatcacg ggccaggtcc    540
cccgccgcat gatcggcacg gatgcgttcc aggagacgcc catcgtggag gtcacgcgct    600
ccatcaccaa gcacaactac ctggtccttg acgtggagga tatcccccgc gtcatccagg    660
aagccttctt cctcgcatcc tctggccgcc cggggccggt gctggttgat atccccaagg    720
acatccagca gcagatggct gtgcctgtct gggacacgcc gatgagtttg ccagggtaca    780
tcgcccgcct gcccaagcca ccatctactg aatcgcttga gcaggtcctg cgtctggttg    840
```

```
gcgagtcacg gcgcccaatt ctgtatgttg gtggtggctg cgctgcatct ggtgaggagt    900
tgcgccgctt tgttgagctc actgggattc cagttacaac tactcttatg ggccttggca    960
acttccccag tgacgaccca ctgtctctgc gcatgctggg gatgcatggc actgtgtatg   1020
caaattatgc agtagataag gctgacctgt tgcttgcatt tggtgtgcgg tttgatgatc   1080
gtgtgaccgg gaaaatcgag gcttttgcaa gcaggtccaa gattgagcac attgacattg   1140
acccagctga gattggcaga acaagcagcc acatgtctcc atttgtgcag atgttaagct   1200
tgctttacag gggttgaatg ctctattaaa tgggagcaaa gcacaacagg gtctggattt   1260
tggtccatgg cacaaggagt tggatcagca gaagagggag tttcctctag gattcaagac   1320
tttttggtgag gccatcccgc cgcaatatgc tatccaggta ctggatgagc tgacaaaagg   1380
ggaggcgatc attgccaccg tgttgggca gcatcagatg tgggcggctc agtattacac   1440
ttacaagcgg ccacggcagt ggctgtcttc atccggtttg ggtgcaatgg gatttgggtt   1500
gccagctgca gctggcgctg ctgtggccaa cccaggtgtt acagttgttg acattgatgg   1560
ggatggtagt ttcctcatga acattcagga gttggcgttg atccgtattg agaacctccc   1620
agtgaaggtg atgatattga acaaccagca tctgggaatg gtggtgcagt gggaggatag   1680
gttttacaag gccaaccggg cgcacacata ccttggcaac ccagaaaatg agagtgagat   1740
atatccagat tttgtgacga ttgctaaagg attcaacgtt ccggcagttc gtgtgacgaa   1800
gaagagcgaa gtcactgcag caatcaagaa gatgcttgag accccagggc atacttgtt    1860
ggatatcatt gtcccgcatc aggagcacgt gctgcctatg atcccaagcg tggtgctttt   1920
taaggacatg atcatggagg gtgatggcag gacctcgtac tgaaatttcg acctacaaga   1980
cctacaagtg tgacatgcgc aatcagcatg ataccctgcgt gttgtatcaa ctactggggg   2040
ttcaactgtg aaccatgcgt tttctagttt gcttgtttca ttcatataag cttgtgttac   2100
ttagttccga accgtgtagt tttgtagtct ctgttctctt ttgtagggat gtgctgtcat   2160
aagatatcat gcaagtttct tgtcctacat atcaataata agcacttcca tgnaanaaaa   2220
aaaaaaaaaa aaaaaaaaaa aaaaaaaaaa aaaaaaaaaa aaaaa                   2265
```

<210> SEQ ID NO 3
<211> LENGTH: 2259
<212> TYPE: DNA
<213> ORGANISM: Artificial Sequence
<220> FEATURE:
<223> OTHER INFORMATION: AHAS homoeologous gene sequence
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t

```
<220> FEATURE:
<221> NAME/KEY: misc_feature
<222> LOCATION: (158)..(158)
<223> OTHER INFORMATION: n is a, c, g, or t
<220> FEATURE:
<221> NAME/KEY: misc_feature
<222> LOCATION: (2207)..(2207)
<223> OTHER INFORMATION: n is a, c, g, or t
<220> FEATURE:
<221> NAME/KEY: misc_feature
<222> LOCATION: (2210)..(2210)
<223> OTHER INFORMATION: n is a, c, g, or t

<400> SEQUENCE: 3
```

| | | | | | |
|---|---|---|---|---|---|
| tcgcccaaac | cctcgccgcc | gccatggccg | cngccacctc | ccccgccgtc | gcattctcgg | 60 |
| gcgccnccgc | cgccgccatn | cccaaacccg | cccgccancc | tctcccgcgc | caccagcccg | 120 |
| nctcgcgccg | cgcgctcccc | gcccgcntcg | tcaggtgntg | cgccgcgtcc | cccgccgcca | 180 |
| cctccgccgc | gcccccgcc | accgcgctcc | ggccctgggg | cccgtccgag | ccccgcaagg | 240 |
| gcgccgacat | cctcgtcgag | gcgctcgagc | gctgcggcat | cgtcgacgta | ttcgcctacc | 300 |
| ccggcggcgc | gtccatggag | atccaccagg | cgctgacgcg | ctcgcccgtc | atcaccaacc | 360 |
| acctcttccg | ccacgagcag | ggggaggcgt | tcgcggcgtc | cggctacgcc | cgcgcgtccg | 420 |
| gccgcgtcgg | cgtctgcgtc | gccacctccg | gcccgggggc | caccaacctc | gtctccgcgc | 480 |
| tcgctgacgc | cctcctcgac | tccatcccca | tggtcgccat | cacgggccag | gtcccccgcc | 540 |
| gcatgatcgg | cacggacgcg | ttccaggaga | cgcccatagt | ggaggtcacg | cgctccatca | 600 |
| ccaagcacaa | ctacctggtc | cttgacgtgg | aggatatccc | ccgcgtcatc | caggaagcct | 660 |
| tcttcctcgc | gtcctctggc | cgcccggggc | cggtgctggt | tgatatcccc | aaggatatcc | 720 |
| agcagcagat | ggccgtgcct | atctgggaca | cgccgatgag | tttgccaggg | tacatcgccc | 780 |
| gcctgcccaa | gccaccatct | actgaatcgc | ttgagcaggt | cctgcgtctg | gttggcgagt | 840 |
| cacggcgccc | aattctgtat | gttggtggtg | gctgcgctgc | atccggcgag | gagttgcgcc | 900 |
| gctttgttga | gctcactggg | attccggtta | caactactct | gatgggcctt | ggcaacttcc | 960 |
| ccagcgacga | cccactgtct | ctgcgcatgc | ttgggatgca | tggcactgtg | tatgcaaatt | 1020 |
| atgcagtcga | taaggctgac | ctgttgcttg | catttggtgt | gcggtttgat | gatcgcgtga | 1080 |
| ctgggaaaat | cgaggccttt | gcaagcaggt | ccaagattga | gcacattgac | attgacccag | 1140 |
| ctgagattgg | cagaacaagc | agccacatgt | ctccatttgt | gcagatgtta | agcttgcttt | 1200 |
| acaggggttg | aatgctctat | taaatgggag | caaagcacaa | cagggtctgg | attttggtcc | 1260 |
| atggcacaag | gagttggatc | agcagaagag | ggagtttcct | ctaggattca | agactttgg | 1320 |
| cgaggccatc | ccgccgcaat | atgctatcca | ggtactggat | gagctgacaa | aggggaggc | 1380 |
| gatcattgct | actggtgttg | ggcagcacca | gatgtgggcg | gctcagtatt | acacttacaa | 1440 |
| gcggccacgg | cagtggctgt | cttcgtctgg | tttgggggca | atgggatttg | ggttaccagc | 1500 |
| tgcagctggc | gctgctgtgg | ccaacccagg | tgttacagtt | gttgacattg | atggagatgg | 1560 |
| tagtttcctc | atgaacattc | aggagttggc | attgatccgt | attgagaacc | tccctgtgaa | 1620 |
| ggtgatgata | ttgaacaacc | agcatctggg | aatggtggtg | caatgggagg | ataggtttta | 1680 |
| caaggccaat | cgggcgcaca | cataccttgg | caacccagaa | aatgagagtg | agatatatcc | 1740 |
| agattttgtg | acgattgcta | aaggattcaa | cgttccggca | gttcgtgtga | cgaagaagag | 1800 |
| cgaagtcact | gcagcaatca | agaagatgct | tgagacccca | gggccatact | tgttggatat | 1860 |
| catcgtcccg | catcaggagc | acgtgctgcc | tatgatccca | gcggtggtg | ctttcaagga | 1920 |

```
catgatcatg gagggtgatg gcaggacctc gtactgaaat ttcgacctac aagacctaca      1980
agtgtgacat gcgcaatcag catggtgccc gcgtgttgta tcaactacta ggggttcaac      2040
tgtgaaccat gcgttttcta gtttgcttgt ttcattcata taagcttgtg ttacttagtt      2100
ccgaaccctg tagctttgta gtctatgctc tcttttgtag ggatgtgctg tcataagata      2160
tcatgcaagt ttcttgtcct acatatcaat aataagtact tccatgnaan aaaaaaaaaa      2220
aaaaaaaaaa aaaaaaaaaa aaaaaaaaaa aaaaaaaaa                             2259

<210> SEQ ID NO 4
<211> LENGTH: 4357
<212> TYPE: DNA
<213> ORGANISM: Artificial Sequence
<220> FEATURE:
<223> OTHER INFORMATION: AHAS homoeologous gene sequence from subgenome
      A

<400> SEQUENCE: 4
cgttgtgcct tggcagtctc aggttgagcc ctcaccattg aagtagcatg ggtcattgga        60
ttgacccgat ttgacggcgg atctattgga tcttcccttt gtgtcgtttt atactggtat       120
agatgtttaa cacatatttg gaaaatatat tcaaaacatg tttctataaa aaagtttaaa       180
ctatacatgt ataatggaag tcatttataa gaaatgtttt acatgtataa aagatgtaca       240
tcatatgtgc aaaagtagac atgtgttaga aaaaataaac aaacaaatac ataaaaagaa       300
aatcaaagaa aaaacaaccc aaaaaaccaa agaaaataaa gaagaagaag aaaaagagaa       360
aaaacattga aaatcaaaga agaaaaaaac ataagaaaaa gaaaaccgaa aaatactggc       420
aaaaacacac aaaaaatgaa aagaaaaaat aaagaaaacc ggactttacc aatcgaacgg       480
agcgatcgga cacgaatgag cgaaggcatg catcgagcaa caccgctaat tgaccggccc       540
gtagtcgttc gcccgtagac cattcataag aatcggtatc ggagagacat aggggttctt       600
tggtttctaa ccatatcttg tcacactttt accatacatca ccttagtcaa atctgatcaa       660
attaggtgag tatttggttc tagccacatc taaggcaaga tttgtttttc tgagcagtga       720
accccatatg tcatagacag aaaaattgtg aaaagattcc tttagacggt caaagcgtgg       780
ttaacaattt aatcaactca agtaagataa atgcgataaa tgtgacaaaa ataatgtgtt       840
atagaagtat gacaaaaata atcacaatcc aaacagtctg atagcttggc gagtgcaaaa       900
tagatacgaa atctctggtg atatcacacg ggtccaaaat aattgcttgt ttgagcatca       960
gcctttctgc acaaaaaaag ctagcccaaa caaacgagtg gcgtcccatc tgaaccacac      1020
gctcacccgc cgcgtgacag cgccaaagac aaaaccatca cccctcccca attccaaccc      1080
tctctccgcc tcacagaaat ctctcccctc gcccaaaccc tcgccgccgc catggccgcc      1140
gccacctccc ccgccgtcgc attctccggc gccgccgccg ccgccgccgc catgcccaag      1200
cccgcccgcc agcctctccc gcgccaccag cccgcctcgc gccgcgcgct cccgcccgc       1260 gtcgtcaggt gctgcgccgc gccccccgct gctgccacct ccgccgcgcc cccgccacc       1320 gcgctccggc cctggggccc gtccgagccc cgcaagggcg ccgacatcct cgtcgaggcg      1380
ctcgagcgct gcggcatcgt cgacgtattc gcctaccccg gcggcgcgtc catggagatc      1440
caccaggcgc tgacgcgctc gcccgtcatc accaaccacc tcttccgcca cgagcagggg      1500
gaggcgttcg cggcgtccgg ctacgcccgc gcgtccggcc gcgtcggcgt ctgcgtcgcc      1560
acctccggcc cgggggccac caacctcgtc tccgcgctcg ctgacgccct cctcgactcc      1620
atccccatgg tcgccatcac gggccaggtc ccccgccgca tgatcggcac ggacgcgttc      1680
```

```
caggagacgc ccatagtgga ggtcacgcgc tccatcacca agcacaacta cctggtcctt    1740
gacgtggagg atatccccg cgtcatccag gaagccttct tcctcgcgtc ctctggccgc     1800
ccggggccgg tgctggttga tatccccaag gatatccagc agcagatggc cgtgcctatc    1860
tgggacacgc cgatgagttt gccagggtac atcgtcccgc ctgcccaagc caccatctac    1920
tgaatcgctt gagcaggtcc tgcgtctggt tggygagtca cggcgcccaa ttctgtatgt    1980
tggtggtggc tgcgctgcat ccggcgagga gttgcgccgc tttgttgagc tcactgggat    2040
tccggttaca actactctga tgggccttgg caacttcccc agcgacgacc cactgtctct    2100
gcgcatgctt gggatgcatg gcactgtgta tgcaaattat gcagtcgata aggctgacct    2160
gttgcttgca tttggtgtgc ggtttgatga tcgcgtgact gggaaaatcg aggcctttgc    2220
aagcaggtcc aagattgtgc acattgacat tgacccagct gagattggca agaacaagca    2280
gccacatgtc tccatttgtg cagatgttaa gcttgcttta caggggttga atgctctatt    2340
aaatgggagc aaagcacaac agggtctgga ttttggtcca tggcacaagg agttggatca    2400
gcagaagagg gagtttcctc taggattcaa gacttttggc gaggccatcc cgccgcaata    2460
tgctatccag gtactggatg agctgacaaa aggggaggcg atcattgcta ctggtgttgg    2520
gcagcaccag atgtgggcgg ctcagtatta cacttacaag cggccacggc agtggctgtc    2580
ttcgtctggt ttgggggcaa tgggatttgg gttaccagct gcagctggcg ctgctgtggc    2640
caacccaggt gttacagttg ttgacattga tggagatggt agtttcctca tgaacattca    2700
ggagttggca ttgatccgta ttgagaacct ccctgtgaag gtgatgatat tgaacaacca    2760
gcatctggga atggtggtgc aatgggagga taggttttac aaggccaatc gggcgcacac    2820
ataccttggc aacccagaaa atgagagtga gatatatcca gattttgtga cgattgctaa    2880
aggattcaac gttccggcag ttcgtgtgac gaagaagagc gaagtcactg cagcaatcaa    2940
gaagatgctt gagaccccag ggccatactt gttggatatc atcgtcccgc atcaggagca    3000
cgtgctgcct atgatcccaa gcggtggtgc tttcaaggac atgatcatgg agggtgatgg    3060
caggacctcg tactgaaatt tcgacctaca agacctacaa gtgtgacatg cgcaatcagc    3120
atggtgcccg cgtgttgtat caactactag gggttcaact gtgaaccatg cgttttctag    3180
tttgcttgtt tcattcatat aagcttgtgt tacttagttc cgaaccctgt agctttgtag    3240
tctatgctct cttttgtagg gatgtgctgt cataagatat catgcaagtt tcttgtccta    3300
catatcaata taagtactt ccatggaata attctcagtt ctgttttgaa ttttgcatct     3360
tctcacaaac agtgtgctgg ttcctttctg ttactttaca tgtctgccgt gtccggttat    3420
gacataatga ccgatggagg gtggtcagca ggttttagac ggggagttga aactttttt    3480 tggggggaag aaatctgaat acagttggga ggaaagataa aagcatatac cttgattaat    3540
ttattgagcc caatatccag cctaatttat caagcaatag gcagtgtagg gtgttggcat    3600
tcttctcttc cttgagatct ggtgtcggga ccccgattct aagtcacacc gatctagcat    3660
gtaacacctc atatcacttt gcggcctcac gcacggtatc ctcacgggtg tcgccttacc    3720
atggcccggg accgtttgcg cctttggct cacgtatatg atggtgtcgc tagyatccat     3780
atgacagaga acccgggccg acatrgctag tcgtgaaccc aaagcggcac agacctatgg    3840
agacaggcat acatgaatca catcgagcat gtcggtcaac agcgtatgaa tccgggctgt    3900
agcactgggc taacaggact ccggggaacc cgggctgtag caggctaggc aggactccgg    3960
aagtcaccgc gtgacatttc cccgaaggga cagacatagg aacgaagtgg aacacatgcc    4020
ggccagtcaa gtgttctgag cagtagtgct gggctagcag gactccggtg aaccgggctg    4080
```

```
tagcggacta ctatggctcg aggtagcact agactacatt tccccataag agaggctkcc    4140
aaggataagc aactagattg tcggrtcycr srywttgtct ccgtgtgttg ttattgttgt    4200
catgcaagta tgtgttgtac aacatggcat cacaacataa cgcaaactca tatagatata    4260
ggctcagaga gccacatagc attaatacga acagggtcac atgacccatc attcagagca    4320
tacagcatga agcatcatgt ctgagtacag acactac                             4357
```

<210> SEQ ID NO 5
<211> LENGTH: 7585
<212> TYPE: DNA
<213> ORGANISM: Artificial Sequence
<220> FEATURE:
<223> OTHER INFORMATION: AHAS homoeologous gene sequence from subgenome B

<400> SEQUENCE: 5

```
ctgaaaattc aatatggccc tcgggcacca atgctcttgc ttccaatttt cataattccc      60
atttgtaaaa aacacaccac aaaaatcaca ctgtagtaat ctacatgttt gttgagccta     120
taaatcttca taaataatt gagattaatg cggtttgtgc aaaaatatgg ggttggtcat     180
gtttctacat atttctattt gcatttcgtt aactggtgct tgttattttt gtacataatg     240
catatctcat tgttattatt tttaaccttt tgagatggta acgaagatcc aaacatgcat     300
agatgattct ccgatgatt ttttgtagcc tgcactagga actcccaaga gccagaaggt     360
tgggtttgta caagataaca tttgtttgaa cacactcata acctgcatgt gacatacatg     420
acgtaactta tagtgatgat tcgacaaatg tctctttgtc caattttgtt atatatcccg     480
tggcaacgca cgggcattcg actagtatat gtaaagatat caatgtgacg agtccccatg     540
gtcgttgcgc ttgtccacta ccggctcgct agaggcgact ctcacctaga agtcgctacg     600
agcaatacat agtcgttctg ggcgcagcta tgttctgcct tttgcgacgc tcaggcacgg     660
cttgcctaca gcctgagggt cgggctagga accactaatt gtgtcatgct gatgtcacaa     720
tgacatcatg catatttta ttttcgtttt tcgctttctc tttaatttta tttgtatttc     780
aaaatatttt atatatttt tgaatttttt caatgttgta tttgaaaaat gttaaacctg     840
tatagagaaa atatttttg atatatataa aagtatataa catgaatgaa aaatgtataa     900
atgttaatta tgtgtaccaa aaatgttgat aacaattagc agtctcacat atttcaaaat     960
aaatgtatgt ggaattaaaa aatatgtgta tttaagttta aaaaaaatgt tcatgtaatg    1020
ttcgtaaaat gtttgataca ttcaataaaa attatgtcac atttgaataa ttcttctcaa    1080
gcttaacaaa tgcgctcatt atattatcaa aaattgtctg tacagtgtac acaaatgttt    1140
atgtagttca aaaaaaatgt tttttcagta aaaatatatt tgatcatgta ttttataaaa    1200
aactgtttaa tatatattta gaaatatatat tcaaacatg tttctgtaaa aagttaaaac    1260
tatacatgta taatgtaagt catttataat aaatgtttta catgtataaa aaatgtacaa    1320
catatgtgca aaagtagaca tgtgttgaaa aaataaacaa ataactaaat aaaaagaaaa    1380
tcaaagaaaa acaccaaaaa ccaaagaaat aaataaaacc aaagtataaa gaagarraaa    1440
ggagaaaaaa cattgaaaat caaagaraaa aacataaaga agaaaaaaac cgaagaaaac    1500
tagcaaaaaa cacacacaca aaaagaaaa tgaaagaaa taataaagaa agccggactg    1560
aaccgatcaa acgcagcgat cgaacatgga tgagctaagg catgcatcga acaacacggc    1620
taattggccg gcccgtagtc gttcgcccgt agaccattcc tacgaatcgg taccggagag    1680
acataggggc tgtatggttc ctaaccatac cttgccacac tttgtcacac ctcatcttag    1740
```

```
gcaaatttaa tcaagttatg taggtgtttg gttttagcca catctaaggc aagatttatt    1800
ttcctgagca gtgaacccca tatgttatag acataaaaag tgtgggaaga ttcccttag     1860 tcaaactgtg gctaacaatt tattaagaat taacttaagt aagataggtg caacaaatgt    1920
agcaaaaata atgtggtata tatagcaaag atagccacaa ccgcgagtgg aaataccaga    1980
tacgagatct ctggtcatat cacacgagtc caaattaatt gctttgtttg aggttcagcc    2040
ttttgcataa aaaagctagc ccaaacaaac gagtggcgtc ccatctgaac cacacactca    2100
cccgccgcgt gacagcgcca aagacaaaac catcacccct ccccaattcc aaccctctct    2160
ctgcctcaca gaaatctctc cctcgcccaa accctcgccg ccgccatggc cgcagccacc    2220
tcccccgccg tcgcattctc gggcgccgcc gccgccgccg ccgccatacc caaacccgcc    2280
cgccagcctc tcccgcgcca ccagcccgcc tcgcgccgcg cgctccccgc ccgcatcgtc    2340
aggtgctgcg ccgcgtcccc cgccgccacc tccgtcgcgc ctcccgccac cgcgctccgg    2400
ccgtggggcc cctccgagcc ccgcaagggc gccgacatcc tcgtcgaggc gctggagcgc    2460
tgcggcatcg tcgacgtctt cgcctaccct ggcggcgcgt ccatggagat ccaccaggcg    2520
ctgacgcgct cgccagtcat caccaaccac ctcttccgcc acgagcaggg ggaggcgttc    2580
gcggcgtccg ggtacgcccg cgcgtccggc cgcgtcggcg tctgcgtcgc cacctccggc    2640
ccgggggcca ccaacctcgt ctccgcgctc gccgacgctc tcctcgactc catccccatg    2700
gtcgccatca cgggccaggt ccccgccgc atgatcggca cggatgcgtt ccaggagacg    2760
cccatcgtgg aggtcacgcg ctccatcacc aagcacaact acctggtcct tgacgtggag    2820 gatatcccc gcgtcatcca ggaagccttc ttcctcgcat cctctggccg cccggggccg    2880
gtgctggttg atatccccaa ggacatccag cagcagatgg ctgtgcctgt ctgggacacg    2940
ccgatgagtt tgccagggta catcgcccgc ctgcccaagc caccatctac tgaatcgctt    3000
gagcaggtcc tgcgtctggt tggcgagtca cggcgcccaa ttctgtatgt tggtggtggc    3060
tgcgctgcat ctggtgagga gttgcgccgc tttgttgagc tcactgggat tccagttaca    3120
actactctta tgggccttgg caacttcccc agtgacgacc cactgtctct gcgcatgctg    3180
gggatgcatg gcactgtgta tgcaaattat gcagtagata aggctgacct gttgcttgca    3240
tttggtgtgc ggtttgatga tcgtgtgacc gggaaaatcg aggcttttgc aagcaggtcc    3300
aagattgtgc acattgacat tgacccagct gagattggca gaacaagca gccacatgtc    3360 tccatttgtg cagatgttaa gcttgcttta caggggttga atgctctatt aaatgggagc    3420
aaagcacaac agggtctgga ttttggtcca tggcacaagg agttggatca gcagaagagg    3480
gagtttcctc taggattcaa gactttggt gaggccatcc cgccgcaata tgctatccag    3540
gtactggatg agctgacaaa agggaggcg atcattgcca ccgtgttgg gcagcatcag    3600 atgtgggcgg ctcagtatta cacttacaag cggccacggc agtggctgtc ttcatccggt    3660
ttgggtgcaa tggatttgg gttgccagct gcagctggcg ctgctgtggc caacccaggt    3720
gttacagttg ttgacattga tggggatggt agtttcctca tgaacattca ggagttggcg    3780
ttgatccgta ttgagaacct cccagtgaag gtgatgatat tgaacaacca gcatctggga    3840
atggtggtgc agtgggagga taggttttac aaggccaacc gggcgcacac ataccttggc    3900
aacccagaaa atgagagtga gatatatcca gattttgtga cgattgctaa aggattcaac    3960
gttccggcag ttcgtgtgac gaagaagagc gaagtcactg cagcaatcaa gaagatgctt    4020 gagacccag ggccatactt gttggatatc attgtcccgc atcaggagca cgtgctgcct    4080
```

```
atgatcccaa gcggtggtgc ttttaaggac atgatcatgg agggtgatgg caggacctcg      4140
tactgaaatt tcgacctaca agacctacaa gtgtgacatg cgcaatcagc atgatacctg      4200
cgtgttgtat caactactgg gggttcaact gtgaaccatg cgttttctag tttgcttgtt      4260
tcattcatat aagcttgtgt tacttagttc cgaaccgtgt agttttgtag tctctgttct      4320
cttttgtagg gatgtgctgt cataagatat catgcaagtt tcttgtccta catatcaata      4380
ataagcactt ccatggaata attctcagtt ctgttttgaa tttcacatct tctcacgaac      4440
agtgtgctgg ttcctttctg ttactttaca tgcctgccgt gtcaggttat gacataacga      4500
ccgatggagg attggaggt ggtcggctgg ttttagacgg ggaattgaaa cattttttctg      4560
gaagaaatct gaatacagtt gggagggaa atggaagcat atatttatcg agcccgctat       4620
ccaggctaat ttatcaagca ctagacagtg tagggtgttg gcattcttct cttccttgat      4680
atccggcttg agaggagaga ttgaggcttc ggctgtgttg gttgctgatt tctacagcat      4740
tttgagagag agagagagat gttgcaactg tgttttgtct tggttgcttg tacagagaaa      4800
gagatgacat ttagagatat gcagatcgtt taccagttgt gctgcgttta ttcgtactga     4860
ttgttgttat tgttgctatc atgtgcaaat tgttgtgatg gaaaatcaac aaaattttga      4920
tattttgcaa agcgagttgg attgaatgat ttgagaaatg gtgacttgtt gagtggcctt      4980
gagaattggt gtttcatagg tgtgcagttg gtaatgaaag cggcggctt gaaatttccg       5040
aaaggcaggc aatgatactt tctgaaagtg atgtttttc ttccaggttt ccggtggaac       5100
aagtctacgt tgagccaatg tttgtcagct tattctgctc tttagtttca gttgttttgt      5160
tcacagattg ctgggcagag ccccatgatc ggctgagcct ccaggagatc cttgattgct      5220
cgactgcgga tacgttgaat cctttaaaat actataagct ccctagtttt agttttagag      5280
aactgagaat caattgaggg caacattagt cgatttggc ttccgatttt gactgggtcg       5340
cctccctggg tcctctacag ttttgtgggc cctatatgta agtgccccag tgttgtgggc      5400
tttctggtct tttctgatga aagcggcgtg gtggctgggg gctttagaat atttcattga      5460
ttaactaaaa caaatcagat ccctttttcc tgcttcatgt gtgtttgacc aatctttttt      5520
taaaaatttc tttgatttta tatttgatgg agtaaatctg gctgtgtcaa cggtagtcca      5580
ttcgaaacct ggaaatcgaa atcattgtac tgcaggtctg ttgcctgtta gtttgttctt      5640
atataagatc tttgacagtt tatgaatttg tctttggaat ttgtataaag tttcacagat      5700
agacaggccc tgttgttaaa tacgttcgtg caattaagtg taaacatatc tgccagtgat      5760
ttttctcggc tcgcattagt acgcataaat ttttagcact tctctgaatt ttctcatatg      5820
cagaccacct atgaaaaaaa cgacatgcaa gtaaataaaa cgatttcagg ttcatttagt      5880
agcaaaccgt ttttatgtcc tttaaaaatc aattagcaga gccactccat tcaccggtca      5940
gcagaaaaga agcatgtgtg tgttttttggg ctatcataga gctaaataaa tttgattccc     6000
atctgtaatg ttcatcgttg tttacatcag tgttggctgt cgtgtggtcg tggagactag      6060
cctgttcaga caatatgttt gacaagagtg ttgttttgtg agatgcggat gcggtgcttg      6120
catctgtact tgttttttgtg aatacagtt agatgatcag ttttttgtgca cttcttgcca    6180
tgaatggctg ttaaattgtc acttttagg aacttgttgc cgtaatatca attaaataat       6240
caattttgt gcatggtata tcaattagat ggtcatttt ttctagtaga gatgtctata       6300
catgccaatg caatgttcag agttgttcaa ggtctcgacg gcgcggcaaa gcgcgtccta      6360
tgcttctagt ttaagatgac aaccaaacac gacccaagtg tatgctatgc tcatccggtt      6420
ggtccttgtt gatgttcaat gggcgtgtct ccatgggcat cgacggcgac aatgttatct      6480
```

```
tcttcaactg tctgctatat gctcattggc atttttgaaa ctttgcaagc aaggtcgata    6540
acttggtctg gggatgttga cgccccctatg tatctagatt agggtgatgc tcccgccagt    6600
attttttgga cgattatcaa catttgcggc tggtatacta ttgtggctaa tcaacaaggt    6660
ttttttgtgt gtggctaatc aacaaggttt ggcgctcgat gttttttttaa tgtatttcga    6720 tgactcaatt tctacgtctg aacatttcat tgagccaaga ggcagaacaa caggtcacat    6780
gtaaccgcca gtgaaaaagg ttcaagaag aaaaagatac gaacgacagc gagtttgtat    6840
kkcagttttc gaactaagag taacacggag trcagtagta cgatccttgt gtmyttctgt    6900
atttggwtak ttttttttccg gagttgagta ttwgwaactt tcttgtgctt tttttaacat    6960
tagtacagat gcaagtgctc atacatacgc gcttttttgat ttgtaacaat attatgaaag    7020
acgtagtaat tatgtttgca gatcaataaa gctagccatc gtgtggtgtt cccaagaaaa    7080
agatattcac tatagattca ctacatcttc taaaaaaact acactgtaga ttcactacag    7140
accaacagaa tattcatggt cacgtggata aaaacttact ttttgaaagt ctcaagcatt    7200
tggtttgatt ttaagaaaaa ataactgact ctattttgt gtactccttg caacgaacct    7260
ggataaagat ggagccagtc cgttcctggt tactaggagt atccatttcc tgaagaccat    7320
ggagcaacca cggcggatcg ggcgatcggc agcctcccag ccggcgacca tggcggatgc    7380
cacgagcgca ggagcgacgc ctctcctccc tggcctcctc gacgacatcg taatctgtga    7440
gatccttgtc cgcctcgccc cccaaagcca tcctccgctg ccgcgccgtc acgccgtgcc    7500
tggcgccgca ccacctccac ccgcgacttc ctcctcgccc accacgcccg ccagcccgcc    7560
ctcctcatca cctccggcca cagtt                                            7585
```

<210> SEQ ID NO 6
<211> LENGTH: 6195
<212> TYPE: DNA
<213> ORGANISM: Artificial Sequence
<220> FEATURE:
<223> OTHER INFORMATION: AHAS homoeologous gene sequence from subgenome
      D

<400> SEQUENCE: 6

```
aaattttat aatattgttt ttccaaattt tatgtttaaa ctcattttg ttcaattttt        60 tgtgaatata ttttaatcca ttgatagatt ttgaaaatat aataatttt ccaaaacatt      120 ctataatttc ataaaccttt ttaacatttc aagaataaga ttaggaaatt ttgattctta      180
aaatatattt ttaatcttgc aactacattt ttatatacaa ttcatgagc caatttattt       240 tggtagaaat caactgaaaa aacaaaagaa aaaattggaa tagcgggagt tctctgcgcg      300
aacttggggg ggggggcga caaccctcta tcaatgagct agggattcct attacatctc      360
gcctacaagc cgcactagtt tttyccccat ttgttttata tcggtttttt actactttg       420 caccggtttt cttctggtat tatttcattt tccttctata ctttctgttg ttttcttcgt      480 ttcccccctcc tgttttttg tcttttcta cagtttcctt gtttctttct ttggtttttca      540 ccgatttact ttgttttca cgtttttaaa tttaattttt aatcttcaga tacataatta      600
acattcatta aattatatac ttttatgtca agttttttca tacacattgt gcatttata      660 catattagga ttcttaaata catgattaat atttattca gacatagagt acttgttttg      720 aacactttt caaatacatg ttgaaataat ttatttatg atatgaaata tgttttttta      780
ttatgcaaac atttttatac actttatgtt ttttgaaat attacaaaat ttttgcttga      840
aacgtgtgaa cattttttaa aatgtaacat aattttttga atggtatgaa acttttttga      900
```

```
actgcgcgaa cattattttt acattgtata ttattttgat tcattttctg taagttatcg      960
cctgaattgc ttgaaaaacg tgatttttt taaatgccac atatattgtt tttgaatggt      1020
tcatgcattt tctgaaagtt gatcgaacat gtttttatat tgcattttta aaatgtaata     1080
accacttttg aaaattaact aatgtatttt cataatatat gtatttaata ttattaaaaa     1140
taaaaaaaag gtaaagaaa aaacagatca acgcgatgag accccatggt tgttgcgctt     1200
gtccactacc ggctcactga agacgtctct cacagtagga gtcgctacga agaatacata     1260
gtcgcgctgg gcgcggttat gttccgcctg ttgcgacgcc caagcatggc ttgcctacag     1320
ctagagggtc gggctaggaa ccactaattg tgtcatgctg atgtcacaat gacatcatac     1380
atgcttttat tttaattttt cgctttctct ttaaattttt ttgtatttca aaatattctg     1440 ttttttaag aatgctagta ttgtatttga aaaatgttaa acctgtatag aaaaatatat      1500
aacatgaatg aaaaatgtat agatgttaat catgtgtaca aaaaatgatt gtgacaatta     1560
agaatgtcac atatttcaaa ataaatgtat gtggaatttt gaaaaatgt gtatataatt      1620 ttttaatggt catgtaattt taaaaaatg tgtgatacat tcaacaaaaa atatttcaca     1680
tttgaataat tcttcttgag cttaagaaat gtgttcatta tgttatcaat tttttttgtac    1740 agtgtacaaa aatgtttaca tagttcaaaa aaatgttttt cagtaaaatt acatttcatt     1800
gtgtatttaa tatttaaca cacatttgga aaatatattt gaaacatgtt tttgtaaaaa     1860
aaaatttaaa actatgcttg tactccctcc gtccgaaaaa ggtttacatg tataaaagtt     1920
ttttcggagg gagggattat aatgttagtc atttataaga aatgtttac atgtatgaaa     1980 atgtatagca tatgtgtaaa agtagacatg tgttgaaaaa aaaaagtaaa acaacccaaa     2040
aaaccaatga aaataaaata aaaccaaagt accaagaaga agaaaaggag aataaaccat     2100
tgaaaaacaa agaaaataaa aaacataaag aagaagaaa cccaagaaa actggcaaaa       2160 attagacaca gaaagaaaa acgaaaaaat atataataaa raaaaccgga ctgaaccgat      2220
cggacacgga tgagcgaagg catgcatcga gcaacacagc taattggccg gcccatagtc     2280
gttcgcccgc agaccattca tacgaatcgg taccggagag acatagggc tatttggttt      2340 gtagccacat tttgtcatac tttgtgacac cgcatcttat gcaagtttga ccaaattagg     2400
tggatgttta gttctaacca catgtaaggg aagatttttt tttatgagca ttgaacccgt     2460 agacacaaa agtgtaggaa gattacttta aacaagctaa agtgtggcta acaattaag     2520 catctcaggt aagataagtg cgacaaatat ggcaaaaata atgtggtata tatgacaaag     2580
atagtcacaa tccaaacagc ccatagcctg gcgagtgcaa atagatacga gatctctggt     2640
gatatcacaa ccgtccaaat taattgcttg tttcagcatc agcctttttg cataaagaag     2700
ctagcccaat ctgaaccaca cactcacccg ccgcgtgaca gcgccaaaga caaaaacatc     2760 accctccc aattccaacc ctctctctgc ctcacagaaa tctcccccct cgcccaaacc       2820
ctcgccgccg ccatggccgc cgccacctcc ccgccgtcg cattctcggg cgccaccgcc      2880
gccgccatgc ccaaacccgc ccgccatcct ctcccgcgcc accagcccgt ctcgcgccgc     2940
gcgctccccg cccgcgtcgt caggtgttgc gccgcgtccc ccgccgccac ctccgccgcg     3000
cctcccgcaa ccgcgctccg gccctggggc ccgtccgagc ccgcaaggg cgccgacatc      3060 ctcgtcgagg cgctcgagcg ctgcggcatc gtcgacgtct tcgcctaccc cggcggcgcc     3120
tccatggaga tccaccaggc gctgacgcgc tcgcccgtca tcaccaacca cctcttccgc     3180
cacgagcagg gggaggcgtt cgcggcgtcc ggctacgccc gcgcgtccgg ccgcgtcggc     3240
```

```
gtctgcgtcg ccacctccgg cccgggggcc accaacctcg tctccgcgct cgccgacgcc    3300
ctcctcgact ccatcccat ggtcgccatc acgggccagg tccccgccg catgatcggc     3360 acggacgcgt tccaggagac gcccatagtg gaggtcacgc gctccatcac caagcacaac    3420
tacctggtcc ttgacgtgga ggatatcccc cgcgtcatcc aggaagcctt cttccttgca    3480
tcctctggcc gcccggggcc ggtgctagtt gatatcccca aggacatcca gcagcagatg    3540
gctgtgcccg tctgggacac tccaatgagt ttgccagggt acatcgcccg cctgcccaag    3600
ccaccatcta ctgaatcgct tgagcaggtc ctgcgtctgg ttggcgagtc acggcgccca    3660
attctgtatg ttggtggtgg ctgcgctgcg tctggcgagg agttgcgccg ctttgttgag    3720
cttactggga ttccagttac aactactctg atgggccttg gcaacttccc cagcgacgac    3780
ccactgtctc tgcgcatgct tgggatgcat ggcactgtgt atgcaaatta tgcagtagat    3840
aaggctgacc tgttgctcgc atttggtgtg cggtttgatg atcgtgtgac tgggaaaatc    3900
gaggcttttg caagcaggtc caagattgtg cacattgaca ttgacccagc tgagattggc    3960
aagaacaagc agccacatgt ctccatttgt gcagatgtta agcttgcttt acaggggttg    4020
aatgatctat taaatgggag caaagcacaa cagggtctgg attttggtcc atggcacaag    4080
gagttggatc agcagaagag ggagtttcct ctaggattca agacttttgg cgaggccatc    4140
ccgccgcaat atgctatcca ggtactggat gagctgacaa aggggaggc gatcattgcc    4200 actggtgttg gcagcacca gatgtgggcg gctcagtatt acacttacaa gcggccacgg    4260
cagtggctgt cttcgtctgg tttgggggca atgggatttg ggttaccagc tgcagctggc    4320
gctgctgtgg ccaacccagg tgttacagtt gttgacattg atggtgatgg tagtttcctc    4380
atgaacattc aggagttggc gttgatccgc attgagaacc tcccagtgaa ggtgatgata    4440
ttgaacaacc agcatctggg aatggtggtg cagtgggagg ataggtttta caaggccaat    4500
cgggcgcaca catacctttgg caacccagaa atgagagtg agatatatcc agattttgtg    4560
acgattgcta aaggattcaa cgttccagca gttcgagtga cgaagaagag cgaagtcact    4620
gcagcaatca agaagatgct tgagaccccca gggccatact tgttggatat catagtcccg    4680
catcaggagc acgtgctgcc tatgatccca agcggtggtg cttttcaagga catgatcatg    4740 gagggtgatg gcaggacctc gtactgaaat ttcgacctac aagacctaca agtgtgacat    4800
gcgcaatcag catgatgccc gcgtgttgta tcaactacta ggggttcaac tgtgagccat    4860
gcgttttcta gtttgcttgt ttcattcata taagcttgta ttacttagtt ccgaaccctg    4920
tagttttgta gtctatgttc tcttttgtag ggatgtgctg tcataagatg tcatgcaagt    4980
ttcttgtcct acatatcaat aataagtact tccatggaat aattctcagt tctgttttga    5040
attttgcatc ttctcacaaa cagtgtgctg gttccttttct gttactttac atgtctgctg    5100
tgtcaggttc tgacataacg accgatggag ggtggtcggc aggttttaga aggggaattg    5160 aaacttttt ttgggaagaa gtctgaatac agttgggagg aaaaatagaa gtatatactt    5220
cgattaattt atcaagcccg ctatccagtc taatttatca agcactagac agtgtagggt    5280
gttggcattc ttctcttcct tgagatccgg cttgagagga gagaccgagg cttcggctgt    5340
gttggttgct gatttctaca gctttttgag atagagagag agatcctgca actgtggttt    5400
gtcttgctgc ttgtacagcg agagagacat tgagagatat gtagatcgtt taccagttgt    5460
gctgctgtta ttcgtactgg tactgattgt tgttactgtt gctatcatgt gcaaattgtt    5520
gtgatggaaa atcaacaaaa ttttgatatt ttgcaaagcg agttggattg aatgatttga    5580
gaaatggtga ctgctttccc tcagacttgt tgagtggcct tgagaattgg tgtttcatag    5640
```

-continued

```
gtggtgtatg cagttgctaa tgaaaggcga cggcttgaaa tttccgaaag gcagccaatg    5700
atactttctg aaagtgatgt ttttttcgtc caggtttccg gtggagcaag tctagacaca    5760
cgttgagcca atgtttgtca gcttattctg ctctttagtt tcagtttagg tgcagttgtt    5820
ttgtttacag attgctgggc agagcccgt gatcggctga gcctcaaga gatccttgct      5880 tgctcgactg cggatacgct gaatccttta aaacgctccc tagttttaag ttttagagaa    5940
ctgagaatca attgggggca acattactgg gtcgcctccc tgggcctcta cagttttgtg    6000
ggccctatat gtaagtgccc cagtgttgtg gggatttgcg gcgtggcggg cggcatttgc    6060
gtcctctctt cggcggcgct gttttcccct ccttcttgct gcttctggag gaggtggtcg    6120
gcggcgggtg ttgtgggggg tcgcattgga gcggcgcgaa cgccggtcct gctgcatctg    6180
ccgccattgg ttgtt                                                     6195

<210> SEQ ID NO 7
<211> LENGTH: 26
<212> TYPE: DNA
<213> ORGANISM: Artificial Sequence
<220> FEATURE:
<223> OTHER INFORMATION: Primer Sequence

<400> SEQUENCE: 7
tctgtaagtt atcgcctgaa ttgctt                                         26

<210> SEQ ID NO 8
<211> LENGTH: 24
<212> TYPE: DNA
<213> ORGANISM: Artificial Sequence
<220> FEATURE:
<223> OTHER INFORMATION: Primer Sequence

<400> SEQUENCE: 8
cattgtgaca tcagcatgac acaa                                           24

<210> SEQ ID NO 9
<211> LENGTH: 20
<212> TYPE: DNA
<213> ORGANISM: Artificial Sequence
<220> FEATURE:
<223> OTHER INFORMATION: Primer Sequence

<400> SEQUENCE: 9
aagcayggct tgcctacagc                                                20

<210> SEQ ID NO 10
<211> LENGTH: 24
<212> TYPE: DNA
<213> ORGANISM: Artificial Sequence
<220> FEATURE:
<223> OTHER INFORMATION: Primer Sequence

<400> SEQUENCE: 10
aaccaaatrc ccctatgtct ctcc                                           24

<210> SEQ ID NO 11
<211> LENGTH: 20
<212> TYPE: DNA
<213> ORGANISM: Artificial Sequence
<220> FEATURE:
<223> OTHER INFORMATION: Primer Sequence

<400> SEQUENCE: 11
```
cgttcgcccg tagaccattc                                               20

<210> SEQ ID NO 12
<211> LENGTH: 23
<212> TYPE: DNA
<213> ORGANISM: Artificial Sequence
<220> FEATURE:
<223> OTHER INFORMATION: Primer Sequence

<400> SEQUENCE: 12 ggagggtga tgkttttgtc ttt                                            23

<210> SEQ ID NO 13
<211> LENGTH: 17
<212> TYPE: DNA
<213> ORGANISM: Artificial Sequence
<220> FEATURE:
<223> OTHER INFORMATION: Primer Sequence

<400> SEQUENCE: 13
tcgcccaaac cctcgcc                                                  17

<210> SEQ ID NO 14
<211> LENGTH: 20
<212> TYPE: DNA
<213> ORGANISM: Artificial Sequence
<220> FEATURE:
<223> OTHER INFORMATION: Primer Sequence

<400> SEQUENCE: 14
gggtcgtcrc tggggaagtt                                               20

<210> SEQ ID NO 15
<211> LENGTH: 23
<212> TYPE: DNA
<213> ORGANISM: Artificial Sequence
<220> FEATURE:
<223> OTHER INFORMATION: Primer Sequence

<400> SEQUENCE: 15
gccttcttcc tygcrtcctc tgg                                           23

<210> SEQ ID NO 16
<211> LENGTH: 23
<212> TYPE: DNA
<213> ORGANISM: Artificial Sequence
<220> FEATURE:
<223> OTHER INFORMATION: Primer Sequence

<400> SEQUENCE: 16
gcccgrttgg ccttgtaaaa cct                                           23

<210> SEQ ID NO 17
<211> LENGTH: 23
<212> TYPE: DNA
<213> ORGANISM: Artificial Sequence
<220> FEATURE:
<223> OTHER INFORMATION: Primer Sequence

<400> SEQUENCE: 17
aycagatgtg ggcggctcag tat                                           23

<210> SEQ ID NO 18
<211> LENGTH: 29
<212> TYPE: DNA
<213> ORGANISM: Artificial Sequence

```
<220> FEATURE:
<223> OTHER INFORMATION: Primer Sequence

<400> SEQUENCE: 18
gggatatgta ggacaagaaa cttgcatga                              29

<210> SEQ ID NO 19
<211> LENGTH: 26
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (25)..(25)
<223> OTHER INFORMATION: n is a, c, g, or t

<400> SEQUENCE: 19
agggccatac ttgttggata tcatnc                                 26

<210> SEQ ID NO 20
<211> LENGTH: 23
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (22)..(22)
<223> OTHER INFORMATION: n is a, c, g, or t

<400> SEQUENCE: 20
gccaacaccc tacactgcct ant                                    23

<210> SEQ ID NO 21
<211> LENGTH: 22
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (21)..(21)
<223> OTHER INFORMATION: n is a, c, g, or t

<400> SEQUENCE: 21
tgcgcaatca gcatgatacc nt                                     22

<210> SEQ ID NO 22
<211> LENGTH: 22
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (21)..(21)
<223> OTHER INFORMATION: n is a, c, g, or t

<400> SEQUENCE: 22
acgtatccgc agtcgagcaa nt                                     22

<210> SEQ ID NO 23
<211> LENGTH: 25
<212> TYPE: DNA
<213> ORGANISM: Artificial Sequence
<220> FEATURE:
<223> OTHER INFORMATION: Primer Sequence
<220> FEATURE:
```

```
<221> NAME/KEY: misc_feature
<222> LOCATION: (24)..(24)
<223> OTHER INFORMATION: n is a, c, g, or t

<400> SEQUENCE: 23
gtagggatgt gctgtcataa gatng                                          25

<210> SEQ ID NO 24
<211> LENGTH: 21
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (20)..(20)
<223> OTHER INFORMATION: n is a, c, g, or t

<400> SEQUENCE: 24
ttggaggctc agccgatcan c                                              21

<210> SEQ ID NO 25
<211> LENGTH: 3053
<212> TYPE: DNA
<213> ORGANISM: Artificial Sequence
<220> FEATURE:
<223> OTHER INFORMATION: Homoeologous gene copy of AHAS from subgenome A

<400> SEQUENCE: 25
cgttcgcccg tagaccattc ataagaatcg gtatcggaga gacatagggg ttctttggtt      60
tctaaccata tcttgtcaca ctttaccata catcaccttta gtcaaatctg atcaaattag    120
gtgagtattt ggttctagcc acatctaagg caagatttgt ttttctgagc agtgaacccc    180
atatgtcata gacagaaaaa ttgtgaaaag attcctttag acggtcaaag cgtggttaac    240
aatttaatca actcaagtaa gataaatgcg ataaatgtga caaaaataat gtgttataga    300
agtatgacaa aataataaac aatccaaaca gtctgatagc ttggcgagtg caaaatagat    360
acgaaatctc tggtgatatc acacgggtcc aaaataattg cttgtttgag catcagcctt    420
tctgcacaaa aaaagctagc ccaaacaaac gagtggcgtc ccatctgaac cacacgctca    480
cccgccgcgt gacagcgcca aagacaaaac catcaccccct ccccaattcc aaccctctct    540
ccgcctcaca gaaatctctc ccctcgccca aaccctcgcc gccgccatgg ccgccgccac    600
ctcccccgcc gtcgcattct ccggcgccgc cgccgccgcc gccgccatgc ccaagcccgc    660
ccgccagcct ctcccgcgcc accagccccgc ctcgcgccgc gcgctccccg cccgcgtcgt    720
caggtgctgc gccgcgcccc ccgctgctgc cacctccgcc gcgcccccccg ccaccgcgct    780 ccggccctcg gggcccgtcc gagccccgca agggcgccga catcctcgtc gaggcgctcg    840
agcgctgcgg catcgtcgac gtattcgcct accccggcgg cgcgtccatg gagatccacc    900
aggcgctgac gcgctcgccc gtcatcacca ccacctcct tccgccacga gcagggggga    960
ggcgttcgcg gcgtccggct acgcccgcgc gtccggccgc gtcggcgtct gcgtcgccac   1020
ctccggcccg ggggccacca acctcgtctc cgcgctcgct gacgccctcc tcgactccat   1080
ccccatggtc gccatcacgg gccaggtccc ccgccgcatg atcggcacgg acgcgttcca   1140
ggagacgccc atagtggagg tcacgcgctc catcaccaag cacaactacc tggtccttga   1200
cgtggaggat atccccccgcg tcatccagga agccttcttc ctcgcgtcct ctggccgccc   1260
ggggccggtg ctggttgata tcccccaagga tatccagcag cagatggccg tgcctatctg   1320
ggacacgccg atgagtttgc cagggtacat cgtcccgcct gcccaagcca ccatctactg   1380
```

```
aatcgcttga gcaggtcctg cgtctggttg gcgagtcacg gcgcccaatt ctgtatgttg   1440
gtggtggctg cgctgcatcc ggcgaggagt tgcgccgctt tgttgagctc actgggattc   1500
cggttacaac tactctgatg ggccttggca acttccccag cgacgaccca ctgtctctgc   1560
gcatgcttgg gatgcatggc actgtgtatg caaattatgc agtcgataag gctgacctgt   1620
tgcttgcatt tggtgtgcgg tttgatgatc gcgtgactgg gaaaatcgag gcctttgcaa   1680
gcaggtccaa gattgtgcac attgacattg acccagctga gattggcaag aacaagcagc   1740
cacatgtctc catttgtgca gatgttaagc ttgctttaca ggggttgaat gctctattaa   1800
atgggagcaa agcacaacag ggtctggatt ttggtccatg gcacaaggag ttggatcagc   1860
agaagaggga gtttcctcta ggattcaaga cttttggcga ggccatcccg ccgcaatatg   1920
ctatccaggt actggatgag ctgacaaaag gggaggcgat cattgctact ggtgttgggc   1980
agcaccagat gtgggcggct cagtattaca cttacaagcg gccacggcag tggctgtctt   2040
cgtctggttg ggggcaatgg gatttgggtt accagctgca gctggcgctg ctgtggccaa   2100
cccaggtgtt acagttgttg acattgatgg agatggtagt ttcctcatga acattcagga   2160
gttggcattg atccgtattg agaacctccc tgtgaaggtg atgatattga acaaccagca   2220
tctgggaatg gtggtgcaat gggaggatag gttttacaag gccaatcggg cgcacacata   2280
ccttggcaac ccagaaaatg agagtgagat atatccagat tttgtgacga ttgctaaagg   2340
attcaacgtt ccggcagttc gtgtgacgaa gaagagcgaa gtcactgcag caatcaagaa   2400
gatgcttgag accccagggc catacttgtt ggatatcatc gtcccgcatc aggagcacgt   2460
gctgcctatg atcccaagcg gtggtgcttt caaggacatg atcatggagg gtgatggcag   2520
gacctcgtac tgaaatttcg acctacaaga cctacaagtg tgacatgcgc aatcagcatg   2580
gtgcccgcgt gttgtatcaa ctactagggg ttcaactgtg aaccatgcgt tttctagttt   2640
gcttgtttca ttcatataag cttgtgttac ttagttccga accctgtagc tttgtagtct   2700
atgctctctt ttgtagggat gtgctgtcat aagatatcat gcaagtttct tgtcctacat   2760
atcaataata agtacttcca tggaataatt ctcagttctg ttttgaattt tgcatcttct   2820
cacaaacagt gtgctggttc cttttctgtta ctttacatgt ctgccgtgtc cggttatgac   2880
ataatgaccg atggagggtg gtcagcaggt tttagacggg gagttgaaac ttttttttgg   2940
ggggaagaaa tctgaataca gttgggagga aagataaaag catatacctt gattaattta   3000
ttgagcccaa tatccagcct aatttatcaa gcaataggca gtgtagggtg ttg          3053
```

<210> SEQ ID NO 26
<211> LENGTH: 3589
<212> TYPE: DNA
<213> ORGANISM: Artificial Sequence
<220> FEATURE:
<223> OTHER INFORMATION: Homoeologous gene copy of AHAS from subgenome B

<400> SEQUENCE: 26

```
cgttcgcccg tagaccattc ctacgaatcg gtaccggaga gacatagggg ctgtatggtt    60
cctaaccata ccttgccaca ctttgtcaca cctcatctta ggcaaattta atcaagttat   120
gtaggtgttt ggttttagcc acatctaagg caagatttat tttcctgagc agtgaacccc   180
atatgttata gacataaaaa gtgtgggaag attcccttta gtcaaactgt ggctaacaat   240
ttattaagaa ttaacttaag taagataggt gcaacaaatg tagcaaaaat aatgtggtat   300
atatagcaaa gatagccaca accgcgagtg gaaataccag atacgagatc tctggtcata   360
```

| | |
|---|---|
| tcacacgagt ccaaattaat tgctttgttt gaggttcagc cttttttgcat aaaaaagcta | 420 |
| gcccaaacaa acgagtggcg tcccatctga accacacact cacccgccgc gtgacagcgc | 480 |
| caaagacaaa accatcaccc ctccccaatt ccaaccctct ctctgcctca cagaaatctc | 540 |
| tccctcgccc aaaccctcgc cgccgccatg gccgcagcca cctcccccgc cgtcgcattc | 600 |
| tcgggcgccg ccgccgccgc cgccgccata cccaaacccg cccgccagcc tctcccgcgc | 660 |
| caccagcccg cctcgcgccg cgcgctcccc gcccgcatcg tcaggtgctg cgccgcgtcc | 720 |
| cccgccgcca cctccgtcgc gcctcccgcc accgcgctcc ggccgtgggg cccctccgag | 780 |
| ccccgcaagg gcgccgacat cctcgtcgag gcgctggagc gctgcggcat cgtcgacgtc | 840 |
| ttcgcctacc ctggcggcgc gtccatggag atccaccagg cgctgacgcg ctcgccagtc | 900 |
| atcaccaacc acctcttccg ccacgagcag ggggaggcgt tcgcggcgtc cgggtacgcc | 960 |
| cgcgcgtccg gccgcgtcgg cgtctgcgtc gccacctccg gcccgggggc caccaacctc | 1020 |
| gtctccgcgc tcgccgacgc tctcctcgac tccatcccca tggtcgccat cacgggccag | 1080 |
| gtcccccgcc gcatgatcgg cacggatgcg ttccaggaga cgcccatcgt ggaggtcacg | 1140 |
| cgctccatca ccaagcacaa ctacctggtc cttgacgtgg aggatatccc ccgcgtcatc | 1200 |
| caggaagcct tcttcctcgc atcctctggc cgcccggggc cggtgctggt tgatatcccc | 1260 |
| aaggacatcc agcagcagat ggctgtgcct gtctgggaca cgccgatgag tttgccaggg | 1320 |
| tacatcgccc gcctgcccaa gccaccatct actgaatcgc ttgagcaggt cctgcgtctg | 1380 |
| gttggcgagt cacggcgccc aattctgtat gttggtggtg gctgcgctgc atctggtgag | 1440 |
| gagttgcgcc gctttgttga gctcactggg attccagtta caactactct tatgggcctt | 1500 |
| ggcaacttcc ccagtgacga cccactgtct ctgcgcatgc tggggatgca tggcactgtg | 1560 |
| tatgcaaatt atgcagtaga taaggctgac ctgttgcttg catttggtgt gcggtttgat | 1620 |
| gatcgtgtga ccgggaaaat cgaggctttt gcaagcaggt ccaagattgt gcacattgac | 1680 |
| attgacccag ctgagattgg caagaacaag cagccacatg tctccatttg tgcagatgtt | 1740 |
| aagcttgctt tacaggggtt gaatgctcta ttaaatggga gcaaagcaca acagggtctg | 1800 |
| gattttggtc catggcacaa ggagttggat cagcagaaga gggagtttcc tctaggattc | 1860 |
| aagacttttg gtgaggccat cccgccgcaa tatgctatcc aggtactgga tgagctgaca | 1920 |
| aaaggggagg cgatcattgc caccggtgtt gggcagcatc agatgtgggc ggctcagtat | 1980 |
| tacacttaca gcggccacg gcagtggctg tcttcatccg gtttgggtgc aatgggattt | 2040 |
| gggttgccag ctgcagctgg cgctgctgtg gccaacccag tgttacagt tgttgacatt | 2100 |
| gatggggatg gtagtttcct catgaacatt caggagttgg cgttgatccg tattgagaac | 2160 |
| ctcccagtga aggtgatgat attgaacaac cagcatctgg gaatggtggt gcagtgggag | 2220 |
| gataggtttt acaaggccaa ccgggcgcac acataccttg caacccaga aaatgagagt | 2280 |
| gagatatatc cagattttgt gacgattgct aaaggattca cgttccggc agttcgtgtg | 2340 |
| acgaagaaga gcgaagtcac tgcagcaatc aagaagatgc ttgagacccc agggccatac | 2400 |
| ttgttggata tcattgtccc gcatcaggag cacgtgctgc ctatgatccc aagcggtggt | 2460 |
| gcttttaagg acatgatcat ggagggtgat ggcaggacct cgtactgaaa tttcgaccta | 2520 |
| caagacctac aagtgtgaca tgcgcaatca gcatgatacc tgcgtgttgt atcaactact | 2580 |
| gggggttcaa ctgtgaacca tgcgttttct agtttgcttg tttcattcat ataagcttgt | 2640 |
| gttacttagt tccgaaccgt gtagtttttgt agtctctgtt ctcttttgta gggatgtgct | 2700 |
| gtcataagat atcatgcaag tttcttgtcc tacatatcaa taataagcac ttccatggaa | 2760 |

```
taattctcag ttctgttttg aatttcacat cttctcacga acagtgtgct ggttcctttc    2820
tgttacttta catgcctgcc gtgtcaggtt atgacataac gaccgatgga ggattggagg    2880
gtggtcggct ggttttagac ggggaattga acattttttc tggaagaaat ctgaatacag    2940
ttgggagggg aaatggaagc atatatttat cgagcccgct atccaggcta atttatcaag    3000
cactagacag tgtagggtgt tggcattctt ctcttccttg atatccggct tgagaggaga    3060
gattgaggct tcggctgtgt tggttgctga tttctacagc attttgagag agagagagag    3120
atgttgcaac tgtgttttgt cttggttgct tgtacagaga aagagatgac atttagagat    3180
atgcagatcg tttaccagtt gtgctgcgtt tattcgtact gattgttgtt attgttgcta    3240
tcatgtgcaa attgttgtga tggaaaatca acaaaatttt gatattttgc aaagcgagtt    3300
ggattgaatg atttgagaaa tggtgacttg ttgagtggcc ttgagaattg gtgtttcata    3360
ggtgtgcagt tggtaatgaa aggcggcggc ttgaaatttc cgaaaggcag gcaatgatac    3420
tttctgaaag tgatgttttt tcttccaggt ttccggtgga acaagtctac gttgagccaa    3480
tgtttgtcag cttattctgc tctttagttt cagttgtttt gttcacagat tgctgggcag    3540
agccccatga tcggctgagc ctccaggaga tccttgattg ctcgactgc                3589

<210> SEQ ID NO 27
<211> LENGTH: 3599
<212> TYPE: DNA
<213> ORGANISM: Artificial Sequence
<220> FEATURE:
<223> OTHER INFORMATION: Homoeologous gene copy of AHAS from subgenome D

<400> SEQUENCE: 27
cgttcgcccg tagaccattc atacgaatcg gtaccggaga gacatagggg ctatttggtt      60
tgtagccaca ttttgtcata ctttgtgaca ccgcatctta tgcaagtttg atcaaattag     120
gtggatgttt agttctaacc acatgtaagg gaagattttt ttttttatga gcattgaacc     180
cgtagacaca aaaagtgtag gaagattact ttaaacaagc taaagtgtgg ctaacaattt     240
aagcatctca ggtaagataa gtgcgacaaa tatggcaaaa ataatgtggt atatatgaca     300
aagatagtca caatccaaac agcccatagc ctggcgagtg caaatagata cgagatctct     360
ggtgatatca caaccgtcca aattaattgc ttgtttcagc atcagccttt ttgcataaag     420
aagctagccc aatctgaacc acacactcac ccgccgcgtg acagcgccaa agacaaaacc     480
atcacccctc cccaattcca accctctctc tgcctcacag aaatctcccc cctcgcccaa     540
accctcgccc ccgccatggc cgccgccacc tccccccgcc tcgcattctc gggcgccacc     600
gccgccgcca tgcccaaacc cgcccgccat cctctcccgc gccaccagcc cgtctcgcgc     660
cgcgcgctcc ccgcccgcgt cgtcaggtgt tgcgccgcgt cccccgccgc cacctccgcc     720
gcgcctcccg caaccgcgct ccggccctgg ggccgtccg agccccgcaa gggcgccgac     780
atcctcgtcg aggcgctcga gcgctgcggc atcgtcgacg tcttcgccta ccccggcggc     840
gcctccatgg agatccacca ggcgctgacg cgctcgcccg tcatcaccaa ccacctcttc     900
cgccacgagc agggggaggc gttcgcggcg tccggctacg cccgcgcgtc cggccgcgtc     960
ggcgtctgcg tcgccacctc cggccgcggg gccaccaacc tcgtctccgc gctcgccgac    1020
gccctcctcg actccatccc catggtcgcc atcacgggcc aggtcccccg ccgcatgatc    1080
ggcacggacg cgttccagga gacgccata gtggaggtca cgcgctccat caccaagcac    1140
aactacctgg tccttgacgt ggaggatatc ccccgcgtca tccaggaagc cttcttcctt    1200
```

```
gcatcctctg gccgcccggg gccggtgcta gttgatatcc ccaaggacat ccagcagcag      1260
atggctgtgc ccgtctggga cactccaatg agtttgccag ggtacatcgc ccgcctgccc      1320
aagccaccat ctactgaatc gcttgagcag gtcctgcgtc tggttggcga gtcacggcgc      1380
ccaattctgt atgttggtgg tggctgcgct gcgtctggcg aggagttgcg ccgctttgtt      1440
gagcttactg ggattccagt tacaactact ctgatgggcc ttggcaactt ccccagcgac      1500
gacccactgt ctctgcgcat gcttgggatg catggcactg tgtatgcaaa ttatgcagta      1560
gataaggctg acctgttgct cgcatttggt gtgcggtttg atgatcgtgt gactgggaaa      1620
atcgaggctt ttgcaagcag gtccaagatt gtgcacattg acattgaccc agctgagatt      1680
ggcaagaaca agcagccaca tgtctccatt tgtgcagatg ttaagcttgc tttacagggg      1740
ttgaatgatc tattaaatgg gagcaaagca caacagggtc tggattttgg tccatggcac      1800
aaggagttgg atcagcagaa gagggagttt cctctaggat tcaagacttt tggcgaggcc      1860
atcccgccgc aatatgctat ccaggtactg gatgagctga caaaagggga ggcgatcatt      1920
gccactggtg ttgggcagca ccagatgtgg gcggctcagt attacactta caagcggcca      1980
cggcagtggc tgtcttcgtc tggtttgggg gcaatgggat ttgggttacc agctgcagct      2040
ggcgctgctg tggccaaccc aggtgttaca gttgttgaca ttgatggtga tggtagtttc      2100
ctcatgaaca ttcaggagtt ggcgttgatc cgcattgaga acctcccagt gaaggtgatg      2160
atattgaaca accagcatct gggaatggtg gtgcagtggg aggataggtt ttacaaggcc      2220
aatcgggcgc acacatacct tggcaaccca gaaaatgaga gtgagatata ccagattttt      2280
gtgacgattg ctaaaggatt caacgttcca gcagttcgag tgacgaagaa gagcgaagtc      2340
actgcagcaa tcaagaagat gcttgagacc ccagggccat acttgttgga tatcatagtc      2400
ccgcatcagg agcacgtgct gcctatgatc ccaagcggtg gtgctttcaa ggacatgatc      2460
atggagggtg atggcaggac ctcgtactga aatttcgacc tacaagacct acaagtgtga      2520
catgcgcaat cagcatgatg cccgcgtgtt gtatcaacta ctaggggttc aactgtgagc      2580
catgcgtttt ctagtttgct tgtttcattc atataagctt gtattactta gttccgaacc      2640
ctgtagtttt gtagtctatg ttctcttttg tagggatgtg ctgtcataag atgtcatgca      2700
agtttcttgt cctacatatc aataataagt acttccatgg aataattctc agttctgttt      2760
tgaattttgc atcttctcac aaacagtgtg ctggttcctt tctgttactt tacatgtctg      2820
ctgtgtcagg ttctgacata cgaccgatg agggtggtc ggcaggtttt agaagggga       2880
```

```
<210> SEQ ID NO 28
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 28

Asp Ser Thr Asn Arg Tyr Arg
1               5

<210> SEQ ID NO 29
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 29

Gln Ser Ala His Arg Thr Asn
1               5

<210> SEQ ID NO 30
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 30

Arg Asn Asp His Arg Ile Asn
1               5

<210> SEQ ID NO 31
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 31

Arg Ser Asp Val Leu Ser Ala
1               5

<210> SEQ ID NO 32
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 32

His Asn Ser Ser Leu Lys Asp
1               5

<210> SEQ ID NO 33
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 33

Gln Trp Gly Thr Arg Tyr Arg
1               5
```

```
<210> SEQ ID NO 34
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 34

Gln Arg Ser Asn Leu Asp Ser
1               5

<210> SEQ ID NO 35
<211> LENGTH: 28
<212> TYPE: DNA
<213> ORGANISM: Artificial Sequence
<220> FEATURE:
<223> OTHER INFORMATION: ZFN Target Site

<400> SEQUENCE: 35
ggatagcata ttgcggcggg atggcctc                                      28

<210> SEQ ID NO 36
<211> LENGTH: 28
<212> TYPE: DNA
<213> ORGANISM: Artificial Sequence
<220> FEATURE:
<223> OTHER INFORMATION: ZFN Target Site

<400> SEQUENCE: 36
gtactggatg agctgacaaa aggggagg                                      28

<210> SEQ ID NO 37
<211> LENGTH: 28
<212> TYPE: DNA
<213> ORGANISM: Artificial Sequence
<220> FEATURE:
<223> OTHER INFORMATION: ZFN Target Site

<400> SEQUENCE: 37
gtacctggat agcatattgc ggcgggat                                      28

<210> SEQ ID NO 38
<211> LENGTH: 28
<212> TYPE: DNA
<213> ORGANISM: Artificial Sequence
<220> FEATURE:
<223> OTHER INFORMATION: ZFN Target Site

<400> SEQUENCE: 38
agtacctgga tagcatattg cggcggga                                      28

<210> SEQ ID NO 39
<211> LENGTH: 28
<212> TYPE: DNA
<213> ORGANISM: Artificial Sequence
<220> FEATURE:
<223> OTHER INFORMATION: ZFN Target Site

<400> SEQUENCE: 39
gatgagctga caaaggggga ggcgatca                                      28

<210> SEQ ID NO 40
<211> LENGTH: 28
<212> TYPE: DNA
<213> ORGANISM: Artificial Sequence
<220> FEATURE:
```

```
<223> OTHER INFORMATION: ZFN Target Site

<400> SEQUENCE: 40
atgagctgac aaaagggggag gcgatcat                                        28

<210> SEQ ID NO 41
<211> LENGTH: 28
<212> TYPE: DNA
<213> ORGANISM: Artificial Sequence
<220> FEATURE:
<223> OTHER INFORMATION: ZFN Target Site

<400> SEQUENCE: 41
tcatccagta cctggatagc atattgcg                                         28

<210> SEQ ID NO 42
<211> LENGTH: 28
<212> TYPE: DNA
<213> ORGANISM: Artificial Sequence
<220> FEATURE:
<223> OTHER INFORMATION: ZFN Target Site

<400> SEQUENCE: 42
ctgacaaaag gggaggcgat cattgcca                                         28

<210> SEQ ID NO 43
<211> LENGTH: 28
<212> TYPE: DNA
<213> ORGANISM: Artificial Sequence
<220> FEATURE:
<223> OTHER INFORMATION: ZFN Target Site

<400> SEQUENCE: 43
aggcagcacg tgctcctgat gcgggact                                         28

<210> SEQ ID NO 44
<211> LENGTH: 28
<212> TYPE: DNA
<213> ORGANISM: Artificial Sequence
<220> FEATURE:
<223> OTHER INFORMATION: ZFN Target Site

<400> SEQUENCE: 44
taggcagcac gtgctcctga tgcgggac                                         28

<210> SEQ ID NO 45
<211> LENGTH: 28
<212> TYPE: DNA
<213> ORGANISM: Artificial Sequence
<220> FEATURE:
<223> OTHER INFORMATION: ZFN Target Site

<400> SEQUENCE: 45
gatcccaagc ggtggtgctt tcaaggac                                         28

<210> SEQ ID NO 46
<211> LENGTH: 28
<212> TYPE: DNA
<213> ORGANISM: Artificial Sequence
<220> FEATURE:
<223> OTHER INFORMATION: ZFN Target Site

<400> SEQUENCE: 46
tgatgcggga ctatgatatc caacaagt                                         28
```

```
<210> SEQ ID NO 47
<211> LENGTH: 28
<212> TYPE: DNA
<213> ORGANISM: Artificial Sequence
<220> FEATURE:
<223> OTHER INFORMATION: ZFN Target Site

<400> SEQUENCE: 47
gagcacgtgc tgcctatgat cccaagcg                                          28

<210> SEQ ID NO 48
<211> LENGTH: 28
<212> TYPE: DNA
<213> ORGANISM: Artificial Sequence
<220> FEATURE:
<223> OTHER INFORMATION: ZFN Target Site

<400> SEQUENCE: 48
tcttgtaggt cgaaatttca gtacgagg                                          28

<210> SEQ ID NO 49
<211> LENGTH: 28
<212> TYPE: DNA
<213> ORGANISM: Artificial Sequence
<220> FEATURE:
<223> OTHER INFORMATION: ZFN Target Site

<400> SEQUENCE: 49
ctacaagtgt gacatgcgca atcagcat                                          28

<210> SEQ ID NO 50
<211> LENGTH: 14
<212> TYPE: DNA
<213> ORGANISM: Artificial Sequence
<220> FEATURE:
<223> OTHER INFORMATION: ZFN Target Site

<400> SEQUENCE: 50
cttgtaggtc gaaa                                                         14

<210> SEQ ID NO 51
<211> LENGTH: 18
<212> TYPE: DNA
<213> ORGANISM: Artificial Sequence
<220> FEATURE:
<223> OTHER INFORMATION: ZFN Target Site

<400> SEQUENCE: 51
caagtgtgac atgcgcaa                                                     18

<210> SEQ ID NO 52
<211> LENGTH: 28
<212> TYPE: DNA
<213> ORGANISM: Artificial Sequence
<220> FEATURE:
<223> OTHER INFORMATION: ZFN Target Site

<400> SEQUENCE: 52
tcttgtaggt cgaaatttca gtacgagg                                          28

<210> SEQ ID NO 53
<211> LENGTH: 28
<212> TYPE: DNA
<213> ORGANISM: Artificial Sequence
<220> FEATURE:
<223> OTHER INFORMATION: ZFN Target Site
```

<400> SEQUENCE: 53
tcttgtaggt cgaaatttca gtacgagg                                28

<210> SEQ ID NO 54
<211> LENGTH: 28
<212> TYPE: DNA
<213> ORGANISM: Artificial Sequence
<220> FEATURE:
<223> OTHER INFORMATION: ZFN Target Site

<400> SEQUENCE: 54
tacaagtgtg acatgcgcaa tcagcatg                                28

<210> SEQ ID NO 55
<211> LENGTH: 28
<212> TYPE: DNA
<213> ORGANISM: Artificial Sequence
<220> FEATURE:
<223> OTHER INFORMATION: ZFN Target Site

<400> SEQUENCE: 55
cagaacctga cacagcagac atgtaaag                                28

<210> SEQ ID NO 56
<211> LENGTH: 28
<212> TYPE: DNA
<213> ORGANISM: Artificial Sequence
<220> FEATURE:
<223> OTHER INFORMATION: ZFN Target Site

<400> SEQUENCE: 56
ataacgaccg atggagggtg gtcggcag                                28

<210> SEQ ID NO 57
<211> LENGTH: 59
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t

<400> SEQUENCE: 57
ancactcttt ccctacacga cgctcttccg atcttcctct aggattcaag acttttgng   59

<210> SEQ ID NO 58
<211> LENGTH: 57
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t

<400> SEQUENCE: 58
gntgactgga gttcagacgt gtgctcttcc gatctcgtgg ccgcttgtaa gtgtana     57

```
<210> SEQ ID NO 59
<211> LENGTH: 56
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t

<400> SEQUENCE: 59
ancactcttt ccctacacga cgctcttccg atctgagacc ccagggccat acttng        56

<210> SEQ ID NO 60
<211> LENGTH: 59
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t

<400> SEQUENCE: 60
gntgactgga gttcagacgt gtgctcttcc gatctcaagc aaactagaaa acgcatgng    59

<210> SEQ ID NO 61
<211> LENGTH: 55
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t

<400> SEQUENCE: 61
ancactcttt ccctacacga cgctcttccg atctatggag ggtgatggca gganc         55

<210> SEQ ID NO 62
<211> LENGTH: 60
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t

<400> SEQUENCE: 62
```
gntgactgga gttcagacgt gtgctcttcc gatctatgac agcacatccc tacaaaagna     60

<210> SEQ ID NO 63
<211> LENGTH: 58
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t

<400> SEQUENCE: 63
ancactcttt ccctacacga cgctcttccg atctaacagt gtgctggttc ctttctng     58

<210> SEQ ID NO 64
<211> LENGTH: 60
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t

<400> SEQUENCE: 64
gntgactgga gttcagacgt gtgctcttcc gatcttytyy cctcccaact gtattcagna     60

<210> SEQ ID NO 65
<211> LENGTH: 1380
<212> TYPE: DNA
<213> ORGANISM: Artificial Sequence
<220> FEATURE:
<223> OTHER INFORMATION: pDAS000132

<400> SEQUENCE: 65
tgcaagcagg tccaagattg tgcacattga cattgaccca gctgagattg gcaagaacaa     60
gcagccacat gtctccattt gtgcagatgt taagcttgct ttacaggggt tgaatgctct    120
attaaatggg agcaaagcac aacagggtct ggattttggt ccatggcaca aggagttgga    180
tcagcagaag agggagtttc ctctaggatt caagactttt ggcgaggcca tcccgccgca    240
atatgctatc caggtactgg atgagctgac aaaaggggag gcgatcattg ctactgtgtgt    300 tgggcagcac cagatgtggg cggctcagta ttacacttac aagcggccac ggcagtggct    360
gtcttcgtct ggttgggggc aatgggattt gggttaccag ctgcagctgg cgctgctgtg    420
gccaacccag gtgttacagt tgttgacatt gatggagatg gtagtttcct catgaacatt    480
caggagttgg cattgatccg tattgagaac ctccctgtga aggtgatgat attgaacaac    540
cagcatctgg gaatggtggt gcaatgggag gataggtttt acaaggccaa tcgggcgcac    600
acataccttg gcaacccaga aaatgagagt gagatatatc cagattttgt gacgattgct    660
aaaggattca acgttccggc agttcgtgtg acgaagaaga gcgaagtcac tgcagcaatc    720
aagaagatgc ttgagacccc agggccatac ttgttggata tcatcgtccc gcatcaggag    780
cacgtgctgc ctatgatccc aaatggtggt gctttcaagg acatgatcat ggagggtgat    840

```
ggcaggacct cgtactgaaa tttcgaccta caagacctac aagtgtgaca tgcgcaatca    900
gcatggtgcc cgcgtgttgt atcaactact aggggttcaa ctgtgaacca tgcgttttct    960
agtttgcttg tttcattcat ataagcttgt gttacttagt tccgaaccct gtagctttgt   1020
agtctatgct ctcttttgta gggatgtgct gtcataagat atcatgcaag tttcttgtcc   1080
tacatatcaa taataagtac ttccatggaa taattctcag ttctgttttg aattttgcat   1140
cttctcacaa acagtgtgct ggttcctttc tgttacttta catgtctgcc gtgtccggtt   1200
atgacataat gaccgatgga gggtggtcag caggttttag acggggagtt gaaacttttt   1260
tttgggggga agaaatctga atacagttgg gaggaaagat aaaagcatat accttgatta   1320
atttattgag cccaatatcc agcctaattt atcaagcaat aggcagtgta gggtgttggc   1380
```

<210> SEQ ID NO 66
<211> LENGTH: 1572
<212> TYPE: DNA
<213> ORGANISM: Artificial Sequence
<220> FEATURE:
<223> OTHER INFORMATION: pDAS000133

<400> SEQUENCE: 66

```
tgcaagcagg tccaagattg tgcacattga cattgaccca gctgagattg caagaacaa     60 gcagccacat gtctccattt gtgcagatgt taagcttgct ttacaggggt tgaatgctct    120
attaaatggg agcaaagcac aacagggtct ggattttggt ccatggcaca aggagttgga    180
tcagcagaag agggagtttc ctctaggatt caagactttt ggtgaggcca tcccgccgca    240
atatgctatc caggtactgg atgagctgac aaaaggggag gcgatcattg ccaccggtgt    300
tgggcagcat cagatgtggg cggctcagta ttacacttac aagcggccac ggcagtggct    360
gtcttcatcc ggtttgggtg caatgggatt tgggttgcca gctgcagctg gcgctgctgt    420
ggccaaccca ggtgttacag ttgttgacat tgatggggat ggtagtttcc tcatgaacat    480
tcaggagttg gcgttgatcc gtattgagaa cctcccagtg aaggtgatga tattgaacaa    540
ccagcatctg ggaatggtgg tgcagtggga ggataggttt tacaaggcca accgggcgca    600
cacataccct tggcaaccca gaaaatgagag tgagatatat ccagattttg tgacgattgc    660
taaaggattc aacgttccgg cagttcgtgt gacgaagaag agcgaagtca ctgcagcaat    720
caagaagatg cttgagaccc cagggccata cttgttggat atcattgtcc cgcatcagga    780
gcacgtgctg cctatgatcc caaatggtgg tgcttttaag gacatgatca tggagggtga    840
tggcaggacc tcgtactgaa atttcgacct acaagaccta caagtgtgac atgcgcaatc    900
agcatgatac ctgcgtgttg tatcaactac tgggggttca actgtgaacc atgcgttttc    960
tagtttgctt gtttcattca tataagcttg tgttacttag ttccgaaccg tgtagttttg   1020
tagtctctgt tctcttttgt agggatgtgc tgtcataaga tatcatgcaa gtttcttgtc   1080
ctacatatca ataatgaagca cttccatgga ataattctca gttctgtttt gaatttcaca   1140
tcttctcacg aacagtgtgc tggttccttt ctgttacttt acatgcctgc cgtgtcaggt   1200
tatgacataa cgaccgatgg aggattggag ggtggtcggc tggttttaga cggggaattg   1260
aaacattttt ctggaagaaa tctgaataca gttgggaggg aaatggaag catatattta   1320 tcgagcccgc tatccaggct aatttatcaa gcactagaca gtgtagggtg ttggcattct   1380
tctcttcctt gatatccggc ttgagaggag agattgaggc ttcggctgtg ttggttgctg   1440
atttctacag catttgtaga gagagagaga gatgttgcaa ctgtgttttg tcttggttgc   1500
```

```
ttgtacagag aaagagatga catttagaga tatgcagatc gtttaccagt tgtgctgcgt    1560
ttattcgtac tg                                                         1572

<210> SEQ ID NO 67
<211> LENGTH: 1571
<212> TYPE: DNA
<213> ORGANISM: Artificial Sequence
<220> FEATURE:
<223> OTHER INFORMATION: pDAS000134

<400> SEQUENCE: 67
tgcaagcagg tccaagattg tgcacattga cattgaccca gctgagattg gcaagaacaa      60
gcagccacat gtctccattt gtgcagatgt taagcttgct ttacaggggt tgaatgatct     120
attaaatggg agcaaagcac aacagggtct ggattttggt ccatggcaca aggagttgga     180
tcagcagaag agggagtttc tctaggatt caagactttt ggcgaggcca tcccgccgca      240
atatgctatc caggtactgg atgagctgac aaaaggggag cgatcattg ccactggtgt      300 tgggcagcac cagatgtggg cggctcagta ttacacttac aagcggccac ggcagtggct     360
gtcttcgtct ggtttggggg caatgggatt tgggttacca gctgcagctg gcgctgctgt     420
ggccaaccca ggtgttacag ttgttgacat tgatggtgat ggtagtttcc tcatgaacat     480
tcaggagttg gcgttgatcc gcattgagaa cctcccagtg aaggtgatga tattgaacaa     540
ccagcatctg ggaatggtgg tgcagtggga ggataggttt tacaaggcca atcgggcgca     600
cacatacctt ggcaacccag aaaatgagag tgagatatat ccagattttg tgacgattgc     660
taaaggattc aacgttccag cagttcgagt gacgaagaag agcgaagtca ctgcagcaat     720
caagaagatg cttgagaccc cagggccata cttgttggat atcatagtcc cgcatcagga     780
gcacgtgctg cctatgatcc caatcggtgg tgctttcaag gacatgatca tggagggtga     840
tggcaggacc tcgtactgaa atttcgacct acaagaccta caagtgtgac atgcgcaatc     900
agcatgatgc ccgcgtgttg tatcaactac taggggttca actgtgagcc atgcgttttc     960
tagtttgctt gtttcattca tataagcttg tattacttag ttccgaaccc tgtagttttg    1020
tagtctatgt tctcttttgt agggatgtgc tgtcataaga tgtcatgcaa gtttcttgtc    1080
ctacatatca ataataagta cttccatgga ataattctca gttctgtttt gaattttgca    1140
tcttctcaca aacagtgtgc tggttccttt ctgttacttt acatgtctgc tgtgtcaggt    1200
tctgacataa cgaccgatgg agggtggtcg gcaggtttta aaggggaat tgaaactttt     1260 ttttgggaag aagtctgaat acagttggga ggaaaaatag aagtatatac ttcgattaat    1320
ttatcaagcc cgctatccag tctaatttat caagcactag acagtgtagg gtgttggcat    1380
tcttctcttc cttgagatcc ggcttgagag gagagaccga ggcttcggct gtgttggttg    1440
ctgatttcta cagctttttg agatagagag agagatcctg caactgtggt ttgtcttgct    1500
gcttgtacag cgagagagac attgagagat atgtagatcg tttaccagtt gtgctgctgt    1560
tattcgtact g                                                         1571

<210> SEQ ID NO 68
<211> LENGTH: 1571
<212> TYPE: DNA
<213> ORGANISM: Artificial Sequence
<220> FEATURE:
<223> OTHER INFORMATION: pDAS000135

<400> SEQUENCE: 68
tgcaagcagg tccaagattg tgcacattga cattgaccca gctgagattg gcaagaacaa      60
```

```
gcagccacat gtctccattt gtgcagatgt taagcttgct ttacaggggt tgaatgatct      120
attaaatggg agcaaagcac aacagggtct ggattttggt ccatggcaca aggagttgga      180
tcagcagaag agggagtttc ctctaggatt caagactttt ggcgaggcca tcccgccgca      240
atatgctatc caggtactgg atgagctgac aaaaggggag gcgatcattg ccactggtgt      300
tgggcagcac cagatgtggg cggctcagta ttacacttac aagcggccac ggcagtggct      360
gtcttcgtct ggtttggggg caatgggatt tgggttacca gctgcagctg gcgctgctgt      420
ggccaaccca ggtgttacag ttgttgacat tgatggtgat ggtagtttcc tcatgaacat      480
tcaggagttg gcgttgatcc gcattgagaa cctcccagtg aaggtgatga tattgaacaa      540
ccagcatctg ggaatggtgg tgcagtggga ggataggttt tacaaggcca atcgggcgca      600
cacataccct ggcaacccag aaaatgagag tgagatatat ccagattttg tgacgattgc      660
taaaggattc aacgttccag cagttcgagt gacgaagaag agcgaagtca ctgcagcaat      720
caagaagatg cttgagaccc agggccata cttgttggat atcatagtcc cgcatcagga      780
gcacgtgatg cctatgatcc caaatggtgg tgctttcaaa gacatgatca tggagggtga      840
tggcaggacc tcgtactgaa atttcgacct acaagaccta caagtgtgac atgcgcaatc      900
agcatgatgc ccgcgtgttg tatcaactac tagggggttca actgtgagcc atgcgttttc      960
tagtttgctt gtttcattca tataagcttg tattacttag ttccgaaccc tgtagttttg     1020
tagtctatgt tctcttttgt agggatgtgc tgtcataaga tgtcatgcaa gtttcttgtc     1080
ctacatatca ataatagta cttccatgga ataattctca gttctgtttt gaattttgca      1140
tcttctcaca aacagtgtgc tggttccttt ctgttacttt acatgtctgc tgtgtcaggt     1200
tctgacataa cgaccgatgg agggtggtcg gcaggtttta gaagggggaat tgaaactttt     1260 ttttgggaag aagtctgaat acagttggga ggaaaaatag aagtatatac ttcgattaat     1320
ttatcaagcc cgctatccag tctaatttat caagcactag acagtgtagg gtgttggcat     1380
tcttctcttc cttgagatcc ggcttgagag gagagaccga ggcttcggct gtgttggttg     1440
ctgatttcta cagcttttttg agatagagag agagatcctg caactgtggt ttgtcttgct     1500
gcttgtacag cgagagagac attgagagat atgtagatcg tttaccagtt gtgctgctgt     1560
tattcgtact g                                                          1571
```

<210> SEQ ID NO 69
<211> LENGTH: 1573
<212> TYPE: DNA
<213> ORGANISM: Artificial Sequence
<220> FEATURE:
<223> OTHER INFORMATION: pDAS000131

<400> SEQUENCE: 69

```
tgcaagcagg tccaagattg tgcacattga cattgaccca gctgagattg gcaagaacaa       60
gcagccacat gtctccattt gtgcagatgt taagcttgct ttacaggggt tgaatgatct      120
attaaatggg agcaaagcac aacagggtct ggattttggt ccatggcaca aggagttgga      180
tcagcagaag agggagtttc ctctaggatt caagactttt ggcgaggcca tcccgccgca      240
atatgctatc caggtactgg atgagctgac aaaaggggag gcgatcattg ccactggtgt      300
tgggcagcac cagatgtggg cggctcagta ttacacttac aagcggccac ggcagtggct      360
gtcttcgtct ggtttggggg caatgggatt tgggttacca gctgcagctg gcgctgctgt      420
ggccaaccca ggtgttacag ttgttgacat tgatggtgat ggtagtttcc tcatgaacat      480
```

-continued

```
tcaggagttg gcgttgatcc gcattgagaa cctcccagtg aaggtgatga tattgaacaa      540
ccagcatctg ggaatggtgg tgcagtggga ggataggttt tacaaggcca atcgggcgca      600
cacataccct ggcaacccag aaaatgagag tgagatatat ccagattttg tgacgattgc      660
taaaggattc aacgttccag cagttcgagt gacgaagaag agcgaagtca ctgcagcaat      720
caagaagatg cttgagaccc agggccata cttgttggat atcatagtcc cgcatcagga       780
gcacgtgctg ccgaattcat cccaagcggg ggtgctttca aggacatgat catggagggt      840
gatggcagga cctcgtactg aaatttcgac ctacaagacc tacaagtgtg acatgcgcaa      900
tcagcatgat gcccgcgtgt tgtatcaact actaggggtt caactgtgag ccatgcgttt      960
tctagtttgc ttgtttcatt catataagct tgtattactt agttccgaac cctgtagttt     1020
tgtagtctat gttctctttt gtagggatgt gctgtcataa gatgtcatgc aagtttcttg     1080
tcctacatat caataataag tacttccatg gaataattct cagttctgtt ttgaattttg     1140
catcttctca caaacagtgt gctggttcct ttctgttact ttacatgtct gctgtgtcag     1200
gttctgacat aacgaccgat ggagggtggt cggcaggttt tagaagggga attgaaactt     1260
ttttttggga agaagtctga atacagttgg gaggaaaaat agaagtatat acttcgatta     1320
atttatcaag cccgctatcc agtctaattt atcaagcact agacagtgta gggtgttggc     1380
attcttctct tccttgagat ccggcttgag aggagagacc gaggcttcgg ctgtgttggt     1440
tgctgatttc tacagctttt tgagatagag agagagatcc tgcaactgtg gtttgtcttg     1500
ctgcttgtac agcgagagag acattgagag atatgtagat cgtttaccag ttgtgctgct     1560
gttattcgta ctg                                                        1573
```

<210> SEQ ID NO 70  
<211> LENGTH: 24  
<212> TYPE: DNA  
<213> ORGANISM: Artificial Sequence  
<220> FEATURE:  
<223> OTHER INFORMATION: Primer Sequence

<400> SEQUENCE: 70

```
tgagcctctc gtcgccgatc acat                                              24
```

<210> SEQ ID NO 71  
<211> LENGTH: 1159  
<212> TYPE: DNA  
<213> ORGANISM: Artificial Sequence  
<220> FEATURE:  
<223> OTHER INFORMATION: pDAS000433

<400> SEQUENCE: 71

```
ccactcttgc cctacacgac actgaagacc ttatgattcc aaacggcggc gccttcaagg       60
acatgatcat ggagggtgat ggcaggacct cgtactgaaa tttcgaccta caagacctac      120
aagtgtgaca tgcgcaatca gcatggtgcc cgcgtgttgt atcaactact aggggttcaa      180
ctgtgaacca tgcgttttct agtttgcttg tttcattcat ataagcttgt gttacttagt      240
tccgaaccct gtagctttgt agtctatgct ctcttttgta gggatgtgct gtcataagat      300
atcatgcaag tttcttgtcc tacatatcaa taataagtac ttccatggaa taattctcag      360
ttctgttttg aattttgcat cttctcacaa acagtgtgct ggttcctttc tgttcgctga      420
cgccctcctc gactccatcc ccatggtcgc catcacgggc caggtccccc gccgcatgat      480
cggtagcgac ttcgtgggcg aggaaagcct ttcgtccaag gtggtccctc ctcgcaatct      540
tgttggatgg tgaatattat aaaagcctgc ccttctcgcg ggtaagactc ccgcccatcc      600
```

```
aggatgagga tgaccagcct tttgcagttt atccactagg gacaggattg catcctgccg    660
aaaccctgcc aagcttgagg tagcctccaa tttgacggtg ccgccagcga cgccgtctgg    720
aactgtcctt tttgaggacc actccgtttg tctagaggta cctggagatc atgacattaa    780
ggatgaccag ttcgtaaagg tcctgcggtg tctattgctt ttcataggtt aataagtgtt    840
tgctagactg tggtgaaagg ccaagactcc cgcccatctc tctatgcccg ggacaagtgc    900
caccccacag tggggcagga tgaggatgac caaagactcc cgcccatctc actagggaca    960
ggattggcct tttgcagttt atctctatgc ccgggacaag tgtatccgaa gtaaataaaa   1020
ccatcggact ctcgtataag actgtcgact cgaccggccg acgcataggt tcatttgaag   1080
ctgctattct atttaaattg aaactcggac ggtagcagtg tggtatgagg tcttcagcac   1140
actcggtaac tccagtcac                                                1159
```

<210> SEQ ID NO 72
<211> LENGTH: 2479
<212> TYPE: DNA
<213> ORGANISM: Artificial Sequence
<220> FEATURE:
<223> OTHER INFORMATION: pDAS000434

<400> SEQUENCE: 72

```
ccactcttgc cctacacgac actgaagacg tcgccattac cgggcaagtg acccgccgca     60
tgatcggcac ggacgcgttc caggagacgc ccatagtgga ggtcacgcgc tccatcacca    120
agcacaacta cctggtcctt gacgtggagg atatcccccg cgtcatccag gaagccttct    180
tccttgcatc ctctggccgc ccggggccgg tgctagttga tatccccaag gacatccagc    240
agcagatggc tgtgcccgtc tgggacactc caatgagttt gccagggtac atcgcccgcc    300
tgcccaagcc accatctact gaatcgcttg agcaggtcct gcgtctggtt ggcgagtcac    360
ggcgcccaat tctgtatgtt ggtggtggct gcgctgcgtc tggcgaggag ttgcgccgct    420
ttgttgagct tactgggatt ccagttacaa ctactctgat gggccttggc aacttcccca    480
gcgacgaccc actgtctctg cgcatgcttg gatgcatgg cactgtgtat gcaaattatg    540
cagtagataa ggctgacctg ttgctcgcat ttggtgtgcg gtttgatgat cgtgtgactg    600
ggaaaatcga ggcttttgca agcaggtcca agattgtgca cattgacatt gacccagctg    660
agattggcaa gaacaagcag ccacatgtct ccatttgtgc agatgttaag cttgctttac    720
aggggttgaa tgatctatta aatgggagca agcacaaca gggtctggat tttggtccat    780
ggcacaagga gttggatcag cagaagaggg agtttcctct aggattcaag acttttggcg    840
aggccatccc gccgcaatat gctatccagg tactggatga gctgacaaaa ggggaggcga    900
tcattgccac tggtgttggg cagcaccaga tgtgggcggc tcagtattac acttacaagc    960
ggccacggca gtggctgtct tcgtctggtt tgggggcaat gggatttggg ttaccagctg   1020
cagctggcgc tgctgtggcc aacccaggtg ttacagttgt tgacattgat ggtgatggta   1080
gtttcctcat gaacattcag gagttggcgt tgatccgcat tgagaacctc ccagtgaagg   1140
tgatgatatt gaacaaccag catctgggaa tggtggtgca gtgggaggat aggttttaca   1200
aggccaatcg ggcgcacaca taccttggca acccagaaaa tgagagtgag atatatccag   1260
attttgtgac gattgctaaa ggattcaacg ttccagcagt tcgagtgacg aagaagagcg   1320
aagtcactgc agcaatcaag aagatgcttg agacccagg gccatacttg ttggatatca   1380
tagtcccgca tcaggagcac gtgctgccta tgatcccaag cggtggtgct ttcaaggaca   1440
```

```
tgatcatgga gggtgatggc aggacctcgt actgaaattt cgacctacaa gacctacaag    1500
tgtgacatgc gcaatcagca tggtgcccgc gtgttgtatc aactactagg ggttcaactg    1560
tgaaccatgc gttttctagt tgcttgttt cattcatata agcttgtgtt acttagttcc    1620
gaaccctgta gctttgtagt ctatgctctc ttttgtaggg atgtgctgtc ataagatatc    1680
atgcaagttt cttgtcctac atatcaataa taagtacttc catggaataa ttctcagttc    1740
tgttttgaat tttgcatctt ctcacaaaca gtgtgctggt tcctttctgt tctacgcccg    1800
cgcgtccggc cgcgtcggcg tctgcgtcgc cacctccggc ccgggggcca ccaacctcgt    1860
ctccgtagcg acttcgtggg cgaggaaagc cttcgtcca agtggtccc tcctcgcaat     1920 cttgttggat ggtgaatatt ataaaagcct gcccttctcg cgggtgagtc catgctcaac    1980
accgtgcact agggacagga ttggccttt gcagtttatc cactagggac aggattgcat    2040
cctgccgaaa ccctgccaag cttgaggtag cctccaattt gacggtgccg ccagcgacgc    2100
cgtctggaac tgtccttttt gaggaccact ccgtttgtct agaggtacct ggagatcatg    2160
acattaagga tgaccagttc gtaaaggtcc tgcggtgtct attgcttttc ataggttaat    2220
aagtgtttgc tagactgtgg tgaaaggccg ccttttgcag tttatctcta gaaagactgg    2280
agttgcagaa agactcccgc ccatccagga tgaggatgac catatccgaa gtaaataaaa    2340
ccatcggact ctcgtataag actgtcgact cgaccggccg acgcataggt tcatttgaag    2400
ctgctattct atttaaattg aaactcggac ggtagcagtg tggtatgagg tcttcagcac    2460
actcggtaac tccagtcac                                                 2479
```

<210> SEQ ID NO 73
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 73

Gln Gln Trp Asp Arg Lys Gln
1               5

<210> SEQ ID NO 74
<211> LENGTH: 47
<212> TYPE: DNA
<213> ORGANISM: Artificial Sequence
<220> FEATURE:
<223> OTHER INFORMATION: pDAS000152
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 74
tnantggtta ggtgctggtg gtccgaaggt ccacgccgcc aactacg                  47

<210> SEQ ID NO 75
<211> LENGTH: 47
<212> TYPE: DNA
<213> ORGANISM: Artificial Sequence
<220> FEATURE:
<223> OTHER INFORMATION: pDAS000152
<220> FEATURE:
<221> NAME/KEY: misc_feature
<222> LOCATION: (2)..(2)

```
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 75
cnantacgta gttggcggcg tggaccttcg gaccaccagc acctaac          47

<210> SEQ ID NO 76
<211> LENGTH: 47
<212> TYPE: DNA
<213> ORGANISM: Artificial Sequence
<220> FEATURE:
<223> OTHER INFORMATION: pDAS000149
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 76
tnantggtta ggtgctggtg gtccgaaggt ccacgccgcc aactacg          47

<210> SEQ ID NO 77
<211> LENGTH: 47
<212> TYPE: DNA
<213> ORGANISM: Artificial Sequence
<220> FEATURE:
<223> OTHER INFORMATION: pDAS000149
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 77
angngtcgta gttggcggcg tggaccttcg gaccaccagc acctaac          47

<210> SEQ ID NO 78
<211> LENGTH: 197
<212> TYPE: DNA
<213> ORGANISM: Artificial Sequence
<220> FEATURE:
<223> OTHER INFORMATION: pDAS000153

<400> SEQUENCE: 78
tggatatcat agtcccgcat caggagcacg tgctgcctat gatcccaagc ggtggtgctt   60
tcaaggacat gatcatgggt taggtgctgg tggtccgaag gtccacgccg ccaactacgt  120
ggatatcata gtcccgcatc aggagcacgt gctgcctatg atcccaagcg tggtgctttc  180
caaggacatg atcatgg                                                 197

<210> SEQ ID NO 79
<211> LENGTH: 197
<212> TYPE: DNA
<213> ORGANISM: Artificial Sequence
<220> FEATURE:
<223> OTHER INFORMATION: pDAS000153

<400> SEQUENCE: 79
ccatgatcat gtccttgaaa gcaccaccgc ttgggatcat aggcagcacg tgctcctgat   60
```

```
gcgggactat gatatccacg tagttggcgg cgtggacctt cggaccacca gcacctaacc    120
catgatcatg tccttgaaag caccaccgct tgggatcata ggcagcacgt gctcctgatg    180
cgggactatg atatcca                                                   197

<210> SEQ ID NO 80
<211> LENGTH: 197
<212> TYPE: DNA
<213> ORGANISM: Artificial Sequence
<220> FEATURE:
<223> OTHER INFORMATION: pDAS000150

<400> SEQUENCE: 80
tggatatcat agtcccgcat caggagcacg tgctgcctat gatcccaagc ggtggtgctt    60
tcaaggacat gatcatgggt taggtgctgg tggtccgaag gtccacgccg ccaactacgg   120
atggcaggac ctcgtactga aatttcgacc tacaagacct acaagtgtga catgcgcaat   180
cagcatgatg cccgcgt                                                   197

<210> SEQ ID NO 81
<211> LENGTH: 197
<212> TYPE: DNA
<213> ORGANISM: Artificial Sequence
<220> FEATURE:
<223> OTHER INFORMATION: pDAS000150

<400> SEQUENCE: 81
acgcgggcat catgctgatt gcgcatgtca cacttgtagg tcttgtaggt cgaaatttca    60
gtacgaggtc ctgccatccg tagttggcgg cgtggacctt cggaccacca gcacctaacc   120
catgatcatg tccttgaaag caccaccgct tgggatcata ggcagcacgt gctcctgatg   180
cgggactatg atatcca                                                   197

<210> SEQ ID NO 82
<211> LENGTH: 20
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (19)..(19)
<223> OTHER INFORMATION: n is a, c, g, or t

<400> SEQUENCE: 82
ggagttggcg ttgatccgnc                                                20

<210> SEQ ID NO 83
<211> LENGTH: 27
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (26)..(26)
<223> OTHER INFORMATION: n is a, c, g, or t

<400> SEQUENCE: 83
aactacaggg ttcggaacta agtaant                                        27

<210> SEQ ID NO 84
<211> LENGTH: 102
<212> TYPE: DNA
```

```
<213> ORGANISM: Artificial Sequence
<220> FEATURE:
<223> OTHER INFORMATION: pDAS000267
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 84
tnantgattc ccaatggcgg cgctttcaag gacatgatca tggagggtga tggcaggacc      60
tcgtactgaa atggtccgaa ggtccacgcc gccaactacg ag                        102

<210> SEQ ID NO 85
<211> LENGTH: 102
<212> TYPE: DNA
<213> ORGANISM: Artificial Sequence
<220> FEATURE:
<223> OTHER INFORMATION: pDAS000267
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 85
cnantactcg tagttggcgg cgtggacctt cggaccattt cagtacgagg tcctgccatc      60
accctccatg atcatgtcct tgaaagcgcc gccattggga at                        102

<210> SEQ ID NO 86
<211> LENGTH: 85
<212> TYPE: DNA
<213> ORGANISM: Artificial Sequence
<220> FEATURE:
<223> OTHER INFORMATION: pDAS000268
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 86
tnantgattc ccaatggcgg cgctttcaag gacatgatca tggagggtga tggcaggacc      60
tcgtactgaa atttgcaggt acaag                                            85

<210> SEQ ID NO 87
<211> LENGTH: 85
<212> TYPE: DNA
<213> ORGANISM: Artificial Sequence
<220> FEATURE:
<223> OTHER INFORMATION: pDAS000268
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 87
```

```
angngtcttg tacctgcaaa tttcagtacg aggtcctgcc atcaccctcc atgatcatgt    60
ccttgaaagc gccgccattg ggaat                                          85

<210> SEQ ID NO 88
<211> LENGTH: 6661
<212> TYPE: DNA
<213> ORGANISM: Artificial Sequence
<220> FEATURE:
<223> OTHER INFORMATION: pDAS000143

<400> SEQUENCE: 88
tggcaggata tattgtggtg taaacaaatt gacgcttaga caacttaata acacattgcg    60
gacgttttta atgtactgaa ttaacgccga attgaattcg agctcggtac cactggattt   120
tggttttagg aattagaaat tttattgata gaagtatttt acaaatacaa atacatacta   180
agggtttctt atatgctcaa cacatgagcg aaaccctata agaaccctaa ttcccttatc   240
tgggaactac tcacacatta ttctggagaa aaatagagag agatagattt gtagagagag   300
actggtgatt tttgcggact ctattagatc tgggtaactg gcctaactgg ccttggagga   360
gctggcaact caaatccct tgccaaaaa ccaacatcat gccatccacc atgcttgtat    420
ccagctgcgc gcaatgtacc ccgggctgtg tatcccaaag cctcatgcaa cctaacagat   480
ggatcgtttg gaaggcctat aacagcaacc acagacttaa aaccttgcgc tccatagac    540 ttaagcaaat gtgtgtacaa tgtggatcct aggcccaacc tttgatgcct atgtgacacg   600
taaacagtac tctcaactgt ccaatcgtaa gcgttcctag ccttccaggg cccagcgtaa   660
gcaataccag ccacaacacc ctcaacctca gcaaccaacc aagggtatct atcttgcaac   720
ctctcgagat catcaatcca ctcttgtggt gtttgtggct ctgtcctaaa gttcactgta   780
gacgtctcaa tgtaatggtt aacgatatca caaaccgcgg ccatatcagc tgctgtagct   840
ggcctaatct caactggtct cctctccgga gacatggctt ctaccacaa aaaagctccg    900 cacgaggctg catttgtcac aaatcatgaa agaaaaact accgatgaac aatgctgagg   960
gattcaaatt ctacccacaa aaagaagaaa gaaagatcta gcacatcaa gcctgacgaa   1020 gcagcagaaa tatataaaaa tataaaccat agtgcccttt tccctcttc ctgatcttgt   1080 ttagcatggc ggaaatttta aaccccccat catctccccc aacaacggcg gatcgcagat   1140
ctacatccga gagcccatt ccccgcgaga tccgggccgg atccacgccg gcgagagccc   1200
cagccgcgag atcccgcccc tcccgcgcac cgatctgggc gcgcacgaag ccgcctctcg   1260
cccacccaaa ctaccaaggc caaagatcga gaccgagacg gaaaaaaaaa acggagaaag   1320
aaagaggaga ggggcgggt ggttaccggc gcggcggcgg cggaggggga gggggagga    1380 gctcgtcgtc cggcagcgag gggggaggag gtggaggtgg tggtggtggt ggtggtaggg   1440 ttgggggat gggaggagag gggggggtat gtatatagtg gcgatggggg gcgtttcttt   1500
ggaagcggag ggagggccgg cctcgtcgct ggctcgcgat cctcctcgcg tttccggccc   1560
ccacgacccg gacccacctg ctgtttttc ttttcttttt tttctttct ttttttttt    1620 ttggctgcga gacgtgcggt gcgtgcggac aactcacggt gatagtgggg gggtgtggag   1680
actattgtcc agttggctgg actggggtgg gttgggttgg gttgggttgg gctgggcttg   1740
ctatggatcg tggatagcac tttgggcttt aggaacttta ggggttgttt ttgtaaatgt   1800
tttgagtcta agtttatctt ttattttac tagaaaaaat acccatgcgc tgcaacgggg    1860
gaaagctatt ttaatcttat tattgttcat tgtgagaatt cgcctgaata tatattttc    1920
```

```
tcaaaaatta tgtcaaatta gcatatgggt ttttttaaag atatttctta tacaaatccc    1980
tctgtattta caaaagcaaa cgaacttaaa acccgactca aatacagata tgcatttcca    2040
aaagcgaata aacttaaaaa ccaattcata caaaaatgac gtatcaaagt accgacaaaa    2100
acatcctcaa tttttataat agtagaaaag agtaaatttc actttgggcc acctttatt    2160
accgatattt tactttatac caccttttaa ctgatgtttt cacttttgac caggtaatct    2220
taccttgtt ttattttgga ctatcccgac tctcttctca agcatatgaa tgacctcgag    2280
tatgctagtc tagagtcgac ctgcagggtg cagcgtgacc cggtcgtgcc cctctctaga    2340
gataatgagc attgcatgtc taagttataa aaaattacca catattttt ttgtcacact    2400
tgtttgaagt gcagtttatc tatctttata catatattta aactttactc tacgaataat    2460
ataatctata gtactacaat aatatcagtg ttttagagaa tcatataaat gaacagttag    2520
acatggtcta aaggacaatt gagtattttg acaacaggac tctacagttt tatctttta    2580
gtgtgcatgt gttctccttt ttttttgcaa atagcttcac ctatataata cttcatccat    2640
tttattagta catccattta gggttaggg ttaatggttt ttatagacta attttttag    2700
tacatctatt ttattctatt ttagcctcta aattaagaaa actaaaactc tattttagtt    2760
tttttattta ataatttaga tataaaatag aataaaataa agtgactaaa aattaaacaa    2820
atacccttta agaaattaaa aaaactaagg aaacattttt cttgtttcga gtagataatg    2880
ccagcctgtt aaacgccgtc gacgagtcta acggacacca accagcgaac cagcagcgtc    2940
gcgtcgggcc aagcgaagca gacggcacgg catctctgtc gctgcctctg accctctc    3000
gagagttccg ctccaccgtt ggacttgctc cgctgtcggc atccagaaat tgcgtggcgg    3060
agcggcagac gtgagccggc acggcaggcg gcctcctcct cctctcacgg cacggcagct    3120
acggggatt cctttcccac cgctccttcg cttccttc ctcgcccgcc gtaataaata    3180
gacaccccct ccacccctc tttccccaac ctcgtgttgt tcggagcgca cacacaca    3240
accagatctc ccccaaatcc acccgtcggc acctccgctt caaggtacgc cgctcgtcct    3300
cccccccccc ccctctctac cttctctaga tcggcgttcc ggtccatggt tagggcccgg    3360
tagttctact tctgttcatg tttgtgttag atccgtgttt gtgttagatc cgtgctgcta    3420
gcgttcgtac acggatgcga cctgtacgtc agacacgttc tgattgctaa cttgccagtg    3480
tttctctttg gggaatcctg ggatggctct agccgttccg cagacgggat cgatttcatg    3540
atttttttg tttcgttgca tagggtttgg tttgcccttt tcctttattt caatatatgc    3600
cgtgcacttg tttgtcgggt catcttttca tgctttttt tgtcttggtt gtgatgatgt    3660
ggtctggttg ggcggtcgtt ctagatcgga gtagaattct gtttcaaact acctggtgga    3720
tttattaatt ttggatctgt atgtgtgtgc catacatatt catagttacg aattgaagat    3780
gatggatgga aatatcgatc taggataggt atacatgttg atgcgggttt tactgatgca    3840
tatacagaga tgctttttgt tcgcttggtt gtgatgatgt ggtgtggttg ggcggtcgtt    3900
cattcgttct agatcggagt agaatactgt ttcaaactac ctggtgtatt tattaatttt    3960
ggaactgtat gtgtgtgtca tacatcttca tagttacgag tttaagatgg atggaaatat    4020
cgatctagga taggtataca tgttgatgtg gttttactg atgcatatac atgatggcat    4080
atgcagcatc tattcatatg ctctaacctt gagtacctat ctattataat aaacaagtat    4140
gttttataat tattttgatc ttgatatact tggatgatgg catatgcagc agctatatgt    4200
ggatttttt agccctgcct tcatacgcta ttatttgct tggtactgtt tcttttgtcg    4260
atgctcaccc tgttgtttgg tgttacttct gcaggaggat cacaagtttg tacaaaaaag    4320
```

```
caggctatgg ccgccgccac ctccccgcc gtcgcattct cgggcgccac cgccgccgcc    4380
atgcccaaac ccgcccgcca tcctctcccg cgccaccagc ccgtctcgcg ccgcgcgctc    4440
cccgcccgcg tcgtcaggtg ttgcgccgcg tccccgccg ccacctccgc cgcgcctccc    4500
gcaaccgcgc tccggccctg gggcccgtcc gagccccgca agggcgccga catcctcgtc    4560
gaggcgctcg agcgctgcgg catcgtcgac gtcttcgcct accccggcgg cgcctccatg    4620
gagatccacc aggcgctgac gcgctcgccc gtcatcacca accacctctt ccgccacgag    4680 caggggagg cgttcgcggc gtccggctac gcccgcgcgt ccggccgcgt cggcgtctgc     4740
gtcgccacct ccgcccggg ggccaccaac ctcgtctccg cgctcgccga cgccctcctc     4800
gactccatcc ccatggtcgc catcacgggc caggtccccc gccgcatgat cggcacggac    4860
gcgttccagg agacgcccat agtggaggtc acgcgctcca tcaccaagca caactacctg    4920
gtccttgacg tggaggatat cccccgcgtc atccaggaag ccttcttcct tgcatcctct    4980
ggccgcccgg ggccggtgct agttgatatc cccaaggaca tccagcagca gatggctgtg    5040
cccgtctggg acactccaat gagtttgcca gggtacatcg cccgcctgcc caagccacca    5100
tctactgaat cgcttgagca ggtcctgcgt ctggttggcg agtcacggcg cccaattctg    5160
tatgttggtg gtggctgcgc tgcgtctggc gaggagttgc gccgctttgt tgagcttact    5220
gggattccag ttacaactac tctgatgggc cttggcaact tccccagcga cgacccactg    5280
tctctgcgca tgcttgggat gcatggcact gtgtatgcaa attatgcagt agataaggct    5340
gacctgttgc tcgcatttgg tgtgcggttt gatgatcgtg tgactgggaa aatcgaggct    5400
tttgcaagca ggtccaagat tgtgcacatt gacattgacc cagctgagat tggcaagaac    5460
aagcagccac atgtctccat ttgtgcagat gttaagcttg ctttacaggg gttgaatgat    5520
ctattaaatg ggagcaaagc acaacagggt ctggattttg gtccatggca caaggagttg    5580
gatcagcaga gagggagtt tcctctagga ttcaagactt ttggcgaggc catcccgccg    5640
caatatgcta tccaggtact ggatgagctg acaaaagggg aggcgatcat tgccactggt    5700
gttgggcagc accagatgtg ggcggctcag tattacactt acaagcggcc acggcagtgg    5760
ctgtcttcgt ctggtttggg ggcaatggga tttgggttac cagctgcagc tggcgctgct    5820
gtggccaacc caggtgttac agttgttgac attgatggtg atggtagttt cctcatgaac    5880
attcaggagt tggcgttgat ccgcattgag aacctcccag tgaaggtgat gatattgaac    5940
aaccagcatc tgggaatggt ggtgcagtgg gaggataggt tttacaaggc caatcgggcg    6000
cacacatacc ttggcaaccc agaaaatgag agtgagatat atccagattt tgtgacgatt    6060
gctaaaggat tcaacgttcc agcagttcga gtgacgaaga gagcgaagt cactgcagca    6120 atcaagaaga tgcttgagac cccagggcca tacttgttgg atatcatagt cccgcatcag    6180
gagcacgtgc tgcctatgat cccaaatggt ggtgctttca aggacatgat catggagggt    6240
gatggcagga cctcgtactg ataccccagct ttccttgtaca aagtggtgat cctactagta    6300
gaaggagtgc gtcgaagcag atcgttcaaa catttggcaa taaagtttct taagattgaa    6360
tcctgttgcc ggtcttgcga tgattatcat ataatttctg ttgaattacg ttaagcatgt    6420
aataattaac atgtaatgca tgacgttatt tatgagatgg ttttttatga ttagagtccc    6480
gcaattatac atttaatacg cgatagaaaa caaaatatag cgcgcaaact aggataaatt    6540
atcgcgcgcg gtgtcatcta tgttactaga tcgaaagctt agcttgagct tggatcagat    6600
tgtcgtttcc cgccttcagt ttaaactatc agtgtttgac aggatatatt ggcgggtaaa    6660
``` c                                                                                      6661

<210> SEQ ID NO 89
<211> LENGTH: 20
<212> TYPE: DNA
<213> ORGANISM: Artificial Sequence
<220> FEATURE:
<223> OTHER INFORMATION: Primer Sequence

<400> SEQUENCE: 89
attttccatt cacttggccc                                                                  20

<210> SEQ ID NO 90
<211> LENGTH: 19
<212> TYPE: DNA
<213> ORGANISM: Artificial Sequence
<220> FEATURE:
<223> OTHER INFORMATION: Primer Sequence

<400> SEQUENCE: 90
tgctatctgg ctcagctgc                                                                   19

<210> SEQ ID NO 91
<211> LENGTH: 21
<212> TYPE: DNA
<213> ORGANISM: Artificial Sequence
<220> FEATURE:
<223> OTHER INFORMATION: Probe Sequence

<400> SEQUENCE: 91
atggtggaag ggcggttgtg a                                                                21

<210> SEQ ID NO 92
<211> LENGTH: 18
<212> TYPE: DNA
<213> ORGANISM: Artificial Sequence
<220> FEATURE:
<223> OTHER INFORMATION: Primer Sequence

<400> SEQUENCE: 92
ctcccgcgca ccgatctg                                                                    18

<210> SEQ ID NO 93
<211> LENGTH: 19
<212> TYPE: DNA
<213> ORGANISM: Artificial Sequence
<220> FEATURE:
<223> OTHER INFORMATION: Primer Sequence

<400> SEQUENCE: 93
cccgcccctc tcctctttc                                                                   19

<210> SEQ ID NO 94
<211> LENGTH: 21
<212> TYPE: DNA
<213> ORGANISM: Artificial Sequence
<220> FEATURE:
<223> OTHER INFORMATION: Probe Sequence

<400> SEQUENCE: 94
aagccgcctc tcgcccaccc a                                                                21

<210> SEQ ID NO 95
<211> LENGTH: 23
<212> TYPE: DNA
<213> ORGANISM: Artificial Sequence
<220> FEATURE:
<223> OTHER INFORMATION: Primer Sequence

<400> SEQUENCE: 95
aycagatgtg ggcggctcag tat                                          23

<210> SEQ ID NO 96
<211> LENGTH: 29
<212> TYPE: DNA
<213> ORGANISM: Artificial Sequence
<220> FEATURE:
<223> OTHER INFORMATION: Primer Sequence

<400> SEQUENCE: 96
gggatatgta ggacaagaaa cttgcatga                                    29

<210> SEQ ID NO 97
<211> LENGTH: 880
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 97
accagatgtg ggcggctcag tattacactt acaagcggcc acggcagtgg ctgtcttcgt    60
ctggttgggg gcaatgggat ttgggttacc agctgcagct ggcgctgctg tggccaaccc   120
aggtgttaca gttgttgaca ttgatggaga tggtagtttc ctcatgaaca ttcaggagtt   180
ggcattgatc cgtattgaga acctccctgt gaaggtgatg atattgaaca accagcatct   240
gggaatggtg gtgcaatggg aggataggtt ttacaaggcc aatcgggcgc acacatacct   300
tggcaaccca gaaaatgaga gtgagatata tccagatttt gtgacgattg ctaaaggatt   360
caacgttccg gcagttcgtg tgacgaagaa gagcgaagtc actgcagcaa tcaagaagat   420
gcttgagacc ccagggccat acttgttgga tatcatcgtc ccgcatcagg agcacgtgct   480
gcctatgatt cccaatggcg gcgctttcaa ggacatgatc atggagggtg atggcaggac   540
ctcgtactga aatggtccga aggtccacgc cgccaactac gagtatgatc caagcggtg    600 gtgctttcaa ggacatgatc atggagggtg atggcaggac ctcgtactga aatttcgacc   660
tacaagacct acaagtgtga catgcgcaat cagcatggtg cccgcgtgtt gtatcaacta   720
ctaggggttc aactgtgaac catgcgtttt ctagtttgct tgtttcattc atataagctt   780
gtgttactta gttccgaacc ctgtagcttt gtagtctatg ctctcttttg tagggatgtg   840
ctgtcataag atatcatgca agtttcttgt cctacatatc                         880

<210> SEQ ID NO 98
<211> LENGTH: 776
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 98
accagatgtg ggcggctcag tattacactt acaagcggcc acggcagtgg ctgtcttcgt    60
ctggttgggg gcaatgggat ttgggttacc agctgcagct ggcgctgctg tggccaaccc   120
aggtgttaca gttgttgaca ttgatggaga tggtagtttc ctcatgaaca ttcaggagtt   180
ggcattgatc cgtattgaga acctccctgt gaaggtgatg atattgaaca accagcatct   240

```
gggaatggtg gtgcaatggg aggataggtt ttacaaggcc aatcgggcgc acacatacct    300
tggcaaccca gaaaatgaga gtgagatata tccagatttt gtgacgattg ctaaaggatt    360
caacgttccg gcagttcgtg tgacgaagaa gagcgaagtc actgcagcaa tcaagaagat    420
gcttgagacc ccagggccat acttgttgga tatcatcgtc ccgcatcagg agcacgtgct    480
gccttcccaa gcggtggtgc tttcaaggac atgatcatgg agggtgatgg caggacctcg    540
tactgaaatt tcgacctaca agacctacaa gtgtgacatg cgcaatcagc atggtgcccg    600
cgtgttgtat caactactag gggttcaact gtgaaccatg cgttttctag tttgcttgtt    660
tcattcatat aagcttgtgt tacttagttc cgaaccctgt agctttgtag tctatgctct    720
cttttgtagg gatgtgctgt cataagatat catgcaagtt tcttgtccta catatc        776
```

<210> SEQ ID NO 99
<211> LENGTH: 866
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 99

```
atcagatgtg gcggctcag tattacactt acaagcggcc acggcagtgg ctgtcttcat      60
ccggtttggg tgcaatggga tttggggttgc cagctgcagc tggcgctgct gtggccaacc    120
caggtgttac agttgttgac attgatgggg atggtagttt cctcatgaac attcaggagt    180
tggcgttgat ccgtattgag aacctcccag tgaaggtgat gatattgaac aaccagcatc    240
tgggaatggt ggtgcagtgg gaggataggt tttacaaggc caaccgggcg cacacatacc    300
ttggcaaccc agaaaatgag agtgagatat atccagattt tgtgacgatt gctaaaggat    360
tcaacgttcc ggcagttcgt gtgacgaaga agagcgaagt cactgcagca atcaagaaga    420
tgcttgagac cccagggcca tacttgttgg atatcattgt cccgcatcag gagcacgtga    480
atggcggcgc tttcaaggac atgatcatgg agggtgatgg caggacctcg tactgaaatg    540
gtccgaaggt ccacgccgcc aactacgagt atgatcccaa gcggtggtgc ttttaaggac    600
atgatcatgg agggtgatgg caggacctcg tactgaaatt tcgacctaca agacctacaa    660
gtgtgacatg cgcaatcagc atgatacctg cgtgttgtat caactactgg gggttcaact    720
gtgaaccatg cgttttctag tttgcttgtt tcattcatat aagcttgtgt tacttagttc    780
cgaaccgtgt agttttgtag tctctgttct cttttgtagg gatgtgctgt cataagatat    840
catgcaagtt tcttgtccta catatc                                          866
```

<210> SEQ ID NO 100
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 100

```
atcagatgtg gcggctcag tattacactt acaagcggcc acggcagtgg ctgtcttcat      60
ccggtttggg tgcaatggga tttggggttgc cagctgcagc tggcgctgct gtggccaacc    120
caggtgttac agttgttgac attgatgggg atggtagttt cctcatgaac attcaggagt    180
tggcgttgat ccgtattgag aacctcccag tgaaggtgat gatattgaac aaccagcatc    240
tgggaatggt ggtgcagtgg gaggataggt tttacaaggc caaccgggcg cacacatacc    300
```
ttggcaaccc agaaaatgag agtgagatat atccagattt tgtgacgatt gctaaaggat     360
tcaacgttcc ggcagttcgt gtgacgaaga agagcgaagt cactgcagca atcaagaaga     420
tgcttgagac cccagggcca tacttgttgg atatcattgt cccgcatcag gagcacgtgc     480
tgcctatgat cccaagcggt ggtgctttta aggacatgat catggagggt gatggcagga     540
cctcgtactg aaatttcgac ctacaagacc tacaagtgtg acatgcgcaa tcagcatgat     600
acctgcgtgt tgtatcaact actgggggtt caactgtgaa ccatgcgttt tctagtttgc     660
ttgtttcatt catataagct tgtgttactt agttccgaac cgtgtagttt tgtagtctct     720
gttctctttt gtagggatgt gctgtcataa gatatcatgc aagtttcttg tcctacatat     780
c                                                                     781

<210> SEQ ID NO 101
<211> LENGTH: 867
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 101
accagatgtg ggcggctcag tattacactt acaagcggcc acggcagtgg ctgtcttcgt      60
ctggtttggg ggcaatggga tttgggttac cagctgcagc tggcgctgct gtggccaacc     120
caggtgttac agttgttgac attgatggtg atggtagttt cctcatgaac attcaggagt     180
tggcgttgat ccgcattgag aacctcccag tgaaggtgat gatattgaac aaccagcatc     240
tgggaatggt ggtgcagtgg gaggataggt tttacaaggc caatcgggcg cacacatacc     300
ttggcaaccc agaaaatgag agtgagatat atccagattt tgtgacgatt gctaaaggat     360
tcaacgttcc agcagttcga gtgacgaaga agagcgaagt cactgcagca atcaagaaga     420
tgcttgagac cccagggcca tacttgttgg atatcatagt cccgcatcag gagcacgtgc     480
tgcctaatgg cggcgctttc aaggacatga tcatggaggg tgatggcagg acctcgtact     540
gaaatggtcc gaaggtccac gccgccaact acgagtccca agcggtggtg ctttcaagga     600
catgatcatg gagggtgatg gcaggacctc gtactgaaat ttcgacctac aagacctaca     660
agtgtgacat gcgcaatcag catgatgccc gcgtgttgta tcaactacta ggggttcaac     720
tgtgagccat gcgttttcta gtttgcttgt tcattcata taagcttgta ttacttagtt     780
ccgaaccctg tagttttgta gtctatgttc tcttttgtag ggatgtgctg tcataagatg     840
tcatgcaagt ttcttgtcct acatatc                                          867

<210> SEQ ID NO 102
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 102
accagatgtg ggcggctcag tattacactt acaagcggcc acggcagtgg ctgtcttcgt      60
ctggtttggg ggcaatggga tttgggttac cagctgcagc tggcgctgct gtggccaacc     120
caggtgttac agttgttgac attgatggtg atggtagttt cctcatgaac attcaggagt     180
tggcgttgat ccgcattgag aacctcccag tgaaggtgat gatattgaac aaccagcatc     240

| | |
|---|---|
| tgggaatggt ggtgcagtgg gaggataggt tttacaaggc caatcggcg cacacatacc | 300 |
| ttggcaaccc agaaaatgag agtgagatat atccagattt tgtgacgatt gctaaaggat | 360 |
| tcaacgttcc agcagttcga gtgacgaaga agagcgaagt cactgcagca atcaagaaga | 420 |
| tgcttgagac cccagggcca tacttgttgg atatcatagt cccgcatcag gagcacgtgc | 480 |
| tgcctatgat cccaagcggt ggtgctttca aggacatgat catggagggt gatggcagga | 540 |
| cctcgtactg aaatttcgac ctacaagacc tacaagtgtg acatgcgcaa tcagcatgat | 600 |
| gcccgcgtgt tgtatcaact actaggggtt caactgtgag ccatgcgttt tctagtttgc | 660 |
| ttgtttcatt catataagct tgtattactt agttccgaac cctgtagttt tgtagtctat | 720 |
| gttctctttt gtagggatgt gctgtcataa gatgtcatgc aagtttcttg tcctacatat | 780 |
| c | 781 |

<210> SEQ ID NO 103
<211> LENGTH: 763
<212> TYPE: DNA
<213> ORGANISM: Artificial Sequence
<220> FEATURE:
<223> OTHER INFORMATION: Donor insertion results from amplified region
of AHAS gene of wheat

<400> SEQUENCE: 103

| | |
|---|---|
| accagatgtg ggcggctcag tattacactt acaagcggcc acggcagtgg ctgtcttcgt | 60 |
| ctggttgggg gcaatgggat ttgggttacc agctgcagct ggcgctgctg tggccaaccc | 120 |
| aggtgttaca gttgttgaca ttgatggaga tggtagtttc ctcatgaaca ttcaggagtt | 180 |
| ggcattgatc cgtattgaga acctccctgt gaaggtgatg atattgaaca accagcatct | 240 |
| gggaatggtg gtgcaatggg aggataggtt ttacaaggcc aatcgggcgc acacatacct | 300 |
| tggcaaccca gaaaatgaga gtgagatata tccagatttt gtgacgattg ctaaaggatt | 360 |
| caacgttccg gcagttcgtg tgacgaagaa gagcgaagtc actgcagcaa tcaagaagat | 420 |
| gcttgagacc ccagggccat acttgttgga tatcatcgtc ccgcatcagg agcacaagcg | 480 |
| gtggtgcttt caaggacatg atcatggagg gtgatggcag gacctcgtac tgaaatttcg | 540 |
| acctacaaga cctacaagtg tgacatgcgc aatcagcatg tgcccgcgt gttgtatcaa | 600 |
| ctactagggg ttcaactgtg aaccatgcgt tttctagttt gcttgtttca ttcatataag | 660 |
| cttgtgttac ttagttccga accctgtagc tttgtagtct atgctctctt ttgtagggat | 720 |
| gtgctgtcat aagatatcat gcaagtttct tgtcctacat atc | 763 |

<210> SEQ ID NO 104
<211> LENGTH: 780
<212> TYPE: DNA
<213> ORGANISM: Artificial Sequence
<220> FEATURE:
<223> OTHER INFORMATION: Donor insertion results from amplified region
of AHAS gene of wheat

<400> SEQUENCE: 104

| | |
|---|---|
| accagatgtg ggcggctcag tattacactt acaagcggcc acggcagtgg ctgtcttcgt | 60 |
| ctggttgggg gcaatgggat ttgggttacc agctgcagct ggcgctgctg tggccaaccc | 120 |
| aggtgttaca gttgttgaca ttgatggaga tggtagtttc ctcatgaaca ttcaggagtt | 180 |
| ggcattgatc cgtattgaga acctccctgt gaaggtgatg atattgaaca accagcatct | 240 |
| gggaatggtg gtgcaatggg aggataggtt ttacaaggcc aatcgggcgc acacatacct | 300 |
| tggcaaccca gaaaatgaga gtgagatata tccagatttt gtgacgattg ctaaaggatt | 360 |

```
caacgttccg gcagttcgtg tgacgaagaa gagcgaagtc actgcagcaa tcaagaagat    420
gcttgagacc ccagggccat acttgttgga tatcatcgtc ccgcatcagg agcacgtgct    480
gcctatgatc ccaagcggtg gtgctttcaa ggacatgatc atggagggtg atggcaggac    540
ctcgtactga aatttcgacc tacaagacct acaagtgtga catgcgcaat cagcatggtg    600
cccgcgtgtt gtatcaacta ctaggggttc aactgtgaac catgcgtttt ctagtttgct    660
tgtttcattc atataagctt gtgttactta gttccgaacc ctgtagcttt gtagtctatg    720
ctctcttttg tagggatgtg ctgtcataag atatcatgca agtttcttgt cctacatatc    780
```

<210> SEQ ID NO 105
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 105

```
atcagatgtg ggcggctcag tattacactt acaagcggcc acggcagtgg ctgtcttcat     60
ccggtttggg tgcaatggga tttggttgc cagctgcagc tggcgctgct gtggccaacc    120
caggtgttac agttgttgac attgatgggg atggtagttt cctcatgaac attcaggagt    180
tggcgttgat ccgtattgag aacctcccag tgaaggtgat gatattgaac aaccagcatc    240
tgggaatggt ggtgcagtgg gaggataggt tttacaaggc caaccgggcg cacacatacc    300
ttggcaaccc agaaaatgag agtgagatat atccagattt tgtgacgatt gctaaaggat    360
tcaacgttcc ggcagttcgt gtgacgaaga agagcgaagt cactgcagca atcaagaaga    420
tgcttgagac cccagggcca tacttgttgg atatcattgt cccgcatcag gagcacgtgc    480
tgcctatgat cccaagcggt ggtgctttta aggacatgat catggagggt gatggcagga    540
cctcgtactg aaatttcgac ctacaagacc tacaagtgtg acatgcgcaa tcagcatgat    600
acctgcgtgt tgtatcaact actgggggtt caactgtgaa ccatgcgttt tctagtttgc    660
ttgtttcatt catataagct tgtgttactt agttccgaac cgtgtagttt tgtagtctct    720
gttctctttt gtagggatgt gctgtcataa gatatcatgc aagtttcttg tcctacatat    780
c                                                                   781
```

<210> SEQ ID NO 106
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 106

```
atcagatgtg ggcggctcag tattacactt acaagcggcc acggcagtgg ctgtcttcat     60
ccggtttggg tgcaatggga tttggttgc cagctgcagc tggcgctgct gtggccaacc    120
caggtgttac agttgttgac attgatgggg atggtagttt cctcatgaac attcaggagt    180
tggcgttgat ccgtattgag aacctcccag tgaaggtgat gatattgaac aaccagcatc    240
tgggaatggt ggtgcagtgg gaggataggt tttacaaggc caaccgggcg cacacatacc    300
ttggcaaccc agaaaatgag agtgagatat atccagattt tgtgacgatt gctaaaggat    360
tcaacgttcc ggcagttcgt gtgacgaaga agagcgaagt cactgcagca atcaagaaga    420
```

```
tgcttgagac cccagggcca tacttgttgg atatcattgt cccgcatcag gagcacgtgc    480
tgcctatgat cccaagcggt ggtgctttta aggacatgat catggagggt gatggcagga    540
cctcgtactg aaatttcgac ctacaagacc tacaagtgtg acatgcgcaa tcagcatgat    600
acctgcgtgt tgtatcaact actgggggtt caactgtgaa ccatgcgttt tctagtttgc    660
ttgtttcatt catataagct tgtgttactt agttccgaac cgtgtagttt tgtagtctct    720
gttctctttt gtagggatgt gctgtcataa gatatcatgc aagtttcttg tcctacatat    780
c                                                                    781
```

<210> SEQ ID NO 107
<211> LENGTH: 876
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 107

```
accagatgtg ggcggctcag tattacactt acaagcggcc acggcagtgg ctgtcttcgt     60
ctggtttggg ggcaatggga tttgggttac cagctgcagc tggcgctgct gtggccaacc    120
caggtgttac agttgttgac attgatggtg atggtagttt cctcatgaac attcaggagt    180
tggcgttgat ccgcattgag aacctcccag tgaaggtgat gatattgaac aaccagcatc    240
tgggaatggt ggtgcagtgg gaggataggt tttacaaggc caatcgggcg cacacatacc    300
ttggcaaccc agaaaatgag agtgagatat atccagattt tgtgacgatt gctaaaggat    360
tcaacgttcc agcagttcga gtgacgaaga agagcgaagt cactgcagca atcaagaaga    420
tgcttgagac cccagggcca tacttgttgg atatcatagt cccgcatcag gagcacgtgc    480
tgcctatgat tcccaatggc ggcgcttttca aggacatgat catggagggt gatggcagga    540
cctcgtactg aaatggtccg aaggtccacg ccgccaacta cgagtcccaa gcggtggtgc    600
tttcaaggac atgatcatgg agggtgatgg caggacctcg tactgaaatt tcgacctaca    660
agacctacaa gtgtgacatg cgcaatcagc atgatgcccg cgtgttgtat caactactag    720
gggttcaact gtgagccatg cgttttctag tttgcttgtt tcattcatat aagcttgtat    780
tacttagttc cgaaccctgt agttttgtag tctatgttct cttttgtagg gatgtgctgt    840
cataagatgt catgcaagtt tcttgtccta catatc                              876
```

<210> SEQ ID NO 108
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 108

```
accagatgtg ggcggctcag tattacactt acaagcggcc acggcagtgg ctgtcttcgt     60
ctggtttggg ggcaatggga tttgggttac cagctgcagc tggcgctgct gtggccaacc    120
caggtgttac agttgttgac attgatggtg atggtagttt cctcatgaac attcaggagt    180
tggcgttgat ccgcattgag aacctcccag tgaaggtgat gatattgaac aaccagcatc    240
tgggaatggt ggtgcagtgg gaggataggt tttacaaggc caatcgggcg cacacatacc    300
ttggcaaccc agaaaatgag agtgagatat atccagattt tgtgacgatt gctaaaggat    360
tcaacgttcc agcagttcga gtgacgaaga agagcgaagt cactgcagca atcaagaaga    420
```

```
tgcttgagac cccagggcca tacttgttgg atatcatagt cccgcatcag gagcacgtgc    480
tgcctatgat cccaagcggt ggtgctttca aggacatgat catggagggt gatggcagga    540
cctcgtactg aaatttcgac ctacaagacc tacaagtgtg acatgcgcaa tcagcatgat    600
gcccgcgtgt tgtatcaact actaggggtt caactgtgag ccatgcgttt tctagtttgc    660
ttgtttcatt catataagct tgtattactt agttccgaac cctgtagttt tgtagtctat    720
gttctctttt gtagggatgt gctgtcataa gatgtcatgc aagtttcttg tcctacatat    780
c                                                                   781
```

<210> SEQ ID NO 109
<211> LENGTH: 880
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 109

```
accagatgtg ggcggctcag tattacactt acaagcggcc acggcagtgg ctgtcttcgt    60
ctggttgggg gcaatgggat ttgggttacc agctgcagct ggcgctgctg tggccaaccc    120
aggtgttaca gttgttgaca ttgatggaga tggtagtttc ctcatgaaca ttcaggagtt    180
ggcattgatc cgtattgaga acctccctgt gaaggtgatg atattgaaca accagcatct    240
gggaatggtg gtgcaatggg aggataggtt ttacaaggcc aatcgggcgc acacatacct    300
tggcaaccca gaaaatgaga gtgagatata tccagatttt gtgacgattg ctaaaggatt    360
caacgttccg gcagttcgtg tgacgaagaa gagcgaagtc actgcagcaa tcaagaagat    420
gcttgagacc ccagggccat acttgttgga tatcatcgtc ccgcatcagg agcacgtgct    480
gcctatgatt cccaatggcg gcgctttcaa ggacatgatc atggagggtg atggcaggac    540
ctcgtactga aatggtccga aggtccacgc cgccaactac gagtatgatc caagcggtg    600 gtgctttcaa ggacatgatc atggagggtg atggcaggac ctcgtactga aatttcgacc    660
tacaagacct acaagtgtga catgcgcaat cagcatggtg cccgcgtgtt gtatcaacta    720
ctaggggttc aactgtgaac catgcgtttt ctagtttgct tgtttcattc atataagctt    780
gtgttactta gttccgaacc ctgtagcttt gtagtctatg ctctcttttg tagggatgtg    840
ctgtcataag atatcatgca agtttcttgt cctacatatc                         880
```

<210> SEQ ID NO 110
<211> LENGTH: 780
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 110

```
accagatgtg ggcggctcag tattacactt acaagcggcc acggcagtgg ctgtcttcgt    60
ctggttgggg gcaatgggat ttgggttacc agctgcagct ggcgctgctg tggccaaccc    120
aggtgttaca gttgttgaca ttgatggaga tggtagtttc ctcatgaaca ttcaggagtt    180
ggcattgatc cgtattgaga acctccctgt gaaggtgatg atattgaaca accagcatct    240
gggaatggtg gtgcaatggg aggataggtt ttacaaggcc aatcgggcgc acacatacct    300
tggcaaccca gaaaatgaga gtgagatata tccagatttt gtgacgattg ctaaaggatt    360
```

| | |
|---|---|
| caacgttccg gcagttcgtg tgacgaagaa gagcgaagtc actgcagcaa tcaagaagat | 420 |
| gcttgagacc ccagggccat acttgttgga tatcatcgtc ccgcatcagg agcacgtgct | 480 |
| gcctatgatc ccaagcggtg gtgctttcaa ggacatgatc atggagggtg atggcaggac | 540 |
| ctcgtactga aatttcgacc tacaagacct acaagtgtga catgcgcaat cagcatggtg | 600 |
| cccgcgtgtt gtatcaacta ctaggggttc aactgtgaac catgcgtttt ctagtttgct | 660 |
| tgtttcattc atataagctt gtgttactta gttccgaacc ctgtagcttt gtagtctatg | 720 |
| ctctcttttg tagggatgtg ctgtcataag atatcatgca agtttcttgt cctacatatc | 780 |

<210> SEQ ID NO 111
<211> LENGTH: 781
<212> TYPE: DNA
<213> ORGANISM: Artificial Sequence
<220> FEATURE:
<223> OTHER INFORMATION: Donor insertion results from amplified region
of AHAS gene of wheat

<400> SEQUENCE: 111

| | |
|---|---|
| atcagatgtg ggcggctcag tattacactt acaagcggcc acggcagtgg ctgtcttcat | 60 |
| ccggtttggg tgcaatggga tttggggttgc cagctgcagc tggcgctgct gtggccaacc | 120 |
| caggtgttac agttgttgac attgatgggg atggtagttt cctcatgaac attcaggagt | 180 |
| tggcgttgat ccgtattgag aacctcccag tgaaggtgat gatattgaac aaccagcatc | 240 |
| tgggaatggt ggtgcagtgg gaggataggt tttacaaggc caaccgggcg cacacatacc | 300 |
| ttggcaaccc agaaaatgag agtgagatat atccagattt tgtgacgatt gctaaaggat | 360 |
| tcaacgttcc ggcagttcgt gtgacgaaga agagcgaagt cactgcagca atcaagaaga | 420 |
| tgcttgagac cccagggcca tacttgttgg atatcattgt cccgcatcag gagcacgtgc | 480 |
| tgcctatgat cccaagcggt ggtgctttta aggacatgat catggagggt gatggcagga | 540 |
| cctcgtactg aaatttcgac ctacaagacc tacaagtgtg acatgcgcaa tcagcatgat | 600 |
| acctgcgtgt tgtatcaact actgggggtt caactgtgaa ccatgcgttt tctagtttgc | 660 |
| ttgtttcatt catataagct tgtgttactt agttccgaac cgtgtagttt tgtagtctct | 720 |
| gttctctttt gtagggatgt gctgtcataa gatatcatgc aagtttcttg tcctacatat | 780 |
| c | 781 |

<210> SEQ ID NO 112
<211> LENGTH: 781
<212> TYPE: DNA
<213> ORGANISM: Artificial Sequence
<220> FEATURE:
<223> OTHER INFORMATION: Donor insertion results from amplified region
of AHAS gene of wheat

<400> SEQUENCE: 112

| | |
|---|---|
| atcagatgtg ggcggctcag tattacactt acaagcggcc acggcagtgg ctgtcttcat | 60 |
| ccggtttggg tgcaatggga tttggggttgc cagctgcagc tggcgctgct gtggccaacc | 120 |
| caggtgttac agttgttgac attgatgggg atggtagttt cctcatgaac attcaggagt | 180 |
| tggcgttgat ccgtattgag aacctcccag tgaaggtgat gatattgaac aaccagcatc | 240 |
| tgggaatggt ggtgcagtgg gaggataggt tttacaaggc caaccgggcg cacacatacc | 300 |
| ttggcaaccc agaaaatgag agtgagatat atccagattt tgtgacgatt gctaaaggat | 360 |
| tcaacgttcc ggcagttcgt gtgacgaaga agagcgaagt cactgcagca atcaagaaga | 420 |
| tgcttgagac cccagggcca tacttgttgg atatcattgt cccgcatcag gagcacgtgc | 480 |

```
tgcctatgat cccaagcggt ggtgctttta aggacatgat catggagggt gatggcagga    540
cctcgtactg aaatttcgac ctacaagacc tacaagtgtg acatgcgcaa tcagcatgat    600
acctgcgtgt tgtatcaact actgggggtt caactgtgaa ccatgcgttt tctagtttgc    660
ttgtttcatt catataagct tgtgttactt agttccgaac cgtgtagttt tgtagtctct    720
gttctctttt gtagggatgt gctgtcataa gatatcatgc aagtttcttg tcctacatat    780
c                                                                   781
```

<210> SEQ ID NO 113
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 113

```
accagatgtg gcggctcag tattacactt acaagcggcc acggcagtgg ctgtcttcgt    60
ctggtttggg ggcaatggga tttgggttac cagctgcagc tggcgctgct gtggccaacc   120
caggtgttac agttgttgac attgatggtg atggtagttt cctcatgaac attcaggagt   180
tggcgttgat ccgcattgag aacctcccag tgaaggtgat gatattgaac aaccagcatc   240
tgggaatggt ggtgcagtgg gaggataggt tttacaaggc caatcgggcg cacacatacc   300
ttggcaaccc agaaaatgag agtgagatat atccagatttt tgtgacgatt gctaaaggat   360
tcaacgttcc agcagttcga gtgacgaaga agagcgaagt cactgcagca atcaagaaga   420
tgcttgagac cccagggcca tacttgttgg atatcatagt cccgcatcag gagcacgtgc   480
tgcctatgat cccaagcggt ggtgctttca aggacatgat catggagggt gatggcagga   540
cctcgtactg aaatttcgac ctacaagacc tacaagtgtg acatgcgcaa tcagcatgat   600
gcccgcgtgt tgtatcaact actaggggtt caactgtgag ccatgcgttt tctagtttgc   660
ttgtttcatt catataagct tgtattactt agttccgaac cctgtagttt tgtagtctat   720
gttctctttt gtagggatgt gctgtcataa gatgtcatgc aagtttcttg tcctacatat   780
c                                                                   781
```

<210> SEQ ID NO 114
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 114

```
accagatgtg gcggctcag tattacactt acaagcggcc acggcagtgg ctgtcttcgt    60
ctggtttggg ggcaatggga tttgggttac cagctgcagc tggcgctgct gtggccaacc   120
caggtgttac agttgttgac attgatggtg atggtagttt cctcatgaac attcaggagt   180
tggcgttgat ccgcattgag aacctcccag tgaaggtgat gatattgaac aaccagcatc   240
tgggaatggt ggtgcagtgg gaggataggt tttacaaggc caatcgggcg cacacatacc   300
ttggcaaccc agaaaatgag agtgagatat atccagatttt tgtgacgatt gctaaaggat   360
tcaacgttcc agcagttcga gtgacgaaga agagcgaagt cactgcagca atcaagaaga   420
tgcttgagac cccagggcca tacttgttgg atatcatagt cccgcatcag gagcacgtgc   480
```

```
tgcctatgat cccaagcggt ggtgctttca aggacatgat catggagggt gatggcagga      540
cctcgtactg aaatttcgac ctacaagacc tacaagtgtg acatgcgcaa tcagcatgat      600
gcccgcgtgt tgtatcaact actaggggtt caactgtgag ccatgcgttt tctagtttgc      660
ttgtttcatt catataagct tgtattactt agttccgaac cctgtagttt tgtagtctat      720
gttctctttt gtagggatgt gctgtcataa gatgtcatgc aagtttcttg tcctacatat      780
c                                                                      781
```

<210> SEQ ID NO 115
<211> LENGTH: 880
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 115

```
accagatgtg ggcggctcag tattacactt acaagcggcc acggcagtgg ctgtcttcgt       60
ctggttgggg gcaatgggat ttgggttacc agctgcagct ggcgctgctg tggccaaccc      120
aggtgttaca gttgttgaca ttgatggaga tggtagtttc ctcatgaaca ttcaggagtt      180
ggcattgatc cgtattgaga acctccctgt gaaggtgatg atattgaaca accagcatct      240
gggaatggtg gtgcaatggg aggataggtt ttacaaggcc aatcgggcgc acacatacct      300
tggcaaccca gaaaatgaga gtgagatata tccagatttt gtgacgattg ctaaaggatt      360
caacgttccg gcagttcgtg tgacgaagaa gagcgaagtc actgcagcaa tcaagaagat      420
gcttgagacc ccagggccat acttgttgga tatcatcgtc ccgcatcagg agcacgtgct      480
gcctatgatt cccaatggcg cgctttcaa ggacatgatc atggagggtg atggcaggac      540
ctcgtactga aatggtccga aggtccacgc cgccaactac gagtatgatc ccaagcggtg      600
gtgctttcaa ggacatgatc atggagggtg atggcaggac ctcgtactga aatttcgacc      660
tacaagacct acaagtgtga catgcgcaat cagcatggtg cccgcgtgtt gtatcaacta      720
ctaggggttc aactgtgaac catgcgtttt ctagtttgct tgtttcattc atataagctt      780
gtgttactta gttccgaacc ctgtagcttt gtagtctatg ctctcttttg tagggatgtg      840
ctgtcataag atatcatgca agtttcttgt cctacatatc                            880
```

<210> SEQ ID NO 116
<211> LENGTH: 780
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 116

```
accagatgtg ggcggctcag tattacactt acaagcggcc acggcagtgg ctgtcttcgt       60
ctggttgggg gcaatgggat ttgggttacc agctgcagct ggcgctgctg tggccaaccc      120
aggtgttaca gttgttgaca ttgatggaga tggtagtttc ctcatgaaca ttcaggagtt      180
ggcattgatc cgtattgaga acctccctgt gaaggtgatg atattgaaca accagcatct      240
gggaatggtg gtgcaatggg aggataggtt ttacaaggcc aatcgggcgc acacatacct      300
tggcaaccca gaaaatgaga gtgagatata tccagatttt gtgacgattg ctaaaggatt      360
caacgttccg gcagttcgtg tgacgaagaa gagcgaagtc actgcagcaa tcaagaagat      420
gcttgagacc ccagggccat acttgttgga tatcatcgtc ccgcatcagg agcacgtgct      480
```
gcctatgatc ccaagcggtg gtgctttcaa ggacatgatc atggagggtg atggcaggac    540
ctcgtactga aatttcgacc tacaagacct acaagtgtga catgcgcaat cagcatggtg    600
cccgcgtgtt gtatcaacta ctaggggttc aactgtgaac catgcgtttt ctagtttgct    660
tgtttcattc atataagctt gtgttactta gttccgaacc ctgtagcttt gtagtctatg    720
ctctcttttg tagggatgtg ctgtcataag atatcatgca agtttcttgt cctacatatc    780

```
<210> SEQ ID NO 117
<211> LENGTH: 1041
<212> TYPE: DNA
<213> ORGANISM: Artificial Sequence
<220> FEATURE:
<223> OTHER INFORMATION: Donor insertion results from amplified region
      of AHAS gene of wheat
<220> FEATURE:
<221> NAME/KEY: misc_feature
<222> LOCATION: (604)..(604)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (607)..(607)
<223> OTHER INFORMATION: n is a, c, g, or t
<220> FEATURE:
<221> NAME/KEY: misc_feature
<222> LOCATION: (608)..(608)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (610)..(610)
<223> OTHER INFORMATION: n is a, c, g, or t
<220> FEATURE:
<221> NAME/KEY: misc_feature
<222> LOCATION: (611)..(611)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (613)..(613)
<223> OTHER INFORMATION: n is a, c, g, or t
<220> FEATURE:
<221> NAME/KEY: misc_feature
<222> LOCATION: (614)..(614)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (616)..(616)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
```

```
<220> FEATURE:
<221> NAME/KEY: misc_feature
<222> LOCATION: (619)..(619)
<223> OTHER INFORMATION: n is a, c, g, or t
<220> FEATURE:
<221> NAME/KEY: misc_feature
<222> LOCATION: (620)..(620)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (622)..(622)
<223> OTHER INFORMATION: n is a, c, g, or t
<220> FEATURE:
<221> NAME/KEY: misc_feature
<222> LOCATION: (623)..(623)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (625)..(625)
<223> OTHER INFORMATION: n is a, c, g, or t
<220> FEATURE:
<221> NAME/KEY: misc_feature
<222> LOCATION: (626)..(626)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (628)..(628)
<223> OTHER INFORMATION: n is a, c, g, or t
<220> FEATURE:
<221> NAME/KEY: misc_feature
<222> LOCATION: (629)..(629)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (631)..(631)
<223> OTHER INFORMATION: n is a, c, g, or t
<220> FEATURE:
<221> NAME/KEY: misc_feature
<222> LOCATION: (632)..(632)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t

<400> SEQUENCE: 117
atcagatgtg ggcggctcag tattacactt acaagcggcc acggcagtgg ctgtcttcat      60
ccggtttggg tgcaatggga tttgggttgc cagctgcagc tggcgctgct gtggccaacc     120
caggtgttac agttgttgac attgatgggg atggtagttt cctcatgaac attcaggagt     180
tggcgttgat ccgtattgag aacctcccag tgaaggtgat gatattgaac aaccagcatc     240
tgggaatggt ggtgcagtgg gaggataggt tttacaaggc caaccgggcg cacacatacc     300
ttggcaaccc agaaaatgag agtgagatat atccagattt tgtgacgatt gctaaaggat     360
tcaacgttcc ggcagttcgt gtgacgaaga agagcgaagt cactgcagca atcaagaaga     420
tgcttgagac cccagggcca tacttgttgg atatcattgt cccgcatcag gagcacgtgc     480
```

```
tgtagttggc ggcgctttca aggacatgat catggagggt gatgkcagga cctcgtactg      540
aaatggtccg aaggtccacg cctcgtatga aatggtccga aggtccacgc cgccaactac      600
gagnnnnnnn nnnnnnnnnn nnnnnnnnnn nnntatgatt cccaatggcg gcttcccaat      660
ggcggcgctt tcaaggacat gatcatggag ggtgatggca ggacctcgta ctgaaatggt      720
ccgaaggtcc acgccgccaa ctacgatgat cccaagcggt ggtgctttta aggacatgat      780
catggagggt gatggcagga cctcgtactg aaatttcgac ctacaagacc tacaagtgtg      840
acatgcgcaa tcagcatgat acctgcgtgt tgtatcaact actggggtt caactgtgaa       900 ccatgcgttt tctagtttgc ttgtttcatt catataagct tgtgttactt agttccgaac      960
cgtgtagttt tgtagtctct gttctctttt gtagggatgt gctgtcataa gatatcatgc     1020
aagtttcttg tcctacatat c                                               1041
```

<210> SEQ ID NO 118
<211> LENGTH: 781
<212> TYPE: DNA
<213> ORGANISM: Artificial Sequence
<220> FEATURE:
<223> OTHER INFORMATION: Donor insertion results from amplified region of AHAS gene of wheat

<400> SEQUENCE: 118

```
atcagatgtg ggcggctcag tattacactt acaagcggcc acggcagtgg ctgtcttcat       60
ccggtttggg tgcaatggga tttggttgc cagctgcagc tggcgctgct gtggccaacc       120
caggtgttac agttgttgac attgatgggg atggtagttt cctcatgaac attcaggagt      180
tggcgttgat ccgtattgag aacctcccag tgaaggtgat gatattgaac aaccagcatc     240
tgggaatggt ggtgcagtgg gaggataggt tttacaaggc caaccgggcg cacacatacc     300
ttggcaaccc agaaaatgag agtgagatat atccagattt tgtgacgatt gctaaaggat     360
tcaacgttcc ggcagttcgt gtgacgaaga gagcgaagt cactgcagca atcaagaaga     420
tgcttgagac cccagggcca tacttgttgg atatcattgt cccgcatcag gagcacgtgc     480
tgcctatgat cccaagcggt ggtgctttta aggacatgat catggagggt gatggcagga     540
cctcgtactg aaatttcgac ctacaagacc tacaagtgtg acatgcgcaa tcagcatgat     600
acctgcgtgt tgtatcaact actggggtt caactgtgaa ccatgcgttt tctagtttgc     660
ttgtttcatt catataagct tgtgttactt agttccgaac cgtgtagttt tgtagtctct     720
gttctctttt gtagggatgt gctgtcataa gatatcatgc aagtttcttg tcctacatat     780
c                                                                     781
```

<210> SEQ ID NO 119
<211> LENGTH: 881
<212> TYPE: DNA
<213> ORGANISM: Artificial Sequence
<220> FEATURE:
<223> OTHER INFORMATION: Donor insertion results from amplified region of AHAS gene of wheat

<400> SEQUENCE: 119

```
accagatgtg ggcggctcag tattacactt acaagcggcc acggcagtgg ctgtcttcgt       60
ctggtttggg ggcaatggga tttggttac cagctgcagc tggcgctgct gtggccaacc       120
caggtgttac agttgttgac attgatggtg atggtagttt cctcatgaac attcaggagt      180
tggcgttgat ccgcattgag aacctcccag tgaaggtgat gatattgaac aaccagcatc     240
tgggaatggt ggtgcagtgg gaggataggt tttacaaggc caatcgggcg cacacatacc     300
```

```
ttggcaaccc agaaaatgag agtgagatat atccagattt tgtgacgatt gctaaaggat      360
tcaacgttcc agcagttcga gtgacgaaga agagcgaagt cactgcagca atcaagaaga      420
tgcttgagac cccagggcca tacttgttgg atatcatagt cccgcatcag gagcacgtgc      480
tgcctatgat tcccaatggc ggcgctttca aggacatgat catggagggt gatggcagga      540
cctcgtactg aaatggtccg aaggtccacg ccgccaacta cgagtatgat cccaagcggt      600
ggtgctttca aggacatgat catggagggt gatggcagga cctcgtactg aaatttcgac      660
ctacaagacc tacaagtgtg acatgcgcaa tcagcatgat gcccgcgtgt tgtatcaact      720
actaggggtt caactgtgag ccatgcgttt tctagtttgc ttgtttcatt catataagct      780
tgtattactt agttccgaac cctgtagttt tgtagtctat gttctctttt gtagggatgt      840
gctgtcataa gatgtcatgc aagtttcttg tcctacatat c                         881
```

<210> SEQ ID NO 120
<211> LENGTH: 918
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 120

```
accagatgtg ggcggctcag tattacactt acaagcggcc acggcagtgg ctgtcttcgt       60
ctggtttggg ggcaatggga tttgggttac cagctgcagc tggcgctgct gtggccaacc      120
caggtgttac agttgttgac attgatggtg atggtagttt cctcatgaac attcaggagt      180
tggcgttgat ccgcattgag aacctcccag tgaaggtgat gatattgaac aaccagcatc      240
tgggaatggt ggtgcagtgg gaggataggt tttacaaggc caatcgggcg cacacatacc      300
ttggcaaccc agaaaatgag agtgagatat atccagattt tgtgacgatt gctaaaggat      360
tcaacgttcc agcagttcga gtgacgaaga agagcgaagt cactgcagca atcaagaaga      420
tgcttgagac cccagggcca tacttgttgg atatcatagt cccgcatcag gagcacgtgc      480
tgcctatgat tcccaatggc ggcgctttca aggacatgat catggagggt gatggcagga      540
cctcgtactg aaaatggtcc gaaggtccac gccgccacct cgtactgaaa tggtccraag      600
gtccacgccg ccaactacga gtatgatccc aagcggtggt gctttcaagg acatgatcat      660
ggagggtgat ggcaggacct cgtactgara tttcgaccta caagacctac aagtgtgaca      720
tgcgcaatca gcatgatgcc cgcgtgttgt atcaactact aggggttcaa ctgtgagcca      780
tgcgttttct agtttgcttg tttcattcat ataagcttgt attacttagt tccgaaccct      840
gtagttttgt agtctatgtt ctcttttgta gggatgtgct gtcataagat gtcatgcaag      900
tttcttgtcc tacatatc                                                   918
```

<210> SEQ ID NO 121
<211> LENGTH: 880
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 121

```
accagatgtg ggcggctcag tattacactt acaagcggcc acggcagtgg ctgtcttcgt       60
ctggttgggg gcaatgggat ttgggttacc agctgcagct ggcgctgctg tggccaaccc      120
```

```
aggtgttaca gttgttgaca ttgatggaga tggtagtttc ctcatgaaca ttcaggagtt    180
ggcattgatc cgtattgaga acctccctgt gaaggtgatg atattgaaca accagcatct    240
gggaatggtg gtgcaatggg aggataggtt ttacaaggcc aatcgggcgc acacatacct    300
tggcaaccca gaaaatgaga gtgagatata tccagatttt gtgacgattg ctaaaggatt    360
caacgttccg gcagttcgtg tgacgaagaa gagcgaagtc actgcagcaa tcaagaagat    420
gcttgagacc ccagggccat acttgttgga tatcatcgtc ccgcatcagg agcacgtgct    480
gcctatgatt cccaatggcg gcgctttcaa ggacatgatc atggagggtg atggcaggac    540
ctcgtactga aatggtccga aggtccacgc cgccaactac gagtatgatc caagcggtg     600 gtgctttcaa ggacatgatc atggagggtg atggcaggac ctcgtactga aatttcgacc    660
tacaagacct acaagtgtga catgcgcaat cagcatggtg cccgcgtgtt gtatcaacta    720
ctaggggttc aactgtgaac catgcgtttt ctagtttgct tgtttcattc atataagctt    780
gtgttactta gttccgaacc ctgtagcttt gtagtctatg ctctcttttg tagggatgtg    840
ctgtcataag atatcatgca agtttcttgt cctacatatc                          880

<210> SEQ ID NO 122
<211> LENGTH: 780
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 122
accagatgtg ggcggctcag tattacactt acaagcggcc acggcagtgg ctgtcttcgt      60
ctggttgggg gcaatgggat ttgggttacc agctgcagct ggcgctgctg tggccaaccc    120
aggtgttaca gttgttgaca ttgatggaga tggtagtttc ctcatgaaca ttcaggagtt    180
ggcattgatc cgtattgaga acctccctgt gaaggtgatg atattgaaca accagcatct    240
gggaatggtg gtgcaatggg aggataggtt ttacaaggcc aatcgggcgc acacatacct    300
tggcaaccca gaaaatgaga gtgagatata tccagatttt gtgacgattg ctaaaggatt    360
caacgttccg gcagttcgtg tgacgaagaa gagcgaagtc actgcagcaa tcaagaagat    420
gcttgagacc ccagggccat acttgttgga tatcatcgtc ccgcatcagg agcacgtgct    480
gcctatgatc ccaagcggtg gtgctttcaa ggacatgatc atggagggtg atggcaggac    540
ctcgtactga aatttcgacc tacaagacct acaagtgtga catgcgcaat cagcatggtg    600
cccgcgtgtt gtatcaacta ctaggggttc aactgtgaac catgcgtttt ctagtttgct    660
tgtttcattc atataagctt gtgttactta gttccgaacc ctgtagcttt gtagtctatg    720
ctctcttttg tagggatgtg ctgtcataag atatcatgca agtttcttgt cctacatatc    780

<210> SEQ ID NO 123
<211> LENGTH: 745
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 123
atcagatgtg ggcggctcag tattacactt acaagcggcc acggcagtgg ctgtcttcat      60
ccggtttggg tgcaatggga tttgggttgc agctgcagc tggcgctgct gtggccaacc     120
caggtgttac agttgttgac attgatgggg atggtagttt cctcatgaac attcaggagt    180
```

```
tggcgttgat ccgtattgag aacctcccag tgaaggtgat gatattgaac aaccagcatc    240
tgggaatggt ggtgcagtgg gaggataggt tttacaaggc caaccgggcg cacacatacc    300
ttggcaaccc agaaaatgag agtgagatat atccagattt tgtgacgatt gctaaaggat    360
tcaacgttcc ggcagttcgt gtgacgaaga agagcgaagt cactgcagca atcaagaaga    420
tgcttgagac cccagggcca tacttgttgg atatcattgt cccgcatgct tttaaggaca    480
tgatcatgga gggtgatggc aggacctcgt actgaaattt cgacctacaa gacctacaag    540
tgtgacatgc gcaatcagca tgatacctgc gtgttgtatc aactactggg ggttcaactg    600
tgaaccatgc gttttctagt ttgcttgttt cattcatata agcttgtgtt acttagttcc    660
gaaccgtgta gttttgtagt ctctgttctc ttttgtaggg atgtgctgtc ataagatatc    720
atgcaagttt cttgtcctac atatc                                          745

<210> SEQ ID NO 124
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 124
atcagatgtg ggcggctcag tattacactt acaagcggcc acggcagtgg ctgtcttcat    60
ccggtttggg tgcaatggga tttggttgc cagctgcagc tggcgctgct gtggccaacc    120
caggtgttac agttgttgac attgatgggg atggtagttt cctcatgaac attcaggagt    180
tggcgttgat ccgtattgag aacctcccag tgaaggtgat gatattgaac aaccagcatc    240
tgggaatggt ggtgcagtgg gaggataggt tttacaaggc caaccgggcg cacacatacc    300
ttggcaaccc agaaaatgag agtgagatat atccagattt tgtgacgatt gctaaaggat    360
tcaacgttcc ggcagttcgt gtgacgaaga agagcgaagt cactgcagca atcaagaaga    420
tgcttgagac cccagggcca tacttgttgg atatcattgt cccgcatcag gagcacgtgc    480
tgcctatgat cccaagcggt ggtgctttta aggacatgat catggagggt gatggcagga    540
cctcgtactg aaatttcgac ctacaagacc tacaagtgtg acatgcgcaa tcagcatgat    600
acctgcgtgt tgtatcaact actgggggtt caactgtgaa ccatgcgttt tctagtttgc    660
ttgtttcatt catataagct tgtgttactt agttccgaac cgtgtagttt tgtagtctct    720
gttctctttt gtagggatgt gctgtcataa gatatcatgc aagtttcttg tcctacatat    780
c                                                                     781

<210> SEQ ID NO 125
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 125
accagatgtg ggcggctcag tattacactt acaagcggcc acggcagtgg ctgtcttcgt    60
ctggtttggg ggcaatggga tttggttac cagctgcagc tggcgctgct gtggccaacc    120
caggtgttac agttgttgac attgatggtg atggtagttt cctcatgaac attcaggagt    180
tggcgttgat ccgcattgag aacctcccag tgaaggtgat gatattgaac aaccagcatc    240
```

```
tgggaatggt ggtgcagtgg gaggataggt tttacaaggc caatcgggcg cacacatacc    300
ttggcaaccc agaaaatgag agtgagatat atccagattt tgtgacgatt gctaaaggat    360
tcaacgttcc agcagttcga gtgacgaaga agagcgaagt cactgcagca atcaagaaga    420
tgcttgagac cccagggcca tacttgttgg atatcatagt cccgcatcag gagcacgtgc    480
tgcctatgat cccaagcggt ggtgctttca aggacatgat catggagggt gatggcagga    540
cctcgtactg aaatttcgac ctacaagacc tacaagtgtg acatgcgcaa tcagcatgat    600
gcccgcgtgt tgtatcaact actagggggtt caactgtgag ccatgcgttt tctagtttgc    660
ttgtttcatt catataagct tgtattactt agttccgaac cctgtagttt tgtagtctat    720
gttctctttt gtagggatgt gctgtcataa gatgtcatgc aagtttcttg tcctacatat    780
c                                                                    781
```

<210> SEQ ID NO 126
<211> LENGTH: 781
<212> TYPE: DNA
<213> ORGANISM: Artificial Sequence
<220> FEATURE:
<223> OTHER INFORMATION: Donor insertion results from amplified region of AHAS gene of wheat

<400> SEQUENCE: 126

```
accagatgtg ggcggctcag tattacactt acaagcggcc acggcagtgg ctgtcttcgt     60
ctggtttggg ggcaatggga tttgggttac cagctgcagc tggcgctgct gtggccaacc    120
caggtgttac agttgttgac attgatggtg atggtagttt cctcatgaac attcaggagt    180
tggcgttgat ccgcattgag aacctcccag tgaaggtgat gatattgaac aaccagcatc    240
tgggaatggt ggtgcagtgg gaggataggt tttacaaggc caatcgggcg cacacatacc    300
ttggcaaccc agaaaatgag agtgagatat atccagattt tgtgacgatt gctaaaggat    360
tcaacgttcc agcagttcga gtgacgaaga agagcgaagt cactgcagca atcaagaaga    420
tgcttgagac cccagggcca tacttgttgg atatcatagt cccgcatcag gagcacgtgc    480
tgcctatgat cccaagcggt ggtgctttca aggacatgat catggagggt gatggcagga    540
cctcgtactg aaatttcgac ctacaagacc tacaagtgtg acatgcgcaa tcagcatgat    600
gcccgcgtgt tgtatcaact actagggggtt caactgtgag ccatgcgttt tctagtttgc    660
ttgtttcatt catataagct tgtattactt agttccgaac cctgtagttt tgtagtctat    720
gttctctttt gtagggatgt gctgtcataa gatgtcatgc aagtttcttg tcctacatat    780
c                                                                    781
```

<210> SEQ ID NO 127
<211> LENGTH: 780
<212> TYPE: DNA
<213> ORGANISM: Artificial Sequence
<220> FEATURE:
<223> OTHER INFORMATION: Donor insertion results from amplified region of AHAS gene of wheat

<400> SEQUENCE: 127

```
accagatgtg ggcggctcag tattacactt acaagcggcc acggcagtgg ctgtcttcgt     60
ctggttgggg gcaatgggat ttgggttacc agctgcagct ggcgctgctg tggccaaccc    120
aggtgttaca gttgttgaca ttgatggaga tggtagtttc ctcatgaaca ttcaggagtt    180
ggcattgatc cgtattgaga acctcccgt gaaggtgatg atattgaaca accagcatct    240
gggaatggtg gtgcaatggg aggataggtt ttacaaggcc aatcgggcgc acacatacct    300
```

```
tggcaaccca gaaaatgaga gtgagatata tccagatttt gtgacgattg ctaaaggatt    360
caacgttccg gcagttcgtg tgacgaagaa gagcgaagtc actgcagcaa tcaagaagat    420
gcttgagacc ccagggccat acttgttgga tatcatcgtc ccgcatcagg agcacgtgct    480
gcctatgatc ccaagcggtg gtgctttcaa ggacatgatc atggagggtg atggcaggac    540
ctcgtactga aatttcgacc tacaagacct acaagtgtga catgcgcaat cagcatggtg    600
cccgcgtgtt gtatcaacta ctaggggttc aactgtgaac catgcgtttt ctagtttgct    660
tgtttcattc atataagctt gtgttactta gttccgaacc ctgtagcttt gtagtctatg    720
ctctcttttg tagggatgtg ctgtcataag atatcatgca agtttcttgt cctacatatc    780
```

<210> SEQ ID NO 128
<211> LENGTH: 780
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 128

```
accagatgtg ggcggctcag tattacactt acaagcggcc acggcagtgg ctgtcttcgt    60
ctggttgggg gcaatgggat ttgggttacc agctgcagct ggcgctgctg tggccaaccc    120
aggtgttaca gttgttgaca ttgatggaga tggtagtttc ctcatgaaca ttcaggagtt    180
ggcattgatc cgtattgaga acctccctgt gaaggtgatg atattgaaca accagcatct    240
gggaatggtg gtgcaatggg aggataggtt ttacaaggcc aatcgggcgc acacatacct    300
tggcaaccca gaaaatgaga gtgagatata tccagatttt gtgacgattg ctaaaggatt    360
caacgttccg gcagttcgtg tgacgaagaa gagcgaagtc actgcagcaa tcaagaagat    420
gcttgagacc ccagggccat acttgttgga tatcatcgtc ccgcatcagg agcacgtgct    480
gcctatgatc ccaagcggtg gtgctttcaa ggacatgatc atggagggtg atggcaggac    540
ctcgtactga aatttcgacc tacaagacct acaagtgtga catgcgcaat cagcatggtg    600
cccgcgtgtt gtatcaacta ctaggggttc aactgtgaac catgcgtttt ctagtttgct    660
tgtttcattc atataagctt gtgttactta gttccgaacc ctgtagcttt gtagtctatg    720
ctctcttttg tagggatgtg ctgtcataag atatcatgca agtttcttgt cctacatatc    780
```

<210> SEQ ID NO 129
<211> LENGTH: 881
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 129

```
atcagatgtg ggcggctcag tattacactt acaagcggcc acggcagtgg ctgtcttcat    60
ccggtttggg tgcaatggga tttgggttgc agctgcagc tggcgctgct gtggccaacc    120
caggtgttac agttgttgac attgatgggg atggtagttt cctcatgaac attcaggagt    180
tggcgttgat ccgtattgag aacctcccag tgaaggtgat gatattgaac aaccagcatc    240
tgggaatggt ggtgcagtgg aggataggtt ttacaaggc caaccgggcg cacacatacc    300
ttggcaaccc agaaaatgag agtgagatat atccagattt tgtgacgatt gctaaaggat    360
tcaacgttcc ggcagttcgt gtgacgaaga agagcgaagt cactgcagca atcaagaaga    420
```

```
tgcttgagac cccagggcca tacttgttgg atatcattgt cccgcatcag gagcacgtgc    480
tgcctatgat tcccaatggc ggcgctttca aggacatgat catggagggt gatggcagga    540
cctcgtactg aaatggtccg aaggtccacg ccgccaacta cgagtatgat cccaagcggt    600
ggtgctttta aggacatgat catggagggt gatggcagga cctcgtactg aaatttcgac    660
ctacaagacc tacaagtgtg acatgcgcaa tcagcatgat acctgcgtgt tgtatcaact    720
actgggggtt caactgtgaa ccatgcgttt tctagtttgc ttgtttcatt catataagct    780
tgtgttactt agttccgaac cgtgtagttt tgtagtctct gttctctttt gtagggatgt    840
gctgtcataa gatatcatgc aagtttcttg tcctacatat c                       881
```

```
<210> SEQ ID NO 130
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 130
atcagatgtg ggcggctcag tattacactt acaagcggcc acggcagtgg ctgtcttcat    60
ccggtttggg tgcaatggga tttgggttgc cagctgcagc tggcgctgct gtggccaacc    120
caggtgttac agttgttgac attgatgggg atggtagttt cctcatgaac attcaggagt    180
tggcgttgat ccgtattgag aacctcccag tgaaggtgat gatattgaac aaccagcatc    240
tgggaatggt ggtgcagtgg gaggataggt tttacaaggc caaccgggcg cacacatacc    300
ttggcaaccc agaaaatgag agtgagatat atccagattt tgtgacgatt gctaaaggat    360
tcaacgttcc ggcagttcgt gtgacgaaga gagcgaagt cactgcagca atcaagaaga    420
tgcttgagac cccagggcca tacttgttgg atatcattgt cccgcatcag gagcacgtgc    480
tgcctatgat cccaagcggt ggtgctttta aggacatgat catggagggt gatggcagga    540
cctcgtactg aaatttcgac ctacaagacc tacaagtgtg acatgcgcaa tcagcatgat    600
acctgcgtgt tgtatcaact actgggggtt caactgtgaa ccatgcgttt tctagtttgc    660
ttgtttcatt catataagct tgtgttactt agttccgaac cgtgtagttt tgtagtctct    720
gttctctttt gtagggatgt gctgtcataa gatatcatgc aagtttcttg tcctacatat    780
c                                                                    781
```

```
<210> SEQ ID NO 131
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 131
accagatgtg ggcggctcag tattacactt acaagcggcc acggcagtgg ctgtcttcgt    60
ctggtttggg ggcaatggga tttgggttac cagctgcagc tggcgctgct gtggccaacc    120
caggtgttac agttgttgac attgatgtg atggtagttt cctcatgaac attcaggagt    180
tggcgttgat ccgcattgag aacctcccag tgaaggtgat gatattgaac aaccagcatc    240
tgggaatggt ggtgcagtgg gaggataggt tttacaaggc caatcgggcg cacacatacc    300
ttggcaaccc agaaaatgag agtgagatat atccagattt tgtgacgatt gctaaaggat    360
tcaacgttcc agcagttcga gtgacgaaga gagcgaagt cactgcagca atcaagaaga    420
```

```
tgcttgagac cccagggcca tacttgttgg atatcatcgt cccgcatcag gagcacgtgc    480
tgcctatgat cccaagcggt ggtgctttca aggacatgat catggagggt gatggcagga    540
cctcgtactg aaatttcgac ctacaagacc tacaagtgtg acatgcgcaa tcagcatggt    600
gcccgcgtgt tgtatcaact actaggggtt caactgtgag ccatgcgttt tctagtttgc    660
ttgtttcatt catataagct tgtattactt agttccgaac cctgtagttt tgtagtctat    720
gttctctttt gtagggatgt gctgtcataa gatgtcatgc aagtttcttg tcctacatat    780
c                                                                    781
```

<210> SEQ ID NO 132
<211> LENGTH: 781
<212> TYPE: DNA
<213> ORGANISM: Artificial Sequence
<220> FEATURE:
<223> OTHER INFORMATION: Donor insertion results from amplified region
       of AHAS gene of wheat

<400> SEQUENCE: 132

```
accagatgtg ggcggctcag tattacactt acaagcggcc acggcagtgg ctgtcttcgt     60
ctggtttggg ggcaatggga tttgggttac cagctgcagc tggcgctgct gtggccaacc    120
caggtgttac agttgttgac attgatggtg atggtagttt cctcatgaac attcaggagt    180
tggcgttgat ccgcattgag aacctcccag tgaaggtgat gatattgaac aaccagcatc    240
tgggaatggt ggtgcagtgg gaggataggt tttacaaggc caatcgggcg cacacatacc    300
ttggcaaccc agaaaatgag agtgagatat atccagattt tgtgacgatt gctaaaggat    360
tcaacgttcc agcagttcga gtgacgaaga gagcgaagt cactgcagca atcaagaaga    420
tgcttgagac cccagggcca tacttgttgg atatcatcgt cccgcatcag gagcacgtgc    480
tgcctatgat cccaagcggt ggtgctttca aggacatgat catggagggt gatggcagga    540
cctcgtactg aaatttcgac ctacaagacc tacaagtgtg acatgcgcaa tcagcatggt    600
gcccgcgtgt tgtatcaact actaggggtt caactgtgag ccatgcgttt tctagtttgc    660
ttgtttcatt catataagct tgtattactt agttccgaac cctgtagttt tgtagtctat    720
gttctctttt gtagggatgt gctgtcataa gatgtcatgc aagtttcttg tcctacatat    780
c                                                                    781
```

<210> SEQ ID NO 133
<211> LENGTH: 880
<212> TYPE: DNA
<213> ORGANISM: Artificial Sequence
<220> FEATURE:
<223> OTHER INFORMATION: Donor insertion results from amplified region
       of AHAS gene of wheat

<400> SEQUENCE: 133

```
accagatgtg ggcggctcag tattacactt acaagcggcc acggcagtgg ctgtcttcgt     60
ctggttgggg gcaatgggat ttgggttacc agctgcagct ggcgctgctg tggccaaccc    120
aggtgttaca gttgttgaca ttgatggaga tggtagtttc ctcatgaaca ttcaggagtt    180
ggcattgatc cgtattgaga acctccctgt gaaggtgatg atattgaaca accagcatct    240
gggaatggtg gtgcaatggg aggataggtt tacaaggcc aatcgggcgc acacatacct    300
tggcaaccca gaaaatgaga gtgagatata tccagatttt gtgacgattg ctaaaggatt    360
caacgttccg gcagttcgtg tgacgaagaa gagcgaagtc actgcagcaa tcaagaagat    420
```

```
gcttgagacc ccagggccat acttgttgga tatcatcgtc ccgcatcagg agcacgtgct    480
gcctatgatt cccaatggcg gcgctttcaa ggacatgatc atggagggtg atggcaggac    540
ctcgtactga aatggtccga aggtccacgc cgccaactac gagtatgatc ccaagcggtg    600
gtgctttcaa ggacatgatc atggagggtg atggcaggac ctcgtactga aatttcgacc    660
tacaagacct acaagtgtga catgcgcaat cagcatggtg cccgcgtgtt gtatcaacta    720
ctaggggttc aactgtgaac catgcgtttt ctagtttgct tgtttcattc atataagctt    780
gtgttactta gttccgaacc ctgtagcttt gtagtctatg ctctcttttg tagggatgtg    840
ctgtcataag atatcatgca agtttcttgt cctacatatc                          880
```

```
<210> SEQ ID NO 134
<211> LENGTH: 780
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 134
accagatgtg ggcggctcag tattacactt acaagcggcc acggcagtgg ctgtcttcgt     60
ctggttgggg gcaatgggat ttgggttacc agctgcagct ggcgctgctg tggccaaccc    120
aggtgttaca gttgttgaca ttgatggaga tggtagtttc ctcatgaaca ttcaggagtt    180
ggcattgatc cgtattgaga acctccctgt gaaggtgatg atattgaaca accagcatct    240
gggaatggtg gtgcaatggg aggataggtt ttacaaggcc aatcgggcgc acacatacct    300 tggcaacccca gaaaatgaga gtgagatata tccagatttt gtgacgattg ctaaaggatt    360
caacgttccg gcagttcgtg tgacgaagaa gagcgaagtc actgcagcaa tcaagaagat    420
gcttgagacc ccagggccat acttgttgga tatcatcgtc ccgcatcagg agcacgtgct    480
gcctatgatc ccaagcggtg gtgctttcaa ggacatgatc atggagggtg atggcaggac    540
ctcgtactga aatttcgacc tacaagacct acaagtgtga catgcgcaat cagcatggtg    600
cccgcgtgtt gtatcaacta ctaggggttc aactgtgaac catgcgtttt ctagtttgct    660
tgtttcattc atataagctt gtgttactta gttccgaacc ctgtagcttt gtagtctatg    720
ctctcttttg tagggatgtg ctgtcataag atatcatgca agtttcttgt cctacatatc    780
```

```
<210> SEQ ID NO 135
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 135
atcagatgtg ggcggctcag tattacactt acaagcggcc acggcagtgg ctgtcttcat     60
ccggtttggg tgcaatggga tttggttgc cagctgcagc tggcgctgct gtggccaacc    120
caggtgttac agttgttgac attgatgggg atggtagttt cctcatgaac attcaggagt    180
tggcgttgat ccgtattgag aacctcccag tgaaggtgat gatattgaac aaccagcatc    240
tgggaatggt ggtgcagtgg gaggataggt tttacaaggc caaccgggcg cacacatacc    300
ttggcaaccc agaaaatgag agtgagatat atccagattt tgtgacgatt gctaaaggat    360
tcaacgttcc ggcagttcgt gtgacgaaga agagcgaagt cactgcagca atcaagaaga    420
tgcttgagac cccagggcca tacttgttgg atatcattgt cccgcatcag gagcacgtgc    480
```

```
tgcctatgat cccaagcggt ggtgctttta aggacatgat catggagggt gatggcagga    540
cctcgtactg aaatttcgac ctacaagacc tacaagtgtg acatgcgcaa tcagcatgat    600
acctgcgtgt tgtatcaact actgggggtt caactgtgaa ccatgcgttt tctagtttgc    660
ttgtttcatt catataagct tgtgttactt agttccgaac cgtgtagttt tgtagtctct    720
gttctctttt gtagggatgt gctgtcataa gatatcatgc aagtttcttg tcctacatat    780
c                                                                    781
```

<210> SEQ ID NO 136
<211> LENGTH: 781
<212> TYPE: DNA
<213> ORGANISM: Artificial Sequence
<220> FEATURE:
<223> OTHER INFORMATION: Donor insertion results from amplified region of AHAS gene of wheat

<400> SEQUENCE: 136

```
atcagatgtg ggcggctcag tattacactt acaagcggcc acggcagtgg ctgtcttcat    60
ccggtttggg tgcaatggga tttggttgc cagctgcagc tggcgctgct gtggccaacc    120
caggtgttac agttgttgac attgatgggg atggtagttt cctcatgaac attcaggagt    180
tggcgttgat ccgtattgag aacctcccag tgaaggtgat gatattgaac aaccagcatc    240
tgggaatggt ggtgcagtgg gaggataggt tttacaaggc caaccgggcg cacacatacc    300
ttggcaaccc agaaaatgag agtgagatat atccagattt tgtgacgatt gctaaaggat    360
tcaacgttcc ggcagttcgt gtgacgaaga gagcgaagt cactgcagca atcaagaaga    420
tgcttgagac cccagggcca tacttgttgg atatcattgt cccgcatcag gagcacgtgc    480
tgcctatgat cccaagcggt ggtgctttta aggacatgat catggagggt gatggcagga    540
cctcgtactg aaatttcgac ctacaagacc tacaagtgtg acatgcgcaa tcagcatgat    600
acctgcgtgt tgtatcaact actgggggtt caactgtgaa ccatgcgttt tctagtttgc    660
ttgtttcatt catataagct tgtgttactt agttccgaac cgtgtagttt tgtagtctct    720
gttctctttt gtagggatgt gctgtcataa gatatcatgc aagtttcttg tcctacatat    780
c                                                                    781
```

<210> SEQ ID NO 137
<211> LENGTH: 781
<212> TYPE: DNA
<213> ORGANISM: Artificial Sequence
<220> FEATURE:
<223> OTHER INFORMATION: Donor insertion results from amplified region of AHAS gene of wheat

<400> SEQUENCE: 137

```
accagatgtg ggcggctcag tattacactt acaagcggcc acggcagtgg ctgtcttcgt    60
ctggtttggg ggcaatggga tttgggttac cagctgcagc tggcgctgct gtggccaacc    120
caggtgttac agttgttgac attgatggtg atggtagttt cctcatgaac attcaggagt    180
tggcgttgat ccgcattgag aacctcccag tgaaggtgat gatattgaac aaccagcatc    240
tgggaatggt ggtgcagtgg gaggataggt tttacaaggc caatcgggcg cacacatacc    300
ttggcaaccc agaaaatgag agtgagatat atccagattt tgtgacgatt gctaaaggat    360
tcaacgttcc agcagttcga gtgacgaaga gagcgaagt cactgcagca atcaagaaga    420
tgcttgagac cccagggcca tacttgttgg atatcatagt cccgcatcag gagcacgtgc    480
```

```
tgcctatgat cccaagcggt ggtgctttca aggacatgat catggagggt gatggcagga    540
cctcgtactg aaatttcgac ctacaagacc tacaagtgtg acatgcgcaa tcagcatgat    600
gcccgcgtgt tgtatcaact actaggggtt caactgtgag ccatgcgttt tctagtttgc    660
ttgtttcatt catataagct tgtattactt agttccgaac cctgtagttt tgtagtctat    720
gttctctttt gtagggatgt gctgtcataa gatgtcatgc aagtttcttg tcctacatat    780
c                                                                    781
```

<210> SEQ ID NO 138
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 138

```
accagatgtg ggcggctcag tattacactt acaagcggcc acggcagtgg ctgtcttcgt    60
ctggtttggg ggcaatggga tttgggttac cagctgcagc tggcgctgct gtggccaacc    120
caggtgttac agttgttgac attgatggtg atggtagttt cctcatgaac attcaggagt    180
tggcgttgat ccgcattgag aacctcccag tgaaggtgat gatattgaac aaccagcatc    240
tgggaatggt ggtgcagtgg gaggataggt tttacaaggc caatcgggcg cacacatacc    300
ttggcaaccc agaaaatgag agtgagatat atccagattt tgtgacgatt gctaaaggat    360
tcaacgttcc agcagttcga gtgacgaaga gagcgaagt cactgcagca atcaagaaga    420
tgcttgagac cccagggcca tacttgttgg atatcatagt cccgcatcag gagcacgtgc    480
tgcctatgat cccaagcggt ggtgctttca aggacatgat catggagggt gatggcagga    540
cctcgtactg aaatttcgac ctacaagacc tacaagtgtg acatgcgcaa tcagcatgat    600
gcccgcgtgt tgtatcaact actaggggtt caactgtgag ccatgcgttt tctagtttgc    660
ttgtttcatt catataagct tgtattactt agttccgaac cctgtagttt tgtagtctat    720
gttctctttt gtagggatgt gctgtcataa gatgtcatgc aagtttcttg tcctacatat    780
c                                                                    781
```

<210> SEQ ID NO 139
<211> LENGTH: 780
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 139

```
accagatgtg ggcggctcag tattacactt acaagcggcc acggcagtgg ctgtcttcgt    60
ctggttgggg gcaatgggat ttgggttacc agctgcagct ggcgctgctg tggccaaccc    120
aggtgttaca gttgttgaca ttgatggaga tggtagtttc ctcatgaaca ttcaggagtt    180
ggcattgatc cgtattgaga acctccctgt gaaggtgatg atattgaaca accagcatct    240
gggaatggtg gtgcaatggg aggataggtt ttacaaggcc aatcgggcgc acacatacct    300
tggcaaccca gaaaatgaga gtgagatata tccagatttt gtgacgattg ctaaaggatt    360
caacgttccg gcagttcgtg tgacgaagaa gagcgaagtc actgcagcaa tcaagaagat    420
gcttgagacc ccagggccat acttgttgga tatcatcgtc ccgcatcagg agcacgtgct    480
gcctatgatc ccaagcggtg gtgctttcaa ggacatgatc atggagggtg atggcaggac    540
```

```
ctcgtactga aatttcgacc tacaagacct acaagtgtga catgcgcaat cagcatggtg    600
cccgcgtgtt gtatcaacta ctaggggttc aactgtgaac catgcgtttt ctagtttgct    660
tgtttcattc atataagctt gtgttactta gttccgaacc ctgtagcttt gtagtctatg    720
ctctcttttg tagggatgtg ctgtcataag atatcatgca agtttcttgt cctacatatc    780
```

<210> SEQ ID NO 140
<211> LENGTH: 780
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 140

```
accagatgtg gcggctcag tattacactt acaagcggcc acggcagtgg ctgtcttcgt    60
ctggttgggg gcaatgggat ttgggttacc agctgcagct ggcgctgctg tggccaaccc    120
aggtgttaca gttgttgaca ttgatggaga tggtagtttc ctcatgaaca ttcaggagtt    180
ggcattgatc cgtattgaga acctccctgt gaaggtgatg atattgaaca accagcatct    240
gggaatggtg gtgcaatggg aggataggtt ttacaaggcc aatcgggcgc acacatacct    300
tggcaaccca gaaaatgaga gtgagatata tccagatttt gtgacgattg ctaaaggatt    360
caacgttccg gcagttcgtg tgacgaagaa gagcgaagtc actgcagcaa tcaagaagat    420
gcttgagacc ccagggccat acttgttgga tatcatcgtc ccgcatcagg agcacgtgct    480
gcctatgatc ccaagcggtg gtgctttcaa ggacatgatc atggagggtg atggcaggac    540
ctcgtactga aatttcgacc tacaagacct acaagtgtga catgcgcaat cagcatggtg    600
cccgcgtgtt gtatcaacta ctaggggttc aactgtgaac catgcgtttt ctagtttgct    660
tgtttcattc atataagctt gtgttactta gttccgaacc ctgtagcttt gtagtctatg    720
ctctcttttg tagggatgtg ctgtcataag atatcatgca agtttcttgt cctacatatc    780
```

<210> SEQ ID NO 141
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 141

```
atcagatgtg gcggctcag tattacactt acaagcggcc acggcagtgg ctgtcttcat    60
ccggtttggg tgcaatggga tttggttgc cagctgcagc tggcgctgct gtggccaacc    120
caggtgttac agttgttgac attgatgggg atggtagttt cctcatgaac attcaggagt    180
tggcgttgat ccgtattgag aacctcccag tgaaggtgat gatattgaac aaccagcatc    240
tgggaatggt ggtgcagtgg gaggataggt tttacaaggc caaccgggcg cacacatacc    300
ttggcaaccc agaaaatgag agtgagatat atccagattt tgtgacgatt gctaaaggat    360
tcaacgttcc ggcagttcgt gtgacgaaga agagcgaagt cactgcagca atcaagaaga    420
tgcttgagac cccagggcca tacttgttgg atatcattgt cccgcatcag gagcacgtgc    480
tgcctatgat cccaagcggt ggtgctttta aggacatgat catggagggt gatggcagga    540
cctcgtactg aaatttcgac ctacaagacc tacaagtgtg acatgcgcaa tcagcatgat    600
acctgcgtgt tgtatcaact actgggggtt caactgtgaa ccatgcgttt tctagtttgc    660
```

```
ttgtttcatt catataagct tgtgttactt agttccgaac cgtgtagttt tgtagtctct    720
gttctctttt gtagggatgt gctgtcataa gatatcatgc aagtttcttg tcctacatat    780
c                                                                    781
```

<210> SEQ ID NO 142
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 142

```
atcagatgtg ggcggctcag tattacactt acaagcggcc acggcagtgg ctgtcttcat     60
ccggtttggg tgcaatggga tttgggttgc cagctgcagc tggcgctgct gtggccaacc    120
caggtgttac agttgttgac attgatgggg atggtagttt cctcatgaac attcaggagt    180
tggcgttgat ccgtattgag aacctcccag tgaaggtgat gatattgaac aaccagcatc    240
tgggaatggt ggtgcagtgg gaggataggt tttacaaggc caaccgggcg cacacatacc    300
ttggcaaccc agaaaatgag agtgagatat atccagattt tgtgacgatt gctaaaggat    360
tcaacgttcc ggcagttcgt gtgacgaaga agagcgaagt cactgcagca atcaagaaga    420
tgcttgagac cccagggcca tacttgttgg atatcattgt cccgcatcag gagcacgtgc    480
tgcctatgat cccaagcggt ggtgctttta aggacatgat catggagggt gatggcagga    540
cctcgtactg aaatttcgac ctacaagacc tacaagtgtg acatgcgcaa tcagcatgat    600
acctgcgtgt tgtatcaact actgggggtt caactgtgaa ccatgcgttt tctagtttgc    660
ttgtttcatt catataagct tgtgttactt agttccgaac cgtgtagttt tgtagtctct    720
gttctctttt gtagggatgt gctgtcataa gatatcatgc aagtttcttg tcctacatat    780
c                                                                    781
```

<210> SEQ ID NO 143
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 143

```
accagatgtg ggcggctcag tattacactt acaagcggcc acggcagtgg ctgtcttcgt     60
ctggtttggg ggcaatggga tttgggttac cagctgcagc tggcgctgct gtggccaacc    120
caggtgttac agttgttgac attgatggtg atggtagttt cctcatgaac attcaggagt    180
tggcgttgat ccgcattgag aacctcccag tgaaggtgat gatattgaac aaccagcatc    240
tgggaatggt ggtgcagtgg gaggataggt tttacaaggc caatcgggcg cacacatacc    300
ttggcaaccc agaaaatgag agtgagatat atccagattt tgtgacgatt gctaaaggat    360
tcaacgttcc agcagttcga gtgacgaaga agagcgaagt cactgcagca atcaagaaga    420
tgcttgagac cccagggcca tacttgttgg atatcatagt cccgcatcag gagcacgtgc    480
tgcctatgat cccaagcggt ggtgctttca aggacatgat catggagggt gatggcagga    540
cctcgtactg aaatttcgac ctacaagacc tacaagtgtg acatgcgcaa tcagcatgat    600
gcccgcgtgt tgtatcaact actaggggtt caactgtgag ccatgcgttt tctagtttgc    660
ttgtttcatt catataagct tgtattactt agttccgaac cctgtagttt tgtagtctat    720
```

```
gttctctttt gtagggatgt gctgtcataa gatgtcatgc aagtttcttg tcctacatat    780
c                                                                    781

<210> SEQ ID NO 144
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 144
accagatgtg gcggctcag tattacactt acaagcggcc acggcagtgg ctgtcttcgt     60
ctggtttggg ggcaatggga tttgggttac cagctgcagc tggcgctgct gtggccaacc   120
caggtgttac agttgttgac attgatggtg atggtagttt cctcatgaac attcaggagt   180
tggcgttgat ccgcattgag aacctcccag tgaaggtgat gatattgaac aaccagcatc   240
tgggaatggt ggtgcagtgg gaggataggt tttacaaggc caatcgggcg cacacatacc   300
ttggcaaccc agaaaatgag agtgagatat atccagattt tgtgacgatt gctaaaggat   360
tcaacgttcc agcagttcga gtgacgaaga gagcgaagt cactgcagca atcaagaaga    420
tgcttgagac cccagggcca tacttgttgg atatcatagt cccgcatcag gagcacgtgc   480
tgcctatgat cccaagcggt ggtgctttca aggacatgat catggagggt gatggcagga   540
cctcgtactg aaatttcgac ctacaagacc tacaagtgtg acatgcgcaa tcagcatgat   600
gcccgcgtgt tgtatcaact actagggggtt caactgtgag ccatgcgttt tctagtttgc   660
ttgtttcatt catataagct tgtattactt agttccgaac cctgtagttt tgtagtctat   720
gttctctttt gtagggatgt gctgtcataa gatgtcatgc aagtttcttg tcctacatat   780
c                                                                    781

<210> SEQ ID NO 145
<211> LENGTH: 880
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 145
accagatgtg gcggctcag tattacactt acaagcggcc acggcagtgg ctgtcttcgt     60
ctggtttggg gcaatgggat ttgggttacc agctgcagct ggcgctgctg tggccaaccc   120
aggtgttaca gttgttgaca ttgatggaga tggtagtttc ctcatgaaca ttcaggagtt   180
ggcattgatc cgtattgaga acctccctgt gaaggtgatg atattgaaca accagcatct   240
gggaatggtg gtgcaatggg aggataggtt ttacaaggcc aatcgggcgc acacatacct   300
tggcaaccca gaaaatgaga gtgagatata tccagatttt gtgacgattg ctaaaggatt   360
caacgttccg gcagttcgtg tgacgaagaa gagcgaagtc actgcagcaa tcaagaagat   420
gcttgagacc ccagggccat acttgttgga tatcatcgtc ccgcatcagg agcacgtgct   480
gcctatgatt cccaatggcg gcgctttcaa ggacatgatc atggagggtg atggcaggac   540
ctcgtactga atggtccga aggtccacgc cgccaactac gagtatgatc ccaagcggtg    600
gtgctttcaa ggacatgatc atggagggtg atggcaggac ctcgtactga aatttcgacc   660
tacaagacct acaagtgtga catgcgcaat cagcatggtg cccgcgtgtt gtatcaacta   720
```

```
ctaggggttc aactgtgaac catgcgtttt ctagtttgct tgtttcattc atataagctt      780
gtgttactta gttccgaacc ctgtagcttt gtagtctatg ctctcttttg tagggatgtg      840
ctgtcataag atatcatgca agtttcttgt cctacatatc                            880

<210> SEQ ID NO 146
<211> LENGTH: 880
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 146
accagatgtg ggcggctcag tattacactt acaagcggcc acggcagtgg ctgtcttcgt       60
ctggttgggg gcaatgggat ttgggttacc agctgcagct ggcgctgctg tggccaaccc      120
aggtgttaca gttgttgaca ttgatggaga tggtagtttc ctcatgaaca ttcaggagtt      180
ggcattgatc cgtattgaga acctccctgt gaaggtgatg atattgaaca accagcatct      240
gggaatggtg gtgcaatggg aggataggtt ttacaaggcc aatcgggcgc acacatacct      300
tggcaaccca gaaaatgaga gtgagatata tccagatttt gtgacgattg ctaaaggatt      360
caacgttccg gcagttcgtg tgacgaagaa gagcgaagtc actgcagcaa tcaagaagat      420
gcttgagacc ccagggccat acttgttgga tatcatcgtc ccgcatcagg agcacgtgct      480
gcctatgatt cccaatggcg cgctttcaa ggacatgatc atggagggtg atggcaggac       540
ctcgtactga atggtccga aggtccacgc cgccaactac gagtatgatc ccaagcggtg       600
gtgctttcaa ggacatgatc atggagggtg atggcaggac ctcgtactga aatttcgacc     660
tacaagacct acaagtgtga catgcgcaat cagcatggtg cccgcgtgtt gtatcaacta      720
ctaggggttc aactgtgaac catgcgtttt ctagtttgct tgtttcattc atataagctt      780
gtgttactta gttccgaacc ctgtagcttt gtagtctatg ctctcttttg tagggatgtg      840
ctgtcataag atatcatgca agtttcttgt cctacatatc                            880

<210> SEQ ID NO 147
<211> LENGTH: 865
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 147
atcagatgtg ggcggctcag tattacactt acaagcggcc acggcagtgg ctgtcttcat       60
ccggtttggg tgcaatggga tttgggttgc agctgcagc tggcgctgct gtggccaacc      120
caggtgttac agttgttgac attgatgggg atggtagttt cctcatgaac attcaggagt      180
tggcgttgat ccgtattgag aacctcccag tgaaggtgat gatattgaac aaccagcatc      240
tgggaatggt ggtgcagtgg gaggataggt tttacaaggc caaccgggcg cacacatacc      300
ttggcaaccc agaaaatgag agtgagatat atccagattt tgtgacgatt gctaaaggat      360
tcaacgttcc ggcagttcgt gtgacgaaga gagcgaagt cactgcagca atcaagaaga       420
tgcttgagac cccagggcca tacttgttgg atatcattgt cccgcatcag gagcacgtgc      480
tgcctgcgct ttcaaggaca tgatcatgga gggtgatggc aggacctcgt actgaaatgg      540
tccgaaggtc cacgccgcca actacgagta tgatcccaag cggtggtgct tttaaggaca      600
tgatcatgga gggtgatggc aggacctcgt actgaaattt cgacctacaa gacctacaag      660
```
tgtgacatgc gcaatcagca tgatacctgc gtgttgtatc aactactggg ggttcaactg    720
tgaaccatgc gttttctagt ttgcttgttt cattcatata agcttgtgtt acttagttcc    780
gaaccgtgta gttttgtagt ctctgttctc ttttgtaggg atgtgctgtc ataagatatc    840
atgcaagttt cttgtcctac atatc                                          865

<210> SEQ ID NO 148
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 148
atcagatgtg gcggctcag tattacactt acaagcggcc acggcagtgg ctgtcttcat     60
ccggtttggg tgcaatggga tttggttgc cagctgcagc tggcgctgct gtggccaacc    120
caggtgttac agttgttgac attgatgggg atggtagttt cctcatgaac attcaggagt    180
tggcgttgat ccgtattgag aacctcccag tgaaggtgat gatattgaac aaccagcatc    240
tgggaatggt ggtgcagtgg gaggataggt tttacaaggc caaccgggcg cacacatacc    300
ttggcaaccc agaaaatgag agtgagatat atccagattt tgtgacgatt gctaaaggat    360
tcaacgttcc ggcagttcgt gtgacgaaga gagcgaagt cactgcagca atcaagaaga    420
tgcttgagac cccagggcca tacttgttgg atatcattgt cccgcatcag gagcacgtgc    480
tgcctatgat cccaagcggt ggtgctttta aggacatgat catggagggt gatggcagga    540
cctcgtactg aaatttcgac ctacaagacc tacaagtgtg acatgcgcaa tcagcatgat    600
acctgcgtgt tgtatcaact actgggggtt caactgtgaa ccatgcgttt tctagtttgc    660
ttgtttcatt catataagct tgtgttactt agttccgaac cgtgtagttt tgtagtctct    720
gttctctttt gtagggatgt gctgtcataa gatatcatgc aagtttcttg tcctacatat    780
c                                                                    781

<210> SEQ ID NO 149
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 149
accagatgtg gcggctcag tattacactt acaagcggcc acggcagtgg ctgtcttcgt     60
ctggtttggg ggcaatggga tttgggttac cagctgcagc tggcgctgct gtggccaacc    120
caggtgttac agttgttgac attgatggtg atggtagttt cctcatgaac attcaggagt    180
tggcgttgat ccgcattgag aacctcccag tgaaggtgat gatattgaac aaccagcatc    240
tgggaatggt ggtgcagtgg gaggataggt tttacaaggc caatcgggcg cacacatacc    300
ttggcaaccc agaaaatgag agtgagatat atccagattt tgtgacgatt gctaaaggat    360
tcaacgttcc agcagttcga gtgacgaaga gagcgaagt cactgcagca atcaagaaga    420
tgcttgagac cccagggcca tacttgttgg atatcatagt cccgcatcag gagcacgtgc    480
tgcctatgat cccaagcggt ggtgctttca aggacatgat catggagggt gatggcagga    540
cctcgtactg aaatttcgac ctacaagacc tacaagtgtg acatgcgcaa tcagcatgat    600

```
gcccgcgtgt tgtatcaact actaggggtt caactgtgag ccatgcgttt tctagtttgc    660
ttgtttcatt catataagct tgtattactt agttccgaac cctgtagttt tgtagtctat    720
gttctctttt gtagggatgt gctgtcataa gatgtcatgc aagtttcttg tcctacatat    780
c                                                                   781
```

```
<210> SEQ ID NO 150
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 150
accagatgtg gcggctcag tattacactt acaagcggcc acggcagtgg ctgtcttcgt    60
ctggtttggg ggcaatggga tttgggttac cagctgcagc tggcgctgct gtggccaacc   120
caggtgttac agttgttgac attgatggtg atggtagttt cctcatgaac attcaggagt   180
tggcgttgat ccgcattgag aacctcccag tgaaggtgat gatattgaac aaccagcatc   240
tgggaatggt ggtgcagtgg gaggataggt tttacaaggc caatcgggcg cacacatacc   300
ttggcaaccc agaaaatgag agtgagatat atccagattt tgtgacgatt gctaaaggat   360
tcaacgttcc agcagttcga gtgacgaaga gagcgaagt cactgcagca atcaagaaga   420
tgcttgagac cccagggcca tacttgttgg atatcatagt cccgcatcag gagcacgtgc   480
tgcctatgat cccaagcggt ggtgcttca aggacatgat catggagggt gatggcagga   540
cctcgtactg aaatttcgac ctacaagacc tacaagtgtg acatgcgcaa tcagcatgat   600
gcccgcgtgt tgtatcaact actaggggtt caactgtgag ccatgcgttt tctagtttgc   660
ttgtttcatt catataagct tgtattactt agttccgaac cctgtagttt tgtagtctat   720
gttctctttt gtagggatgt gctgtcataa gatgtcatgc aagtttcttg tcctacatat   780
c                                                                  781
```

```
<210> SEQ ID NO 151
<211> LENGTH: 880
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 151
accagatgtg gcggctcag tattacactt acaagcggcc acggcagtgg ctgtcttcgt    60
ctggttgggg gcaatgggat ttgggttacc agctgcagct ggcgctgctg tggccaaccc   120
aggtgttaca gttgttgaca ttgatggaga tggtagtttc ctcatgaaca ttcaggagtt   180
ggcattgatc cgtattgaga acctccctgt gaaggtgatg atattgaaca accagcatct   240
gggaatggtg gtgcaatggg aggataggtt ttacaaggcc aatcgggcgc acacatacct   300
tggcaaccca gaaaatgaga gtgagatata tccagatttt gtgacgattg ctaaaggatt   360
caacgttccg gcagttcgtg tgacgaagaa gagcgaagtc actgcagcaa tcaagaagat   420
gcttgagacc ccagggccat acttgttgga tatcatcgtc ccgcatcagg agcacgtgct   480
gcctatgatt cccaatggcg gcgctttcaa ggacatgatc atggagggtg atggcaggac   540
ctcgtactga aatggtccga aggtccacgc cgccaactac gagtatgatc ccaagcggtg   600
gtgctttcaa ggacatgatc atggagggtg atggcaggac ctcgtactga aatttcgacc   660
```

```
tacaagacct acaagtgtga catgcgcaat cagcatggtg cccgcgtgtt gtatcaacta    720
ctaggggttc aactgtgaac catgcgtttt ctagtttgct tgtttcattc atataagctt    780
gtgttactta gttccgaacc ctgtagcttt gtagtctatg ctctcttttg tagggatgtg    840
ctgtcataag atatcatgca agtttcttgt cctacatatc                          880
```

<210> SEQ ID NO 152
<211> LENGTH: 780
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 152

```
accagatgtg gcggctcag tattacactt acaagcggcc acggcagtgg ctgtcttcgt     60
ctggttgggg gcaatgggat ttgggttacc agctgcagct ggcgctgctg tggccaaccc   120
aggtgttaca gttgttgaca ttgatggaga tggtagtttc ctcatgaaca ttcaggagtt   180
ggcattgatc cgtattgaga acctccctgt gaaggtgatg atattgaaca accagcatct   240
gggaatggtg gtgcaatggg aggataggtt ttacaaggcc aatcgggcgc acacatacct   300
tggcaaccca gaaaatgaga gtgagatata tccagatttt gtgacgattg ctaaaggatt   360
caacgttccg gcagttcgtg tgacgaagaa gagcgaagtc actgcagcaa tcaagaagat   420
gcttgagacc ccagggccat acttgttgga tatcatcgtc ccgcatcagg agcacgtgct   480
gcctatgatc ccaagcggtg gtgctttcaa ggacatgatc atggagggtg atggcaggac   540
ctcgtactga aatttcgacc tacaagacct acaagtgtga catgcgcaat cagcatggtg   600
cccgcgtgtt gtatcaacta ctaggggttc aactgtgaac catgcgtttt ctagtttgct   660
tgtttcattc atataagctt gtgttactta gttccgaacc ctgtagcttt gtagtctatg   720
ctctcttttg tagggatgtg ctgtcataag atatcatgca agtttcttgt cctacatatc   780
```

<210> SEQ ID NO 153
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 153

```
atcagatgtg ggcggctcag tattacactt acaagcggcc acggcagtgg ctgtcttcat     60
ccggtttggg tgcaatggga tttggggttgc cagctgcagc tggcgctgct gtggccaacc   120
caggtgttac agttgttgac attgatgggg atggtagttt cctcatgaac attcaggagt   180
tggcgttgat ccgtattgag aacctcccag tgaaggtgat gatattgaac aaccagcatc   240
tgggaatggt ggtgcagtgg gaggataggt tttacaaggc caaccgggcg cacacatacc   300
ttggcaaccc agaaaatgag agtgagatat atccagattt tgtgacgatt gctaaaggat   360
tcaacgttcc ggcagttcgt gtgacgaaga gagcgaagt cactgcagca atcaagaaga   420
tgcttgagac cccagggcca tacttgttgg atatcattgt cccgcatcag gagcacgtgc   480
tgcctatgat cccaagcggt ggtgctttta aggacatgat catggagggt gatggcagga   540
cctcgtactg aaatttcgac ctacaagacc tacaagtgtg acatgcgcaa tcagcatgat   600
acctgcgtgt tgtatcaact actggggggtt caactgtgaa ccatgcgttt tctagtttgc   660
```

```
ttgtttcatt catataagct tgtgttactt agttccgaac cgtgtagttt tgtagtctct    720
gttctctttt gtagggatgt gctgtcataa gatatcatgc aagtttcttg tcctacatat    780
c                                                                    781
```

<210> SEQ ID NO 154
<211> LENGTH: 781
<212> TYPE: DNA
<213> ORGANISM: Artificial Sequence
<220> FEATURE:
<223> OTHER INFORMATION: Donor insertion results from amplified region
       of AHAS gene of wheat

<400> SEQUENCE: 154

```
atcagatgtg gcggctcag tattacactt acaagcggcc acggcagtgg ctgtcttcat    60
ccggtttggg tgcaatggga tttgggttgc cagctgcagc tggcgctgct gtggccaacc   120
caggtgttac agttgttgac attgatgggg atggtagttt cctcatgaac attcaggagt   180
tggcgttgat ccgtattgag aacctcccag tgaaggtgat gatattgaac aaccagcatc   240
tgggaatggt ggtgcagtgg gaggataggt tttacaaggc caaccgggcg cacacatacc   300
ttggcaaccc agaaaatgag agtgagatat atccagattt tgtgacgatt gctaaaggat   360
tcaacgttcc ggcagttcgt gtgacgaaga agagcgaagt cactgcagca atcaagaaga   420
tgcttgagac cccagggcca tacttgttgg atatcattgt cccgcatcag gagcacgtgc   480
tgcctatgat cccaagcggt ggtgcttttta aggacatgat catggagggt gatggcagga   540
cctcgtactg aaatttcgac ctacaagacc tacaagtgtg acatgcgcaa tcagcatgat   600
acctgcgtgt tgtatcaact actgggggtt caactgtgaa ccatgcgttt tctagtttgc   660
ttgtttcatt catataagct tgtgttactt agttccgaac cgtgtagttt tgtagtctct   720
gttctctttt gtagggatgt gctgtcataa gatatcatgc aagtttcttg tcctacatat   780
c                                                                    781
```

<210> SEQ ID NO 155
<211> LENGTH: 781
<212> TYPE: DNA
<213> ORGANISM: Artificial Sequence
<220> FEATURE:
<223> OTHER INFORMATION: Donor insertion results from amplified region
       of AHAS gene of wheat

<400> SEQUENCE: 155

```
accagatgtg gcggctcag tattacactt acaagcggcc acggcagtgg ctgtcttcgt    60
ctggtttggg ggcaatggga tttgggttac cagctgcagc tggcgctgct gtggccaacc   120
caggtgttac agttgttgac attgatggtg atggtagttt cctcatgaac attcaggagt   180
tggcgttgat ccgcattgag aacctcccag tgaaggtgat gatattgaac aaccagcatc   240
tgggaatggt ggtgcagtgg gaggataggt tttacaaggc caatcgggcg cacacatacc   300
ttggcaaccc agaaaatgag agtgagatat atccagattt tgtgacgatt gctaaaggat   360
tcaacgttcc agcagttcga gtgacgaaga agagcgaagt cactgcagca atcaagaaga   420
tgcttgagac cccagggcca tacttgttgg atatcatagt cccgcatcag gagcacgtgc   480
tgcctatgat cccaagcggt ggtgctttca aggacatgat catggagggt gatggcagga   540
cctcgtactg aaatttcgac ctacaagacc tacaagtgtg acatgcgcaa tcagcatgat   600
gcccgcgtgt tgtatcaact actaggggtt caactgtgag ccatgcgttt tctagtttgc   660
ttgtttcatt catataagct tgtattactt agttccgaac cctgtagttt tgtagtctat   720
```

```
gttctcttttt gtagggatgt gctgtcataa gatgtcatgc aagtttcttg tcctacatat    780
c                                                                    781

<210> SEQ ID NO 156
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400 ctctctttg tagggatgtg ctgtcataag atatcatgca agtttcttgt cctacatatc    780

<210> SEQ ID NO 158
<211> LENGTH: 780
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 158
accagatgtg gcggctcag tattacactt acaagcggcc acggcagtgg ctgtcttcgt     60
ctggttgggg gcaatgggat ttgggttacc agctgcagct ggcgctgctg tggccaaccc   120
aggtgttaca gttgttgaca ttgatggaga tggtagtttc ctcatgaaca ttcaggagtt   180
ggcattgatc cgtattgaga acctccctgt gaaggtgatg atattgaaca accagcatct   240
gggaatggtg gtgcaatggg aggataggtt ttacaaggcc aatcgggcgc acacatacct   300
tggcaaccca gaaaatgaga gtgagatata tccagatttt gtgacgattg ctaaaggatt   360
caacgttccg gcagttcgtg tgacgaagaa gagcgaagtc actgcagcaa tcaagaagat   420
gcttgagacc ccagggccat acttgttgga tatcatcgtc ccgcatcagg agcacgtgct   480
gcctatgatc ccaagcggtg gtgctttcaa ggacatgatc atggagggtg atggcaggac   540
ctcgtactga aatttcgacc tacaagacct acaagtgtga catgcgcaat cagcatggtg   600
cccgcgtgtt gtatcaacta ctaggggttc aactgtgaac catgcgtttt ctagtttgct   660
tgtttcattc atataagctt gtgttactta gttccgaacc ctgtagcttt gtagtctatg   720 ctctctttg tagggatgtg ctgtcataag atatcatgca agtttcttgt cctacatatc    780

<210> SEQ ID NO 159
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 159
atcagatgtg gcggctcag tattacactt acaagcggcc acggcagtgg ctgtcttcat     60
ccggtttggg tgcaatggga tttgggttgc agctgcagc tggcgctgct gtggccaacc   120
caggtgttac agttgttgac attgatgggg atggtagttt cctcatgaac attcaggagt   180
tggcgttgat ccgtattgag aacctcccag tgaaggtgat gatattgaac aaccagcatc   240
tgggaatggt ggtgcagtgg gaggataggt tttacaaggc caaccgggcg cacacatacc   300
ttggcaaccc agaaaatgag agtgagatat atccagattt tgtgacgatt gctaaaggat   360
tcaacgttcc ggcagttcgt gtgacgaaga agagcgaagt cactgcagca atcaagaaga   420
tgcttgagac cccagggcca tacttgttgg atatcattgt cccgcatcag gagcacgtgc   480
tgcctatgat cccaagcggt ggtgctttta aggacatgat catggagggt gatggcagga   540
cctcgtactg aaatttcgac ctacaagacc tacaagtgtg acatgcgcaa tcagcatgat   600
acctgcgtgt tgtatcaact actgggggtt caactgtgaa ccatgcgttt tctagtttgc   660
ttgtttcatt catataagct tgtgttactt agttccgaac cgtgtagttt tgtagtctct   720
gttctctttt gtagggatgt gctgtcataa gatatcatgc aagtttcttg tcctacatat   780
c                                                                   781

<210> SEQ ID NO 160
<211> LENGTH: 781
<212> TYPE: DNA
<213> ORGANISM: Artificial Sequence
<220> FEATURE:
<223> OTHER INFORMATION: Donor insertion results from amplified region of AHAS gene of wheat

<400> SEQUENCE: 160

```
atcagatgtg gcggctcag tattacactt acaagcggcc acggcagtgg ctgtcttcat    60
ccggtttggg tgcaatggga tttgggttgc cagctgcagc tggcgctgct gtggccaacc  120
caggtgttac agttgttgac attgatgggg atggtagttt cctcatgaac attcaggagt  180
tggcgttgat ccgtattgag aacctcccag tgaaggtgat gatattgaac aaccagcatc  240
tgggaatggt ggtgcagtgg gaggataggt tttacaaggc caaccgggcg cacacatacc  300
ttggcaaccc agaaaatgag agtgagatat atccagattt tgtgacgatt gctaaaggat  360
tcaacgttcc ggcagttcgt gtgacgaaga gagcgaagt cactgcagca atcaagaaga  420
tgcttgagac cccagggcca tacttgttgg atatcattgt cccgcatcag gagcacgtgc  480
tgcctatgat cccaagcggt ggtgctttta aggacatgat catggagggt gatggcagga  540
cctcgtactg aaatttcgac ctacaagacc tacaagtgtg acatgcgcaa tcagcatgat  600
acctgcgtgt tgtatcaact actggggttt caactgtgaa ccatgcgttt tctagtttgc  660
ttgtttcatt catataagct tgtgttactt agttccgaac cgtgtagttt tgtagtctct  720
gttctctttt gtagggatgt gctgtcataa gatatcatgc aagtttcttg tcctacatat  780
c                                                                  781
```

<210> SEQ ID NO 161
<211> LENGTH: 881
<212> TYPE: DNA
<213> ORGANISM: Artificial Sequence
<220> FEATURE:
<223> OTHER INFORMATION: Donor insertion results from amplified region of AHAS gene of wheat

<400> SEQUENCE: 161

```
accagatgtg gcggctcag tattacactt acaagcggcc acggcagtgg ctgtcttcgt    60
ctggtttggg ggcaatggga tttgggttac cagctgcagc tggcgctgct gtggccaacc  120
caggtgttac agttgttgac attgatggtg atggtagttt cctcatgaac attcaggagt  180
tggcgttgat ccgcattgag aacctcccag tgaaggtgat gatattgaac aaccagcatc  240
tgggaatggt ggtgcagtgg gaggataggt tttacaaggc caatcgggcg cacacatacc  300
ttggcaaccc agaaaatgag agtgagatat atccagattt tgtgacgatt gctaaaggat  360
tcaacgttcc agcagttcga gtgacgaaga gagcgaagt cactgcagca atcaagaaga  420
tgcttgagac cccagggcca tacttgttgg atatcatagt cccgcatcag gagcacgtgc  480
tgcctatgat tcccaatggc ggcgctttca aggacatgat catggagggt gatggcagga  540
cctcgtactg aaatggtccg aaggtccacg ccgccaacta cgagtatgat cccaagcggt  600
ggtgctttca aggacatgat catggagggt gatggcagga cctcgtactg aaatttcgac  660
ctacaagacc tacaagtgtg acatgcgcaa tcagcatgat gcccgcgtgt tgtatcaact  720
actggggttt caactgtgag ccatgcgttt tctagtttgc ttgtttcatt catataagct  780
tgtattactt agttccgaac cctgtagttt tgtagtctat gttctctttt gtagggatgt  840
gctgtcataa gatgtcatgc aagtttcttg tcctacatat c                      881
```

<210> SEQ ID NO 162
<211> LENGTH: 781
<212> TYPE: DNA
<213> ORGANISM: Artificial Sequence
<220> FEATURE:
<223> OTHER INFORMATION: Donor insertion results from amplified region of AHAS gene of wheat

<400> SEQUENCE: 162

```
accagatgtg ggcggctcag tattacactt acaagcggcc acggcagtgg ctgtcttcgt    60
ctggtttggg ggcaatggga tttgggttac cagctgcagc tggcgctgct gtggccaacc   120
caggtgttac agttgttgac attgatggtg atggtagttt cctcatgaac attcaggagt   180
tggcgttgat ccgcattgag aacctcccag tgaaggtgat gatattgaac aaccagcatc   240
tgggaatggt ggtgcagtgg gaggataggt tttacaaggc caatcgggcg cacacatacc   300
ttggcaaccc agaaaatgag agtgagatat atccagattt tgtgacgatt gctaaaggat   360
tcaacgttcc agcagttcga gtgacgaaga gagcgaagt cactgcagca atcaagaaga    420
tgcttgagac cccagggcca tacttgttgg atatcatagt cccgcatcag gagcacgtgc   480
tgcctatgat cccaagcggt ggtgctttca aggacatgat catggagggt gatggcagga   540
cctcgtactg aaatttcgac ctacaagacc tacaagtgtg acatgcgcaa tcagcatgat   600
gcccgcgtgt tgtatcaact actagggggt caactgtgag ccatgcgttt tctagtttgc   660
ttgtttcatt catataagct tgtattactt agttccgaac cctgtagttt tgtagtctat   720
gttctctttt gtagggatgt gctgtcataa gatgtcatgc aagtttcttg tcctacatat   780
c                                                                   781
```

<210> SEQ ID NO 163
<211> LENGTH: 780
<212> TYPE: DNA
<213> ORGANISM: Artificial Sequence
<220> FEATURE:
<223> OTHER INFORMATION: Donor insertion results from amplified region of AHAS gene of wheat

<400> SEQUENCE: 163

```
accagatgtg ggcggctcag tattacactt acaagcggcc acggcagtgg ctgtcttcgt    60
ctggttgggg gcaatgggat ttgggttacc agctgcagct ggcgctgctg tggccaaccc   120
aggtgttaca gttgttgaca ttgatggaga tggtagtttc ctcatgaaca ttcaggagtt   180
ggcattgatc cgtattgaga acctccctgt gaaggtgatg atattgaaca accagcatct   240
gggaatggtg gtgcaatggg aggataggtt ttacaaggcc aatcgggcgc acacatacct   300
tggcaaccca gaaaatgaga gtgagatata tccagatttt gtgacgattg ctaaaggatt   360
caacgttccg gcagttcgtg tgacgaagaa gagcgaagtc actgcagcaa tcaagaagat   420
gcttgagacc ccagggccat acttgttgga tatcatcgtc ccgcatcagg agcacgtgct   480
gcctatgatc ccaagcggtg gtgctttcaa ggacatgatc atggagggtg atggcaggac   540
ctcgtactga aatttcgacc tacaagacct acaagtgtga catgcgcaat cagcatggtg   600
cccgcgtgtt gtatcaacta ctaggggttc aactgtgaac catgcgtttt ctagtttgct   660
tgtttcattc atataagctt gtgttactta gttccgaacc ctgtagcttt gtagtctatg   720
ctctcttttg tagggatgtg ctgtcataag atatcatgca agtttcttgt cctacatatc   780
```

<210> SEQ ID NO 164
<211> LENGTH: 780

<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 164

```
accagatgtg ggcggctcag tattacactt acaagcggcc acggcagtgg ctgtcttcgt      60
ctggttgggg gcaatgggat ttgggttacc agctgcagct ggcgctgctg tggccaaccc     120
aggtgttaca gttgttgaca ttgatggaga tggtagtttc ctcatgaaca ttcaggagtt     180
ggcattgatc cgtattgaga acctccctgt gaaggtgatg atattgaaca accagcatct     240
gggaatggtg gtgcaatggg aggataggtt ttacaaggcc aatcgggcgc acacatacct     300
tggcaaccca gaaaatgaga gtgagatata tccagatttt gtgacgattg ctaaaggatt     360
caacgttccg gcagttcgtg tgacgaagaa gagcgaagtc actgcagcaa tcaagaagat     420
gcttgagacc ccagggccat acttgttgga tatcatcgtc ccgcatcagg agcacgtgct     480
gcctatgatc ccaagcggtg gtgctttcaa ggacatgatc atggagggtg atggcaggac     540
ctcgtactga aatttcgacc tacaagacct acaagtgtga catgcgcaat cagcatggtg     600
cccgcgtgtt gtatcaacta ctaggggttc aactgtgaac catgcgtttt ctagtttgct     660
tgtttcattc atataagctt gtgttactta gttccgaacc ctgtagcttt gtagtctatg     720
ctctcttttg tagggatgtg ctgtcataag atatcatgca agtttcttgt cctacatatc     780
```

<210> SEQ ID NO 165
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 165

```
atcagatgtg ggcggctcag tattacactt acaagcggcc acggcagtgg ctgtcttcat      60
ccggtttggg tgcaatggga tttgggttgc agctgcagc tggcgctgct gtggccaacc      120
caggtgttac agttgttgac attgatgggg atggtagttt cctcatgaac attcaggagt     180
tggcgttgat ccgtattgag aacctcccag tgaaggtgat gatattgaac aaccagcatc     240
tgggaatggt ggtgcagtgg gaggataggt tttacaaggc caaccgggcg cacacatacc     300
ttggcaaccc agaaaatgag agtgagatat atccagattt tgtgacgatt gctaaaggat     360
tcaacgttcc ggcagttcgt gtgacgaaga agagcgaagt cactgcagca atcaagaaga     420
tgcttgagac cccagggcca tacttgttgg atatcattgt cccgcatcag gagcacgtgc     480
tgcctatgat cccaagcggt ggtgctttta aggacatgat catggagggt gatggcagga     540
cctcgtactg aaatttcgac ctacaagacc tacaagtgtg acatgcgcaa tcagcatgat     600
acctgcgtgt tgtatcaact actgggggtt caactgtgaa ccatgcgttt tctagtttgc     660
ttgtttcatt catataagct tgtgttactt agttccgaac cgtgtagttt tgtagtctct     720
gttctctttt gtagggatgt gctgtcataa gatatcatgc aagtttcttg tcctacatat     780
c                                                                     781
```

<210> SEQ ID NO 166
<211> LENGTH: 781
<212> TYPE: DNA
<213> ORGANISM: Artificial Sequence
<220> FEATURE:

<223> OTHER INFORMATION: Donor insertion results from amplified region of AHAS gene of wheat

<400> SEQUENCE: 166

```
atcagatgtg ggcggctcag tattacactt acaagcggcc acggcagtgg ctgtcttcat    60
ccggtttggg tgcaatggga tttggttgc cagctgcagc tggcgctgct gtggccaacc   120
caggtgttac agttgttgac attgatgggg atggtagttt cctcatgaac attcaggagt   180
tggcgttgat ccgtattgag aacctcccag tgaaggtgat gatattgaac aaccagcatc   240
tgggaatggt ggtgcagtgg gaggataggt tttacaaggc caaccgggcg cacacatacc   300
ttggcaaccc agaaaatgag agtgagatat atccagattt tgtgacgatt gctaaaggat   360
tcaacgttcc ggcagttcgt gtgacgaaga gagcgaagt cactgcagca atcaagaaga   420
tgcttgagac cccagggcca tacttgttgg atatcattgt cccgcatcag gagcacgtgc   480
tgcctatgat cccaagcggt ggtgctttta aggacatgat catggagggt gatggcagga   540
cctcgtactg aaatttcgac ctacaagacc tacaagtgtg acatgcgcaa tcagcatgat   600
acctgcgtgt tgtatcaact actgggggtt caactgtgaa ccatgcgttt tctagtttgc   660
ttgtttcatt catataagct tgtgttactt agttccgaac cgtgtagttt tgtagtctct   720
gttctctttt gtagggatgt gctgtcataa gatatcatgc aagtttcttg tcctacatat   780
c                                                                   781
```

<210> SEQ ID NO 167
<211> LENGTH: 771
<212> TYPE: DNA
<213> ORGANISM: Artificial Sequence
<220> FEATURE:
<223> OTHER INFORMATION: Donor insertion results from amplified region of AHAS gene of wheat

<400> SEQUENCE: 167

```
accagatgtg ggcggctcag tattacactt acaagcggcc acggcagtgg ctgtcttcgt    60
ctggtttggg ggcaatggga tttggttac cagctgcagc tggcgctgct gtggccaacc   120
caggtgttac agttgttgac attgatggtg atggtagttt cctcatgaac attcaggagt   180
tggcgttgat ccgcattgag aacctcccag tgaaggtgat gatattgaac aaccagcatc   240
tgggaatggt ggtgcagtgg gaggataggt tttacaaggc caatcgggcg cacacatacc   300
ttggcaaccc agaaaatgag agtgagatat atccagattt tgtgacgatt gctaaaggat   360
tcaacgttcc agcagttcga gtgacgaaga gagcgaagt cactgcagca atcaagaaga   420
tgcttgagac cccagggcca tacttgttgg atatcatagt cccgcatcag gagcacgtgt   480
cccaagcggt ggtgctttca aggacatgat catggagggt gatggcagga cctcgtactg   540
aaatttcgac ctacaagacc tacaagtgtg acatgcgcaa tcagcatgat gcccgcgtgt   600
tgtatcaact actaggggtt caactgtgag ccatgcgttt tctagtttgc ttgtttcatt   660
catataagct tgtattactt agttccgaac cctgtagttt tgtagtctat gttctctttt   720
gtagggatgt gctgtcataa gatgtcatgc aagtttcttg tcctacatat c             771
```

<210> SEQ ID NO 168
<211> LENGTH: 854
<212> TYPE: DNA
<213> ORGANISM: Artificial Sequence
<220> FEATURE:
<223> OTHER INFORMATION: Donor insertion results from amplified region of AHAS gene of wheat

<400> SEQUENCE: 168

```
accagatgtg ggcggctcag tattacactt acaagcggcc acggcagtgg ctgtcttcgt      60
ctggtttggg ggcaatggga tttgggttac cagctgcagc tggcgctgct gtggccaacc     120
caggtgttac agttgttgac attgatggtg atggtagttt cctcatgaac attcaggagt     180
tggcgttgat ccgcattgag aacctcccag tgaaggtgat gatattgaac aaccagcatc     240
tgggaatggt ggtgcagtgg gaggataggt tttacaaggc caatcgggcg cacacatacc     300
ttggcaaccc agaaaatgag agtgagatat atccagattt tgtgacgatt gctaaaggat     360
tcaacgttcc agcagttcga gtgacgaaga gagcgaagt cactgcagca atcaagaaga     420
tgcttgagac cccagggcca tacttgttgg atatcatagt cccgcatcag gagcacgtgc     480
tgcctatgat tcccaatggc ggcgctttca aggacatgat catggagggt gatggcagga     540
cctcgtactg aaatggtccg aaggtcaagc ggtggtgctt tcaaggacat gatcatggag     600
ggtgatggca ggacctcgta ctgaaatttc gacctacaag acctacaagt gtgacatgcg     660
caatcagcat gatgcccgcg tgttgtatca actactaggg gttcaactgt gagccatgcg     720
tttctagtt tgcttgtttc attcatataa gcttgtatta cttagttccg aaccctgtag     780
ttttgtagtc tatgttctct tttgtaggga tgtgctgtca taagatgtca tgcaagtttc     840
ttgtcctaca tatc                                                       854
```

<210> SEQ ID NO 169
<211> LENGTH: 843
<212> TYPE: DNA
<213> ORGANISM: Artificial Sequence
<220> FEATURE:
<223> OTHER INFORMATION: Donor insertion results from amplified region of AHAS gene of wheat

<400> SEQUENCE: 169

```
accagatgtg ggcggctcag tattacactt acaagcggcc acggcagtgg ctgtcttcgt      60
ctggttgggg gcaatgggat ttgggttacc agctgcagct ggcgctgctg tggccaaccc     120
aggtgttaca gttgttgaca ttgatggaga tggtagtttc ctcatgaaca ttcaggagtt     180
ggcattgatc cgtattgaga acctccctgt gaaggtgatg atattgaaca accagcatct     240
gggaatggtg gtgcaatggg aggataggtt ttacaaggcc aatcgggcgc acacatacct     300
tggcaaccca gaaaatgaga gtgagatata tccagatttt gtgacgattg ctaaaggatt     360
caacgttccg gcagttcgtg tgacgaagaa gagcgaagtc actgcagcaa tcaagaagat     420
gcttgagacc ccagggccat acttgttgga tatcatcgtc ccgcatcagg agcacgtgct     480
gcctatgatt cccaatggcg gcgctttcaa ggacatgatc atggagggtg atggcaggac     540
ctcgtactga aatttgcagg gtggtgcttt caaggacatg atcatggagg gtgatggcag     600
gacctcgtac tgaaatttcg acctacaaga cctacaagtg tgacatgcgc aatcagcatg     660
gtgcccgcgt gttgtatcaa ctactagggg ttcaactgtg aaccatgcgt tttctagttt     720
gcttgtttca ttcatataag cttgtgttac ttagttccga accctgtagc tttgtagtct     780
atgctctctt ttgtagggat gtgctgtcat aagatatcat gcaagtttct tgtcctacat     840
atc                                                                    843
```

<210> SEQ ID NO 170
<211> LENGTH: 780
<212> TYPE: DNA
<213> ORGANISM: Artificial Sequence
<220> FEATURE:

<223> OTHER INFORMATION: Donor insertion results from amplified region of AHAS gene of wheat

<400> SEQUENCE: 170

```
accagatgtg ggcggctcag tattacactt acaagcggcc acggcagtgg ctgtcttcgt    60
ctggttgggg gcaatgggat ttgggttacc agctgcagct ggcgctgctg tggccaaccc   120
aggtgttaca gttgttgaca ttgatggaga tggtagtttc ctcatgaaca ttcaggagtt   180
ggcattgatc cgtattgaga acctccctgt gaaggtgatg atattgaaca accagcatct   240
gggaatggtg gtgcaatggg aggataggtt ttacaaggcc aatcgggcgc acacatacct   300
tggcaaccca gaaaatgaga gtgagatata tccagatttt gtgacgattg ctaaaggatt   360
caacgttccg gcagttcgtg tgacgaagaa gagcgaagtc actgcagcaa tcaagaagat   420
gcttgagacc ccagggccat acttgttgga tatcatcgtc ccgcatcagg agcacgtgct   480
gcctatgatc ccaagcggtg gtgctttcaa ggacatgatc atggagggtg atggcaggac   540
ctcgtactga aatttcgacc tacaagacct acaagtgtga catgcgcaat cagcatggtg   600
cccgcgtgtt gtatcaacta ctaggggttc aactgtgaac catgcgtttt ctagtttgct   660
tgtttcattc atataagctt gtgttactta gttccgaacc ctgtagcttt gtagtctatg   720
ctctcttttg tagggatgtg ctgtcataag atatcatgca agtttcttgt cctacatatc   780
```

<210> SEQ ID NO 171
<211> LENGTH: 781
<212> TYPE: DNA
<213> ORGANISM: Artificial Sequence
<220> FEATURE:
<223> OTHER INFORMATION: Donor insertion results from amplified region of AHAS gene of wheat

<400> SEQUENCE: 171

```
atcagatgtg ggcggctcag tattacactt acaagcggcc acggcagtgg ctgtcttcat    60
ccggtttggg tgcaatggga tttgggttgc cagctgcagc tggcgctgct gtggccaacc   120
caggtgttac agttgttgac attgatgggg atggtagttt cctcatgaac attcaggagt   180
tggcgttgat ccgtattgag aacctcccag tgaaggtgat gatattgaac aaccagcatc   240
tgggaatggt ggtgcagtgg gaggataggt tttacaaggc caaccgggcg cacacatacc   300
ttggcaaccc agaaaatgag agtgagatat atccagattt tgtgacgatt gctaaaggat   360
tcaacgttcc ggcagttcgt gtgacgaaga gagcgaagt cactgcagca atcaagaaga   420
tgcttgagac cccagggcca tacttgttgg atatcattgt cccgcatcag gagcacgtgc   480
tgcctatgat cccaagcggt ggtgctttta aggacatgat catggagggt gatggcagga   540
cctcgtactg aaatttcgac ctacaagacc tacaagtgtg acatgcgcaa tcagcatgat   600
acctgcgtgt tgtatcaact actgggggtt caactgtgaa ccatgcgttt tctagtttgc   660
ttgtttcatt catataagct tgtgttactt agttccgaac cgtgtagttt tgtagtctct   720
gttctctttt gtagggatgt gctgtcataa gatatcatgc aagtttcttg tcctacatat   780
c                                                                  781
```

<210> SEQ ID NO 172
<211> LENGTH: 781
<212> TYPE: DNA
<213> ORGANISM: Artificial Sequence
<220> FEATURE:
<223> OTHER INFORMATION: Donor insertion results from amplified region of AHAS gene of wheat

<400> SEQUENCE: 172

```
atcagatgtg ggcggctcag tattacactt acaagcggcc acggcagtgg ctgtcttcat    60
ccggtttggg tgcaatggga tttgggttgc cagctgcagc tggcgctgct gtggccaacc   120
caggtgttac agttgttgac attgatgggg atggtagttt cctcatgaac attcaggagt   180
tggcgttgat ccgtattgag aacctcccag tgaaggtgat gatattgaac aaccagcatc   240
tgggaatggt ggtgcagtgg gaggataggt tttacaaggc caaccgggcg cacacatacc   300
ttggcaaccc agaaaatgag agtgagatat atccagattt tgtgacgatt gctaaaggat   360
tcaacgttcc ggcagttcgt gtgacgaaga gagcgaagt cactgcagca atcaagaaga   420
tgcttgagac cccagggcca tacttgttgg atatcattgt cccgcatcag gagcacgtgc   480
tgcctatgat cccaagcggt ggtgctttta aggacatgat catggagggt gatggcagga   540
cctcgtactg aaatttcgac ctacaagacc tacaagtgtg acatgcgcaa tcagcatgat   600
acctgcgtgt tgtatcaact actggggtt caactgtgaa ccatgcgttt tctagtttgc   660
ttgtttcatt catataagct tgtgttactt agttccgaac cgtgtagttt tgtagtctct   720
gttctctttt gtagggatgt gctgtcataa gatatcatgc aagtttcttg tcctacatat   780
c                                                                  781
```

<210> SEQ ID NO 173
<211> LENGTH: 854
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 173

```
accagatgtg ggcggctcag tattacactt acaagcggcc acggcagtgg ctgtcttcgt    60
ctggtttggg ggcaatggga tttgggttac cagctgcagc tggcgctgct gtggccaacc   120
caggtgttac agttgttgac attgatggtg atggtagttt cctcatgaac attcaggagt   180
tggcgttgat ccgcattgag aacctcccag tgaaggtgat gatattgaac aaccagcatc   240
tgggaatggt ggtgcagtgg gaggataggt tttacaaggc caatcgggcg cacacatacc   300
ttggcaaccc agaaaatgag agtgagatat atccagattt tgtgacgatt gctaaaggat   360
tcaacgttcc agcagttcga gtgacgaaga gagcgaagt cactgcagca atcaagaaga   420
tgcttgagac cccagggcca tacttgttgg atatcatagt cccgcatcag gagcacgtgc   480
tgcctatgat tcccaatggc ggcgctttca aggacatgat catggagggt gatggcagga   540
cctcgtactg aaatggtccg aaggtcaagc ggtggtgctt tcaaggacat gatcatggag   600
ggtgatggca ggacctcgta ctgaaatttc gacctacaag acctacaagt gtgacatgcg   660
caatcagcat gatgcccgcg tgttgtatca actactaggg gttcaactgt gagccatgcg   720
ttttctagtt tgcttgtttc attcatataa gcttgtatta cttagttccg aaccctgtag   780
ttttgtagtc tatgttctct tttgtaggga tgtgctgtca taagatgtca tgcaagtttc   840
ttgtcctaca tatc                                                    854
```

<210> SEQ ID NO 174
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 174

```
accagatgtg ggcggctcag tattacactt acaagcggcc acggcagtgg ctgtcttcgt    60
ctggtttggg ggcaatggga tttgggttac cagctgcagc tggcgctgct gtggccaacc   120
caggtgttac agttgttgac attgatggtg atggtagttt cctcatgaac attcaggagt   180
tggcgttgat ccgcattgag aacctcccag tgaaggtgat gatattgaac aaccagcatc   240
tgggaatggt ggtgcagtgg gaggataggt tttacaaggc caatcgggcg cacacatacc   300
ttggcaaccc agaaaatgag agtgagatat atccagattt tgtgacgatt gctaaaggat   360
tcaacgttcc agcagttcga gtgacgaaga gagcgaagt cactgcagca atcaagaaga   420
tgcttgagac cccagggcca tacttgttgg atatcatagt cccgcatcag gagcacgtgc   480
tgcctatgat cccaagcggt ggtgctttca aggacatgat catggagggt gatggcagga   540
cctcgtactg aaatttcgac ctacaagacc tacaagtgtg acatgcgcaa tcagcatgat   600
gcccgcgtgt tgtatcaact actagggggt caactgtgag ccatgcgttt tctagtttgc   660
ttgtttcatt catataagct tgtattactt agttccgaac cctgtagttt tgtagtctat   720
gttctctttt gtagggatgt gctgtcataa gatgtcatgc aagtttcttg tcctacatat   780
c                                                                  781
```

<210> SEQ ID NO 175
<211> LENGTH: 859
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 175

```
accagatgtg ggcggctcag tattacactt acaagcggcc acggcagtgg ctgtcttcgt    60
ctggtttgggg gcaatgggat ttgggttacc agctgcagct ggcgctgctg tggccaaccc   120
aggtgttaca gttgttgaca ttgatggaga tggtagtttc ctcatgaaca ttcaggagtt   180
ggcattgatc cgtattgaga acctccctgt gaaggtgatg atattgaaca accagcatct   240
gggaatggtg gtgcaatggg aggataggtt ttacaaggcc aatcgggcgc acacatacct   300
tggcaaccca gaaaatgaga gtgagatata tccagatttt gtgacgattg ctaaaggatt   360
caacgttccg gcagttcgtg tgacgaagaa gagcgaagtc actgcagcaa tcaagaagat   420
gcttgagacc ccagggccat acttgttgga tatcatcgtc ccgcatcagg agcacgtgct   480
gcctatgatt cccaatggcg cgctttcaa ggacatgatc atggagggtg atggcaggac   540
ctcgtactga aatttgcagg tacaagatcc aagcggtgg tgctttcaag gacatgatca   600
tggagggtga tggcaggacc tcgtactgaa atttcgacct acaagaccta caagtgtgac   660
atgcgcaatc agcatggtgc cgcgtgttg tatcaactac tagggggttca actgtgaacc   720
atgcgttttc tagtttgctt gtttcattca tataagcttg ttacttag ttccgaaccc   780
tgtagctttg tagtctatgc tctcttttgt agggatgtgc tgtcataaga tcatgcaa    840
gtttcttgtc ctacatatc                                                859
```

<210> SEQ ID NO 176
<211> LENGTH: 780
<212> TYPE: DNA
<213> ORGANISM: Artificial Sequence
<220> FEATURE:
<223> OTHER INFORMATION: Donor insertion results from amplified region of AHAS gene of wheat

<400> SEQUENCE: 176

| | | | | | |
|---|---|---|---|---|---|
| accagatgtg | ggcggctcag | tattacactt | acaagcggcc | acggcagtgg | ctgtcttcgt | 60 |
| ctggttgggg | gcaatgggat | ttgggttacc | agctgcagct | ggcgctgctg | tggccaaccc | 120 |
| aggtgttaca | gttgttgaca | ttgatggaga | tggtagtttc | ctcatgaaca | ttcaggagtt | 180 |
| ggcattgatc | cgtattgaga | acctccctgt | gaaggtgatg | atattgaaca | accagcatct | 240 |
| gggaatggtg | gtgcaatggg | aggataggtt | ttacaaggcc | aatcgggcgc | acacatacct | 300 |
| tggcaacccca | gaaaatgaga | gtgagatata | tccagatttt | gtgacgattg | ctaaaggatt | 360 |
| caacgttccg | gcagttcgtg | tgacgaagaa | gagcgaagtc | actgcagcaa | tcaagaagat | 420 |
| gcttgagacc | ccagggccat | acttgttgga | tatcatcgtc | ccgcatcagg | agcacgtgct | 480 |
| gcctatgatc | ccaagcggtg | gtgctttcaa | ggacatgatc | atggagggtg | atggcaggac | 540 |
| ctcgtactga | aatttcgacc | tacaagacct | acaagtgtga | catgcgcaat | cagcatggtg | 600 |
| cccgcgtgtt | gtatcaacta | ctaggggttc | aactgtgaac | catgcgtttt | ctagtttgct | 660 |
| tgtttcattc | atataagctt | gtgttactta | gttccgaacc | ctgtagcttt | gtagtctatg | 720 |
| ctctctttttg | tagggatgtg | ctgtcataag | atatcatgca | agtttcttgt | cctacatatc | 780 |

<210> SEQ ID NO 177
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 177

| | | | | | |
|---|---|---|---|---|---|
| atcagatgtg | ggcggctcag | tattacactt | acaagcggcc | acggcagtgg | ctgtcttcat | 60 |
| ccggtttggg | tgcaatggga | tttgggttgc | cagctgcagc | tggcgctgct | gtggccaacc | 120 |
| caggtgttac | agttgttgac | attgatgggg | atggtagttt | cctcatgaac | attcaggagt | 180 |
| tggcgttgat | ccgtattgag | aacctcccag | tgaaggtgat | gatattgaac | aaccagcatc | 240 |
| tgggaatggt | ggtgcagtgg | gaggataggt | tttacaaggc | caaccgggcg | cacacatacc | 300 |
| ttggcaaccc | agaaaatgag | agtgagatat | atccagattt | tgtgacgatt | gctaaaggat | 360 |
| tcaacgttcc | ggcagttcgt | gtgacgaaga | agagcgaagt | cactgcagca | atcaagaaga | 420 |
| tgcttgagac | cccagggcca | tacttgttgg | atatcattgt | cccgcatcag | gagcacgtgc | 480 |
| tgcctatgat | cccaagcggt | ggtgctttta | aggacatgat | catggagggt | gatggcagga | 540 |
| cctcgtactg | aaatttcgac | ctacaagacc | tacaagtgtg | acatgcgcaa | tcagcatgat | 600 |
| acctgcgtgt | tgtatcaact | actgggggtt | caactgtgaa | ccatgcgttt | tctagtttgc | 660 |
| ttgtttcatt | catataagct | tgtgttactt | agttccgaac | cgtgtagttt | tgtagtctct | 720 |
| gttctctttt | gtagggatgt | gctgtcataa | gatatcatgc | aagtttcttg | tcctacatat | 780 |
| c | | | | | | 781 |

<210> SEQ ID NO 178
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 178

```
atcagatgtg ggcggctcag tattacactt acaagcggcc acggcagtgg ctgtcttcat      60
ccggtttggg tgcaatggga tttgggttgc cagctgcagc tggcgctgct gtggccaacc     120
caggtgttac agttgttgac attgatgggg atggtagttt cctcatgaac attcaggagt     180
tggcgttgat ccgtattgag aacctcccag tgaaggtgat gatattgaac aaccagcatc     240
tgggaatggt ggtgcagtgg gaggataggt tttacaaggc caaccgggcg cacacatacc     300
ttggcaaccc agaaaatgag agtgagatat atccagattt tgtgacgatt gctaaaggat     360
tcaacgttcc ggcagttcgt gtgacgaaga agagcgaagt cactgcagca atcaagaaga     420
tgcttgagac cccagggcca tacttgttgg atatcattgt cccgcatcag gagcacgtgc     480
tgcctatgat cccaagcggt ggtgctttta aggacatgat catggagggt gatggcagga     540
cctcgtactg aaatttcgac ctacaagacc tacaagtgtg acatgcgcaa tcagcatgat     600
acctgcgtgt tgtatcaact actgggggtt caactgtgaa ccatgcgttt tctagtttgc     660
ttgtttcatt catataagct tgtgttactt agttccgaac cgtgtagttt tgtagtctct     720
gttctctttt gtagggatgt gctgtcataa gatatcatgc aagtttcttg tcctacatat     780
c                                                                     781

<210> SEQ ID NO 179
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 179
accagatgtg ggcggctcag tattacactt acaagcggcc acggcagtgg ctgtcttcgt      60
ctggtttggg ggcaatggga tttgggttac cagctgcagc tggcgctgct gtggccaacc     120
caggtgttac agttgttgac attgatggtg atggtagttt cctcatgaac attcaggagt     180
tggcgttgat ccgcattgag aacctcccag tgaaggtgat gatattgaac aaccagcatc     240
tgggaatggt ggtgcagtgg gaggataggt tttacaaggc caatcgggcg cacacatacc     300
ttggcaaccc agaaaatgag agtgagatat atccagattt tgtgacgatt gctaaaggat     360
tcaacgttcc agcagttcga gtgacgaaga agagcgaagt cactgcagca atcaagaaga     420
tgcttgagac cccagggcca tacttgttgg atatcatagt cccgcatcag gagcacgtgc     480
tgcctatgat cccaagcggt ggtgctttca aggacatgat catggagggt gatggcagga     540
cctcgtactg aaatttcgac ctacaagacc tacaagtgtg acatgcgcaa tcagcatgat     600
gcccgcgtgt tgtatcaact actagggggtt caactgtgag ccatgcgttt tctagtttgc     660
ttgtttcatt catataagct tgtattactt agttccgaac cctgtagttt tgtagtctat     720
gttctctttt gtagggatgt gctgtcataa gatgtcatgc aagtttcttg tcctacatat     780
c                                                                     781

<210> SEQ ID NO 180
<211> LENGTH: 781
<212> TYPE: DNA
<213> ORGANISM: Artificial Sequence
<220> FEATURE:
<223> OTHER INFORMATION: Donor insertion results from amplified region
      of AHAS gene of wheat

<400> SEQUENCE: 180
```

-continued

```
accagatgtg ggcggctcag tattacactt acaagcggcc acggcagtgg ctgtcttcgt    60
ctggtttggg ggcaatggga tttgggttac cagctgcagc tggcgctgct gtggccaacc   120
caggtgttac agttgttgac attgatggtg atggtagttt cctcatgaac attcaggagt   180
tggcgttgat ccgcattgag aacctcccag tgaaggtgat gatattgaac aaccagcatc   240
tgggaatggt ggtgcagtgg gaggataggt tttacaaggc caatcgggcg cacacatacc   300
ttggcaaccc agaaaatgag agtgagatat atccagattt tgtgacgatt gctaaaggat   360
tcaacgttcc agcagttcga gtgacgaaga agagcgaagt cactgcagca atcaagaaga   420
tgcttgagac cccagggcca tacttgttgg atatcatagt cccgcatcag gagcacgtgc   480
tgcctatgat cccaagcggt ggtgctttca aggacatgat catggagggt gatggcagga   540
cctcgtactg aaatttcgac ctacaagacc tacaagtgtg acatgcgcaa tcagcatgat   600
gcccgcgtgt tgtatcaact actaggggtt caactgtgag ccatgcgttt tctagtttgc   660
ttgtttcatt catataagct tgtattactt agttccgaac cctgtagttt tgtagtctat   720
gttctctttt gtagggatgt gctgtcataa gatgtcatgc aagtttcttg tcctacatat   780
c                                                                    781
```

<210> SEQ ID NO 181
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 181

Gln Ser Ser His Leu Thr Arg
1               5

<210> SEQ ID NO 182
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 182

Arg Ser Asp Asp Leu Thr Arg
1               5

<210> SEQ ID NO 183
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 183

Tyr Arg Trp Leu Leu Arg Ser
1               5

<210> SEQ ID NO 184
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 184

Gln Ser Gly Asp Leu Thr Arg
1               5

<210> SEQ ID NO 185
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 185

Gln Arg Asn Ala Arg Thr Leu
1               5

<210> SEQ ID NO 186
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 186

Arg Ser Asp Asn Leu Ser Val
1               5

<210> SEQ ID NO 187
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 187

Gln Lys Ile Asn Leu Gln Val
1               5

<210> SEQ ID NO 188
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 188

Asp Asp Trp Asn Leu Ser Gln
1               5

<210> SEQ ID NO 189
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 189

Arg Ser Ala Asn Leu Thr Arg
1               5

<210> SEQ ID NO 190
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 190

Gln Ser Gly His Leu Ala Arg
1               5

<210> SEQ ID NO 191
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 191

Asn Asp Trp Asp Arg Arg Val
1               5

<210> SEQ ID NO 192
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 192

Arg Ser Asp His Leu Ser Gln
1               5

<210> SEQ ID NO 193
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 193

Asp Ser Ser Thr Arg Lys Lys
1               5

<210> SEQ ID NO 194
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 194

Arg Ser Asp Val Leu Ser Glu
1               5

<210> SEQ ID NO 195
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 195

Asp Arg Ser Asn Arg Ile Lys
1               5

<210> SEQ ID NO 196
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 196

Arg Ser Asp Asn Leu Ser Asn
1               5

```
<210> SEQ ID NO 197
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 197

Thr Ser Ser Ser Arg Ile Asn
1               5

<210> SEQ ID NO 198
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 198

Asp Arg Ser Asn Leu Thr Arg
1               5

<210> SEQ ID NO 199
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 199

Gln Ser Ser Asp Leu Ser Arg
1               5

<210> SEQ ID NO 200
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 200

Gln Ser Ala His Arg Lys Asn
1               5

<210> SEQ ID NO 201
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 201

Asp Arg Ser His Leu Thr Arg
1               5

<210> SEQ ID NO 202
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 202

Gln Ser Gly His Leu Ser Arg
1               5

<210> SEQ ID NO 203
```

<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 203

Arg Ser Asp Asn Leu Ser Glu
1               5

<210> SEQ ID NO 204
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 204

His Ser Asn Ala Arg Lys Thr
1               5

<210> SEQ ID NO 205
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 205

Thr Ser Gly Asn Leu Thr Arg
1               5

<210> SEQ ID NO 206
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 206

His Arg Thr Ser Leu Thr Asp
1               5

<210> SEQ ID NO 207
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 207

His Lys Tyr His Leu Arg Ser
1               5

<210> SEQ ID NO 208
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 208

Gln Trp Ser Thr Arg Lys Arg
1               5

<210> SEQ ID NO 209
<211> LENGTH: 7

-continued

```
<212> TYPE: PRT
<213> ORGANISM: Artificial Sequence
<220> FEATURE:
<223> OTHER INFORMATION: ZFN Binding Motif

<400> SEQUENCE: 209

Ser Pro Ser Ser Arg Arg Thr
1               5

<210> SEQ ID NO 210
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 210

Thr Ala Arg Gln Arg Asn Arg
1               5

<210> SEQ ID NO 211
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 211

Asp Arg Ser His Leu Ala Arg
1               5

<210> SEQ ID NO 212
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 212

Arg Ser Asp Ser Leu Ser Ala
1               5

<210> SEQ ID NO 213
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 213

Arg Ser Asp Ala Leu Ala Arg
1               5

<210> SEQ ID NO 214
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 214

Gln Lys Ser Asn Leu Ser Ser
1               5

<210> SEQ ID NO 215
<211> LENGTH: 7
<212> TYPE: PRT
```

```
<213> ORGANISM: Artificial Sequence
<220> FEATURE:
<223> OTHER INFORMATION: ZFN Binding Motif

<400> SEQUENCE: 215

Asp Ser Ser Asp Arg Lys Lys
1               5

<210> SEQ ID NO 216
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 216

Trp Trp Thr Ser Arg Ala Leu
1               5

<210> SEQ ID NO 217
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 217

Asp Arg Ser Asp Leu Ser Arg
1               5

<210> SEQ ID NO 218
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 218

Arg Ser Asp His Leu Ser Glu
1               5

<210> SEQ ID NO 219
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 219

Tyr Ser Trp Arg Leu Ser Gln
1               5

<210> SEQ ID NO 220
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 220

Arg Ser Asp Ser Leu Ser Val
1               5

<210> SEQ ID NO 221
<211> LENGTH: 7
<212> TYPE: PRT
<213> ORGANISM: Artificial Sequence
```

```
<220> FEATURE:
<223> OTHER INFORMATION: ZFN Binding Motif

<400> SEQUENCE: 221

Arg Asn Gln Asp Arg Lys Asn
1               5

<210> SEQ ID NO 222
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 222

Gln Ser Gly Asn Leu Ala Arg
1               5

<210> SEQ ID NO 223
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 223

Asp Arg Ser Ala Leu Ala Arg
1               5

<210> SEQ ID NO 224
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 224

Arg Ser Asp Asn Leu Ser Thr
1               5

<210> SEQ ID NO 225
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 225

Ala Gln Trp Gly Arg Thr Ser
1               5

<210> SEQ ID NO 226
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 226

Arg Ser Ala Asp Leu Thr Arg
1               5

<210> SEQ ID NO 227
<211> LENGTH: 7
<212> TYPE: PRT
<213> ORGANISM: Artificial Sequence
<220> FEATURE:
```

<223> OTHER INFORMATION: ZFN Binding Motif

<400> SEQUENCE: 227

Thr Asn Gln Asn Arg Ile Thr
1               5

<210> SEQ ID NO 228
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 228

Arg Ser Asp Ser Leu Leu Arg
1               5

<210> SEQ ID NO 229
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 229

Leu Gln His His Leu Thr Asp
1               5

<210> SEQ ID NO 230
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 230

Gln Asn Ala Thr Arg Ile Asn
1               5

<210> SEQ ID NO 231
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 231

Met Arg Asn Arg Leu Asn Arg
1               5

<210> SEQ ID NO 232
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 232

Asp Arg Ser Asn Leu Ser Arg
1               5

<210> SEQ ID NO 233
<211> LENGTH: 7
<212> TYPE: PRT
<213> ORGANISM: Artificial Sequence
<220> FEATURE:
<223> OTHER INFORMATION: ZFN Binding Motif

```
<400> SEQUENCE: 233

Trp Arg Ser Cys Arg Ser Ala
1               5

<210> SEQ ID NO 234
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 234

Gln Trp Phe Gly Arg Lys Asn
1               5

<210> SEQ ID NO 235
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 235

Gln Trp Phe Gly Arg Lys Asn
1               5

<210> SEQ ID NO 236
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 236

Arg Ser Asp Ala Leu Thr Gln
1               5

<210> SEQ ID NO 237
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 237

Glu Arg Gly Thr Leu Ala Arg
1               5

<210> SEQ ID NO 238
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 238

Asp Thr Gly Ala Arg Leu Lys
1               5

<210> SEQ ID NO 239
<211> LENGTH: 7
<212> TYPE: PRT
<213> ORGANISM: Artificial Sequence
<220> FEATURE:
<223> OTHER INFORMATION: ZFN Binding Motif
```

```
<400> SEQUENCE: 239

His Arg Arg Ser Arg Asp Gln
1               5

<210> SEQ ID NO 240
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 240

Asp Arg Ser Tyr Arg Asn Thr
1               5

<210> SEQ ID NO 241
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 241

Arg Ser Ala Asp Leu Ser Arg
1               5

<210> SEQ ID NO 242
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 242

Arg Ser Asp His Leu Ser Ala
1               5

<210> SEQ ID NO 243
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 243

Gln Ser Ser Asp Leu Arg Arg
1               5

<210> SEQ ID NO 244
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 244

Arg Ser Asp Asp Arg Lys Thr
1               5

<210> SEQ ID NO 245
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 245
```

```
Arg Arg Ala Asp Arg Ala Lys
1               5

<210> SEQ ID NO 246
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 246

Thr Ser Ser Asp Arg Lys Lys
1               5

<210> SEQ ID NO 247
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 247

Arg Asn Asp Asp Arg Lys Lys
1               5

<210> SEQ ID NO 248
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 248

Asp Ser Ser Thr Arg Arg Arg
1               5

<210> SEQ ID NO 249
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 249

His Ser Arg Thr Arg Thr Lys
1               5

<210> SEQ ID NO 250
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 250

Asn Asn Arg Asp Arg Thr Lys
1               5

<210> SEQ ID NO 251
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 251
```

```
Val Ser Ser Asn Leu Thr Ser
1               5

<210> SEQ ID NO 252
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 252

Arg Ser Asp Ala Leu Ser Val
1               5

<210> SEQ ID NO 253
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 253

Asp Ser Ser His Arg Thr Arg
1               5

<210> SEQ ID NO 254
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 254

Arg Ser Asp Asn Leu Thr Arg
1               5

<210> SEQ ID NO 255
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 255

Arg Ser Asp Asn Leu Ala Arg
1               5

<210> SEQ ID NO 256
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 256

Asp Arg Ser His Leu Ser Arg
1               5

<210> SEQ ID NO 257
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 257

Thr Ser Ser Asn Arg Lys Thr
```

```
1               5

<210> SEQ ID NO 258
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 258

Arg Ser Asp Asp Leu Ser Lys
1               5

<210> SEQ ID NO 259
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 259

Arg Ser Ala His Leu Ser Arg
1               5

<210> SEQ ID NO 260
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 260

Arg Ser Asp Ala Leu Ser Thr
1               5

<210> SEQ ID NO 261
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 261

Asp Arg Ser Thr Arg Thr Lys
1               5

<210> SEQ ID NO 262
<211> LENGTH: 7
<212> TYPE: PRT
<213> ORGANISM: Artificial Sequence
<220> FEATURE:
<223> OTHER INFORMATION: ZFN Binding Motif

<400> SEQUENCE: 262

Thr Ser Ser Asp Arg Thr Lys
1               5

<210> SEQ ID NO 263
<211> LENGTH: 28
<212> TYPE: DNA
<213> ORGANISM: Artificial Sequence
<220> FEATURE:
<223> OTHER INFORMATION: ZFN Target Site
<220> FEATURE:
<221> NAME/KEY: misc_feature
<222> LOCATION: (2)..(2)
<223> OTHER INFORMATION: n is a, c, g, or t
```

```
<400> SEQUENCE: 263
cngcggccat ggcggcggcg agggtttg                                            28

<210> SEQ ID NO 264
<211> LENGTH: 28
<212> TYPE: DNA
<213> ORGANISM: Artificial Sequence
<220> FEATURE:
<223> OTHER INFORMATION: ZFN Target Site
<220> FEATURE:
<221> NAME/KEY: misc_feature
<222> LOCATION: (24)..(24)
<223> OTHER INFORMATION: n is a, c, g, or t

<400> SEQUENCE: 264
acctcccccg ccgtcgcatt ctcnggcg                                            28

<210> SEQ ID NO 265
<211> LENGTH: 28
<212> TYPE: DNA
<213> ORGANISM: Artificial Sequence
<220> FEATURE:
<223> OTHER INFORMATION: ZFN Target Site
<220> FEATURE:
<221> NAME/KEY: misc_feature
<222> LOCATION: (20)..(20)
<223> OTHER INFORMATION: n is a, c, g, or t

<400> SEQUENCE: 265
ggccggacgc gcgggcgtan ccggacgc                                            28

<210> SEQ ID NO 266
<211> LENGTH: 28
<212> TYPE: DNA
<213> ORGANISM: Artificial Sequence
<220> FEATURE:
<223> OTHER INFORMATION: ZFN Target Site

<400> SEQUENCE: 266
cgtcggcgtc tgcgtcgcca cctccggc                                            28

<210> SEQ ID NO 267
<211> LENGTH: 28
<212> TYPE: DNA
<213> ORGANISM: Artificial Sequence
<220> FEATURE:
<223> OTHER INFORMATION: ZFN Target Site

<400> SEQUENCE: 267
acgccgacgc ggccggacgc gcgggcgt                                            28

<210> SEQ ID NO 268
<211> LENGTH: 28
<212> TYPE: DNA
<213> ORGANISM: Artificial Sequence
<220> FEATURE:
<223> OTHER INFORMATION: ZFN Target Site

<400> SEQUENCE: 268
gcgtcgccac ctccggcccg ggggccac                                            28

<210> SEQ ID NO 269
<211> LENGTH: 28
<212> TYPE: DNA
<213> ORGANISM: Artificial Sequence
<220> FEATURE:
<223> OTHER INFORMATION: ZFN Target Site
```

```
<400> SEQUENCE: 269
cagacgccga cgcggccgga cgcgcggg                                          28

<210> SEQ ID NO 270
<211> LENGTH: 28
<212> TYPE: DNA
<213> ORGANISM: Artificial Sequence
<220> FEATURE:
<223> OTHER INFORMATION: ZFN Target Site

<400> SEQUENCE: 270
gtcgccacct ccggcccggg ggccacca                                          28

<210> SEQ ID NO 271
<211> LENGTH: 28
<212> TYPE: DNA
<213> ORGANISM: Artificial Sequence
<220> FEATURE:
<223> OTHER INFORMATION: ZFN Target Site

<400> SEQUENCE: 271
gcgacgcaga cgccgacgcg gccggacg                                          28

<210> SEQ ID NO 272
<211> LENGTH: 28
<212> TYPE: DNA
<213> ORGANISM: Artificial Sequence
<220> FEATURE:
<223> OTHER INFORMATION: ZFN Target Site

<400> SEQUENCE: 272
cctccggccc gggggccacc aacctcgt                                          28

<210> SEQ ID NO 273
<211> LENGTH: 28
<212> TYPE: DNA
<213> ORGANISM: Artificial Sequence
<220> FEATURE:
<223> OTHER INFORMATION: ZFN Target Site
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 273
gggatggagt cgaggagngc gtcngcga                                          28

<210> SEQ ID NO 274
<211> LENGTH: 28
<212> TYPE: DNA
<213> ORGANISM: Artificial Sequence
<220> FEATURE:
<223> OTHER INFORMATION: ZFN Target Site

<400> SEQUENCE: 274
tggtcgccat cacgggccag gtcccccg                                          28

<210> SEQ ID NO 275
<211> LENGTH: 28
<212> TYPE: DNA
<213> ORGANISM: Artificial Sequence
<220> FEATURE:
```

<223> OTHER INFORMATION: ssss
<220> FEATURE:
<221> NAME/KEY: misc_feature
<222> LOCATION: (24)..(24)
<223> OTHER INFORMATION: n is a, c, g, or t

<400> SEQUENCE: 275
accatgggga tggagtcgag gagngcgt                                28

<210> SEQ ID NO 276
<211> LENGTH: 28
<212> TYPE: DNA
<213> ORGANISM: Artificial Sequence
<220> FEATURE:
<223> OTHER INFORMATION: ZFN Target Site

<400> SEQUENCE: 276
ccatcacggg ccaggtcccc cgccgcat                                28

<210> SEQ ID NO 277
<211> LENGTH: 28
<212> TYPE: DNA
<213> ORGANISM: Artificial Sequence
<220> FEATURE:
<223> OTHER INFORMATION: ZFN Target Site
<220> FEATURE:
<221> NAME/KEY: misc_feature
<222> LOCATION: (26)..(26)
<223> OTHER INFORMATION: n is a, c, g, or t

<400> SEQUENCE: 277
cgaccatggg gatggagtcg aggagngc                                28

<210> SEQ ID NO 278
<211> LENGTH: 28
<212> TYPE: DNA
<213> ORGANISM: Artificial Sequence
<220> FEATURE:
<223> OTHER INFORMATION: ZFN Target Site

<400> SEQUENCE: 278
catcacgggc caggtccccc gccgcatg                                28

<210> SEQ ID NO 279
<211> LENGTH: 55
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t

<400> SEQUENCE: 279
ancactcttt ccctacacga cgctcttccg atcttcccca attccaaccc tctnc      55

<210> SEQ ID NO 280
<211> LENGTH: 56
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature

```
<222> LOCATION: (2)..(2)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t

<400> SEQUENCE: 280
gntgactgga gttcagacgt gtgctcttcc gatctcgtca gcgcctggtg gatcnt      56

<210> SEQ ID NO 281
<211> LENGTH: 54
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t

<400> SEQUENCE: 281
ancactcttt ccctacacga cgctcttccg atctgcccgt ccgagccccg cana         54

<210> SEQ ID NO 282
<211> LENGTH: 56
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t

<400> SEQUENCE: 282
gntgactgga gttcagacgt gtgctcttcc gatctcgtca gcgcctggtg gatcnt      56

<210> SEQ ID NO 283
<211> LENGTH: 53
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 283
ancactcttt ccctacacga cgctcttccg atctgcgctc gcccgtcatc anc          53

<210> SEQ ID NO 284
<211> LENGTH: 56
<212> TYPE: DNA
<213> ORGANISM: Artificial Sequence
<220> FEATURE:
<223> OTHER INFORMATION: Primer Sequence
<220> FEATURE:
```

```
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t

<400> SEQUENCE: 284
gntgactgga gttcagacgt gtgctcttcc gatctatggg gatggagtcg aggang    56

<210> SEQ ID NO 285
<211> LENGTH: 53
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 285
ancactcttt ccctacacga cgctcttccg atctcttccg ccacgagcag gng    53

<210> SEQ ID NO 286
<211> LENGTH: 56
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t

<400> SEQUENCE: 286
gntgactgga gttcagacgt gtgctcttcc gatctatggg gatggagtcg aggang    56

<210> SEQ ID NO 287
<211> LENGTH: 54
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t

<400> SEQUENCE: 287
ancactcttt ccctacacga cgctcttccg atcttcgtct ccgcgctcgc tgna    54

<210> SEQ ID NO 288
<211> LENGTH: 56
<212> TYPE: DNA
<213> ORGANISM: Artificial Sequence
<220> FEATURE:
<223> OTHER INFORMATION: Primer Sequence
```

```
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t

<400> SEQUENCE: 288
gntgactgga gttcagacgt gtgctcttcc gatcttccac tatgggcgtc tcctng        56

<210> SEQ ID NO 289
<211> LENGTH: 6661
<212> TYPE: DNA
<213> ORGANISM: Artificial Sequence
<220> FEATURE:
<223> OTHER INFORMATION: pDAS000164

<400> SEQUENCE: 289
tggcaggata tattgtggtg taaacaaatt gacgcttaga caacttaata acacattgcg    60
gacgttttta atgtactgaa ttaacgccga attgaattcg agctcggtac cactggattt   120
tggttttagg aattagaaat tttattgata gaagtatttt acaaatacaa atacatacta   180
agggtttctt atatgctcaa cacatgagcg aaaccctata agaaccctaa ttcccttatc   240
tgggaactac tcacacatta ttctggagaa aaatagagag agatagattt gtagagagag   300
actggtgatt tttgcggact ctattagatc tgggtaactg gcctaactgg ccttggagga   360
gctggcaact caaaatccct tgccaaaaa ccaacatcat gccatccacc atgcttgtat    420
ccagctgcgc gcaatgtacc ccgggctgtg tatcccaaag cctcatgcaa cctaacagat   480
ggatcgtttg gaaggcctat aacagcaacc acagacttaa aaccttgcgc tccatagac    540 ttaagcaaat gtgtgtacaa tgtggatcct aggcccaacc tttgatgcct atgtgacacg   600
taaacagtac tctcaactgt ccaatcgtaa gcgttcctag ccttcagggg cccagcgtaa   660
gcaataccag ccacaacacc ctcaacctca gcaaccaacc aagggtatct atcttgcaac   720
ctctcgagat catcaatcca ctcttgtggt gtttgtggct ctgtcctaaa gttcactgta   780
gacgtctcaa tgtaatggtt aacgatatca caaaccgcgg ccatatcagc tgctgtagct   840
ggcctaatct caactggtct cctctccgga gacatggctt ctacctacaa aaaagctccg   900
cacgaggctg catttgtcac aaatcatgaa agaaaaact accgatgaac aatgctgagg    960
gattcaaatt ctacccacaa aaagaagaaa gaaagatcta gcacatctaa gcctgacgaa   1020
gcagcagaaa tatataaaaa tataaaccat agtgcccttt tcccctcttc ctgatcttgt   1080
ttagcatggc ggaaatttta aaccccccat catctccccc aacaacggcg gatcgcagat   1140
ctacatccga gagcccattt ccccgcgaga tccgggccgg atccacgccg gcgagagccc   1200
cagccgcgag atcccgcccc tcccgcgcac cgatctgggc gcgcacgaag ccgcctctcg   1260
cccacccaaa ctaccaaggc caaagatcga gaccgagacg gaaaaaaaaa acggagaaag   1320
aaagaggaga ggggcggggt ggttaccggc gcggcggcgg cggaggggga gggggagga    1380 gctcgtcgtc cggcagcgag gggggaggag gtggaggtgg tggtggtggt ggtggtaggg   1440 ttgggggggat gggaggagag gggggggtat gtatatagtg gcgatggggg gcgtttcttt   1500
ggaagcggag ggagggccgg cctcgtcgct ggctcgcgat cctcctcgcg tttccggccc   1560
ccacgacccg gacccacctg ctgttttttc tttttctttt tttctttct ttttttttt    1620 ttggctgcga gacgtgcggt gcgtgcggac aactcacggt gatagtgggg gggtgtggag   1680
```

```
actattgtcc agttggctgg actggggtgg gttgggttgg gttgggttgg gctgggcttg    1740
ctatggatcg tggatagcac tttgggcttt aggaacttta ggggttgttt ttgtaaatgt    1800
tttgagtcta agtttatctt ttattttttac tagaaaaaat acccatgcgc tgcaacgggg   1860
gaaagctatt ttaatcttat tattgttcat tgtgagaatt cgcctgaata tatattttc    1920 tcaaaaatta tgtcaaatta gcatatgggt tttttaaag atatttctta tacaaatccc    1980
tctgtattta caaagcaaa cgaacttaaa acccgactca aatacagata tgcatttcca    2040
aaagcgaata aacttaaaaa ccaattcata caaaaatgac gtatcaaagt accgacaaaa   2100
acatcctcaa ttttttataat agtagaaaag agtaaatttc actttgggcc acctttatt   2160 accgatattt tactttatac cacctttaa ctgatgtttt cacttttgac caggtaatct    2220
tacctttgtt ttattttgga ctatcccgac tctcttctca agcatatgaa tgacctcgag    2280
tatgctagtc tagagtcgac ctgcagggtg cagcgtgacc cggtcgtgcc cctctctaga    2340
gataatgagc attgcatgtc taagttataa aaaattacca catatttttt ttgtcacact    2400
tgtttgaagt gcagtttatc tatctttata catatattta aactttactc tacgaataat    2460
ataatctata gtactacaat aatatcagtt ttttagagaa tcatataaat gaacagttag    2520
acatggtcta aaggacaatt gagtattttg acaacaggac tctacagttt tatcttttta    2580
gtgtgcatgt gttctccttt tttttttgcaa atagcttcac ctatataata cttcatccat    2640
tttattagta catccattta gggtttaggg ttaatggttt ttatagacta atttttttag    2700
tacatctatt ttattctatt ttagcctcta aattaagaaa actaaaactc tattttagtt    2760
tttttattta ataattaga tataaaatag aataaaataa agtgactaaa aattaaacaa    2820
atacccttta agaaattaaa aaaactaagg aaacattttt cttgtttcga gtagataatg   2880
ccagcctgtt aaacgccgtc gacgagtcta acggacacca accagcgaac cagcagcgtc    2940
gcgtcgggcc aagcgaagca gacggcacgg catctctgtc gctgcctctg gacccctctc    3000
gagagttccg ctccaccgtt ggacttgctc cgctgtcggc atccagaaat tgcgtggcgg    3060
agcggcagac gtgagccggc acggcaggcg gcctcctcct cctctcacgg cacggcagct    3120
acgggggatt cctttcccac cgctccttcg ctttcccttc ctcgcccgcc gtaataaata    3180 gacacccct ccacaccctc tttccccaac ctcgtgttgt tcggagcgca cacacacaca     3240
accagatctc ccccaaatcc acccgtcggc acctccgctt caaggtacgc cgctcgtcct    3300
cccccccccc ccctctctac cttctctaga tcggcgttcc ggtccatggt tagggcccgg    3360
tagttctact tctgttcatg tttgtgttag atccgtgttt gtgttagatc cgtgctgcta    3420
gcgttcgtac acggatgcga cctgtacgtc agacacgttc tgattgctaa cttgccagtg    3480
tttctctttg gggaatcctg ggatggctct agccgttccg cagacgggat cgatttcatg    3540
attttttttg tttcgttgca tagggtttgg tttgcccttt tcctttatt caatatatgc     3600 cgtgcacttg tttgtcgggt catctttca tgctttttt tgtcttggtt gtgatgatgt     3660
ggtctggttg ggcggtcgtt ctagatcgga gtagaattct gtttcaaact acctggtgga    3720
tttattaatt ttggatctgt atgtgtgtgc catacatatt catagttacg aattgaagat    3780
gatggatgga aatatcgatc taggataggt atacatgttg atgcgggttt tactgatgca    3840
tatacagaga tgcttttgt tcgcttggtt gtgatgatgt ggtgtggttg ggcggtcgtt     3900
cattcgttct agatcggagt agaatactgt ttcaaactac ctggtgtatt tattaatttt    3960
ggaactgtat gtgtgtgtca tacatcttca tagttacgag tttaagatgg atggaaatat    4020
cgatctagga taggtataca tgttgatgtg ggttttactg atgcatatac atgatggcat    4080
```

-continued

```
atgcagcatc tattcatatg ctctaacctt gagtacctat ctattataat aaacaagtat    4140
gttttataat tattttgatc ttgatatact tggatgatgg catatgcagc agctatatgt    4200
ggattttttt agccctgcct tcatacgcta tttatttgct tggtactgtt tcttttgtcg    4260
atgctcaccc tgttgtttgg tgttacttct gcaggaggat cacaagtttg tacaaaaaag    4320
caggctatgg ccgccgccac ctcccccgcc gtcgcattct cgggcgccac cgccgccgcc    4380
atgcccaaac ccgccgcca tcctctcccg cgccaccagc ccgtctcgcg ccgcgcgctc    4440
cccgcccgcg tcgtcaggtg ttgcgccgcg tccccgccg ccacctccgc cgcgcctccc    4500
gcaaccgcgc tccggccctg gggcccgtcc gagccccgca agggcgccga catcctcgtc    4560
gaggcgctcg agcgctgcgg catcgtcgac gtcttcgcct accccggcgg cgcctccatg    4620
gagatccacc aggcgctgac gcgctcgccc gtcatcacca accacctctt ccgccacgag    4680
caggggagg cgttcgcggc gtccggctac gcccgcgcgt ccggccgcgt cggcgtctgc    4740
gtcgccacct ccgccccggg ggccaccaac ctcgtctccg cgctcgccga cgccctcctc    4800
gactccatcc ccatggtcgc catcacgggc caggtctccc gccgcatgat cggcacggac    4860
gcgttccagg agacgcccat agtggaggtc acgcgctcca tcaccaagca caactacctg    4920
gtccttgacg tggaggatat cccccgcgtc atccaggaag ccttcttcct tgcatcctct    4980
ggccgcccgg ggccggtgct agttgatatc cccaaggaca tccagcagca gatggctgtg    5040
cccgtctggg acactccaat gagtttgcca gggtacatcg cccgcctgcc caagccacca    5100
tctactgaat cgcttgagca ggtcctgcgt ctggttggcg agtcacggcg cccaattctg    5160
tatgttggtg gtggctgcgc tgcgtctggc gaggagttgc gccgctttgt tgagcttact    5220
gggattccag ttacaactac tctgatgggc cttggcaact tccccagcga cgacccactg    5280
tctctgcgca tgcttgggat gcatggcact gtgtatgcaa attatgcagt agataaggct    5340
gacctgttgc tcgcatttgg tgtgcggttt gatgatcgtg tgactgggaa aatcgaggct    5400
tttgcaagca ggtccaagat tgtgcacatt gacattgacc cagctgagat tggcaagaac    5460
aagcagccac atgtctccat ttgtgcagat gttaagcttg ctttacaggg gttgaatgat    5520
ctattaaatg ggagcaaagc acaacagggt ctggattttg gtccatggca caaggagttg    5580
gatcagcaga agagggagtt tcctctagga ttcaagactt ttggcgaggc catcccgccg    5640
caatatgcta tccaggtact ggatgagctg acaaaagggg aggcgatcat tgccactggt    5700
gttgggcagc accagatgtg ggcggctcag tattacactt acaagcggcc acggcagtgg    5760
ctgtcttcgt ctggtttggg ggcaatggga tttgggttac cagctgcagc tggcgctgct    5820
gtggccaacc caggtgttac agttgttgac attgatggtg atggtagttt cctcatgaac    5880
attcaggagt tggcgttgat ccgcattgag aacctcccag tgaaggtgat gatattgaac    5940
aaccagcatc tgggaatggt ggtgcagtgg gaggataggt tttacaaggc caatcgggcg    6000
cacacatacc ttggcaaccc agaaaatgag agtgagatat atccagattt tgtgacgatt    6060
gctaaaggat tcaacgttcc agcagttcga gtgacgaaga gagcgaagt cactgcagca    6120
atcaagaaga tgcttgagac cccagggcca tacttgttgg atatcatagt cccgcatcag    6180
gagcacgtgc tgcctatgat cccaagcggt ggtgcttttca aggacatgat catggagggt    6240
gatggcagga cctcgtactg ataccccagct ttcttgtaca aagtggtgat cctactagta    6300
gaaggagtgc gtcgaagcag atcgttcaaa catttggcaa taaagtttct taagattgaa    6360
tcctgttgcc ggtcttgcga tgattatcat ataatttctg ttgaattacg ttaagcatgt    6420
```

-continued

```
aataattaac atgtaatgca tgacgttatt tatgagatgg gtttttatga ttagagtccc    6480
gcaattatac atttaatacg cgatagaaaa caaaatatag cgcgcaaact aggataaatt    6540
atcgcgcgcg gtgtcatcta tgttactaga tcgaaagctt agcttgagct tggatcagat    6600
tgtcgtttcc cgccttcagt ttaaactatc agtgtttgac aggatatatt ggcgggtaaa    6660
c                                                                    6661
```

<210> SEQ ID NO 290
<211> LENGTH: 20
<212> TYPE: DNA
<213> ORGANISM: Artificial Sequence
<220> FEATURE:
<223> OTHER INFORMATION: Primer Sequence

<400> SEQUENCE: 290
gcgaagatcc aggacaagga                                                   20

<210> SEQ ID NO 291
<211> LENGTH: 21
<212> TYPE: DNA
<213> ORGANISM: Artificial Sequence
<220> FEATURE:
<223> OTHER INFORMATION: Primer Sequence

<400> SEQUENCE: 291
ctgcttaccg gcaaagatga g                                                 21

<210> SEQ ID NO 292
<211> LENGTH: 20
<212> TYPE: DNA
<213> ORGANISM: Artificial Sequence
<220> FEATURE:
<223> OTHER INFORMATION: Primer Sequence

<400> SEQUENCE: 292
ttcccccgga ccagcagcgt                                                   20

<210> SEQ ID NO 293
<211> LENGTH: 20
<212> TYPE: DNA
<213> ORGANISM: Artificial Sequence
<220> FEATURE:
<223> OTHER INFORMATION: Primer Sequence

<400> SEQUENCE: 293
ccgacgagaa agaccagcaa                                                   20

<210> SEQ ID NO 294
<211> LENGTH: 23
<212> TYPE: DNA
<213> ORGANISM: Artificial Sequence
<220> FEATURE:
<223> OTHER INFORMATION: Primer Sequence

<400> SEQUENCE: 294
cttaagttgt cgatcgggac tgt                                               23

<210> SEQ ID NO 295
<211> LENGTH: 2571
<212> TYPE: DNA
<213> ORGANISM: Artificial Sequence
<220> FEATURE:
<223> OTHER INFORMATION: pDAS000435

<400> SEQUENCE: 295

-continued

```
tgagattggc aagaacaagc agccacatgt ctccatttgt gcagatgtta agcttgcttt       60
acaggggttg aatgatctat taaatgggag caaagcacaa cagggtctgg attttggtcc      120
atggcacaag gagttggatc agcagaagag ggagtttcct ctaggattca agacttttgg      180
cgaggccatc ccgccgcaat atgctatcca ggtactggat gagctgacaa aaggggaggc      240
gatcattgcc actggtgttg ggcagcacca gatgtgggcg gctcagtatt acacttacaa      300
gcggccacgg cagtggctgt cttcgtctgg tttgggggca atgggatttg ggttaccagc      360
tgcagctggc gctgctgtgg ccaacccagg tgttacagtt gttgacattg atggtgatgg      420
tagtttcctc atgaacattc aggagttggc gttgatccgc attgagaacc tcccagtgaa      480
ggtgatgata ttgaacaacc agcatctggg aatggtggtg cagtgggagg ataggtttta      540
caaggccaat cgggcgcaca catacccttgg caacccagaa atgagagtg agatatatcc      600 agattttgtg acgattgcta aaggattcaa cgttccagca gttcgagtga cgaagaagag      660
cgaagtcact gcagcaatca agaagatgct tgagaccca gggccatact tgttggatat      720
catagtcccg catcaggagc acgtgctgcc tatgattcca aacggcggcg ccttcaagga      780
catgatcatg gagggtgatg gcaggacctc gtactgaaat ttcgacctac aagacctaca      840
agtgtgacat gcgcaatcag catggtgccc gcgtgttgta tcaactacta ggggttcaac      900
tgtgaaccat gcgttttcta gtttgcttgt tcattcata taagcttgtg ttacttagtt      960
ccgaaccctg tagctttgta gtctatgctc tcttttgtag ggatgtgctg tcataagata     1020
tcatgcaagt ttcttgtcct acatatcaat aataagtact tccatggaat aattctcagt     1080
tctgttttga attttgcatc ttctcacaaa cagtgtgctg gttcctttct gttcgctgac     1140
gccctcctcg actccatccc catggtcgcc atcacgggcc aggtccccg ccgcatgatc      1200 ggtagcgact tcgtgggcga ggaaagcctt tcgtccaagg tggtccctcc tcgcaatctt     1260
gttggatggt gaatattata aaagcctgcc cttctcgcgg gtaagactcc cgcccatcca     1320
ggatgaggat gaccagcctt ttgcagttta tccactaggg acaggattgc atcctgccga     1380
aaccctgcca agcttgaggt agcctccaat ttgacggtgc cgccagcgac gccgtctgga     1440
actgtccttt ttgaggacca ctccgtttgt ctagaggtac ctggagatca tgacattaag     1500
gatgaccagt tcgtaaaggt cctgcggtgt ctattgcttt tcataggtta ataagtgttt     1560
gctagactgt ggtgaaaggc caagactccc gcccatctct ctatgcccgg acaagtgcc      1620 accccacagt ggggcaggat gaggatgacc aaagactccc gcccatctca ctagggacag     1680
gattggcctt ttgcagttta tctctatgcc cgggacaagt gtatccgaag taaataaaac     1740
catcggactc tcgtataaga ctgtcgactc gaccggccga cgcataggtt catttgaagc     1800
tgctattcta tttaaattga atcccaagc ggtggtgctt tcaaggacat gatcatggag      1860
ggtgatggca ggacctcgta ctgaaatttc gacctacaag acctacaagt gtgacatgcg     1920
caatcagcat gatgcccgcg tgttgtatca actactaggg gttcaactgt gagccatgcg     1980
ttttctagtt tgcttgtttc attcatataa gcttgtatta cttagttccg aaccctgtag     2040
ttttgtagtc tatgttctct tttgtaggga tgtgctgtca taagatgtca tgcaagtttc     2100
ttgtcctaca tatcaataat aagtactcc atggaataat tctcagttct gttttgaatt      2160
ttgcatcttc tcacaaacag tgtgctggtt cctttctgtt actttacatg tctgctgtgt     2220
caggttctga cataacgacc gatggagggt ggtcggcagg tttagaagg ggaattgaaa      2280 cttttttttg ggaagaagtc tgaatacagt tgggaggaaa aatagaagta tatacttcga     2340
```

```
ttaatttatc aagcccgcta tccagtctaa tttatcaagc actagacagt gtagggtgtt    2400
ggcattcttc tcttccttga gatccggctt gagaggagag accgaggctt cggctgtgtt    2460
ggttgctgat ttctacagct ttttgagata gagagagaga tcctgcaact gtggtttgtc    2520
ttgctgcttg tacagcgaga gagacattga gagatatgta gatcgtttac c             2571
```

<210> SEQ ID NO 296
<211> LENGTH: 3893
<212> TYPE: DNA
<213> ORGANISM: Artificial Sequence
<220> FEATURE:
<223> OTHER INFORMATION: pDAS000436

<400> SEQUENCE: 296

```
atgacaaaga tagtcacaat ccaaacagcc catagcctgg cgagtgcaaa tagatacgag      60
atctctggtg atatcacaac cgtccaaatt aattgcttgt ttcagcatca gccttttgc     120 ataaagaagc tagcccaatc tgaaccacac actcacccgc cgcgtgacag cgccaaagac     180
aaaaccatca cccctcccca attccaaccc tctctctgcc tcacagaaat ctcccccctc     240
gcccaaaccc tcgccgccgc catggccgcc gccacctccc ccgccgtcgc attctcgggc     300
gccaccgccg ccgccatgcc caaacccgcc cgccatcctc tcccgcgcca ccagcccgtc     360
tcgcgccgcg cgctcccgc ccgcgtcgtc aggtgttgcg ccgcgtcccc cgccgccacc     420
tccgccgcgc ctcccgcaac cgcgctccgg ccctggggcc cgtccgagcc ccgcaagggc     480
gccgacatcc tcgtcgaggc gctcgagcgc tgcggcatcg tcgacgtctt cgcctacccc     540
ggcggcgcct ccatggagat ccaccaggcg ctgacgcgct cgcccgtcat caccaaccac     600
ctcttccgcc acgagcaggg ggaggcgttc gcggcgtccg gctacgcccg cgcgtccggc     660
cgcgtcggcg tctgcgtcgc cacctccggc ccggggggcca ccaacctcgt ctccgcgctc     720
gccgacgccc tcctcgactc catccccatg gtcgccatta ccgggcaagt gacccgccgc     780
atgatcggca cggacgcgtt ccaggagacg cccatagtgg aggtcacgcg ctccatcacc     840
aagcacaact acctggtcct tgacgtggag gatatccccc gcgtcatcca ggaagccttc     900
ttccttgcat cctctggccg cccgggggccg gtgctagttg atatccccaa ggacatccag     960
cagcagatgg ctgtgcccgt ctgggacact ccaatgagtt tgccagggta catcgcccgc    1020
ctgcccaagc caccatctac tgaatcgctt gagcaggtcc tgcgtctggt tggcgagtca    1080
cggcgcccaa ttctgtatgt tggtggtggc tgcgctgcgt ctggcgagga gttgcgccgc    1140
tttgttgagc ttactgggat tccagttaca actactctga tgggccttgg caacttcccc    1200
agcgacgacc cactgtctct gcgcatgctt gggatgcatg gcactgtgta tgcaaattat    1260
gcagtagata aggctgacct gttgctcgca tttggtgtgc ggtttgatga tcgtgtgact    1320
gggaaaatcg aggcttttgc aagcaggtcc aagattgtgc acattgacat tgacccagct    1380
gagattggca agaacaagca gccacatgtc tccatttgtg cagatgttaa gcttgcttta    1440 cagggggttga atgatctatt aaatgggagc aaagcacaac agggtctgga ttttggtcca    1500
tggcacaagg agttggatca gcagaagagg gagtttcctc taggattcaa gacttttggc    1560
gaggccatcc cgccgcaata tgctatccag gtactggatg agctgacaaa agggaggcg    1620 atcattgcca ctggtgttgg gcagcaccag atgtgggcgg ctcagtatta cacttacaag    1680
cggccacggc agtggctgtc ttcgtctggt ttgggggcaa tgggatttgg gttaccagct    1740
gcagctggcg ctgctgtggc caacccaggt gttacagttg ttgacattga tggtgatggt    1800
agtttcctca tgaacattca ggagttggcg ttgatccgca ttgagaacct cccagtgaag    1860
```

-continued

```
gtgatgatat tgaacaacca gcatctggga atggtggtgc agtgggagga taggttttac     1920
aaggccaatc gggcgcacac ataccttggc aacccagaaa atgagagtga gatatatcca     1980
gattttgtga cgattgctaa aggattcaac gttccagcag ttcgagtgac gaagaagagc     2040
gaagtcactg cagcaatcaa gaagatgctt gagaccccag gccatactt gttggatatc      2100
atagtcccgc atcaggagca cgtgctgcct atgatcccaa gcggtggtgc tttcaaggac     2160
atgatcatgg agggtgatgg caggacctcg tactgaaatt tcgacctaca agacctacaa     2220
gtgtgacatg cgcaatcagc atggtgcccg cgtgttgtat caactactag gggttcaact     2280
gtgaaccatg cgttttctag tttgcttgtt tcattcatat aagcttgtgt tacttagttc     2340
cgaaccctgt agctttgtag tctatgctct cttttgtagg gatgtgctgt cataagatat     2400
catgcaagtt tcttgtccta catatcaata ataagtactt ccatgaaata attctcagtt     2460
ctgttttgaa ttttgcatct tctcacaaac agtgtgctgg ttcctttctg ttctacgccc     2520
gcgcgtccgg ccgcgtcggc gtctgcgtcg ccacctccgg cccggggggcc accaacctcg    2580
tctccgtagc gacttcgtgg gcgaggaaag cctttcgtcc aaggtggtcc ctcctcgcaa     2640
tcttgttgga tggtgaatat tataaaagcc tgcccttctc gcgggtgagt ccatgctcaa     2700
caccgtgcac tagggacagg attggccttt tgcagtttat ccactaggga caggattgca     2760
tcctgccgaa accctgccaa gcttgaggta gcctccaatt tgacggtgcc gccagcgacg     2820
ccgtctggaa ctgtcctttt tgaggaccac tccgtttgtc tagaggtacc tggagatcat     2880
gacattaagg atgaccagtt cgtaaaggtc ctgcggtgtc tattgctttt cataggttaa     2940
taagtgtttg ctagactgtg gtgaaaggcc gccttttgca gtttatctct agaaagactg     3000
gagttgcaga aagactcccg cccatccagg atgaggatga ccatatccga agtaaataaa     3060
accatcggac tctcgtataa gactgtcgac tcgaccggcc gacgcatagg ttcatttgaa     3120
gctgctattc tatttaaatt gaactcgact ccatccccat ggtcgccatc acgggccagg     3180
tcccccgccg catgatcggt agcgacttcg tgggcgagga aagcctttcg tccaaggtgg     3240
tccctcctcg caatcttgtt ggatggtgaa tattataaaa gcctgccctt ctcgcgggta     3300
agactcccgc ccatccagga tgaggatgac cagccttttg cagtttatcc actagggaca     3360
ggattgcatc ctgccgaaac cctgccaagc ttgaggtagc ctccaatttg acggtgccgc     3420
cagcgacgcc gtctggaact gtccttttt g aggaccactc cgtttgactg gattttggtt    3480
ttaggaatta gaaattttat tgatagaagt attttacaaa tacaaataca tactaagggt     3540
ttcttatatg ctcaacacat gagcgaaacc ctataagaac cctaattccc ttatctggga     3600
actactcaca cattattctg gagaaaaata gagagagata gatttgtaga gagagactgg     3660
tgattttgc ggactctatt agatctgggt aactggccta actggccttg gaggagctgg      3720
caactcaaaa tccctttgcc aaaaaccaac atcatgccat ccaccatgct tgtatccagc     3780
tgcgcgcaat gtaccccggg ctgtgtatcc caaagcctca tgcaacctaa cagatggatc     3840
gtttggaagg cctataacag caaccacaga cttaaaacct tgcgcctcca tag            3893
```

<210> SEQ ID NO 297
<211> LENGTH: 24
<212> TYPE: DNA
<213> ORGANISM: artificial sequence
<220> FEATURE:
<223> OTHER INFORMATION: AHASs653ZFN.F2 primer

<400> SEQUENCE: 297

```
gcaatcaaga agatgcttga gacc                                              24

<210> SEQ ID NO 298
<211> LENGTH: 24
<212> TYPE: DNA
<213> ORGANISM: artificial sequence
<220> FEATURE:
<223> OTHER INFORMATION: AHASs653ZFN.R1 primer sequence

<400> SEQUENCE: 298
tcttttgtag ggatgtgctg tcat                                              24

<210> SEQ ID NO 299
<211> LENGTH: 21
<212> TYPE: DNA
<213> ORGANISM: artificial sequence
<220> FEATURE:
<223> OTHER INFORMATION: Forward Primer pDAS434

<400> SEQUENCE: 299
gccaacccag gtgttacagt t                                                 21

<210> SEQ ID NO 300
<211> LENGTH: 20
<212> TYPE: DNA
<213> ORGANISM: artificial sequence
<220> FEATURE:
<223> OTHER INFORMATION: Reverse Primer pDAS434

<400> SEQUENCE: 300
ggctggtcat cctcatcctg                                                   20

<210> SEQ ID NO 301
<211> LENGTH: 57
<212> TYPE: DNA
<213> ORGANISM: artificial sequence
<220> FEATURE:
<223> OTHER INFORMATION: Primer AHASs653ZFN.F2

<400> SEQUENCE: 301
acactctttc cctacacgac gctcttccga tctgcaatca agaagatgct tgagacc          57

<210> SEQ ID NO 302
<211> LENGTH: 57
<212> TYPE: DNA
<213> ORGANISM: artificial sequence
<220> FEATURE:
<223> OTHER INFORMATION: AHASs653ZFN.R3 primer sequence

<400> SEQUENCE: 302
gtgactggag ttcagacgtg tgctcttccg atctcaagca aactagaaaa cgcatgg          57

<210> SEQ ID NO 303
<211> LENGTH: 11938
<212> TYPE: DNA
<213> ORGANISM: artificial sequence
<220> FEATURE:
<223> OTHER INFORMATION: pDAS0000004

<400> SEQUENCE: 303
tgatcacagg cagcaacgct ctgtcatcgt tacaatcaac atgctaccct ccgcgagatc       60
atccgtgttt caaacccggc agcttagttg ccgttcttcc gaatagcatc ggtaacatga      120
gcaaagtctg ccgccttaca acggctctcc cgctgacgcc gtcccggact gatgggctgc      180
ctgtatcgag tggtgatttt gtgccgagct gccggtcggg gagctgttgg ctggctggtg      240
```

```
gcaggatata ttgtggtgta aacaaattga cgcttagaca acttaataac acattgcgga    300 cgttttaat  gtactgaatt aacgccgaat tgaattcgag ctcggtacca ctggattttg   360
gttttaggaa ttagaaattt tattgataga agtattttac aaatacaaat acatactaag   420
ggtttcttat atgctcaaca catgagcgaa accctataag aaccctaatt cccttatctg   480
ggaactactc acacattatt ctggagaaaa atagagagag atagatttgt agagagagac   540
tggtgatttt tgcggactct attagatctg ggtaactggc ctaactggcc ttggaggagc   600
tggcaactca aaatcccttt gccaaaaacc aacatcatgc catccaccat gcttgtatcc   660
agctgcgcgc aatgtacccc gggctgtgta tcccaaagcc tcatgcaacc taacagatgg   720
atcgtttgga aggcctataa cagcaaccac agacttaaaa ccttgcgcct ccatagactt   780
aagcaaatgt gtgtacaatg tggatcctag gcccaacctt tgatgcctat gtgacacgta   840
aacagtactc tcaactgtcc aatcgtaagc gttcctagcc ttccagggcc cagcgtaagc   900
aataccagcc acaacaccct caacctcagc aaccaaccaa gggtatctat cttgcaacct   960
ctcgagatca tcaatccact cttgtggtgt ttgtggctct gtcctaaagt tcactgtaga  1020
cgtctcaatg taatggttaa cgatatcaca aaccgcggcc atatcagctg ctgtagctgg  1080
cctaatctca actggtctcc tctccggaga catggcttct acctacaaaa aagctccgca  1140
cgaggctgca tttgtcacaa atcatgaaaa gaaaaactac cgatgaacaa tgctgaggga  1200
ttcaaattct acccacaaaa agaagaaaga aagatctagc acatctaagc ctgacgaagc  1260
agcagaaata tataaaaata taaaccatag tgccctttc ccctcttcct gatcttgttt   1320
agcatggcgg aaattttaaa cccccccatca tctcccccaa caacggcgga tcgcagatct  1380
acatccgaga gccccattcc ccgcgagatc cgggccggat ccacgccggc gagagcccca  1440
gccgcgagat cccgcccctc ccgcgcaccg atctgggcgc gcacgaagcc gcctctcgcc  1500
cacccaaact accaaggcca aagatcgaga ccgagacgga aaaaaaaaac ggagaaagaa  1560
agaggagagg ggcggggtgg ttaccggcgc ggcggcggcg gaggggggagg ggggaggagc  1620 tcgtcgtccg gcagcgaggg gggaggaggt ggaggtggtg gtggtggtgg tggtagggtt  1680
ggggggatgg gaggagaggg ggggtatgt atatagtggc gatgggggc gtttctttgg    1740 aagcggaggg agggccggcc tcgtcgctgg ctcgcgatcc tcctcgcgtt tccggccccc  1800
acgacccgga cccacctgct gttttttctt tttcttttt ttctttcttt tttttttttt  1860
ggctgcgaga cgtgcggtgc gtgcggacaa ctcacggtga tagtgggggg gtgtggagac  1920
tattgtccag ttggctggac tggggtgggt tgggttgggt tgggttgggc tgggcttgct  1980
atggatcgtg gatagcactt tgggctttag gaactttagg ggttgttttt gtaaatgttt  2040
tgagtctaag tttatctttt atttttacta gaaaaaatac ccatgcgctg caacggggga  2100
aagctatttt aatcttatta ttgttcattg tgagaattcg cctgaatata tattttctc   2160 aaaaattatg tcaaattagc atatgggttt tttaaagat atttcttata caaatccctc   2220
tgtatttaca aaagcaaacg aacttaaaac ccgactcaaa tacagatatg catttccaaa  2280
agcgaataaa cttaaaaacc aattcataca aaaatgacgt atcaaagtac cgacaaaaac  2340
atcctcaatt tttataatag tagaaaagag taaatttcac tttgggccac cttttattac  2400 cgatattta  ctttatacca ccttttaact gatgttttca cttttgacca ggtaatctta  2460
cctttgtttt attttggact atcccgactc tcttctcaag catatgaatg acctcgagta  2520
tgctagtcta gagtcgacct gcaggcatgc aagcttagct tgagcttgga tcagattgtc  2580
```

```
gtttcccgcc ttcagtttat cacaagtttg tacaaaaaag caggctctgc agtgcagcgt    2640
gacccggtcg tgcccctctc tagagataat gagcattgca tgtctaagtt ataaaaaatt    2700
accacatatt tttttgtca cacttgtttg aagtgcagtt tatctatctt tatacatata    2760
tttaaacttt actctacgaa taatataatc tatagtacta caataatatc agtgttttag    2820
agaatcatat aaatgaacag ttagacatgg tctaaaggac aattgagtat tttgacaaca    2880
ggactctaca gttttatctt tttagtgtgc atgtgttctc cttttttttt gcaaatagct    2940
tcacctatat aatacttcat ccatttatt agtacatcca tttagggttt agggttaatg    3000
gtttttatag actaatttt ttagtacatc tattttattc tattttagcc tctaaattaa    3060
gaaaactaaa actctatttt agtttttta tttaataatt tagatataaa atagaataaa    3120
ataaagtgac taaaaattaa acaaataccc tttaagaaat taaaaaaact aaggaaacat    3180
ttttcttgtt tcgagtagat aatgccagcc tgttaaacgc cgtcgacgag tctaacggac    3240
accaaccagc gaaccagcag cgtcgcgtcg ggccaagcga agcagacggc acggcatctc    3300
tgtcgctgcc tctggacccc tctcgagagt tccgctccac cgttggactt gctccgctgt    3360
cggcatccag aaattgcgtg gcggagcggc agacgtgagc cggcacggca ggcggcctcc    3420
tcctcctctc acggcacggc agctacgggg gattcctttc ccaccgctcc ttcgctttcc    3480
cttcctcgcc cgccgtaata aatagacacc ccctccacac cctctttccc caacctcgtg    3540
ttgttcggag cgcacacaca cacaaccaga tctcccccaa atccacccgt cggcacctcc    3600
gcttcaaggt acgccgctcg tcctccccccc cccccctct ctaccttctc tagatcggcg    3660
ttccggtcca tggttagggc ccggtagttc tacttctgtt catgtttgtg ttagatccgt    3720
gtttgtgtta gatccgtgct gctagcgttc gtacacggat gcgacctgta cgtcagacac    3780
gttctgattg ctaacttgcc agtgtttctc tttggggaat cctgggatgg ctctagccgt    3840
tccgcagacg ggatcgattt catgattttt tttgtttcgt tgcatagggt ttggtttgcc    3900
cttttccttt atttcaatat atgccgtgca cttgtttgtc gggtcatctt ttcatgcttt    3960
tttttgtctt ggttgtgatg atgtggtctg gttgggcggt cgttctagat cggagtagaa    4020
ttctgtttca aactacctgg tggatttatt aattttggat ctgtatgtgt gtgccataca    4080
tattcatagt tacgaattga agatgatgga tggaaatatc gatctaggat aggtatacat    4140
gttgatgcgg gttttactga tgcatataca gagatgcttt ttgttcgctt ggttgtgatg    4200
atgtggtgtg gttgggcggt cgttcattcg ttctagatcg gagtagaata ctgtttcaaa    4260
ctacctggtg tatttattaa ttttggaact gtatgtgtgt gtcatacatc ttcatagtta    4320
cgagtttaag atggatggaa atatcgatct aggataggta tacatgttga tgtgggtttt    4380
actgatgcat atacatgatg gcatatgcag catctattca tatgctctaa ccttgagtac    4440
ctatctatta taataaacaa gtatgtttta taattatttt gatcttgata tacttggatg    4500
atggcatatg cagcagctat atgtggattt ttttagccct gccttcatac gctatttatt    4560
tgcttggtac tgtttctttt gtcgatgctc accctgttgt ttggtgttac ttctgcagga    4620
tggcctcctc cgagaacgtg atcaccgagt tcatgcgctt caaggtgcgc atggagggca    4680
ccgtgaacgg ccacgagttc gagatcgagg gcgaggggga gggcaggcca tacgagggcc    4740
acaacaccgt gaagctcaag gtgaccaagg gaggcccact cccattcgcc tgggacatcc    4800
tcagcccaca gttccagtac ggctccaagg tgtacgtgaa gcaccagccc gacatcccag    4860
actacaagaa gctcagcttc ccagagggct tcaagtggga gcgcgtgatg aacttcgagg    4920
acggcggcgt ggccaccgtg acccaagact ccagcctcca ggacggctgc ttcatctaca    4980
```

```
aggtgaagtt catcggcgtg aacttcccat ccgacggccc agtgatgcaa aagaagacca    5040
tgggctggga ggcctccacc gagaggctct acccaaggga cggcgtgctc aagggcgaga    5100
cccacaaggc cctcaagctc aaggacggcg gccactacct cgtcgagttc aagtccatct    5160
acatggccaa gaagccagtc cagctcccag gctactacta cgtggacgcc aagctcgaca    5220
tcacctccca caacgaggac tacaccatcg tcgagcagta cgagcgcacc gagggccgcc    5280
accacctgtt cctctgaaga aggagtgcgt cgaagcagat cgttcaaaca tttggcaata    5340
aagtttctta agattgaatc ctgttgccgg tcttgcgatg attatcatat aatttctgtt    5400
gaattacgtt aagcatgtaa taattaacat gtaatgcatg acgttattta tgagatgggt    5460
ttttatgatt agagtcccgc aattatacat ttaatacgcg atagaaaaca aaatatagcg    5520
cgcaaactag gataaattat cgcgcgcggt gtcatctatg ttactagatc gaacccagct    5580
ttcttgtaca aagtggtgat aaactatcag tgtttgacag gatatattgg cgggtaaacc    5640
taagagaaaa gagcgtttat tagaataatc ggatatttaa aagggcgtga aaaggtttat    5700
ccgttcgtcc atttgtatgt gcatgccaac acagggttcc cctcgggat caaagtactt    5760
taaagtactt taaagtactt taaagtactt tgatccaacc cctccgctgc tatagtgcag    5820
tcggcttctg acgttcagtg cagccgtctt ctgaaaacga catgtcgcac aagtcctaag    5880
ttacgcgaca ggctgccgcc ctgccctttt cctggcgttt tcttgtcgcg tgttttagtc    5940
gcataaagta gaatacttgc gactagaacc ggagacatta cgccatgaac aagagcgccg    6000
ccgctggcct gctgggctat gcccgcgtca gcaccgacga ccaggacttg accaaccaac    6060
gggccgaact gcacgcggcc ggctgcacca agctgttttc cgagaagatc accggcacca    6120
ggcgcgaccg cccggagctg gccaggatgc ttgaccacct acgccctggc gacgttgtga    6180
cagtgaccag gctagaccgc ctggcccgca gcacccgcga cctactggac attgccgagc    6240
gcatccagga ggccggcgcg ggcctgcgta gcctggcaga gccgtgggcc gacaccacca    6300
cgccggccgg ccgcatggtg ttgaccgtgt cgccggcat tgccgagttc gagcgttccc    6360
taatcatcga ccgcacccgg agcgggcgcg aggccgccaa ggcccgaggc gtgaagtttg    6420
gcccccgccc taccctcacc ccggcacaga tcgcgcacgc ccgcgagctg atcgaccagg    6480
aaggccgcac cgtgaaagag gcggctgcac tgcttggcgt gcatcgctcg accctgtacc    6540
gcgcacttga gcgcagcgag gaagtgacgc ccaccgagc caggcggcgc ggtgccttcc    6600
gtgaggacgc attgaccgag gccgacgccc tggcggccgc cgagaatgaa cgccaagagg    6660
aacaagcatg aaaccgcacc aggacggcca ggacgaaccc ttttcatta ccgaagagat    6720
cgaggcggag atgatcgcgg ccgggtacgt gttcgagccg cccgcgcacg tctcaaccgt    6780
gcggctgcat gaaatcctgg ccggtttgtc tgatgccaag ctggcggcct ggccggccag    6840
cttggccgct gaagaaaccg agcgccgccg tctaaaaagg tgatgtgtat ttgagtaaaa    6900
cagcttgcgt catgcggtcg ctgcgtatat gatgcgatga gtaaataaac aaatacgcaa    6960
ggggaacgca tgaaggttat cgctgtactt aaccagaaag gcgggtcagg caagacgacc    7020
atcgcaaccc atctagcccg cgccctgcaa ctcgccgggg ccgatgttct gttagtcgat    7080
tccgatcccc agggcagtgc ccgcgattgg gcggccgtgc gggaagatca accgctaacc    7140
gttgtcggca tcgaccgccc gacgattgac cgcgacgtga aggccatcgg ccggcgcgac    7200
ttcgtagtga tcgacggagc gccccaggcg gcggacttgg ctgtgtccgc gatcaaggca    7260
gccgacttcg tgctgattcc ggtgcagcca agcccttacg acatatgggc caccgccgac    7320
```

-continued

```
ctggtggagc tggttaagca gcgcattgag gtcacggatg gaaggctaca agcggccttt     7380
gtcgtgtcgc gggcgatcaa aggcacgcgc atcggcggtg aggttgccga ggcgctggcc     7440
gggtacgagc tgcccattct tgagtcccgt atcacgcagc gcgtgagcta cccaggcact     7500
gccgccgccg gcacaaccgt tcttgaatca gaacccgagg gcgacgctgc ccgcgaggtc     7560
caggcgctgg ccgctgaaat taaatcaaaa ctcatttgag ttaatgaggt aaagagaaaa     7620
tgagcaaaag cacaaacacg ctaagtgccg gccgtccgag cgcacgcagc agcaaggctg     7680
caacgttggc cagcctggca gacacgccag ccatgaagcg ggtcaacttt cagttgccgg     7740
cggaggatca caccaagctg aagatgtacg cggtacgcca aggcaagacc attaccgagc     7800
tgctatctga atacatcgcg cagctaccag agtaaatgag caaatgaata aatgagtaga     7860
tgaattttag cggctaaagg aggcggcatg gaaaatcaag aacaaccagg caccgacgcc     7920
gtggaatgcc ccatgtgtgg aggaacgggc ggttggccag gcgtaagcgg ctgggttgtc     7980
tgccggccct gcaatggcac tggaaccccc aagcccgagg aatcggcgtg agcggtcgca     8040
aaccatccgg cccggtacaa atcggcgcgg cgctgggtga tgacctggtg gagaagttga     8100
aggccgcgca ggccgcccag cggcaacgca tcgaggcaga agcacgcccc ggtgaatcgt     8160
ggcaagcggc cgctgatcga atccgcaaag aatcccggca accgccggca gccggtgcgc     8220
cgtcgattag gaagccgccc aagggcgacg agcaaccaga ttttttcgtt ccgatgctct     8280
atgacgtggg caccccgcgat agtcgcagca tcatggacgt ggccgttttc cgtctgtcga     8340
agcgtgaccg acgagctggc gaggtgatcc gctacgagct tccagacggg cacgtagagg     8400
tttccgcagg gccggccggc atggccagtg tgtgggatta cgacctggta ctgatggcgg     8460
tttcccatct aaccgaatcc atgaaccgat accgggaagg aagggagac aagcccggcc     8520 gcgtgttccg tccacacgtt gcggacgtac tcaagttctg ccggcgagcc gatggcggaa     8580
agcagaaaga cgacctggta gaaacctgca ttcggttaaa caccacgcac gttgccatgc     8640
agcgtacgaa gaaggccaag aacggccgcc tggtgacggt atccgagggt gaagccttga     8700
ttagccgcta caagatcgta aagagcgaaa ccgggcggcc ggagtacatc gagatcgagc     8760
tagctgattg gatgtaccgc gagatcacag aaggcaagaa cccggacgtg ctgacggttc     8820
accccgatta cttttttgatc gatcccggca tcggccgttt tctctaccgc ctggcacgcc     8880
gcgccgcagg caaggcagaa gccagatggt tgttcaagac gatctacgaa cgcagtggca     8940
gcgccggaga gttcaagaag ttctgtttca ccgtgcgcaa gctgatcggg tcaaatgacc     9000
tgccggagta cgatttgaag gaggaggcgg ggcaggctgg cccgatccta gtcatgcgct     9060
accgcaacct gatcgagggc gaagcatccg ccggttccta atgtacggag cagatgctag     9120
ggcaaattgc cctagcaggg gaaaaaggtc gaaaaggtct ctttcctgtg gatagcacgt     9180
acattgggaa cccaaagccg tacattggga accggaaccc gtacattggg aacccaaagc     9240
cgtacattgg gaaccggtca cacatgtaag tgactgatat aaaagagaaa aaaggcgatt     9300
tttccgccta aaactcttta aaacttatta aaactcttaa acccgcctg gcctgtgcat     9360 aactgtctgg ccagcgcaca gccgaagagc tgcaaaaagc gcctaccctt cggtcgctgc     9420 gctcctacg ccccgccgct tcgcgtcggc ctatcgcggc cgctggccgc tcaaaaatgg     9480
ctggcctacg gccaggcaat ctaccagggc gcggacaagc cgcgccgtcg ccactcgacc     9540
gccggcgccc acatcaaggc accctgcctc gcgcgtttcg gtgatgacgg tgaaaacctc     9600
tgacacatgc agctcccgga gacggtcaca gcttgtctgt aagcggatgc cgggagcaga     9660
caagcccgtc agggcgcgtc agcgggtgtt ggcgggtgtc ggggcgcagc catgacccag     9720
```

```
tcacgtagcg atagcggagt gtatactggc ttaactatgc ggcatcgagg cagattgtac   9780
tgagagtgca ccatatgcgg tgtgaaatac cgcacagatg cgtaaggaga aaataccgca   9840
tcaggcgctc ttccgcttcc tcgctcactg actcgctgcg ctcggtcgtt cggctgcggc   9900
gagcggtatc agctcactca aaggcggtaa tacggttatc cacagaatca ggggataacg   9960
caggaaagaa catgtgagca aaaggccagc aaaaggccag gaaccgtaaa aaggccgcgt  10020
tgctggcgtt tttccatagg ctccgccccc ctgacgagca tcacaaaaat cgacgctcaa  10080
gtcagaggtg gcgaaacccg acaggactat aaagatacca ggcgtttccc cctggaagct  10140
ccctcgtgcg ctctcctgtt ccgaccctgc cgcttaccgg atacctgtcc gcctttctcc  10200
cttcgggaag cgtggcgctt tctcatagct cacgctgtag gtatctcagt tcggtgtagg  10260
tcgttcgctc caagctgggc tgtgtgcacg aaccccccgt tcagcccgac cgctgcgcct  10320
tatccggtaa ctatcgtctt gagtccaacc cggtaagaca cgacttatcg ccactggcag  10380
cagccactgg taacaggatt agcagagcga ggtatgtagg cggtgctaca gagttcttga  10440
agtggtggcc taactacggc tacactagaa ggacagtatt tggtatctgc gctctgctga  10500
agccagttac cttcggaaaa agagttggta gctcttgatc cggcaaacaa accaccgctg  10560
gtagcggtgg tttttttgtt tgcaagcagc agattacgcg cagaaaaaaa ggatctcaag  10620
aagatccttt gatcttttct acggggtctg acgctcagtg gaacgaaaac tcacgttaag  10680
ggattttggt catgcatgat atatctccca atttgtgtag ggcttattat gcacgcttaa  10740
aaataataaa agcagacttg acctgatagt ttggctgtga gcaattatgt gcttagtgca  10800
tctaacgctt gagttaagcc gcgccgcgaa gcggcgtcgg cttgaacgaa tttctagcta  10860
gacattattt gccgactacc ttggtgatct cgcctttcac gtagtggaca aattcttcca  10920
actgatctgc gcgcgaggcc aagcgatctt cttcttgtcc aagataagcc tgtctagctt  10980
caagtatgac gggctgatac tgggccggca ggcgctccat tgcccagtcg gcagcgacat  11040
ccttcggcgc gattttgccg gttactgcgc tgtaccaaat gcgggacaac gtaagcacta  11100
catttcgctc atcgccagcc cagtcggggcg gcgagttcca tagcgttaag gtttcattta  11160
gcgcctcaaa tagatcctgt tcaggaaccg gatcaaagag ttcctccgcc gctggaccta  11220
ccaaggcaac gctatgttct cttgcttttg tcagcaagat agccagatca atgtcgatcg  11280
tggctggctc gaagatacct gcaagaatgt cattgcgctg ccattctcca aattgcagtt  11340
cgcgcttagc tggataacgc cacggaatga tgtcgtcgtg cacaacaatg gtgacttcta  11400
cagcgcggag aatctcgctc tctccagggg aagccgaagt ttccaaaagg tcgttgatca  11460
aagctcgccg cgttgtttca tcaagcctta cggtcaccgt aaccagcaaa tcaatatcac  11520
tgtgtggctt caggccgcca tccactgcgg agccgtacaa atgtacggcc agcaacgtcg  11580
gttcgagatg cgctcgatg acgccaacta cctctgatag ttgagtcgat acttcggcga  11640
tcaccgcttc ccccatgatg tttaactttg ttttagggcg actgccctgc tgcgtaacat  11700
cgttgctgct ccataacatc aaacatcgac ccacggcgta acgcgcttgc tgcttggatg  11760
cccgaggcat agactgtacc ccaaaaaaac agtcataaca agccatgaaa accgccactg  11820
cgccgttacc accgctgcgt tcggtcaagg ttctggacca gttgcgtgag cgcatacgct  11880
acttgcatta cagcttacga accgaacagg cttatgtcca ctgggttcgt gcccgaat    11938
```

<210> SEQ ID NO 304  
<211> LENGTH: 341  
<212> TYPE: DNA

```
<213> ORGANISM: artificial sequence
<220> FEATURE:
<223> OTHER INFORMATION: yc06-9110-1 (A-genome ; WT allele)

<400> SEQUENCE: 304
gcaatcaaga agatgcttga accccaggg ccatacttgt tggatatcat cgtcccgcat      60
caggagcacg tgctgcctat gatcccaagc ggtggtgctt tcaaggacat gatcatggag    120
ggtgatggca ggacctcgta ctgaaatttc gacctacaag acctacaagt gtgacatgcg    180
caatcagcat ggtgcccgcg tgttgtatca actactaggg gttcaactgt gaaccatgcg    240
ttttctagtt tgcttgtttc attcatataa gcttgtgtta cttagttccg aaccctgtag    300
ctttgtagtc tatgctctct tttgtaggga tgtgctgtca t                        341

<210> SEQ ID NO 305
<211> LENGTH: 341
<212> TYPE: DNA
<213> ORGANISM: artificial sequence
<220> FEATURE:
<223> OTHER INFORMATION: yc06-9110-1 (A-genome ; WT allele)

<400> SEQUENCE: 305
gcaatcaaga agatgcttga accccaggg ccatacttgt tggatatcat cgtcccgcat      60
caggagcacg tgctgcctat gatcccaagc ggtggtgctt tcaaggacat gatcatggag    120
ggtgatggca ggacctcgta ctgaaatttc gacctacaag acctacaagt gtgacatgcg    180
caatcagcat ggtgcccgcg tgttgtatca actactaggg gttcaactgt gaaccatgcg    240
ttttctagtt tgcttgtttc attcatataa gcttgtgtta cttagttccg aaccctgtag    300
ctttgtagtc tatgctctct tttgtaggga tgtgctgtca t                        341

<210> SEQ ID NO 306
<211> LENGTH: 341
<212> TYPE: DNA
<213> ORGANISM: artificial sequence
<220> FEATURE:
<223> OTHER INFORMATION: yc06-9110-1 (B-genome ; WT allele)

<400> SEQUENCE: 306
gcaatcaaga agatgcttga accccaggg ccatacttgt tggatatcat cgtcccgcat      60
caggagcacg tgctgcctat gatcccaagc ggtggtgctt tcaaggacat gatcatggag    120
ggtgatggca ggacctcgta ctgaaatttc gacctacaag acctacaagt gtgacatgcg    180
caatcagcat ggtgcccgcg tgttgtatca actactaggg gttcaactgt gaaccatgcg    240
ttttctagtt tgcttgtttc attcatataa gcttgtgtta cttagttccg aaccctgtag    300
ctttgtagtc tatgctctct tttgtaggga tgtgctgtca t                        341

<210> SEQ ID NO 307
<211> LENGTH: 440
<212> TYPE: DNA
<213> ORGANISM: artificial sequence
<220> FEATURE:
<223> OTHER INFORMATION: yc06-9110-1 (B-genome ; ED allele)

<400> SEQUENCE: 307
gcaatcaaga agatgcttga accccaggg ccatacttgt tggatatcat tgtcccgcat      60
caggagcacg tgctgcctat gattcccaat ggcggcgctt tcaaggacat gatcatggag    120
ggtgatggca ggacctcgta ctgaaatggt ccgaagtcca cgccgccaac tacgagtatg    180
atcccaagcg gtggtgcttt taaggacatg atcatggagg gtgatggcag gacctcgtac    240
```

```
tgaaatttcg acctacaaga cctacaagtg tgacatgcgc aatcagcatg atacctgcgt        300
gttgtatcaa ctactggggg ttcaactgtg aaccatgcgt tttctagttt gcttgtttca        360
ttcatataag cttgtgttac ttagttccga accgtgtagt tttgtagtct ctgttctctt        420
ttgtagggat gtgctgtcat                                                    440

<210> SEQ ID NO 308
<211> LENGTH: 346
<212> TYPE: DNA
<213> ORGANISM: artificial sequence
<220> FEATURE:
<223> OTHER INFORMATION: yc06-9110-1 (D-genome ; WT allele)

<400> SEQUENCE: 308
gcaatcaaga agatgcttga gaccccaggg ccatacttgt tggatatcat agtcccgcat         60
caggagcacg tgctgcctat gatcccaagc ggtggtgctt tcaaggacat gatcatggag        120
ggtgatggca ggacctcgta ctgaaatttc gacctacaag acctacaagt gtgacatgcg        180
caatcagcat gatgcccgcg tgttgtatca actactaggg gttcaactgt gagccatgcg        240
ttttctagtt tgcttgtttc attcatataa gcttgtatta cttagttccg aaccctgtag        300
ttttgtagtc tatgttctct tttgtaggga tgtgctgtca taagat                       346

<210> SEQ ID NO 309
<211> LENGTH: 346
<212> TYPE: DNA
<213> ORGANISM: artificial sequence
<220> FEATURE:
<223> OTHER INFORMATION: yc06-9110-1 (D-genome ; WT allele

<400> SEQUENCE: 309
gcaatcaaga agatgcttga gaccccaggg ccatacttgt tggatatcat agtcccgcat         60
caggagcacg tgctgcctat gatcccaagc ggtggtgctt tcaaggacat gatcatggag        120
ggtgatggca ggacctcgta ctgaaatttc gacctacaag acctacaagt gtgacatgcg        180
caatcagcat gatgcccgcg tgttgtatca actactaggg gttcaactgt gagccatgcg        240
ttttctagtt tgcttgtttc attcatataa gcttgtatta cttagttccg aaccctgtag        300
ttttgtagtc tatgttctct tttgtaggga tgtgctgtca taagat                       346

<210> SEQ ID NO 310
<211> LENGTH: 437
<212> TYPE: DNA
<213> ORGANISM: artificial sequence
<220> FEATURE:
<223> OTHER INFORMATION: yr00-9311-1 (A-genome ; ED allele)

<400> SEQUENCE: 310
gcaatcaaga agatgcttga gaccccaggg ccatacttgt tggatatcat cgtcccgcat         60
caggagcacg tgctgcctat gattcccaat ggcggcgctt tcaaggacat gatcatggag        120
ggtgatggca ggacctcgta ctgaaatggt ccgaaggtcc caagcggtgg tgctttcaag        180
gacatgatca tggagggtga tgcaggacc tcgtactgaa atttcgacct acaagaccta        240
cgacctacaa gacctacaag tgtgacatgc gcaatcagca tggtgcccgc gtgttgtatc        300
aactactagg ggttcaactg tgaaccatgc gttttctagt ttgcttgttt cattcatata        360
agcttgtgtt acttagttcc gaaccctgta gctttgtagt ctatgctctc ttttgtaggg        420
atgtgctgtc ataagat                                                       437
```

<210> SEQ ID NO 311
<211> LENGTH: 387
<212> TYPE: DNA
<213> ORGANISM: artificial sequence
<220> FEATURE:
<223> OTHER INFORMATION: yr00-9311-1 (A-genome ; ED allele)

<400> SEQUENCE: 311

```
gcaatcaaga agatgcttga daccccaggg ccatacttgt tggatatcat cgtcccgcat      60
caggagcacg tgctgcccca tcaccctcca tgatcatgtc cttgaaagcg ccgcattggg     120
aataataatc ccaagcggtg gtgctttcaa ggacatgatc atggagggtg atggcaggac     180
ctcgtactga aatttcgacc tacaagacct acaagtgtga catgcgcaat cagcatggtg     240
cccgcgtgtt gtatcaacta ctagggttc aactgtgaac catgcgtttt ctagtttgct     300
tgtttcattc atataagctt gtgttactta gttccgaacc ctgtagcttt gtagtctatg     360
ctctcttttg tagggatgtg ctgtcat                                         387
```

<210> SEQ ID NO 312
<211> LENGTH: 346
<212> TYPE: DNA
<213> ORGANISM: artificial sequence
<220> FEATURE:
<223> OTHER INFORMATION: yr00-9311-1 (D-genome ; WT allele)

<400> SEQUENCE: 312

```
gcaatcaaga agatgcttga daccccaggg ccatacttgt tggatatcat agtcccgcat      60
caggagcacg tgctgcctat gatcccaagc ggtggtgctt tcaaggacat gatcatggag     120
ggtgatggca ggacctcgta ctgaaatttc gacctacaag acctacaagt gtgacatgcg     180
caatcagcat gatgcccgcg tgttgtatca actactaggg gttcaactgt gagccatgcg     240
ttttctagtt tgcttgtttc attcatataa gcttgtatta cttagttccg aaccctgtag     300
ttttgtagtc tatgttctct tttgtaggga tgtgctgtca taagat                    346
```

<210> SEQ ID NO 313
<211> LENGTH: 346
<212> TYPE: DNA
<213> ORGANISM: artificial sequence
<220> FEATURE:
<223> OTHER INFORMATION: yr00-9311-1 (D-genome ; WT allele)

<400> SEQUENCE: 313

```
gcaatcaaga agatgcttga daccccaggg ccatacttgt tggatatcat agtcccgcat      60
caggagcacg tgctgcctat gatcccaagc ggtggtgctt tcaaggacat gatcatggag     120
ggtgatggca ggacctcgta ctgaaatttc gacctacaag acctacaagt gtgacatgcg     180
caatcagcat gatgcccgcg tgttgtatca actactaggg gttcaactgt gagccatgcg     240
ttttctagtt tgcttgtttc attcatataa gcttgtatta cttagttccg aaccctgtag     300
ttttgtagtc tatgttctct tttgtaggga tgtgctgtca taagat                    346
```

<210> SEQ ID NO 314
<211> LENGTH: 3336
<212> TYPE: DNA
<213> ORGANISM: artificial sequence
<220> FEATURE:
<223> OTHER INFORMATION: QA_pDAS000434

<400> SEQUENCE: 314

```
ccactcttgc cctacacgac actgaagacc ttatgattcc aaacggcggc gccttcaagg      60
```

```
acatgatcat ggagggtgat ggcaggacct cgtactgaaa tttcgaccta caagacctac      120
aagtgtgaca tgcgcaatca gcatggtgcc cgcgtgttgt atcaactact aggggttcaa      180
ctgtgaacca tgcgttttct agtttgcttg tttcattcat ataagcttgt gttacttagt      240
tccgaaccct gtagctttgt agtctatgct ctcttttgta gggatgtgct gtcataagat      300
atcatgcaag tttcttgtcc tacatatcaa taataagtac ttccatggaa taattctcag      360
ttctgttttg aattttgcat cttctcacaa acagtgtgct ggttcctttc tgttcgctga      420
cgccctcctc gactccatcc ccatggtcgc catcacgggc caggtccccc gccgcatgat      480
cggtagcgac ttcgtgggcg aggaaagcct ttcgtccaag gtggtccctc ctcgcaatct      540
tgttggatgg tgaatattat aaaagcctgc ccttctcgcg ggtaagactc ccgcccatcc      600
aggatgagga tgaccagcct tttgcagttt atccactagg gacaggattg catcctgccg      660
aaaccctgcc aagcttgagg tagcctccaa tttgacggtg ccgccagcga cgccgtctgg      720
aactgtcctt tttgaggacc actccgtttg tctagactag catactcgag gtcattcata      780
tgcttgagaa gagagtcggg atagtccaaa ataaaacaaa ggtaagatta cctggtcaaa      840
agtgaaaaca tcagttaaaa ggtggtataa agtaaaatat cggtaataaa aggtggccca      900
aagtgaaatt tactcttttc tactattata aaaattgagg atgtttttgt cggtactttg      960
atacgtcatt tttgtatgaa ttggttttta agtttattcg cttttggaaa tgcatatctg     1020
tatttgagtc gggttttaag ttcgtttgct tttgtaaata cagagggatt tgtataagaa     1080
atatctttaa aaaacccat atgctaattt gacataattt ttgagaaaaa tatatattca     1140
ggcgaattct cacaatgaac aataataaga ttaaaatagc tttcccccgt tgcagcgcat     1200 gggtatttt tctagtaaaa ataaaagata aacttagact caaaacattt acaaaaacaa     1260
cccctaaagt tcctaaagcc caaagtgcta tccacgatcc atagcaagcc cagcccaacc     1320
caacccaacc caacccaccc cagtccagcc aactggacaa tagtctccac acccccccac     1380
tatcaccgtg agttgtccgc acgcaccgca cgtctcgcag ccaaaaaaaa aaaagaaag     1440 aaaaaaaaga aaaagaaaaa acagcaggtg ggtccgggtc gtgggggccg gaaacgcgag     1500
gaggatcgcg agccagcgac gaggccggcc ctccctccgc ttccaaagaa acgccccca     1560 tcgccactat atacatacc cccccctctcc tcccatcccc caacccetac caccaccacc     1620 accaccacct ccacctcctc cccccctcgct gccggacgac gagctcctcc cccctcccce     1680 tccgccgccg ccgcgccggt aaccaccccg cccctctcct cttcttctct ccgtttttt     1740 tttccgtctc ggtctcgatc tttggccttg gtagttgggg tgggcgagag gcggcttcgt     1800
gcgcgcccag atcggtgcgc gggaggggcg ggatctcgcg gctgggctc tcgccggcgt     1860 ggatccggcc cggatctcgc ggggaatggg gctctcggat gtagatctgc gatccgccgt     1920
tgttggggga gatgatgggg ggtttaaaat ttccgccatg ctaaacaaga tcaggaagag     1980
gggaaaaggg cactatggtt tatatttta tatatttctg ctgcttcgtc aggcttagat     2040
gtgctagatc tttctttctt cttttttgtgg gtagaatttg aatccctcag cattgttcat     2100
cggtagtttt tcttttcatg atttgtgaca aatgcagcct cgtgcggagc tttttttgtag     2160 gtagaagcca tgtctccgga gaggagacca gttgagatta ggccagctac agcagctgat     2220
atggccgcgg tttgtgatat cgttaaccat tacattgaga cgtctacagt gaactttagg     2280
acagagccac aaaccaccaca agagtggatt gatgatctcg agaggttgca agatagatac     2340
ccttggttgg ttgctgaggt tgagggtgtt gtggctggta ttgcttacgc tgggccctgg     2400
```

-continued

```
aaggctagga acgcttacga ttggacagtt gagagtactg tttacgtgtc acataggcat    2460
caaaggttgg gcctaggatc cacattgtac acacatttgc ttaagtctat ggaggcgcaa    2520
ggttttaagt ctgtggttgc tgttataggc cttccaaacg atccatctgt taggttgcat    2580
gaggctttgg gatacacagc ccggggtaca ttgcgcgcag ctggatacaa gcatggtgga    2640
tggcatgatg ttggtttttg gcaaagggat tttgagttgc cagctcctcc aaggccagtt    2700
aggccagtta cccagatcta atagagtccg caaaaatcac cagtctctct ctacaaatct    2760
atctctctct atttttctcc agaataatgt gtgagtagtt cccagataag ggaattaggg    2820
ttcttatagg gtttcgctca tgtgttgagc atataagaaa cccttagtat gtatttgtat    2880
ttgtaaaata cttctatcaa taaaatttct aattcctaaa accaaaatcc agtggtacct    2940
ggagatcatg acattaagga tgaccagttc gtaaaggtcc tgcggtgtct attgcttttc    3000
ataggttaat aagtgtttgc tagactgtgg tgaaaggcca agactcccgc ccatctctct    3060
atgcccggga caagtgccac cccacagtgg ggcaggatga ggatgaccaa agactcccgc    3120
ccatctcact agggacagga ttggccttt gcagtttatc tctatgcccg ggacaagtgt     3180
atccgaagta aataaaacca tcggactctc gtataagact gtcgactcga ccggccgacg    3240
cataggttca tttgaagctg ctattctatt taaattgaaa ctcggacggt agcagtgtgg    3300
tatgaggtct tcagcacact cggtaactcc agtcac                              3336
```

METHODS AND COMPOSITIONS FOR INTEGRATION OF AN EXOGENOUS SEQUENCE WITHIN THE GENOME OF PLANTS

CROSS-REFERENCE TO RELATED APPLICATIONS

The present application is a divisional of U.S. application Ser. No. 14/243,553, filed Apr. 2, 2014 which claims the benefit of U.S. Provisional Application No. 61/809,097, filed on Apr. 5, 2013 and U.S. Provisional Application No. 61/820,461, filed on May 7, 2013, the disclosures of which are hereby incorporated by reference in their entireties herein.

STATEMENT OF RIGHTS TO INVENTIONS MADE UNDER FEDERALLY SPONSORED RESEARCH

Not applicable.

REFERENCE TO SEQUENCE LISTING SUBMITTED ELECTRONICALLY

The official copy of the sequence listing is submitted electronically via EFS-Web as an ASCII formatted sequence listing concurrently with the specification. The sequence listing contained in this ASCII formatted document is part of the specification and is herein incorporated by reference in its entirety.

TECHNICAL FIELD

The present disclosure is in the field of genomic engineering, particularly in the integration of exogenous sequences into plants, including simultaneous genomic editing of multiple alleles over multiple genomes, including in polyploid plants.

BACKGROUND

To meet the challenge of increasing global demand for food production, many effective approaches to improving agricultural productivity (e.g., enhanced yield or engineered pest resistance) rely on either mutation breeding or introduction of novel genes into the genomes of crop species by transformation. Both processes are inherently non-specific and relatively inefficient. For example, conventional plant transformation methods deliver exogenous DNA that integrates into the genome at random locations. The random nature of these methods makes it necessary to generate and screen hundreds of unique random-integration events per construct in order to identify and isolate transgenic lines with desirable attributes. Moreover, conventional transformation methods create several challenges for transgene evaluation including: (a) difficulty for predicting whether pleiotropic effects due to unintended genome disruption have occurred; and (b) difficulty for comparing the impact of different regulatory elements and transgene designs within a single transgene candidate, because such comparisons are complicated by random integration into the genome. As a result, conventional plant trait engineering is a laborious and cost intensive process with a low probability of success.

Precision gene modification overcomes the logistical challenges of conventional practices in plant systems, and as such has been a longstanding but elusive goal in both basic plant biology research and agricultural biotechnology. However, with the exception of "gene targeting" via positive-negative drug selection in rice or the use of pre-engineered restriction sites, targeted genome modification in all plant species, both model and crop, has until recently proven very difficult. Terada et al. (2002) *Nat Biotechnol* 20(10):1030; Terada et al. (2007) *Plant Physiol* 144(2):846; D'Halluin et al. (2008) *Plant Biotechnology J.* 6(1):93.

Recently, methods and compositions for targeted cleavage of genomic DNA have been described. Such targeted cleavage events can be used, for example, to induce targeted mutagenesis, induce targeted deletions of cellular DNA sequences, and facilitate targeted recombination and integration at a predetermined chromosomal locus. See, for example, Urnov et al. (2010) *Nature* 435(7042):646-51; U.S. Pat. Nos. 8,586,526; 8,586,363; 8,409,861; 8,106,255; 7,888,121; 8,409,861 and U.S. Patent Publications 20030232410; 20050026157; 20090263900; 20090117617; 20100047805; 20100257638; 20110207221; 20110239315; 20110145940, the disclosures of which are incorporated by reference in their entireties for all purposes. Cleavage can occur through the use of specific nucleases such as engineered zinc finger nucleases (ZFN), transcription-activator like effector nucleases (TALENs), or using the CRISPR/Cas system with an engineered crRNA/tracr RNA ('single guide RNA') to guide specific cleavage. U.S. Patent Publication No. 20080182332 describes the use of non-canonical zinc finger nucleases (ZFNs) for targeted modification of plant genomes; U.S. Pat. No. 8,399,218 describes ZFN-mediated targeted modification of a plant EPSPS locus; U.S. Pat. No. 8,329,986 describes targeted modification of a plant Zp15 locus and U.S. Pat. No. 8,592,645 describes targeted modification of plant genes involved in fatty acid biosynthesis. In addition, Moehle et al. (2007) *Proc. Natl. Acad, Sci. USA* 104(9):3055-3060 describes using designed ZFNs for targeted gene addition at a specified locus. U.S. Patent Publication 20110041195 describes methods of making homozygous diploid organisms.

Transgene (or trait) stacking has great potential for production of plants, but has proven difficult. See, e.g., Halpin (2005) *Plant Biotechnology Journal* 3:141-155. In addition, polyploidy, where the organism has two or more duplicated (autoploidy) or related (alloploid) paired sets of chromosomes, occurs more often in plant species than in animals. For example, wheat has lines that are diploid (two sets of chromosomes), tetraploid (four sets of chromosomes) and hexaploid (six sets of chromosomes). In addition, many agriculturally important plants of the genus *Brassica* are also allotetraploids.

Thus, there remains a need for compositions and methods for the identification, selection and rapid advancement of stable targeted integration into precise locations within a plant genome, including simultaneous modification of multiple alleles across different genomes of polyploid plants, for establishing stable, heritable genetic modifications in a plant and its progeny.

SUMMARY

The present disclosure provides methods and compositions for precision transformation, gene targeting, targeted genomic modification and protein expression in plants. In particular, the present disclosure describes a novel, transgenic marker-free strategy for integrating an exogenous sequence and to stack traits that exploit differential selection at an endogenous locus (e.g., the acetohydroxyacid synthase (AHAS) locus) in plant genomes. The strategy facilitates generation of plants that have one or more transgenes (or one or more genes of interest (GOI), wherein the transgenes do not include transgenic selectable marker genes) precisely positioned at an endogenous plant locus, for example, at one or more AHAS paralogs. The methods and compositions described herein enable both parallel and sequential transgene stacking in plant genomes at precisely the same genomic location, including simultaneous editing of multiple alleles across multiple genomes of polyploid plant species. In addition, the methods and compositions of the invention allow for exogenous transgenic selectable marker-free selection and/or genomic modification of an endogenous gene in which the genomic modification produces a mutation in the endogenous gene such that the endogenous gene produces a product that results in an herbicide tolerant plant (e.g., by virtue of exploiting known mutations in an endogenous gene such as known mutations in AHAS gene that confer tolerance to Group B herbicides, or ALS inhibitor herbicides such as imidazolinone or sulfonylurea). Also provided are cells (e.g., seeds), cell lines, organisms (e.g., plants), etc. comprising these transgene-stacked and/or simultaneously-modified alleles. The targeted genomic editing (insertions, deletions, mutations, transgene stacking) can result, for example, in increased crop yield, a protein encoding disease resistance, a protein that increases growth, a protein encoding insect resistance, a protein encoding herbicide tolerance and the like. Increased yield can include, for example, increased amount of fruit or grain yield, increased biomass of the plant (or fruit or grain of the plant), higher content of fruit flesh, larger plants, increased dry weight, increased solids context, higher total weight at harvest, enhanced intensity and/or uniformity of color of the crop, altered chemical (e.g., oil, fatty acid, carbohydrate, protein) characteristics, etc.

Thus, in one aspect, disclosed herein are methods and compositions for precise, genomic modification (e.g., transgene stacking) at one or more endogenous alleles of a plant gene. In certain embodiments, the transgene(s) is(are) integrated into an endogenous locus of a plant genome (e.g., polyploid plant). Transgene integration includes integration of multiple transgenes, which may be in parallel (simultaneous integration of one or more transgenes into one or more alleles) or sequential. In certain embodiments, the transgene does not include a transgenic marker, but is integrated into an endogenous locus that is modified upon integration of the transgene comprising a trait, for example, integration of the transgene(s) into an endogenous acetohydroxyacid synthase (AHAS) locus (e.g., the 3' untranslated region of the AHAS locus) such that the transgene is expressed and the AHAS locus is modified to alter herbicide tolerance (e.g., Group B herbicides, or ALS inhibitor herbicides such as imidazolinone or sulfonylurea). The transgene(s) is(are) integrated in a targeted manner using one or more non-naturally occurring nucleases, for example zinc finger nucleases, meganucleases, TALENs and/or a CRISPR/Cas system with an engineered single guide RNA. The transgene can comprise one or more coding sequences (e.g., proteins), non-coding sequences and/or may produce one or more RNA molecules (e.g., mRNA, RNAi, siRNA, shRNA, etc.). In certain embodiments, the transgene integration is simultaneous (parallel). In other embodiments, sequential integration of one or more transgenes (GOIs) is achieved, for example by the AHAS locus, by alternating between different herbicide (Group B, or ALS inhibitor herbicides such as imidazolinone or sulfonylurea) chemical selection agents and known AHAS mutations conferring tolerance to those specific herbicides. Furthermore, any of the plant cells described herein may further comprise one or more additional transgenes, in which the additional transgenes are integrated into the genome at a different locus (or different loci) than the target allele(s) for transgene stacking. Thus, a plurality of endogenous loci may include integrated transgenes in the cells described herein.

In another aspect, disclosed herein are polyploid plant cells in which multiple alleles of one or more genes across the different genomes (sub-genomes) have been simultaneously modified. The targeted modifications may enhance or reduce gene activity (e.g., endogenous gene activity and/or activity of an integrated transgene) in the polyploid plant, for example mutations in AHAS that alter (e.g., increase) herbicide tolerance.

In certain embodiments, the targeted genomic modification in the polyploid plant cell comprises a small insertion and/or deletion, also known as an indel. Any of the plant cells described herein may be within a plant or plant part (e.g., seeds, flower, fruit), for example, any variety of: wheat, soy, maize, potato, alfalfa, rice, barley, sunflower, tomato, *Arabidopsis*, cotton, *Brassica* species (including but not limited to *B. napus, B. rapa, B. oleracea, B. nigra, B. juncea, B. carinata*), *Brachypodium*, timothy grass and the like.

In another aspect, described herein is a DNA-binding domain (e.g., zinc finger protein (ZFP)) that specifically binds to a gene involved in herbicide tolerance, for example, an AHAS gene. The zinc finger protein can comprise one or more zinc fingers (e.g., 2, 3, 4, 5, 6, 7, 8, 9 or more zinc fingers), and can be engineered to bind to any sequence within a polyploid plant genome. Any of the zinc finger proteins described herein may bind to a target site within the coding sequence of the target gene or within adjacent sequences (e.g., promoter or other expression elements). In certain embodiments, the zinc finger protein binds to a target site in an AHAS gene, for example, as shown in Table 3 and Table 13. The recognition helix regions of exemplary AHAS-binding zinc fingers are shown in Table 2 and Table 12. One or more of the component zinc finger binding domains of the zinc finger protein can be a canonical (C2H2) zinc finger or a non-canonical (e.g., C3H) zinc finger (e.g., the N-terminal and/or C-terminal zinc finger can be a non-canonical finger).

In another aspect, disclosed herein are fusion proteins, each fusion protein comprising a DNA-binding domain (e.g., a zinc finger protein) that specifically binds to multiple alleles of a gene in polyploid plant genomes. In certain embodiments, the proteins are fusion proteins comprising a zinc finger protein and a functional domain, for example a transcriptional activation domain, a transcriptional repression domain and/or a cleavage domain (or cleavage half-domain). In certain embodiments, the fusion protein is a zinc finger nuclease (ZFN). Cleavage domains and cleavage half domains can be obtained, for example, from various restriction endonucleases and/or homing endonucleases. In one embodiment, the cleavage half-domains are derived from a Type IIS restriction endonuclease (e.g., Fok I).

In other aspects, provided herein are polynucleotides encoding any of the DNA-binding domains and/or fusion proteins described herein. In certain embodiments, described herein is an expression vector comprising a polynucleotide, encoding one or more DNA-binding domains and/or fusion proteins described herein, operably linked to a promoter. In one embodiment, one or more of the fusion proteins are ZFNs.

The DNA-binding domains and fusion proteins comprising these DNA-binding domains bind to and/or cleave two or more endogenous genes in a polyploid genome (e.g., an AHAS gene) within the coding region of the gene or in a non-coding sequence within or adjacent to the gene, such as, for example, a leader sequence, trailer sequence or intron, or promoter sequence, or within a non-transcribed region, either upstream or downstream of the coding region, for example the 3' untranslated region. In certain embodiments, the DNA-binding domains and/or fusion proteins bind to and/or cleave a coding sequence or a regulatory sequence of the target gene.

In another aspect, described herein are compositions comprising one or more proteins, fusion proteins or polynucleotides as described herein. Polyploid plant cells contain multiple genomic allelic targets. Thus, compositions described herein may comprise one or more DNA-binding proteins (and polynucleotides encoding same) that target (and simultaneously modify) multiple alleles present in multiple genomes (also referred to as sub-genomes) of a polyploid plant cell. The DNA-binding proteins may target all genes (paralogs), one or multiple (but less than all) selected alleles.

In another aspect, provided herein is a method for simultaneously altering multiple alleles across the multiple genomes of a polyploid plant cell, the method comprising, expressing one or more DNA-binding domain proteins (e.g., zinc finger proteins such as zinc finger nucleases) in the cell such that multiple alleles of the polyploid plant are altered. In certain embodiments, altering expression of one or more AHAS genes in a plant cell, the method comprising, expressing one or more DNA-binding domain containing proteins (e.g., zinc finger proteins) in the cell such that expression of AHAS is altered. In certain embodiments, the methods comprise using a pair of zinc finger nucleases to create a small insertion and/or deletion ("indel") that disrupts endogenous gene expression. In other embodiments, the methods comprise using a pair of zinc finger nucleases to enhance gene expression, for example via targeted insertion of an exogenous sequence (e.g., donor sequence, GOI, or transgene) or expression enhancing element. The altered gene expression/function can result in increased photosynthesis, increased herbicide tolerance and/or modifications in growth within plant cells.

In another aspect, provided herein are nucleic acids and antibodies, and methods of using the same, for detecting and/or measuring altered expression of and modifications to multiples alleles of a gene (e.g., AHAS).

In another aspect, described herein is a method for simultaneously modifying one or more endogenous genes in a polyploid plant cell. In certain embodiments, the method comprising: (a) introducing, into the polyploid plant cell, one or more expression vectors encoding one or more nucleases (e.g., ZFNs, TALENs, meganucleases and/or CRISPR/Cas systems) that bind to a target site in the one or more genes under conditions such that the nucleases cleave the one or more endogenous genes, thereby modifying the one or more endogenous (e.g., AHAS) genes. In other embodiments, more than one allele of an endogenous gene is cleaved, for example in polyploid plants. In other embodiments, one or more alleles of more than one endogenous gene is cleaved. Furthermore, in any of the methods described herein, cleavage of the one or more genes may result in deletion, addition and/or substitution of nucleotides in the cleaved region, for example such that AHAS activity is altered (e.g., enhanced or reduced), thereby allowing for assessment of, for example, transgene integration at or near the modified endogenous genes.

In yet another aspect, described herein is a method for introducing one or more exogenous sequences into the genome of a plant cell, the method comprising the steps of: (a) contacting the cell with the one or more exogenous sequences (e.g., donor vector, transgene or GOI, or combinations thereof); and (b) expressing one or more nucleases (e.g., ZFNs, TALENs, meganucleases and/or CRISPR/Cas systems) as described herein in the cell, wherein the one or more nucleases cleave chromosomal DNA; such that cleavage of chromosomal DNA in step (b) stimulates incorporation of the exogenous sequence into the genome by homologous recombination. In certain embodiments, the chromsomal DNA is modified such that the chromosomal sequence (e.g., endogenous gene) is mutated to expresses a product that produces a selectable phenotype (e.g., herbicide tolerance). Multiple exogenous sequences may be integrated simultaneously (in parallel) or the steps may be repeated for sequential addition of transgenes (transgene stacking). In certain embodiments, the one or more transgenes are introduced within an AHAS gene, for example the 3' untranslated region. In any of the methods described herein, the one or more nucleases may be fusions between a nuclease (cleavage) domain (e.g., a cleavage domain of a Type IIs restriction endonuclease or a meganuclease) and an engineered zinc finger binding domain. In other embodiments, the nuclease comprises a TAL effector domain, a homing endonuclease and/or a Crispr/Cas single guide RNA. In any of the methods described herein, the exogenous sequence may encode a protein product and/or produce an RNA molecule. In any of the methods described herein, the exogenous sequence may be integrated such that endogenous locus into which the exogenous sequence(s) is(are) inserted is modified to produce one or more measurable phenotypes or markers (e.g., herbicide tolerance by mutation of endogenous AHAS).

In yet another aspect, disclosed herein is a plant cell comprising a targeted genomic modification to one or more alleles of an endogenous gene in the plant cell, wherein the genomic modification follows cleavage by a site specific nuclease, and wherein the genomic modification produces a mutation in the endogenous gene such that the endogenous gene produces a product that results in an herbicide tolerant plant cell. In an embodiment, the genomic modification comprises integration of one or more exogenous sequences. In a further embodiment, the genomic modification comprises introduction of one or more indels that mutate the endogenous gene. In an additional embodiment, the endogenous gene with the genomic modification encodes a protein that confers tolerance to sulfonylurea herbicides. In an embodiment, the endogenous gene with the genomic modification encodes a protein that confers tolerance to imidazolinone herbicides. In a further embodiment, the exogenous sequence does not encode a transgenic selectable marker. In an additional embodiment, the exogenous sequence encodes a protein selected from the group consisting of a protein that increases crop yield, a protein encoding disease resistance, a protein that increases growth, a protein encoding insect resistance, a protein encoding herbicide tolerance, and combinations thereof. In subsequent embodiments, the increased crop yield comprises an increase in fruit yield, grain yield, biomass, fruit flesh content, size, dry weight, solids content, weight, color intensity, color uniformity, altered chemical characteristics, or combinations thereof. In certain embodiments, the endogenous gene is an endogenous acetohydroxyacid synthase (AHAS) gene. In additional embodiments, the two or more exogenous sequences are integrated into the endogenous gene. In a further aspect, the plant cell is a polyploid plant cell. In an embodiment, the site specific nuclease comprises a zinc finger DNA-binding domain, and a FokI cleavage domain. In yet another embodiment, the zinc finger DNA-binding domain encodes a protein that binds to a target site selected from the group consisting of SEQ ID NOs:35-56 and 263-278. In a further embodiment, the plant is selected from the group consisting of wheat, soy, maize, potato, alfalfa, rice, barley, sunflower, tomato, *Arabidopsis*, cotton, *Brassica* species, and timothy grass.

In yet another aspect, disclosed herein is a plant, plant part, seed, or fruit comprising one or more plant cells comprising a targeted genomic modification to one or more alleles of an endogenous gene in the plant cell, wherein the genomic modification follows cleavage by a site specific nuclease, and wherein the genomic modification produces a mutation in the endogenous gene such that the endogenous gene produces a product that results in an herbicide tolerant plant cell.

In yet another aspect, disclosed herein is a method for making a plant cell as disclosed herein above, the method comprising: expressing one or more site specific nucleases in the plant cell; and, modifying one or more alleles of an endogenous gene across multiple genomes of a polyploid plant cell. In an embodiment, the endogenous gene is an acetohydroxyacid synthase (AHAS) gene. In a further embodiment, the modification disrupts expression of the endogenous gene. In yet another embodiment, the modification comprises integration of one or more exogenous sequences into one or more alleles of the endogenous gene. Furthermore, a plant, plant part, seed, or fruit comprising one or more plant cells produced by the method are disclosed herein as an aspect of the disclosure.

In yet another aspect, disclosed herein is a zinc finger protein that binds to a target site selected from the group consisting of SEQ ID NOs:35-56 and 263-278. In a further embodiment, the zinc finger proteins comprise the recognition helix regions shown in a single row of Table 2 or Table 12.

In yet another aspect, described herein is a method of integrating one or more exogenous sequences into the genome of a plant cell, the method comprising: expressing one or more site specific nucleases in the plant cell, wherein the one or more nucleases target and cleave chromosomal DNA of one or more endogenous loci; integrating one or more exogenous sequences into the one or more endogenous loci within the genome of the plant cell, wherein the one or more endogenous loci are modified such that the endogenous gene is mutated to expresses a product that results in a selectable phenotype in the plant cell; and, selecting plant cells that express the selectable phenotype, wherein plant cells are selected which incorporate the one or more exogenous sequences. In a further embodiment, the one or more exogenous sequences are selected from the group consisting of a donor polynucleotide, a transgene, or any combination thereof. In a subsequent embodiment, the integration of the one or more exogenous sequences occurs by homologous recombination or non-homologous end joining. In an additional embodiment, the one or more exogenous sequences are incorporated simultaneously or sequentially into the one or more endogenous loci. In further embodiments, the one or more endogenous loci comprise an acetohydroxyacid synthase (AHAS) gene. In an embodiment, the AHAS gene is located on an A, B, or D genome of a polyploidy genome. In another embodiment, the one or more exogenous sequences are integrated into the AHAS gene. In yet another embodiment, the one or more exogenous sequences encode a S653N AHAS mutation. In an additional embodiment, the one or more exogenous sequences encode a P197S AHAS mutation. In a subsequent embodiment, the site specific nuclease is selected from the group consisting of a zinc finger nuclease, a TAL effector domain nuclease, a homing endonuclease, and a Crispr/Cas single guide RNA nuclease. In a further embodiment, the site specific nuclease comprises a zinc finger DNA-binding domain, and a FokI cleavage domain. In an embodiment, the one or more exogenous sequences encode a transgene or produce an RNA molecule. In a subsequent embodiment, the transgene encodes a protein selected from the group consisting of a protein that increases crop yield, a protein encoding disease resistance, a protein that increases growth, a protein encoding insect resistance, a protein encoding herbicide tolerance, and combinations thereof. In further embodiments, the integration of the transgene further comprises introduction of one or more indels that disrupt expression of the one or more endogenous loci and produce the selectable phenotype. Subsequent embodiments of the method further comprise the steps of; culturing the selected plant cells comprising the one or more exogenous sequences; and, obtaining a whole plant comprising the one or more exogenous sequences integrated within the one or more endogenous loci of the plant genome. In an additional embodiment, a selection agent comprising an imidazolinone, or a sulfonylurea selection agent is used to select the plant cells. In other embodiments, the whole plant comprising the one or more exogenous sequences integrated within the one or more endogenous loci of the plant genome is further modified to incorporate an additional exogenous sequence within the endogenous loci of the plant genome. In further embodiments, the one or more exogenous sequences do not encode a transgenic selectable marker.

In a still further aspect, a plant cell obtained according to any of the methods described herein is also provided.

In another aspect, provided herein is a plant comprising a plant cell as described herein.

In another aspect, provided herein is a seed from a plant comprising the plant cell that is obtained as described herein.

In another aspect, provided herein is fruit obtained from a plant comprising plant cell obtained as described herein.

In any of the compositions (cells or plants) or methods described herein, the plant cell can comprise a monocotyledonous or dicotyledonous plant cell. In certain embodiments, the plant cell is a crop plant, for example, wheat, tomato (or other fruit crop), potato, maize, soy, alfalfa, etc.

BRIEF DESCRIPTION OF THE DRAWINGS

FIG. 1 is a plasmid map of pDAB109350.
FIG. 2 is a plasmid map of pDAB109360.
FIG. 3 is a plasmid map of pDAS000132.
FIG. 4 is a plasmid map of pDAS000133.
FIG. 5 is a plasmid map of pDAS000134.
FIG. 6 is a plasmid map of pDAS000135.
FIG. 7 is a plasmid map of pDAS000131.
FIG. 8 is a plasmid map of pDAS000153.
FIG. 9 is a plasmid map of pDAS000150.
FIG. 10 is a plasmid map of pDAS000143.
FIG. 11 is a plasmid map of pDAS000164.
FIG. 12 is a plasmid map of pDAS000433.
FIG. 13 is a plasmid map of pDAS000434.
FIG. 14A depicts a first transgene stack;
FIG. 14B depicts a second transgene stack.

FIG. 15A depicts a first transgene stack; FIG. 15B depicts a second transgene stack.

FIG. 18 is a plasmid map of pDAS0000004.

FIG. 19 is a plasmid map of QA_pDAS000434.

DETAILED DESCRIPTION

Figure 14A:
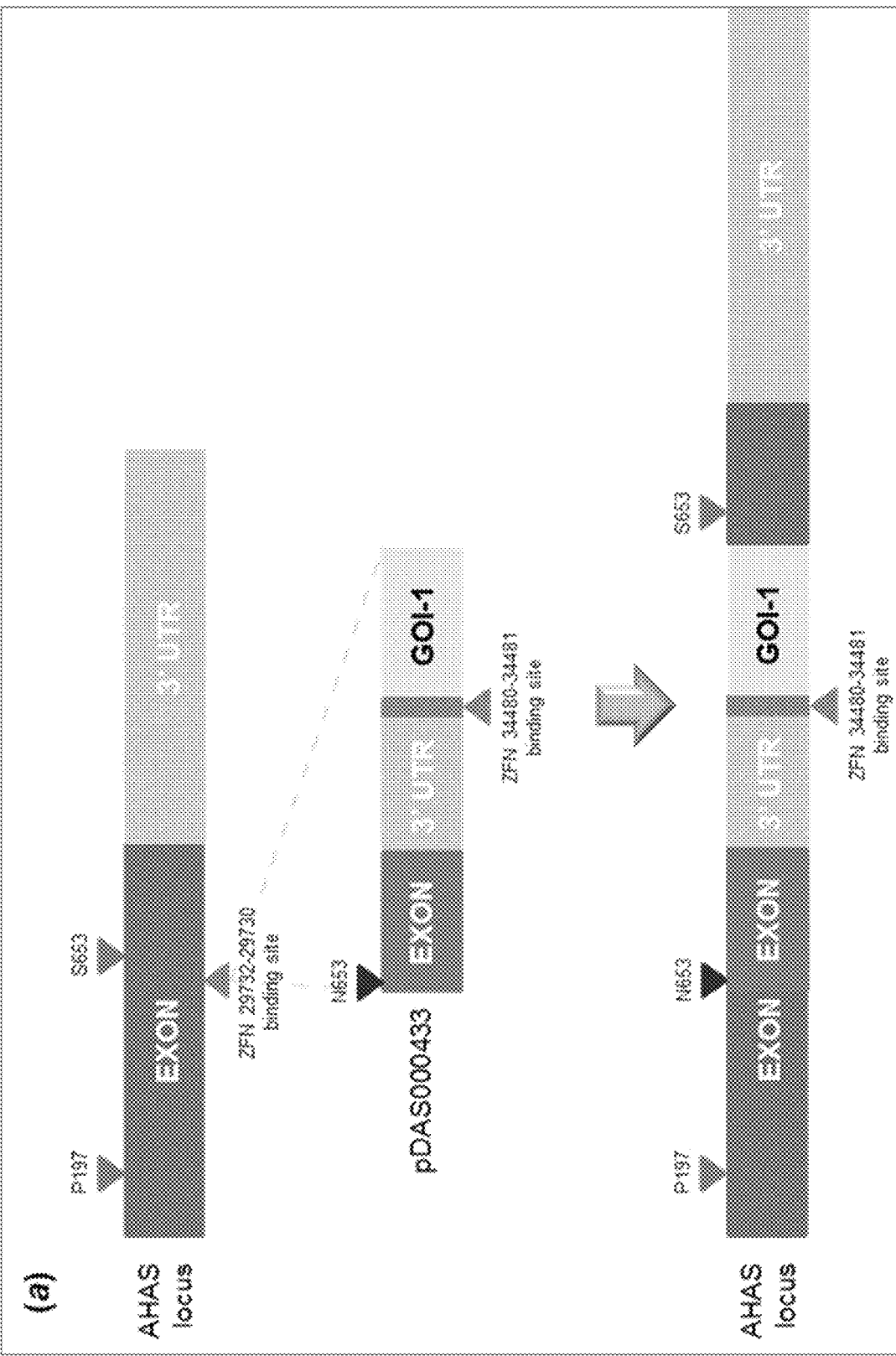
FIGS. 14A and 14B are schematics depicting exogenous marker-free, sequential transgene stacking at an endogenous AHAS locus in the wheat genome of *Triticum aestivum* using ZFN-mediated, NHEJ-directed DNA repair.

The present disclosure relates to methods and compositions for exogenous sequence integration, including parallel (simultaneous) or sequential exogenous sequence integration (including transgene stacking) in a plant species, including in a polyploid plant. The methods and compositions described herein are advantageous in providing targeted integration into a selected locus without the use of an exogenous transgenic marker to assess integration. In particular, differential selection at an endogenous locus, with a transgenic marker-free donor design, has been demonstrated to bias selection for targeted transgenic events by reducing the number of illegitimate integrated events recovered (Shukla et al. (2009) *Nature* 459(7245):437-41). In addition, the disclosure relates to genomic modification (e.g., mutation) of an endogenous locus, which mutation can result in production of a product that serves as a marker (phenotype). Thus, the present disclosure provides for exogenous sequence integration, including transgene stacking, into an endogenous locus, which endogenous locus can serve as a marker for integration (e.g., the AHAS locus in which single mutations can impart herbicide tolerance).

Integration of the exogenous sequence(s) (e.g., into the AHAS locus) is facilitated by targeted double-strand cleavage of endogenous sequence, for example by cleavage of a sequence located in the 3' untranslated region. Cleavage is targeted to this region through the use of fusion proteins comprising a DNA-binding domain, such as a meganuclease DNA-binding domain, a leucine zipper DNA-binding domain, a TAL DNA-binding domain, a zinc finger protein (ZFP); or through the use of a Crispr/Cas RNA or chimeric combinations of the aforementioned. Such cleavage stimulates integration of the donor nucleic acid sequence(s) at, or near the endogenous cleavage site. Integration of exogenous sequences can proceed through both homology-dependent and homology-independent mechanisms, and the selection of precisely targeted events is achieved through screening for a selectable marker (e.g., tolerance to a specific Group B herbicide, or ALS inhibitor herbicides such as imidazolinone or sulfonylurea) which is only functional in correctly targeted events.

In certain embodiments, the nuclease(s) comprise one or more ZFNs, one or more TALENs, one or more meganucleases and/or one or more CRISPR/Cas nuclease systems. ZFNs and TALENs typically comprise a cleavage domain (or a cleavage half-domain) and a zinc finger DNA binding or TALE-effector DNA binding domain and may be introduced as proteins, as polynucleotides encoding these proteins or as combinations of polypeptides and polypeptide-encoding polynucleotides. ZFNs and TALENs can function as dimeric proteins following dimerization of the cleavage half-domains. Obligate heterodimeric nucleases, in which the nuclease monomers bind to the "left" and "right" recognition domains can associate to form an active nuclease have been described. See, e.g., U.S. Pat. Nos. 8,623,618; 7,914,796; 8,034,598. Thus, given the appropriate target sites, a "left" monomer could form an active nuclease with any "right" monomer. This significantly increases the number of useful nuclease sites based on proven left and right domains that can be used in various combinations. For example, recombining the binding sites of four homodimeric nucleases yields an additional twelve heterodimeric nucleases. More importantly, it enables a systematic approach to transgenic design such that every new introduced sequence becomes flanked with a unique nuclease binding site that can be used to excise the gene back out or to target additional genes next to it. Additionally, this method can simplify strategies of stacking into a single locus that is driven by nuclease-dependent double-strand breaks.

A zinc finger binding domain can be a canonical (C2H2) zinc finger or a non-canonical (e.g., C3H) zinc finger. See, e.g., U.S. Patent Publication No. 20080182332. Furthermore, the zinc finger binding domain can comprise one or more zinc fingers (e.g., 2, 3, 4, 5, 6, 7, 8, 9 or more zinc fingers), and can be engineered to bind to any sequence within any endogenous gene, for example an AHAS gene. The presence of such a fusion protein (or proteins) in a cell results in binding of the fusion protein(s) to its (their) binding site(s) and cleavage within the target gene(s).

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids and includes hypervariable diresidues at positions 12 and/or 13 referred to as the Repeat Variable Diresidue (RVD) involved in DNA-binding specificity. TALE repeats exhibit at least some sequence homology with other TALE repeat sequences within a naturally occurring TALE protein. See, e.g., U.S. Pat. No. 8,586,526.

Zinc finger binding and TALE domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 8,586,526, 5,789, 538; 5,925,523; 6,007,988; 6,013,453; 6,200,759; WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. Suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62 (for BLASTP); Descriptions=50 sequences; sort by =HIGH SCORE; Databases=non-redundant, GenBank+EMBL+DDBJ+PDB+GenBank CDS translations+Swiss protein+Spupdate+PIR. Details of these programs can be found on the internet.

With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is known to those with skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe.

Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the probe sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, that uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage domain" comprises one or more polypeptide sequences which possesses catalytic activity for DNA cleavage. A cleavage domain can be contained in a single polypeptide chain or cleavage activity can result from the association of two (or more) polypeptides.

A "cleavage half-domain" is a polypeptide sequence which, in conjunction with a second polypeptide (either identical or different) forms a complex having cleavage activity (preferably double-strand cleavage activity).

An "engineered cleavage half-domain" is a cleavage half-domain that has been modified so as to form obligate heterodimers with another cleavage half-domain (e.g., another engineered cleavage half-domain). See, also, U.S. Pat. Nos. 7,914,796; 8,034,598; 8,623,618 and U.S. Patent Publication No. 2011/0201055, incorporated herein by reference in their entireties.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease. In addition Table 3 and 13 list the target sites for the binding of the ZFP recognition helices of Table 2 and Table 12.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present in cells only during the early stages of development of a flower is an exogenous molecule with respect to the cells of a fully developed flower. Similarly, a molecule induced by heat shock is an exogenous molecule with respect to a non-heat-shocked cell. An exogenous molecule can comprise, for example, a coding sequence for any polypeptide or fragment thereof, a functioning version of a malfunctioning endogenous molecule or a malfunctioning version of a normally-functioning endogenous molecule. Additionally, an exogenous molecule can comprise a coding sequence from another species that is an ortholog of an endogenous gene in the host cell.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases. Thus, the term includes "transgenes" or "genes of interest" which are exogenous sequences introduced into a plant cell.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, protoplast transformation, silicon carbide (e.g., WHISKERS™), *Agrobacterium*-mediated transformation, lipid-mediated transfer (i.e., liposomes, including neutral and cationic lipids), electroporation, direct injection, cell fusion, particle bombardment (e.g., using a "gene gun"), calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins, for example, a fusion between a DNA-binding domain (e.g., ZFP, TALE and/or meganuclease DNA-binding domains) and a nuclease (cleavage) domain (e.g., endonuclease, meganuclease, etc. and fusion nucleic acids (for example, a nucleic acid encoding the fusion protein described herein). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristoylation, and glycosylation.

"Modulation" of gene expression refers to a change in the activity of a gene. Modulation of expression can include, but is not limited to, gene activation and gene repression.

A "transgenic selectable marker" refers to an exogenous sequence comprising a marker gene operably linked to a promoter and 3'-UTR to comprise a chimeric gene expression cassette. Non-limiting examples of transgenic selectable markers include herbicide tolerance, antibiotic resistance, and visual reporter markers. The transgenic selectable marker can be integrated along with a donor sequence via targeted integration. As such, the transgenic selectable marker expresses a product that is used to assess integration of the donor. In contrast, the methods and compositions described herein allow for integration of any donor sequence without the need for co-integration of a transgenic selectable marker, for example by using a donor which mutates the endogenous gene into which it is integrated to produce a selectable marker (i.e., the selectable marker as used in this instance is not transgenic) from the endogenous target locus. Non-limiting examples of selectable markers include herbicide tolerance markers, including a mutated AHAS gene as described herein.

"Plant" cells include, but are not limited to, cells of monocotyledonous (monocots) or dicotyledonous (dicots) plants. Non-limiting examples of monocots include cereal plants such as maize, rice, barley, oats, wheat, sorghum, rye, sugarcane, pineapple, onion, banana, and coconut. Non-limiting examples of dicots include tobacco, tomato, sunflower, cotton, sugarbeet, potato, lettuce, melon, soy, canola (rapeseed), and alfalfa. Plant cells may be from any part of the plant and/or from any stage of plant development.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a DNA-binding domain (ZFP, TALE) is fused to a cleavage domain (e.g., endonuclease domain such as FokI, meganuclease domain, etc.), the DNA-binding domain and the cleavage domain are in operative linkage if, in the fusion polypeptide, the DNA-binding domain portion is able to bind its target site and/or its binding site, while the cleavage (nuclease) domain is able to cleave DNA in the vicinity of the target site. The nuclease domain may also exhibit DNA-binding capability (e.g., a nuclease fused to a ZFP or TALE domain that also can bind to DNA). Similarly, with respect to a fusion polypeptide in which a DNA-binding domain is fused to an activation or repression domain, the DNA-binding domain and the activation or repression domain are in operative linkage if, in the fusion polypeptide, the DNA-binding domain portion is able to bind its target site and/or its binding site, while the activation domain is able to upregulate gene expression or the repression domain is able to downregulate gene expression. A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobilityshift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

DNA-Binding Domains

Any DNA-binding domain can be used in the methods disclosed herein. In certain embodiments, the DNA binding domain comprises a zinc finger protein. A zinc finger binding domain comprises one or more zinc fingers. Miller et al. (1985) *EMBO J.* 4:1609-1614; Rhodes (1993) *Scientific American* February: 56-65; U.S. Pat. No. 6,453,242. The zinc finger binding domains described herein generally include 2, 3, 4, 5, 6 or even more zinc fingers.

Typically, a single zinc finger domain is about 30 amino acids in length. Structural studies have demonstrated that each zinc finger domain (motif) contains two beta sheets (held in a beta turn which contains the two invariant cysteine residues) and an alpha helix (containing the two invariant histidine residues), which are held in a particular conformation through coordination of a zinc atom by the two cysteines and the two histidines.

Zinc fingers include both canonical $C_2H_2$ zinc fingers (i.e., those in which the zinc ion is coordinated by two cysteine and two histidine residues) and non-canonical zinc fingers such as, for example, $C_3H$ zinc fingers (those in which the zinc ion is coordinated by three cysteine residues and one histidine residue) and $C_4$ zinc fingers (those in which the zinc ion is coordinated by four cysteine residues). See also WO 02/057293 and also U.S. Patent Publication No. 20080182332 regarding non-canonical ZFPs for use in plants.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Enhancement of binding specificity for zinc finger binding domains has been described, for example, in U.S. Pat. No. 6,794,136.

Since an individual zinc finger binds to a three-nucleotide (i.e., triplet) sequence (or a four-nucleotide sequence which can overlap, by one nucleotide, with the four-nucleotide binding site of an adjacent zinc finger), the length of a sequence to which a zinc finger binding domain is engineered to bind (e.g., a target sequence) will determine the number of zinc fingers in an engineered zinc finger binding domain. For example, for ZFPs in which the finger motifs do not bind to overlapping subsites, a six-nucleotide target sequence is bound by a two-finger binding domain; a nine-nucleotide target sequence is bound by a three-finger binding domain, etc. As noted herein, binding sites for individual zinc fingers (i.e., subsites) in a target site need not be contiguous, but can be separated by one or several nucleotides, depending on the length and nature of the amino acids sequences between the zinc fingers (i.e., the inter-finger linkers) in a multi-finger binding domain.

In a multi-finger zinc finger binding domain, adjacent zinc fingers can be separated by amino acid linker sequences of approximately 5 amino acids (so-called "canonical" inter-finger linkers) or, alternatively, by one or more non-canonical linkers. See, e.g., U.S. Pat. Nos. 6,453,242 and 6,534,261. For engineered zinc finger binding domains comprising more than three fingers, insertion of longer ("non-canonical") inter-finger linkers between certain of the zinc fingers may be desirable in some instances as it may increase the affinity and/or specificity of binding by the binding domain. See, for example, U.S. Pat. No. 6,479,626 and WO 01/53480. Accordingly, multi-finger zinc finger binding domains can also be characterized with respect to the presence and location of non-canonical inter-finger linkers. For example, a six-finger zinc finger binding domain comprising three fingers (joined by two canonical inter-finger linkers), a long linker and three additional fingers (joined by two canonical inter-finger linkers) is denoted a 2×3 configuration. Similarly, a binding domain comprising two fingers (with a canonical linker therebetween), a long linker and two additional fingers (joined by a canonical linker) is denoted a 2×2 configuration. A protein comprising three two-finger units (in each of which the two fingers are joined by a canonical linker), and in which each two-finger unit is joined to the adjacent two finger unit by a long linker, is referred to as a 3×2 configuration.

The presence of a long or non-canonical inter-finger linker between two adjacent zinc fingers in a multi-finger binding domain often allows the two fingers to bind to subsites which are not immediately contiguous in the target sequence. Accordingly, there can be gaps of one or more nucleotides between subsites in a target site; i.e., a target site can contain one or more nucleotides that are not contacted by a zinc finger. For example, a 2×2 zinc finger binding domain can bind to two six-nucleotide sequences separated by one nucleotide, i.e., it binds to a 13-nucleotide target site. See also Moore et al. (2001a) *Proc. Natl. Acad. Sci. USA* 98:1432-1436; Moore et al. (2001b) *Proc. Natl. Acad. Sci. USA* 98:1437-1441 and WO 01/53480.

As discussed previously, a target subsite is a three- or four-nucleotide sequence that is bound by a single zinc finger. For certain purposes, a two-finger unit is denoted a "binding module." A binding module can be obtained by, for example, selecting for two adjacent fingers in the context of a multi-finger protein (generally three fingers) which bind a particular six-nucleotide target sequence. Alternatively, modules can be constructed by assembly of individual zinc fingers. See also WO 98/53057 and WO 01/53480.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905;

Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous DNA-binding domain (e.g., zinc finger protein or TALE) or to a heterologous cleavage domain. DNA-binding domains derived from meganucleases may also exhibit DNA-binding activity.

In other embodiments, the DNA-binding domain comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like effectors (TALE) which mimic plant transcriptional activators and manipulate the plant transcriptome (see Kay et al (2007) *Science* 318:648-651). These proteins contain a DNA binding domain and a transcriptional activation domain. One of the most well characterized TALEs is AvrBs3 from *Xanthomonas campestgris* pv. *Vesicatoria* (see Bonas et al (1989) *Mol Gen Genet* 218: 127-136 and WO2010079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appland Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Thus, in some embodiments, the DNA binding domain that binds to a target site in a target locus is an engineered domain from a TAL effector similar to those derived from the plant pathogens *Xanthomonas* (see Boch et al, (2009) *Science* 326: 1509-1512 and Moscou and Bogdanove, (2009) *Science* 326: 1501) and *Ralstonia* (see Heuer et al (2007) *Applied and Environmental Microbiology* 73(13): 4379-4384); U.S. Pat. Nos. 8,586,526; 8,420,782 and 8,440,431. TALENs may include C-cap and/or N-cap sequences (e.g., C-terminal and/or N-terminal truncations of the TALE backbone (e.g., "+17", "+63" C-caps). See, e.g., U.S. Pat. No. 8,586,526.

As another alternative, the DNA-binding domain may be derived from a leucine zipper protein. Leucine zippers are a class of proteins that are involved in protein-protein interactions in many eukaryotic regulatory proteins that are important transcriptional factors associated with gene expression. The leucine zipper refers to a common structural motif shared in these transcriptional factors across several kingdoms including animals, plants, yeasts, etc. The leucine zipper is formed by two polypeptides (homodimer or heterodimer) that bind to specific DNA sequences in a manner where the leucine residues are evenly spaced through an α-helix, such that the leucine residues of the two polypeptides end up on the same face of the helix. The DNA binding specificity of leucine zippers can be utilized in the DNA-binding domains disclosed herein.

Cleavage Domains

As noted above, any DNA-binding domain may be associated with a cleavage (nuclease) domain. For example, homing endonucleases may be modified in their DNA-binding specificity while retaining nuclease function. In addition, zinc finger proteins may also be fused to a nuclease (cleavage) domain to form a zinc finger nuclease (ZFN). TALE proteins may be linked to a nuclease (cleavage) domain to form a TALEN.

The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). Non limiting examples of homing endonucleases and meganucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. One or more of these enzymes (or functional fragments thereof) can be used as a source of cleavage domains and cleavage half-domains.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is FokI. This particular enzyme is active as a dimer. Bitinaite et al. (1998) *Proc. Natl. Acad. Sci. USA* 95: 10,570-10,575. Accordingly, for the purposes of the present disclosure, the portion of the FokI enzyme used in the disclosed fusion proteins is considered a cleavage half-domain. Thus, for targeted double-stranded cleavage and/or targeted replacement of cellular sequences using zinc finger-FokI fusions, two fusion proteins, each comprising a FokI cleavage half-domain, can be used to reconstitute a catalytically active cleavage domain. Alternatively, a single polypeptide molecule containing a zinc finger binding domain and two FokI cleavage half-domains can also be used. Parameters for targeted cleavage and targeted sequence alteration using zinc finger-FokI fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Publication No. 20070134796, incorporated by reference herein in its entirety.

To enhance cleavage specificity, cleavage domains may also be modified. In certain embodiments, variants of the cleavage half-domain are employed these variants minimize or prevent homodimerization of the cleavage half-domains. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains. Non-limiting examples of such modified cleavage half-domains are described in detail in U.S. Pat. Nos. 7,888,121; 7,914,796 and 8,034,598, incorporated by reference herein. See, also, Examples.

Additional engineered cleavage half-domains of FokI that form obligate heterodimers can also be used in the ZFNs described herein. Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., U.S. Pat. Nos. 7,914,796 and 8,034,598, the disclosures of which are incorporated by reference for all purposes. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See U.S. Patent Publication No. 20110201055). In other embodiments, the engineered cleavage half domain comprises the "Sharkey" and/or "Sharkey" mutations (see Guo et al, (2010) *J. Mol. Biol.* 400(1):96-107).

Engineered cleavage half-domains described herein can be prepared using any suitable method, for example, by site-directed mutagenesis of wild-type cleavage half-domains (Fok I) as described in U.S. Pat. Nos. 7,914,796; 8,034,598 and 8,623,618; and U.S. Patent Publication No. 20110201055.

In other embodiments, the nuclease comprises an engineered TALE DNA-binding domain and a nuclease domain (e.g., endonuclease and/or meganuclease domain), also referred to as TALENs. Methods and compositions for engineering these TALEN proteins for robust, site specific interaction with the target sequence of the user's choosing have been published (see U.S. Pat. No. 8,586,526). In some embodiments, the TALEN comprises a endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al., (2013) *Nucl Acid Res:* 1-13, doi: 10.1093/nar/gkt1224). In addition, the nuclease domain may also exhibit DNA-binding functionality.

In still further embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley et al (2013) *Nat Comm:* 1-8 DOI: 10.1038/ncomms2782). Any TALENs may be used in combination with additional TALENs (e.g., one or more TALENs (cTALENs or FokI-TALENs) with one or more mega-TALs).

Nucleases may be assembled using standard techniques, including in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in U.S. Pat. No. 8,563,314. Nuclease expression constructs can be readily designed using methods known in the art. See, e.g., United States Patent Publications 20030232410; 20050208489; 20050026157; 20050064474; 20060188987; 20060063231; and International Publication WO 07/014275. Expression of the nuclease may be under the control of a constitutive promoter or an inducible promoter, for example the galactokinase promoter which is activated (de-repressed) in the presence of raffinose and/or galactose and repressed in presence of glucose.

In certain embodiments, the nuclease comprises a CRISPR/Cas system. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of foreign DNA sequences into the CRISPR array to prevent future attacks, in a process called 'adaptation', (ii) expression of the relevant proteins, as well as expression and processing of the array, followed by (iii) RNA-mediated interference with the foreign nucleic acid. Thus, in the bacterial cell, several of the so-called 'Cas' proteins are involved with the natural function of the CRISPR/Cas system and serve roles in functions such as insertion of the foreign DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein. See, e.g., U.S. Pat. No. 9,873,894.

Thus, the nuclease comprises a DNA-binding domain in that specifically binds to a target site in any gene in combination with a nuclease domain that cleaves DNA at or near the binding site.

Fusion Proteins

Methods for design and construction of fusion proteins (and polynucleotides encoding same) are known to those of skill in the art. For example, methods for the design and construction of fusion proteins comprising DNA-binding domains (e.g., zinc finger domains, TALEs) and regulatory or cleavage domains (or cleavage half-domains), and polynucleotides encoding such fusion proteins, are described in U.S. Pat. Nos. 8,586,526; 8,592,645; 8,399,218; 8,329,986; 7,888,121; 6,453,242; and 6,534,261 and U.S. Patent Publications 2007/0134796 and, herein incorporated by reference in their entireties. In certain embodiments, polynucleotides encoding the fusion proteins are constructed. These polynucleotides can be inserted into a vector and the vector can be introduced into a cell (see below for additional disclosure regarding vectors and methods for introducing polynucleotides into cells).

In certain embodiments of the methods described herein, a zinc finger nuclease or TALEN comprises a fusion protein comprising a zinc finger binding domain or a TALE DNA binding domain and a nuclease domain (e.g., Type IIS restriction enzyme and/or meganuclease domain). In certain embodiments, the ZFN or TALEN comprise a cleavage half-domain from the FokI restriction enzyme, and two such fusion proteins are expressed in a cell. Expression of two fusion proteins in a cell can result from delivery of the two proteins to the cell; delivery of one protein and one nucleic acid encoding one of the proteins to the cell; delivery of two nucleic acids, each encoding one of the proteins, to the cell; or by delivery of a single nucleic acid, encoding both proteins, to the cell. In additional embodiments, a fusion protein comprises a single polypeptide chain comprising two cleavage half domains and a zinc finger or TALE binding domain. In this case, a single fusion protein is expressed in a cell and, without wishing to be bound by theory, is believed to cleave DNA as a result of formation of an intramolecular dimer of the cleavage half-domains.

In certain embodiments, the components of the fusion proteins (e.g., ZFP-FokI fusions) are arranged such that the DNA-binding domain is nearest the amino terminus of the fusion protein, and the cleavage half-domain is nearest the carboxy-terminus. This mirrors the relative orientation of the cleavage domain in naturally-occurring dimerizing cleavage domains such as those derived from the FokI enzyme, in which the DNA-binding domain is nearest the amino terminus and the cleavage half-domain is nearest the carboxy terminus. In these embodiments, dimerization of the cleavage half-domains to form a functional nuclease is brought about by binding of the fusion proteins to sites on opposite DNA strands, with the 5' ends of the binding sites being proximal to each other.

In additional embodiments, the components of the fusion proteins (e.g., ZFP-FokI fusions) are arranged such that the cleavage half-domain is nearest the amino terminus of the fusion protein, and the zinc finger domain is nearest the carboxy-terminus. In these embodiments, dimerization of the cleavage half-domains to form a functional nuclease is brought about by binding of the fusion proteins to sites on opposite DNA strands, with the 3' ends of the binding sites being proximal to each other.

In yet additional embodiments, a first fusion protein contains the cleavage half-domain nearest the amino terminus of the fusion protein, and the zinc finger domain nearest the carboxy-terminus, and a second fusion protein is arranged such that the zinc finger domain is nearest the amino terminus of the fusion protein, and the cleavage half-domain is nearest the carboxy-terminus. In these embodiments, both fusion proteins bind to the same DNA strand, with the binding site of the first fusion protein containing the zinc finger domain nearest the carboxy terminus located to the 5' side of the binding site of the second fusion protein containing the zinc finger domain nearest the amino terminus.

In certain embodiments of the disclosed fusion proteins, the amino acid sequence between the zinc finger domain and the cleavage domain (or cleavage half-domain) is denoted the "ZC linker." The ZC linker is to be distinguished from the inter-finger linkers discussed above. See, e.g., U.S. Pat. No. 7,888,121 for details on obtaining ZC linkers that optimize cleavage.

In one embodiment, the disclosure provides a ZFN comprising a zinc finger protein having one or more of the recognition helix amino acid sequences shown in Table 2 (e.g., a zinc finger protein made up of component zinc finger domains with the recognition helices as shown in a single row of Table 2). In another embodiment, provided herein is a ZFP expression vector comprising a nucleotide sequence encoding a ZFP having one or more recognition helices shown in Tables 2 or 12. In another embodiment, provided herein is a ZFP that binds to a target site as shown in Tables 3 or 13 or a polynucleotide encoding a ZFP that binds to a target site shown in Tables 3 or 13.

Target Sites

The disclosed methods and compositions include fusion proteins comprising a DNA-binding domain (e.g., ZFP, TALE, etc.) and a regulatory domain or cleavage (e.g., nuclease) domain (or a cleavage half-domain), in which the DNA-binding domain, by binding to a sequence in cellular chromatin in one or more plant genes, induces cleavage and targeted integration of one or more exogenous sequences (including transgenes) into the vicinity of the target sequence.

As set forth elsewhere in this disclosure, a DNA-binding domain can be engineered to bind to virtually any desired sequence. Accordingly, after identifying a region of interest containing a sequence at which gene regulation, cleavage, or recombination is desired, one or more DNA-binding domains can be engineered to bind to one or more sequences in the region of interest. In certain embodiments, the DNA-binding domain comprises a zinc finger protein that binds to a target site in one or more AHAS genes as shown in Table 3 or Table 13.

Selection of a target site in a genomic region of interest in cellular chromatin of any gene for binding by a DNA-binding domain (e.g., a target site) can be accomplished, for example, according to the methods disclosed in U.S. Pat. No. 6,453,242. It will be clear to those skilled in the art that simple visual inspection of a nucleotide sequence can also be used for selection of a target site. Accordingly, any means for target site selection can be used in the claimed methods.

Target sites are generally composed of a plurality of adjacent target subsites. In the case of zinc finger proteins, a target subsite refers to the sequence (usually either a nucleotide triplet, or a nucleotide quadruplet that can overlap by one nucleotide with an adjacent quadruplet) bound by an individual zinc finger. See, for example, U.S. Pat. No. 6,794,136. If the strand with which a zinc finger protein makes most contacts is designated the target strand "primary recognition strand," or "primary contact strand," some zinc finger proteins bind to a three base triplet in the target strand and a fourth base on the non-target strand. A target site generally has a length of at least 9 nucleotides and, accordingly, is bound by a zinc finger binding domain comprising at least three zinc fingers. However binding of, for example, a 4-finger binding domain to a 12-nucleotide target site, a 5-finger binding domain to a 15-nucleotide target site or a 6-finger binding domain to an 18-nucleotide target site, is also possible. As will be apparent, binding of larger binding domains (e.g., 7-, 8-, 9-finger and more) to longer target sites is also possible.

It is not necessary for a target site to be a multiple of three nucleotides. For example, in cases in which cross-strand interactions occur (see, e.g., U.S. Pat. Nos. 6,453,242 and 6,794,136), one or more of the individual zinc fingers of a multi-finger binding domain can bind to overlapping quadruplet subsites. As a result, a three-finger protein can bind a 10-nucleotide sequence, wherein the tenth nucleotide is part of a quadruplet bound by a terminal finger, a four-finger protein can bind a 13-nucleotide sequence, wherein the thirteenth nucleotide is part of a quadruplet bound by a terminal finger, etc.

In certain embodiments, the target site is in an AHAS locus (including untranslated regions such as the 3' untranslated region of AHAS). Non-limiting examples of suitable AHAS target sites are shown in Table 3 and Table 13. The AHAS (also known as AHAS/ALS) genes are present in all major plant species including but not limited to maize, soybean, cotton, *Arabidopsis*, rice, sunflower, wheat, barley, sugarbeet and *Brassica*. Specific amino acid modifications to the AHAS structural gene sequence have been described that alter the resulting proteins sensitivity to various structural classes of herbicides without a negative penalty on plant performance. For example, imidazolinone-tolerant maize (*Zea mays* L.) [Currie R S, Kwon C S and Penner D, Magnitude of imazethapyr resistance of corn (*Zea mays*) hybrids with altered acetolactate synthase. *Weed Sci* 43:578-582 (1995), Wright T R and Penner D, Corn (*Zea mays*) acetolactate synthase sensitivity to four classes of ALS-inhibiting herbicides. *Weed Sci* 46:8-12 (1998), Siehl D L, Bengtson A S, Brockman J P, Butler J H, Kraatz G W, Lamoreaux R J and Subramanian M V, Patterns of cross tolerance to herbicides inhibiting acetohydroxyacid synthase in commercial corn hybrids designed for tolerance to imidazolinones. *Crop Sci* 36:274-278 (1996), and Bailey W A and Wilcut J W, Tolerance of imidazolinone-resistant corn (*Zea mays*) to diclosulam. *Weed Technol* 17:60-64 (2003)], rice (*Oryza sativa* L.) [Webster E P and Masson J A, Acetolactate synthase-inhibiting herbicides on imidazolinone-tolerant rice. *Weed Sci* 49:652-657 (2001) and, Gealy D R, Mitten D H and Rutger J N, Gene flow between red rice (*Oryza sativa*) and herbicide-resistant rice (*O. sativa*): implications for weed management. *Weed Technol* 17:627-645 (2003)], bread wheat (*Triticum aestivum* L.) [Newhouse K, Smith W A, Starrett M A, Schaefer T J and Singh B K, Tolerance to imidazolinone herbicides in wheat. *Plant Physiol* 100:882-886 (1992), and Pozniak C J and Hucl P J, Genetic analysis of imidazolinone resistance in mutation-derived lines of common wheat. *Crop Sci* 44:23-30 (2004)], and oilseed rape (*Brassica napus* and *B. juncea* L. Czern.) [Shaner D L, Bascomb N F and Smith W, Imidazolinoneresistant crops: selection, characterization and management, in *Herbicide resistant crops*, edited by Duke S O, CRC Press, Boca Raton, pp 143-157 (1996) and Swanson E B, Herrgesell M J, Arnoldo M, Sippell D W and Wong R S C, Microspore mutagenesis and selection: canola plants with field tolerance to the imidazolinones. *Theor Appl Genet* 78:525-530 (1989)], were developed through mutagenesis, selection, and conventional breeding technologies and have been commercialized since 1992, 2003, 2002, and 1996, respectively. Several AHAS genes encoding AHAS enzymes that are tolerant to imidazolinone herbicides have been discovered in plants as naturally occurring mutations and through the process of chemically-induced mutagenesis. The S653N mutation is among the five most common single-point mutations in AHAS genes that result in tolerance to imidazolinone herbicides in plants (Tan, S., Evans, R. R., Dahmer, M. L., Singh, B. K., and Shaner, D. L. (2005) Imidazolinone-tolerant crops: History, current status and future. *Pest Manag. Sci.* 61:246-257).

The length and nature of amino acid linker sequences between individual zinc fingers in a multi-finger binding domain also affects binding to a target sequence. For example, the presence of a so-called "non-canonical linker," "long linker" or "structured linker" between adjacent zinc fingers in a multi-finger binding domain can allow those fingers to bind subsites which are not immediately adjacent. Non-limiting examples of such linkers are described, for example, in U.S. Pat. Nos. 6,479,626 and 7,851,216. Accordingly, one or more subsites, in a target site for a zinc finger binding domain, can be separated from each other by 1, 2, 3, 4, 5 or more nucleotides. To provide but one example, a four-finger binding domain can bind to a 13-nucleotide target site comprising, in sequence, two contiguous 3-nucleotide subsites, an intervening nucleotide, and two contiguous triplet subsites. See, also, U.S. Patent Publication Nos. 20090305419 and 20110287512 for compositions and methods for linking artificial nucleases to bind to target sites separated by different numbers of nucleotides. Distance between sequences (e.g., target sites) refers to the number of nucleotides or nucleotide pairs intervening between two sequences, as measured from the edges of the sequences nearest each other.

In certain embodiments, DNA-binding domains with transcription factor function are designed, for example by constructing fusion proteins comprising a DNA-binding domain (e.g., ZFP or TALE) and a transcriptional regulatory domain (e.g., activation or repression domain). For transcription factor function, simple binding and sufficient proximity to the promoter are all that is generally needed. Exact positioning relative to the promoter, orientation, and within limits, distance does not matter greatly. This feature allows considerable flexibility in choosing target sites for constructing artificial transcription factors. The target site recognized by the DNA-binding domain therefore can be any suitable site in the target gene that will allow activation or repression of gene expression, optionally linked to a regulatory domain. Preferred target sites include regions adjacent to, downstream, or upstream of the transcription start site. In addition, target sites that are located in enhancer regions, repressor sites, RNA polymerase pause sites, and specific regulatory sites (e.g., SP-1 sites, hypoxia response elements, nuclear receptor recognition elements, p53 binding sites), sites in the cDNA encoding region or in an expressed sequence tag (EST) coding region.

In other embodiments, ZFPs with nuclease activity are designed. Expression of a ZFN comprising a fusion protein comprising a zinc finger binding domain and a cleavage domain (or of two fusion proteins, each comprising a zinc finger binding domain and a cleavage half-domain), in a cell, effects cleavage in the vicinity of the target sequence. In certain embodiments, cleavage depends on the binding of two zinc finger domain/cleavage half-domain fusion molecules to separate target sites. The two target sites can be on opposite DNA strands, or alternatively, both target sites can be on the same DNA strand.

A variety of assays can be used to determine whether a ZFP modulates gene expression. The activity of a particular ZFP can be assessed using a variety of in vitro and in vivo assays, by measuring, e.g., protein or mRNA levels, product levels, enzyme activity, transcriptional activation or repression of a reporter gene, using, e.g., immunoassays (e.g., ELISA and immunohistochemical assays with antibodies), hybridization assays (e.g., RNase protection, northerns, in situ hybridization, oligonucleotide array studies), colorimetric assays, amplification assays, enzyme activity assays, phenotypic assays, and the like.

ZFPs are typically first tested for activity in vitro using ELISA assays and then using a yeast expression system. The ZFP is often first tested using a transient expression system with a reporter gene, and then regulation of the target endogenous gene is tested in cells and in whole plants, both in vivo and ex vivo. The ZFP can be recombinantly expressed in a cell, recombinantly expressed in cells transplanted into a plant, or recombinantly expressed in a transgenic plant, as well as administered as a protein to plant or cell using delivery vehicles described below. The cells can be immobilized, be in solution, be injected into a plant, or be naturally occurring in a transgenic or non-transgenic plant.

Transgenic and non-transgenic plants are also used as a preferred embodiment for examining regulation of endogenous gene expression in vivo. Transgenic plants can stably express the ZFP of choice. Alternatively, plants that transiently express the ZFP of choice, or to which the ZFP has been administered in a delivery vehicle, can be used. Regulation of endogenous gene expression is tested using any one of the assays described herein.

Methods for Targeted Cleavage

The disclosed methods and compositions can be used to cleave DNA at a region of interest in cellular chromatin (e.g., at a desired or predetermined site in a genome, for example, within or adjacent to an AHAS gene). For such targeted DNA cleavage, a DNA-binding domain (e.g., zinc finger protein or TALE) is engineered to bind a target site at or near the predetermined cleavage site, and a fusion protein comprising the engineered zinc finger binding domain and a cleavage domain is expressed in a cell. Upon binding of the DNA-binding portion of the fusion protein to the target site, the DNA is cleaved near the target site by the cleavage domain.

Alternatively, two fusion proteins, each comprising a DNA-binding domain and a cleavage half-domain, are expressed in a cell, and bind to target sites which are juxtaposed in such a way that a functional cleavage domain is reconstituted and DNA is cleaved in the vicinity of the target sites. In one embodiment, cleavage occurs between the target sites of the two DNA-binding domains. One or both of the zinc finger binding domains can be engineered.

For targeted cleavage using a zinc finger binding domain-cleavage domain fusion polypeptide, the binding site can encompass the cleavage site, or the near edge of the binding site can be 1, 2, 3, 4, 5, 6, 10, 25, 50 or more nucleotides (or any integral value between 1 and 50 nucleotides) from the cleavage site. The exact location of the binding site, with respect to the cleavage site, will depend upon the particular cleavage domain, and the length of the ZC linker. For methods in which two fusion polypeptides, each comprising a zinc finger binding domain and a cleavage half-domain, are used, the binding sites generally straddle the cleavage site. Thus the near edge of the first binding site can be 1, 2, 3, 4, 5, 6, 10, 25 or more nucleotides (or any integral value between 1 and 50 nucleotides) on one side of the cleavage site, and the near edge of the second binding site can be 1, 2, 3, 4, 5, 6, 10, 25 or more nucleotides (or any integral value between 1 and 50 nucleotides) on the other side of the cleavage site. Methods for mapping cleavage sites in vitro and in vivo are known to those of skill in the art.

Thus, the methods described herein can employ an engineered zinc finger binding domain fused to a cleavage domain. In these cases, the binding domain is engineered to bind to a target sequence, at or near where cleavage is desired. The fusion protein, or a polynucleotide encoding same, is introduced into a plant cell. Once introduced into, or expressed in, the cell, the fusion protein binds to the target sequence and cleaves at or near the target sequence. The exact site of cleavage depends on the nature of the cleavage domain and/or the presence and/or nature of linker sequences between the binding and cleavage domains. In cases where two fusion proteins, each comprising a cleavage half-domain, are used, the distance between the near edges of the binding sites can be 1, 2, 3, 4, 5, 6, 7, 8, 9, 10, 25 or more nucleotides (or any integral value between 1 and 50 nucleotides). Optimal levels of cleavage can also depend on both the distance between the binding sites of the two fusion proteins (see, for example, Smith et al. (2000) *Nucleic Acids Res.* 28:3361-3369; Bibikova et al. (2001)*Mol. Cell. Biol.* 21:289-297) and the length of the ZC linker in each fusion protein. See, also, U.S. Patent Publication 20050064474A1 and International Patent Publications WO05/084190, WO05/014791 and WO03/080809.

In certain embodiments, the cleavage domain comprises two cleavage half-domains, both of which are part of a single polypeptide comprising a binding domain, a first cleavage half-domain and a second cleavage half-domain. The cleavage half-domains can have the same amino acid sequence or different amino acid sequences, so long as they function to cleave the DNA.

Cleavage half-domains may also be provided in separate molecules. For example, two fusion polypeptides may be introduced into a cell, wherein each polypeptide comprises a binding domain and a cleavage half-domain. The cleavage half-domains can have the same amino acid sequence or different amino acid sequences, so long as they function to cleave the DNA. Further, the binding domains bind to target sequences which are typically disposed in such a way that, upon binding of the fusion polypeptides, the two cleavage half-domains are presented in a spatial orientation to each other that allows reconstitution of a cleavage domain (e.g., by dimerization of the half-domains), thereby positioning the half-domains relative to each other to form a functional cleavage domain, resulting in cleavage of cellular chromatin in a region of interest. Generally, cleavage by the reconstituted cleavage domain occurs at a site located between the two target sequences. One or both of the proteins can be engineered to bind to its target site.

The two fusion proteins can bind in the region of interest in the same or opposite polarity, and their binding sites (i.e., target sites) can be separated by any number of nucleotides, e.g., from 0 to 200 nucleotides or any integral value therebetween. In certain embodiments, the binding sites for two fusion proteins, each comprising a zinc finger binding domain and a cleavage half-domain, can be located between 5 and 18 nucleotides apart, for example, 5-8 nucleotides apart, or 15-18 nucleotides apart, or 6 nucleotides apart, or 16 nucleotides apart, as measured from the edge of each binding site nearest the other binding site, and cleavage occurs between the binding sites.

The site at which the DNA is cleaved generally lies between the binding sites for the two fusion proteins. Double-strand breakage of DNA often results from two single-strand breaks, or "nicks," offset by 1, 2, 3, 4, 5, 6 or more nucleotides, (for example, cleavage of double-stranded DNA by native Fok I results from single-strand breaks offset by 4 nucleotides). Thus, cleavage does not necessarily occur at exactly opposite sites on each DNA strand. In addition, the structure of the fusion proteins and the distance between the target sites can influence whether cleavage occurs adjacent a single nucleotide pair, or whether cleavage occurs at several sites. However, for many applications, including targeted recombination and targeted mutagenesis (see infra) cleavage within a range of nucleotides is generally sufficient, and cleavage between particular base pairs is not required.

As noted above, the fusion protein(s) can be introduced as polypeptides and/or polynucleotides. For example, two polynucleotides, each comprising sequences encoding one of the aforementioned polypeptides, can be introduced into a cell, and when the polypeptides are expressed and each binds to its target sequence, cleavage occurs at or near the target sequence. Alternatively, a single polynucleotide comprising sequences encoding both fusion polypeptides is introduced into a cell. Polynucleotides can be DNA, RNA or any modified forms or analogues or DNA and/or RNA.

To enhance cleavage specificity, additional compositions may also be employed in the methods described herein. For example, single cleavage half-domains can exhibit limited double-stranded cleavage activity. In methods in which two fusion proteins, each containing a three-finger zinc finger domain and a cleavage half-domain, are introduced into the cell, either protein specifies an approximately 9-nucleotide target site. Although the aggregate target sequence of 18 nucleotides is likely to be unique in a mammalian and plant genomes, any given 9-nucleotide target site occurs, on average, approximately 23,000 times in the human genome. Thus, non-specific cleavage, due to the site-specific binding of a single half-domain, may occur. Accordingly, the methods described herein contemplate the use of a dominant-negative mutant of a nuclease (or a nucleic acid encoding same) that is expressed in a cell along with the two fusion proteins. The dominant-negative mutant is capable of dimerizing but is unable to induce double-stranded cleavage when dimerized. By providing the dominant-negative mutant in molar excess to the fusion proteins, only regions in which both fusion proteins are bound will have a high enough local concentration of functional cleavage half-domains for dimerization and double-stranded cleavage to occur.

In other embodiments, the nuclease domain(s) are nickases in that they induce single-stranded break. In certain embodiments, the nickase comprises two nucleases domains one of which is modified (e.g., to be catalytically inactive) such that the nuclease makes only a single-stranded break. Such nickases are described for example in U.S. Patent Publication No. 20100047805. Two nickases may be used to induce a double-stranded break.

Expression Vectors

A nucleic acid encoding one or more fusion proteins (e.g., ZFNs, TALENs, etc.) as described herein can be cloned into a vector for transformation into prokaryotic or eukaryotic cells for replication and/or expression. Vectors can be prokaryotic vectors (e.g., plasmids, or shuttle vectors, insect vectors) or eukaryotic vectors. A nucleic acid encoding a fusion protein can also be cloned into an expression vector, for administration to a cell.

To express the fusion proteins, sequences encoding the fusion proteins are typically subcloned into an expression vector that contains a promoter to direct transcription. Suitable prokaryotic and eukaryotic promoters are well known in the art and described, e.g., in Sambrook et al., *Molecular Cloning, A Laboratory Manual* (2nd ed. 1989; 3$^{rd}$ ed., 2001); Kriegler, Gene *Transfer and Expression: A Laboratory Manual* (1990); and *Current Protocols in Molecular Biology* (Ausubel et al., supra. Bacterial expression systems for expressing the ZFP are available in, e.g., *E. coli, Bacillus* sp., and *Salmonella* (Palva et al., *Gene* 22:229-235 (1983)). Kits for such expression systems are commercially available. Eukaryotic expression systems for mammalian cells, yeast, and insect cells are well known by those of skill in the art and are also commercially available.

The promoter used to direct expression of a fusion protein-encoding nucleic acid depends on the particular application. For example, a strong constitutive promoter suited to the host cell is typically used for expression and purification of fusion proteins.

In contrast, when a fusion protein is administered in vivo for regulation of a plant gene (see, "Nucleic Acid Delivery to Plant Cells" section below), either a constitutive, regulated (e.g., during development, by tissue or cell type, or by the environment) or an inducible promoter is used, depending on the particular use of the fusion protein. Non-limiting examples of plant promoters include promoter sequences derived from *A. thaliana* ubiquitin-3 (ubi-3) (Callis, et al., 1990, *J. Biol. Chem.* 265-12486-12493); *A. tumefaciens* mannopine synthase (Δmas) (Petolino et al., U.S. Pat. No. 6,730,824); and/or Cassava Vein Mosaic Virus (CsVMV) (Verdaguer et al., 1996, *Plant Molecular Biology* 31:1129-1139). See, also, Examples.

In addition to the promoter, the expression vector typically contains a transcription unit or expression cassette that contains all the additional elements required for the expression of the nucleic acid in host cells, either prokaryotic or eukaryotic. A typical expression cassette thus contains a promoter (comprising ribosome binding sites) operably linked, e.g., to a nucleic acid sequence encoding the fusion protein, and signals required, e.g., for efficient polyadenylation of the transcript, transcriptional termination, or translation termination. Additional elements of the cassette may include, e.g., enhancers, heterologous splicing signals, the 2A sequence from *Thosea asigna* virus (Mattion et al. (1996) *J. Virol.* 70:8124-8127), and/or a nuclear localization signal (NLS).

The particular expression vector used to transport the genetic information into the cell is selected with regard to the intended use of the fusion proteins, e.g., expression in plants, animals, bacteria, fungus, protozoa, etc. (see expression vectors described below). Standard bacterial and animal expression vectors are known in the art and are described in detail, for example, U.S. Patent Publication 20050064474A1 and International Patent Publications WO 05/084190, WO 05/014791 and WO 03/080809.

Standard transfection methods can be used to produce bacterial, plant, mammalian, yeast or insect cell lines that express large quantities of protein, which can then be purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds., 1983).

Any of the well-known procedures for introducing foreign nucleotide sequences into such host cells may be used. These include the use of calcium phosphate transfection, polybrene, protoplast fusion, electroporation, ultrasonic methods (e.g., sonoporation), liposomes, microinjection, naked DNA, plasmid vectors, viral vectors, *Agrobacterium*-mediated transformation, silicon carbide (e.g., WHISKERS™) mediated transformation, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Donors

As noted above, insertion of one or more exogenous sequence (also called a "donor sequence" or "donor" or "transgene"), for example for stacking can also be completed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded or double-stranded and can be introduced into a cell in linear or circular form. See, e.g., U.S. Patent Publication Nos. 20100047805; 20110281361; and 20110207221. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)). See, e.g., U. S, Patent Publication No. 20090117617.

The donor is generally inserted so that its expression is driven by the endogenous promoter at the integration site, namely the promoter that drives expression of the endogenous gene into which the donor is inserted. However, it will be apparent that the donor may comprise a promoter and/or enhancer, for example a constitutive promoter or an inducible or tissue specific promoter. Furthermore, the donor molecule may be inserted into an endogenous gene such that all, some or none of the endogenous gene is expressed.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

The donor sequence is introduced into an endogenous gene (or multiple alleles of the gene) such that the function of the endogenous gene is altered to act as an endogenous marker for transgene integration, thereby resulting in a genomic modification. In certain embodiments, the endogenous locus into which the transgene(s) is (are) introduced is an AHAS locus. Several mutations in the AHAS gene are known to confer Group B, or ALS inhibitor herbicide tolerance (for example imidazolinone or sulfonylurea), including a single mutation of serine at position 653 to asparagine (S653N). See, e.g., Lee et al. (2011) *Proc. Nat'l. Acad. Sci. USA* 108: 8909-8913, and Tan, S., Evans, R. R., Dahmer, M. L., Singh, B. K., and Shaner, D. L. (2005) Imidazolinone-tolerant crops: History, current status and future. *Pest Manag. Sci.* 61:246-257.

AHAS is one desirable locus because the gene is transcriptionally active at all stages of plant development, it is not prone to gene silencing (e.g., by DNA, Histone Methylation, iRNA, etc.), where the insertion of a new gene or plant transformation unit into this locus does not have a negative impact on the agronomic or quality properties of the host plant. The ubiquitous nature of the AHAS locus and clear commercial evidence that alteration AHAS locus or loci in canola, corn, sunflower, cotton, soybean, sugar beet, wheat, and any other plant does not carry an agronomic or quality penalty means the AHAS loci represents broad class of a preferred target loci across all commercially relevant plant species.

Integration of the donor DNA into the wild type (herbicide susceptible) AHAS locus typically both introduces an exogenous sequence (e.g., a transgene) and a mutation to the endogenous AHAS to produce a genomic modification that confers tolerance to imidazolinones (i.e., a product that results in an herbicide tolerant plant cell), thus allowing regeneration of correctly targeted plants using an endogenous imidazolinone selection system rather than a transgenic selection marker system. Stacking of a second transgene at the AHAS locus can be achieved by integration of a donor DNA that introduces one or more additional transgenes, confers susceptibility to imidazolines but tolerance to sulfonylureas (i.e., a product that results in an herbicide tolerant plant cell), thus allowing regeneration of correctly targeted plants using a sulfonylurea selection agent. Stacking of a third transgene can be achieved by integration of a donor DNA that introduces further transgene(s) and confers susceptibility to sulfonylurea and tolerance to imidazolinones, thus allowing regeneration of correctly targeted plants using an imidazolinone selection agent. As such, continued rounds of sequential transgene stacking are possible by the use of donor molecules that introduce mutations (e.g., genomic modification) to wild-type AHAS thus allowing differential cycling between sulfonylurea and imidazolinone chemical selection agents.

Nucleic Acid Delivery to Plant Cells

As noted above, DNA constructs (e.g., nuclease(s) and/or donor(s)) may be introduced into (e.g., into the genome of) a desired plant host by a variety of conventional techniques. For reviews of such techniques see, for example, Weissbach & Weissbach *Methods for Plant Molecular Biology* (1988, Academic Press, N.Y.) Section VIII, pp. 421-463; and Grierson & Corey, *Plant Molecular Biology* (1988, 2d Ed.), Blackie, London, Ch. 7-9. See, also, U.S. Patent Publication Nos. 20090205083; 20100199389; 20110167521 and 20110189775, incorporated herein by reference in their entireties. It will be apparent that one or more DNA constructs can be employed in the practice of the present invention, for example the nuclease(s) may be carried by the same construct or different constructs as the construct(s) carrying the donor(s).

The DNA construct(s) may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al. (1987) *Nature* 327:70-73). Alternatively, the DNA construct can be introduced into the plant cell via nanoparticle transformation (see, e.g., U.S. Patent Publication No. 20090104700, which is incorporated herein by reference in its entirety). Alternatively, the DNA constructs may be combined with suitable T-DNA border/flanking regions and introduced into a conventional *Agrobacterium tumefaciens* host vector. *Agrobacterium tumefaciens*-mediated transformation techniques, including disarming of oncogenes and the development and use of binary vectors, are well described in the scientific literature. See, for example Horsch et al. (1984) *Science* 233:496-498, and Fraley et al. (1983) *Proc. Nat'l. Acad. Sci. USA* 80:4803.

In addition, gene transfer may be achieved using non-*Agrobacterium* bacteria or viruses such as *Rhizobium* sp. NGR234, *Sinorhizoboium meliloti*, *Mesorhizobium loti*, potato virus X, cauliflower mosaic virus and cassava vein mosaic virus and/or tobacco mosaic virus, See, e.g., Chung et al. (2006) *Trends Plant Sci.* 11(1):1-4.

The virulence functions of the *Agrobacterium tumefaciens* host will direct the insertion of a T-strand containing the construct and adjacent marker into the plant cell DNA when the cell is infected by the bacteria using binary T-DNA vector (Bevan (1984) *Nuc. Acid Res.* 12:8711-8721) or the co-cultivation procedure (Horsch et al. (1985) *Science* 227: 1229-1231). Generally, the *Agrobacterium* transformation system is used to engineer dicotyledonous plants (Bevan et al. (1982) *Ann. Rev. Genet* 16:357-384; Rogers et al. (1986) *Methods Enzymol.* 118:627-641). The *Agrobacterium* transformation system may also be used to transform, as well as transfer, DNA to monocotyledonous plants and plant cells. See U.S. Pat. No. 5,591,616; Hernalsteen et al. (1984) *EMBO J* 3:3039-3041; Hooykass-Van Slogteren et al. (1984) *Nature* 311:763-764; Grimsley et al. (1987) *Nature* 325:1677-179; Boulton et al. (1989) *Plant Mol. Biol.* 12:31-40; and Gould et al. (1991) *Plant Physiol.* 95:426-434.

Alternative gene transfer and transformation methods include, but are not limited to, protoplast transformation through calcium-, polyethylene glycol (PEG)- or electroporation-mediated uptake of naked DNA (see Paszkowski et al. (1984) *EMBO J* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505). Additional methods for plant cell transformation include microinjection, silicon carbide (e.g., WHISKERS™) mediated DNA uptake (Kaeppler et al. (1990) *Plant Cell Reporter* 9:415-418), and microprojectile bombardment (see Klein et al. (1988) *Proc. Nat. Acad. Sci. USA* 85:4305-4309; and Gordon-Kamm et al. (1990) *Plant Cell* 2:603-618). Finally, nanoparticles, nanocarriers and cell penetrating peptides can be utilized to deliver DNA, RNA, peptides and/or proteins into plant cells (see WO/2011/26644, WO/2009/046384, and WO/2008/148223).

The disclosed methods and compositions can be used to insert exogenous sequences into an AHAS gene. This is useful inasmuch as expression of an introduced transgene into a plant genome depends critically on its integration site and, as noted above, AHAS provides a suitable site for transgene integration. Accordingly, genes encoding, e.g., herbicide tolerance, insect resistance, nutrients, antibiotics or therapeutic molecules can be inserted, by targeted recombination, into regions of a plant genome favorable to their expression.

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al. (1987) *Ann. Rev. of Plant Phys.* 38:467-486.

Nucleic acids introduced into a plant cell can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., *petunia*, rose, *chrysanthemum*), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna*, and *Zea*.

The introduction of nucleic acids introduced into a plant cell can be used to confer desired traits on essentially any plant. In certain embodiments, the integrated transgene(s) in plant cells results in plants having increased amount of fruit yield, increased biomass of plant (or fruit of the plant), higher content of fruit flesh, concentrated fruit set, larger plants, increased fresh weight, increased dry weight, increased solids context, higher total weight at harvest, enhanced intensity and/or uniformity of color of the crop, altered chemical (e.g., oil, fatty acid, carbohydrate, protein) characteristics, etc.

One with skill in the art will recognize that an exogenous sequence can be transiently incorporated into a plant cell. The introduction of an exogenous polynucleotide sequence can utilize the cell machinery of the plant cell in which the sequence has been introduced. The expression of an exogenous polynucleotide sequence comprising a ZFN that is transiently incorporated into a plant cell can be assayed by analyzing the genomic DNA of the target sequence to identify and determine any indels, inversions, or insertions. These types of rearrangements result from the cleavage of the target site within the genomic DNA sequence, and the subsequent DNA repair. In addition, the expression of an exogenous polynucleotide sequence can be assayed using methods which allow for the testing of marker gene expression known to those of ordinary skill in the art. Transient expression of marker genes has been reported using a variety of plants, tissues, and DNA delivery systems. Transient analyses systems include but are not limited to direct gene delivery via electroporation or particle bombardment of tissues in any transient plant assay using any plant species of interest. Such transient systems would include but are not limited to electroporation of protoplasts from a variety of tissue sources or particle bombardment of specific tissues of interest. The present disclosure encompasses the use of any transient expression system to evaluate a site specific endonuclease (e.g., ZFN) and to introduce transgenes and/or mutations within a target gene (e.g., AHAS) to result in a genomic modification. Examples of plant tissues envisioned to test in transients via an appropriate delivery system would include but are not limited to leaf base tissues, callus, cotyledons, roots, endosperm, embryos, floral tissue, pollen, and epidermal tissue.

One of skill in the art will recognize that an exogenous polynucleotide sequence can be stably incorporated in transgenic plants. Once the exogenous polynucleotide sequence is confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for a phenotype encoded by the markers present on the exogenous DNA sequence. Markers may also be described and referred to as selectable markers, or reporter markers. The markers can be utilized for the identification and selection of transformed plants ("transformants"). Typically, the marker is incorporated into the genome of a plant cell as an exogenous sequence. In some examples, the exogenous marker sequence is incorporated into the plant genome at a site specific target loci as a donor sequence, wherein the donor sequence contains mutations which result in tolerance to a selection agent (e.g., herbicides, etc.). In other examples, the exogenous marker sequence is incorporated into the plant genome as a transgene (i.e., "transgenic selectable marker"), wherein the marker gene is operably linked to a promoter and 3'-UTR to comprise a chimeric gene expression cassette. The expression of the marker gene results in expression of a visual marker protein or in tolerance to a selection agent (e.g., herbicide, antibiotics, etc.).

For instance, selection can be performed by growing the engineered plant material on media containing an inhibitory amount of the antibiotic or herbicide (i.e., also described as a selective agent) to which the transforming gene construct confers tolerance. In an embodiment, selectable marker genes include herbicide tolerance genes.

Herbicide tolerance markers code for a modified target protein insensitive to the herbicide, or for an enzyme that degrades and detoxifies the herbicide in the plant before it can act. For example, a modified target protein insensitive to an herbicide would include tolerance to glyphosate. Plants tolerant to glyphosate have been obtained by using genes coding for mutant target enzyme 5-enolpyruvylshikimate-3-phosphate synthase (EPSPS). Genes and mutants for EPSPS are well known, and include mutant 5-enolpyruvyl-shikimate-3-phosphate synthase (EPSPs), dgt-28, and aroA genes. Such genes provide tolerance to glyphosate via the introduction of recombinant nucleic acids and/or various forms of in vivo mutagenesis of the native EPSPs genes. An example of enzymes that degrade and detoxify herbicides in the plant would include tolerance to glufosinate ammonium, bromoxynil, and 2,4-dichlorophenoxyacetate (2,4-D). Tolerance to these herbicides has been obtained by expressing bacterial genes that encode pat or DSM-2, a nitrilase, an aad-1 or an aad-12 gene within a plant cell as a transgene. Tolerance genes for phosphono compounds include bar and pat genes from *Streptomyces* species, including *Streptomyces hygroscopicus* and *Streptomyces viridichromogenes*, and pyridinoxy or phenoxy proprionic acids and cyclohexones (ACCase inhibitor-encoding genes). Exemplary genes conferring tolerance to cyclohexanediones and/or aryloxyphenoxypropanoic acid (including Haloxyfop, Diclofop, Fenoxyprop, Fluazifop, Quizalofop) include genes of acetyl coenzyme A carboxylase (ACCase), such as; Acc1-S1, Acc1-S2 and Acc1-S3. In an embodiment, herbicides can inhibit photosynthesis, including triazine (psbA and 1s+ genes) or benzonitrile (nitrilase gene). Other herbicide tolerant gene sequences are known by those with skill in the art.

Antibiotic resistant markers code for an enzyme that degrades and detoxifies an antibiotic in the plant before it can act on the plant. Various types of antibiotics are known that can impede plant growth and development when used at proper concentrations, such as kanamycin, chloramphenicol, spectinomycin, and hygromycin. Exogenous sequences can be obtained (e.g., bacterial genes) and expressed as a transgene to breakdown the antibiotic. For example, antibiotic resistant marker genes include exogenous sequences encoding antibiotic resistance, such as the genes encoding neomycin phosphotransferase II (NEO), chloramphenicol acetyltransferase (CAT), alkaline phosphatase, spectinomycin resistance, kanamycin resistance, and hygromycin phosphotransferase (HPT).

Further, transformed plants and plant cells can also be identified by screening for the activities of a reporter gene that encode a visible marker gene. Reporter genes are typically provided as recombinant nucleic acid constructs and integrated into the plant cell as a transgene. Visual observation of proteins such as reporter genes encoding β-glucuronidase (GUS), luciferase, green fluorescent protein (GFP), yellow fluorescent protein (YFP), DsRed, β-galactosidase may be used to identify and select transformants. Such selection and screening methodologies are well known to those skilled in the art.

The above list of marker genes is not meant to be limiting. Any reporter or selectable marker gene is encompassed by the present disclosure. Moreover, it should be appreciated that markers (e.g., herbicide tolerant markers) are primarily utilized for the identification and selection of transformed plants, as compared to a trait (e.g., herbicide tolerant traits) that are utilized for providing tolerance to herbicides applied in a field environment to control weed species.

Physical and biochemical methods also may be used to identify plant or plant cell transformants containing stably inserted gene constructs, or plant cell containing target gene altered genomic DNA which results from the transient expression of a site-specific endonuclease (e.g., ZFN). These methods include but are not limited to: 1) Southern analysis or PCR amplification for detecting and determining the structure of the recombinant DNA insert; 2) Northern blot, 51 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays (ELISA), where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, northern blots of the RNA (e.g., mRNA) isolated from the tissues of interest. Typically, if the mRNA is present or the amount of mRNA has increased, it can be assumed that the corresponding transgene is being expressed. Other methods of measuring gene and/or encoded polypeptide activity can be used. Different types of enzymatic assays can be used, depending on the substrate used and the method of detecting the increase or decrease of a reaction product or by-product. In addition, the levels of polypeptide expressed can be measured immunochemically, i.e., ELISA, RIA, EIA and other antibody based assays well known to those of skill in the art, such as by electrophoretic detection assays (either with staining or western blotting). As one non-limiting example, the detection of the AAD-1 and PAT proteins using an ELISA assay is described in U.S. Patent Publication No. 20090093366, which reference is hereby incorporated by reference in its entirety herein. A transgene may be selectively expressed in some tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct. The present disclosure further encompasses the progeny, clones, cell lines or cells of the transgenic plants described above wherein said progeny, clone, cell line or cell has the transgene or gene construct.

Fusion proteins (e.g., ZFNs) and expression vectors encoding fusion proteins can be administered directly to the plant for gene regulation, targeted cleavage, and/or recombination. In certain embodiments, the plant contains multiple paralogous target genes. For example, for AHAS, *Brassica napus* includes 5 paralogs and wheat includes 3 paralogs. Thus, one or more different fusion proteins or expression vectors encoding fusion proteins may be administered to a plant in order to target one or more of these paralogous genes in the plant.

Administration of effective amounts is by any of the routes normally used for introducing fusion proteins into ultimate contact with the plant cell to be treated. The ZFPs are administered in any suitable manner, preferably with acceptable carriers. Suitable methods of administering such modulators are available and well known to those of skill in the art, and, although more than one route can be used to administer a particular composition, a particular route can often provide a more immediate and more effective reaction than another route.

Carriers may also be used and are determined in part by the particular composition being administered, as well as by the particular method used to administer the composition. Accordingly, there is a wide variety of suitable formulations of carriers that are available.

EXAMPLES

Example 1: Characterization of AHAS Genomic Target Sequences Identification of AHAS Sequences The transcribed regions for three homoeologous AHAS genes were identified and determined. These novel sequences are listed as SEQ ID NO:1, SEQ ID NO:2, and SEQ ID NO:3. Previous sequencing efforts identified and genetically mapped homoeologous copies of AHAS genes from *Triticum aestivum* to the long arms of chromosomes 6A, 6B and 6D (Anderson et al., (2004) Weed Science 52:83-90; and, Li et al., (2008) Molecular Breeding 22:217-225). Sequence analysis of Expressed Sequence Tags (EST) and genomic sequences available in Genbank (Accession Numbers: AY210405.1, AY210407.1, AY210406.1, AY210408.1, FJ997628.1, FJ997629.1, FJ997631.1, FJ997630.1, FJ997627.1, AY273827.1) were used to determine the transcribed region for the homoeologous copies of the AHAS gene (SEQ ID NOs: 1-3).

The novel, non-coding sequences located upstream and downstream of the transcribed region were characterized for the first time. To completely characterize theses non-coding sequences, the transcribed sequences for each of the three homoeologous copies of the AHAS gene were used as BLASTN™ queries to screen unassembled ROCHE 454™ sequence reads that had been generated from whole genome shotgun sequencing of *Triticum aestivum* cv. Chinese Spring. The ROCHE 454™ sequence reads of *Triticum aestivum* cv. Chinese Spring had been generated to 5-fold sequence coverage. Sequence assembly was completed using the SEQUENCHER SOFTWARE™ (GeneCodes, Ann Arbor, Mich.) of the ROCHE 454™ Sequence reads with a significant BLASTN™ hit (E-value <0.0001) were used to characterize these non-transcribed region. Iterative rounds of BLASTN™ analysis and sequence assembly were performed. Each iteration incorporated the assembled AHAS sequence from the previous iteration so that all of the sequences were compiled as a single contiguous sequence. Overall, 4,384, 7,590 and 6,205 of genomic sequences for the homoeologous AHAS genes located on chromosomes 6A, 6B and 6D, respectively, were characterized (SEQ ID NOs:4-6).

Sequence Analysis of AHAS Genes Isolated from *Triticum aestivum* cv. Bobwhite MPB26RH The homoeologous copies of the AHAS gene were cloned and sequenced from *Triticum aestivum* cv. Bobwhite MPB26RH to obtain nucleotide sequence suitable for designing specific zinc finger proteins that could bind the sequences with a high degree of specificity. The sequence analysis of the AHAS nucleotide sequences obtained from *Triticum aestivum* cv. Bobwhite MPB26RH was required to confirm the annotation of nucleotides present in Genbank and ROCHE 454™ AHAS gene sequences and due to allelic variation between cv. Bobwhite MPB26RH and the other wheat varieties from which the Genbank and ROCHE 454™ sequences were obtained.

A cohort of PCR primers (Table 1) were designed for amplification of the AHAS genes. The primers were designed from a consensus sequence which was produced from multiple sequence alignments generated using CLUSTALW™ (Thompson et al., (1994) Nucleic Acids Research 22:4673-80). The sequence alignments were assembled from the cv. Chinese Spring sequencing data generated from ROCHE 454™ sequencing which was completed at a 5-fold coverage.

As indicated in Table 1, the PCR primers were designed to amplify all three homoeologous sequences or to amplify only a single homoeologous sequence. For example, the PCR primers used to amplify the transcribed region of the AHAS gene were designed to simultaneously amplify all three homoeologous copies in a single multiplex PCR reaction. The PCR primers used to amplify the non-transcribed region were either designed to amplify all three homoeologous copies or to amplify only a single homoeologous copy. All of the PCR primers were designed to be between 18 and 27 nucleotides in length and to have a melting temperature of 60 to 65° C., optimal 63° C. In addition, several primers were designed to position the penultimate base (which contained a phosphorothioate linkage and is indicated in Table 1 as an asterisk [*]) over a nucleotide sequence variation that distinguished the gene copies from each wheat sub-genome. Table 1 lists the PCR primers that were designed and synthesized.

TABLE 1

Primer sequences used for PCR amplification of AHAS sequences

| Primer Name | Genome Region Amplified | SEQ ID NO. | Sequence (5'→3') |
|---|---|---|---|
| AHAS-p_Fwd5 | 5' UTR D | 7 | TCTGTAAGTTATCGCCTGAATTGCTT |
| AHAS-p_Rvs6 | 5' UTR D | 8 | CATTGTGACATCAGCATGACACAA |
| AHAS-p_Fwd4 | 5' UTR D | 9 | AAGCAYGGCTTGCCTACAGC |
| AHAS-p_Rvs3 | 5' UTR D | 10 | AACCAAATRCCCCTATCTCTCTCC |
| AHAS-p_Fwd1 | 5' UTR A, B, and D | 11 | CGTTCGCCCGTAGACCATTC |
| AHAS-p_Rvs1 | 5' UTR A, B, and D | 12 | GGAGGGGTGATGKTTTTGTCTTT |
| AHAS_1F1_transcribed | Coding A, B, and D | 13 | TCG CCC AAA CCC TCG CC |
| AHAS_1R1_transcribed | Coding A, B, and D | 14 | GGG TCG TCR CTG GGG AAG TT |

TABLE 1-continued

Primer sequences used for PCR amplification of AHAS sequences

| Primer Name | Genome Region Amplified | SEQ ID NO. | Sequence (5'→3') |
|---|---|---|---|
| AHAS_2F2_transcribed | Coding A, B, and D | 15 | GCC TTC TTC CTY GCR TCC TCT GG |
| AHAS_2R2_transcribed | Coding A, B, and D | 16 | GCC CGR TTG GCC TTG TAA AAC CT |
| AHAS_3F1_transcribed | Coding A, B, and D | 17 | AYC AGA TGT GGG CGG CTC AGT AT |
| AHAS_3R1_transcribed | Coding A, B, and D | 18 | GGG ATA TGT AGG ACA AGA AAC TTG CAT GA |
| AHAS-6A.PS.3'.F1 | 3'UTR A | 19 | AGGGCCATACTTGTTGGATATCAT*C |
| AHAS-6A.PS.3'.R2 | 3'UTR A | 20 | GCCAACACCCTACACTGCCTA*T |
| AHAS-6B.PS.3'.F1 | 3'UTR B | 21 | TGCGCAATCAGCATGATACC*T |
| AHAS-6B.PS.3'.R1 | 3'UTR B | 22 | ACGTATCCGCAGTCGAGCAA*T |
| AHAS-6D.PS.3'.F1 | 3'UTR D | 23 | GTAGGGATGTGCTGTCATAAGAT*G |
| AHAS-6D.PS.3'.R3 | 3'UTR D | 24 | TTGGAGGCTCAGCCGATCA*C |

UTR = untranslated region
Coding = primers designed for the transcribed regions
asterisk (*) indicates the incorporation of a phosphorothioate sequence Sub-genome-specific amplification was achieved using on-off PCR (Yang et al., (2005) Biochemical and Biophysical Research Communications 328:265-72) with primers that were designed to position the penultimate base (which contained a phosphorothioate linkage) over a nucleotide sequence variation that distinguished the gene copies from each wheat sub-genome. Two different sets of PCR conditions were used to amplify the homoeologous copies of the AHAS gene from cv. Bobwhite MPB26RH. For the transcribed regions, the PCR reaction contained 0.2 mM dNTPs, 1× IMMOLASE PCR™ buffer (Bioline, Taunton, Mass.), 1.5 mM $MgCl_2$, 0.25 units IMMOLASE DNA POLYIMERASE™ (Bioline, Taunton, Mass.), 0.2 µM each of forward and reverse primer, and about 50 ng genomic DNA. Reactions containing the AHAS_1F1 and AHAS_1R1 primers were supplemented with 8% (v/v) DMSO. For the non-transcribed regions, the PCR reactions contained 0.2 mM dNTP, 1× PHUSION GC BUFFER™ (New England Biolabs Ipswich, Mass.), 0.5 units HOT-START PHUSION DNA™ polymerase (New England Biolabs), 0.2 µM each of forward and reverse primer, and about 50 ng genomic DNA. PCR was performed in a final 25 µl reaction volume using an MJ PTC200® thermocycler (BioRad, Hercules, Calif.). Following PCR cycling, the reaction products were purified and cloned using PGEM-T EASY VECTOR™ (Promega, Madison, Wis.) into E. coli JM109 cells. Plasmid DNA was extracted using a DNAEASY PLASMID DNA PURIFICATION KIT™ (Qiagen, Valencia, Calif.) and Sanger sequenced using BIGDYE® v3.1 chemistry (Applied Biosystems, Carlsbad, Calif.) on an ABI3730XL® automated capillary electrophoresis platform. Sequence analysis performed using SEQUENCHER SOFTWARE™ (GeneCodes, Ann Arbor, Mich.) was used to generate a consensus sequence for each homoeologous gene copy (SEQ ID NO:25, SEQ ID NO:26, and SEQ ID NO:27) from cv. Bobwhite MPB26RH. CLUSTALW™ was used to produce a multiple consensus sequence alignment from which homoeologous sequence variation distinguishing between the AHAS gene copies was confirmed.

Example 2: Design of Zinc Finger Binding Domains Specific to AHAS Gene Sequences Zinc finger proteins directed against the identified DNA sequences of the homoeologous copies of the AHAS genes were designed as previously described. See, e.g., Urnov et al., (2005) Nature 435:646-551. Exemplary target sequence and recognition helices are shown in Table 2 (recognition helix regions designs) and Table 3 (target sites). In Table 3, nucleotides in the target site that are contacted by the ZFP recognition helices are indicated in uppercase letters; non-contacted nucleotides are indicated in lowercase. Zinc Finger Nuclease (ZFN) target sites were in 4 regions in the AHAS gene: a region about 500-bp upstream of the serine 653 amino acid residue, an upstream region adjacent (within 30-bp) to the serine 653 amino acid residue, a downstream region adjacent (within 80-bp) to the serine 653 amino acid residue, and a region about 400-bp downstream of the serine 653 amino acid residue.

TABLE 2

AHAS zinc finger designs (N/A indicates "not applicable")

| ZFP # | F1 | F2 | F3 | F4 | F5 | F6 |
|---|---|---|---|---|---|---|
| 299 64 | QSSHLTR SEQ ID NO: 181 | RSDDLTR SEQ ID NO: 182 | RSDDLTR SEQ ID NO: 182 | YRWLLRS SEQ ID NO: 183 | QSGDLTR SEQ ID NO: 184 | QRNARTL SEQ ID NO: 185 |
| 299 65 | RSDNLSV SEQ ID NO: 186 | QKINLQV SEQ ID NO: 187 | DDWNLSQ SEQ ID NO: 188 | RSANLTR SEQ ID NO: 189 | QSGHLAR SEQ ID NO: 190 | NDWDRRV SEQ ID NO: 191 |

TABLE 2-continued

AHAS zinc finger designs (N/A indicates "not applicable")

| ZFP # | F1 | F2 | F3 | F4 | F5 | F6 |
|---|---|---|---|---|---|---|
| 29966 | RSDDLTR SEQ ID NO: 182 | YRWLLRS_ SEQ ID NO: 183 | QSGDLTR SEQ ID NO: 184 | QRNARTL_ SEQ ID NO: 185 | RSDHLSQ_ SEQ ID NO: 192 | DSSTRKK SEQ ID NO: 193 |
| 29967 | RSDDLTR SEQ ID NO: 182 | YRWLLRS_ SEQ ID NO: 183 | QSGDLTR SEQ ID NO: 184 | QRNARTL SEQ ID NO: 185 | RSDVLSE SEQ ID NO: 194 | DRSNRIK SEQ ID NO: 195 |
| 29968 | RSDNLSN SEQ ID NO: 196 | TSSSRIN SEQ ID NO: 197 | DRSNLTR SEQ ID NO: 198 | QSSDLSR SEQ ID NO: 199 | QSAHRKN SEQ ID NO: 200 | N/A |
| 29969 | DRSHLTR SEQ ID NO: 201 | QSGHLSR SEQ ID NO: 202 | RSDNLSV SEQ ID NO: 186 | QKINLQV SEQ ID NO: 187 | DDWNLSQ SEQ ID NO: 188 | RSANLTR SEQ ID NO: 189 |
| 29970 | QSGDLTR SEQ ID NO: 184 | QRNARTL SEQ ID NO: 185 | RSDVLSE SEQ ID NO: 194 | DRSNRIK SEQ ID NO: 195 | RSDNLSE SEQ ID NO: 203 | HSNARKT SEQ ID NO: 204 |
| 29971 | DRSHLTR SEQ ID NO: 201 | QSGHLSR SEQ ID NO: 202 | RSDNLSN SEQ ID NO: 196 | TSSSRIN SEQ ID NO: 197 | DRSNLTR SEQ ID NO: 198 | N/A |
| 29730 | TSGNLTR SEQ ID NO: 205 | HRTSLTD SEQ ID NO: 206 | QSSDLSR SEQ ID NO: 199 | HKYHLRS SEQ ID NO: 207 | QSSDLSR SEQ ID NO: 199 | QWSTRKR SEQ ID NO: 208 |
| 29731 | RSDVLSE SEQ ID NO: 194 | SPSSRRT SEQ ID NO: 209 | RSDTLSE SEQ ID NO: 210 | TARQRNR SEQ ID NO: 211 | DRSHLAR SEQ ID NO: 212 | N/A |
| 29732 | RSDSLSA_ SEQ ID NO: 213 | RSDALAR_ SEQ ID NO: 214 | RSDDLTR_ SEQ ID NO: 182 | QKSNLSS_ SEQ ID NO: 215 | DSSDRKK_ SEQ ID NO: 216 | N/A |
| 30006 | TSGNLTR_ SEQ ID NO: 205 | WWTSRAL_ SEQ ID NO: 217 | DRSDLSR_ SEQ ID NO: 218 | RSDHLSE_ SEQ ID NO: 219 | YSWRLSQ_ SEQ ID NO: 220 | N/A |
| 30008 | RSDSLSV_ SEQ ID NO: 221 | RNQDRKN_ SEQ ID NO: 222 | QSSDLSR SEQ ID NO: 199 | HKYHLRS SEQ ID NO: 207 | QSGDLTR_ SEQ ID NO: 184 | N/A |
| 29753 | QSGNLAR_ SEQ ID NO: 223 | DRSALAR_ SEQ ID NO: 224 | RSDNLST_ SEQ ID NO: 225 | AQWGRTS_ SEQ ID NO: 226 | N/A | N/A |
| 29754 | RSADLTR_ SEQ ID NO: 227 | TNQNRIT_ SEQ ID NO: 228 | RSDSLLR_ SEQ ID NO: 229 | LQHHLTD_ SEQ ID NO: 230 | QNATRIN_ SEQ ID NO: 231 | N/A |
| 29769 | QSGNLAR_ SEQ ID NO: 223 | DRSALAR_ SEQ ID NO: 224 | RSDNLST_ SEQ ID NO: 225 | AQWGRTS_ SEQ ID NO: 226 | N/A | N/A |
| 29770 | QSGDLTR SEQ ID NO: 184 | MRNRLNR_ SEQ ID NO: 232 | DRSNLSR_ SEQ ID NO: 233 | WRSCRSA SEQ ID NO: 234 | RSDNLSV_ SEQ ID NO: 186 | N/A |
| 30012 | HSNARKT SEQ ID NO: 204 | QSGNLAR SEQ ID NO: 223 | DRSALAR SEQ ID NO: 224 | RSDNLST SEQ ID NO: 225 | AQWGRTS_ SEQ ID NO: 226 | N/A |
| 30014 | HSNARKT SEQ ID NO: 204 | QSGNLAR SEQ ID NO: 223 | DRSALAR SEQ ID NO: 224 | RSDHLSQ SEQ ID NO: 192 | QWFGRKN_ SEQ ID NO: 235 | N/A |
| 30018 | QSGDLTR SEQ ID NO: 184 | MRNRLNR SEQ ID NO: 232 | DRSNLSR SEQ ID NO: 233 | WRSCRSA SEQ ID NO: 234 | QRSNLDS_ SEQ ID NO: 34 | N/A |
| 29988 | QSGDLTR SEQ ID NO: 184 | QWGTRYR SEQ ID NO: 33 | DRSNLSR SEQ ID NO: 233 | HNSSLKD SEQ ID NO: 32 | QSGNLAR_ SEQ ID NO: 223 | N/A |
| 29989 | RSDVLSA SEQ ID NO: 31 | RNDHRIN SEQ ID NO: 30 | RSDHLSQ SEQ ID NO: 192 | QSAHRTN SEQ ID NO: 29 | DRSNLSR_ SEQ ID NO: 233 | DSTNRYR_ SEQ ID NO: 28 |

TABLE 3

Target site of AHAS zinc fingers

| ZFP | AHAS Region | Target Site (5'→3') | SEQ ID NO: |
|---|---|---|---|
| 29964 | 500-bp upstream of S653 | ggATAGCAtATTGCGGCGGGAtggcctc | 35 |
| 29965 | 500-bp upstream of S653 | gtACTGGAtGAGCTGaCAAAAGgggagg | 36 |

TABLE 3-continued

Target site of AHAS zinc fingers

| ZFP | AHAS Region | Target Site (5'→3') | SEQ ID NO: |
|---|---|---|---|
| 29966 | 500-bp upstream of S653 | gtACCTGGATAGCAtATTGCGgcgggat | 37 |
| 29967 | 500-bp upstream of S653 | agTACCTGgATAGCAtATTGCGgcggga | 38 |
| 29968 | 500-bp upstream of S653 | gaTGAGCTGACAAAAGGggaggcgatca | 39 |
| 29969 | 500-bp upstream of S653 | atGAGCTGaCAAAAGgGGAGGCgatcat | 40 |
| 29970 | 500-bp upstream of S653 | tcATCCAGTACCTGgATAGCAtattgcg | 41 |
| 29971 | 500-bp upstream of S653 | ctGACAAAAGGGGAGGCgatcattgcca | 42 |
| 29730 | Within 30-bp upstream of S653 | AGgcagcacgtgctcctgatGCGGGACT | 43 |
| 29731 | Within 30-bp upstream of S653 | taGGCAGCACGtgCTCCTGatgcgggac | 44 |
| 29732 | Within 30-bp upstream of S653 | gaTCCCAAGCGGTGGTGctttcaaggac | 45 |
| 30006 | Within 30-bp upstream of S653 | tgATGCGGGACTATGATatccaacaagt | 46 |
| 30008 | Within 30-bp upstream of S653 | gaGCACGTGCTgCCTATGatcccaagcg | 47 |
| 29753 | Within 80-bp downstream of S653N | tcTTGTAGGTCGAAatttcagtacgagg | 48 |
| 29754 | Within 80-bp downstream of S653N | ctACAAGTGTGaCATGCGcaatcagcat | 49 |
| 29769 | Within 80-bp downstream of S653N | cTTGTAGGTCGAAa | 50 |
| 29770 | Within 80-bp downstream of S653N | cAAGTGTGACaTGCGCAa | 51 |
| 30012 | Within 80-bp downstream of S653N | tcTTGTAGGTCGAAATTtcagtacgagg | 52 |
| 30014 | Within 80-bp downstream of S653N | tcTTGTAGGTCGAAATTtcagtacgagg | 53 |
| 30018 | Within 80-bp downstream of S653N | taCAAgTGTGACaTGCGCAatcagcatg | 54 |
| 29988 | 400-bp downstream of S653 | caGAACCTGACACAGCAgacatgtaaag | 55 |
| 29989 | 400-bp downstream of S653 | atAACGACCGATGGAGGGTGgtcggcag | 56 |

The AHAS zinc finger designs were incorporated into zinc finger expression vectors encoding a protein having at least one finger with a CCHC structure. See, U.S. Patent Publication No. 2008/0182332. In particular, the last finger in each protein had a CCHC backbone for the recognition helix. The non-canonical zinc finger-encoding sequences were fused to the nuclease domain of the type IIS restriction enzyme FokI (amino acids 384-579 of the sequence of Wah et al., (1998) Proc. Natl. Acad. Sci. USA 95:10564-10569) via a four amino acid ZC linker and an opaque-2 nuclear localization signal derived from Zea mays to form AHAS zinc-finger nucleases (ZFNs). See, U.S. Pat. No. 7,888,121.

The optimal zinc fingers were verified for cleavage activity using a budding yeast based system previously shown to identify active nucleases. See, e.g., U.S. Patent Publication No. 2009/0111119; Doyon et al., (2008) Nat Biotechnology 26:702-708; Geurts et al., (2009) Science 325:433. Zinc fingers for the various functional domains were selected for in vivo use. Of the numerous ZFNs that were designed, produced and tested to bind to the putative AHAS genomic polynucleotide target sites, 13 ZFNs were identified as having in vivo activity at high levels, and selected for further experimentation. Eleven of the ZFNs were designed to bind to the three homoeologous gene copies and two ZFNs (29989-2A-29988 and 30006-2A-30008) were designed to only bind the gene copy on chromosome 6D. The 13 ZFNs were characterized as being capable of efficiently binding and cleaving the unique AHAS genomic polynucleotide target sites in planta. Exemplary vectors are described below.

Example 3: Evaluation of Zinc Finger Nuclease Cleavage of AHAS Genes Using Transient Assays ZFN Construct Assembly Plasmid vectors containing ZFN gene expression constructs, which were identified using the yeast assay as described in Example 2, were designed and completed using skills and techniques commonly known in the art. Each ZFN-encoding sequence was fused to a sequence encoding an opaque-2 nuclear localization signal (Maddaloni et al., (1989) Nuc. Acids Res. 17:7532), that was positioned upstream of the zinc finger nuclease.

Expression of the fusion proteins was driven by the constitutive promoter from the *Zea mays* Ubiquitin gene which includes the 5' untranslated region (UTR) (Toki et al., (1992) Plant Physiology 100; 1503-07). The expression cassette also included the 3' UTR (comprising the transcriptional terminator and polyadenylation site) from the *Zea mays* peroxidase (Per5) gene (US Patent Publication No. 2004/0158887). The self-hydrolyzing 2A encoding the nucleotide sequence from *Thosea asigna* virus (Szymczak et al., (2004) Nat Biotechnol. 22:589-760) was added between the two Zinc Finger Nuclease fusion proteins that were cloned into the construct.

The plasmid vectors were assembled using the IN-FUSION™ Advantage Technology (Clontech, Mountain View, Calif.). Restriction endonucleases were obtained from New England BioLabs (Ipswich, Mass.) and T4 DNA Ligase (Invitrogen, Carlsbad, Calif.) was used for DNA ligation. Plasmid preparations were performed using NUCLEO-SPIN® Plasmid Kit (Macherey-Nagel Inc., Bethlehem, Pa.) or the Plasmid Midi Kit (Qiagen) following the instructions of the suppliers. DNA fragments were isolated using QIA-QUICK GEL EXTRACTION KIT™ (Qiagen) after agarose tris-acetate gel electrophoresis. Colonies of ligation reactions were initially screened by restriction digestion of miniprep DNA. Plasmid DNA of selected clones was sequenced by a commercial sequencing vendor (Eurofins MWG Operon, Huntsville, Ala.). Sequence data were assembled and analyzed using the SEQUENCHER™ software (Gene Codes Corp., Ann Arbor, Mich.).

The resulting 13 plasmid constructs: pDAB109350 (ZFNs 29732-2A-29730), pDAB109351 (ZFNs 29732-2A-29731), pDAB109352 (ZFNs 29753-2A-29754), pDAB109353 (ZFNs 29968-2A-29967), pDAB109354 (ZFNs 29965-2A-29964), pDAB109355 (ZFNs 29968-2A-29966), pDAB109356 (ZFNs 29969-2A-29967), pDAB109357 (ZFNs 29971-2A-29970), pDAB109358 (ZFNs 29989-2A-29988), pDAB109359 (ZFNs 30006-2A-30008), pDAB109360 (ZFNs 30012-2A-30018), pDAB109361 (ZFNs 30014-2A-30018) and pDAB109385 (ZFNs 29770-2A-29769) were confirmed via restriction enzyme digestion and via DNA sequencing.

Representative plasmids pDAB109350 and pDAB109360 are shown in FIG. 1 and FIG. 2.

Preparation of DNA from ZFN Constructs for Transfection

Before delivery to *Triticum aestivum* protoplasts, plasmid DNA for each ZFN construct was prepared from cultures of *E. coli* using the PURE YIELD PLASMID MAXIPREP SYSTEM® (Promega Corporation, Madison, Wis.) or PLASMID MAXI KIT® (Qiagen, Valencia, Calif.) following the instructions of the suppliers.

Isolation of Wheat Mesophyll Protoplasts

Mesophyll protoplasts were prepared from the wheat line cv. Bobwhite MPB26RH were prepared for transfection using polyethylene glycol (PEG)-mediated DNA delivery as follows.

Mature seed was surface sterilized by immersing in 80% (v/v) ethanol for 30 secs, rinsing twice with tap water, followed by washing in 20% DOMESTOS® (0.8% v/v available chlorine) on a gyratory shaker at 140 rpm for 20 mins. The DOMESTOS® was removed by decanting and the seeds were rinsed four times with sterile water. Excess water was removed by placing the seed on WHATMAN™ filter paper. The seeds were placed in a sterile PETRI™ dish on several sheets of dampened sterile WHATMAN™ filter paper and incubated for 24 h at 24° C. Following incubation, the seeds were surface sterilized a second time in 15% DOMESTOS® with 15 min shaking, followed by rinsing with sterile water as described previously. The seeds were placed on Murashige and Skooge (MS) solidified media for 24 hr at 24° C. Finally, the seeds were surface sterilized a third time in 10% DOMESTOS® with 10 min shaking, followed by rinsing in sterile water as previously described. The seeds were placed, crease side down, onto MS solidified media with 10 seeds per PETRI™ dish and germinated in the dark at 24° C. for 14-21 days.

About 2-3 grams of leaf material from the germinated seeds was cut into 2-3 cm lengths and placed in a pre-weighed PETRI™ dish. Leaf sheath and yellowing leaf material was discarded. Approximately 10 mL of leaf enzyme digest mix (0.6 M mannitol, 10 mM MES, 1.5% w/v cellulase R10, 0.3% w/v macerozyme, 1 mM $CaCl_2$, 0.1% bovine serum albumin, 0.025% v/v pluronic acid, 5 mM β-mercaptoethanol, pH 5.7) was pipetted into the PETRI™ dish and the leaf material was chopped transversely into 1-2 mm segments using a sharp scalpel blade. The leaf material was chopped in the presence of the leaf digest mix to prevent cell damage resulting from the leaf material drying out. Additional leaf enzyme digest mix was added to the PETRI™ dish to a volume of 10 mL per gram fresh weight of leaf material and subject to vacuum (20" Hg) pressure for 30 min. The PETRI™ dish was sealed with PARAFILM® and incubated at 28° C. with gentle rotational shaking for 4-5 hours.

Mesophyll protoplasts released from the leaf segments into the enzyme digest mix were isolated from the plant debris by passing the digestion suspension through a 100 micron mesh and into a 50 mL collection tube. To maximize the yield of protoplasts, the digested leaf material was washed three times. Each wash was performed by adding 10 mL wash buffer (20 mM KCl, 4 mM MES, 0.6 M mannitol, pH 5.6) to the PETRI™ dish, swirling gently for 1 min, followed by passing of the wash buffer through the 100 micron sieve into the same 50 mL collection tube. Next, the filtered protoplast suspension was passed through a 70 micron sieve, followed by a 40 micron sieve. Next, 6 mL aliquots of the filtered protoplast suspension were transferred to 12 mL round bottomed centrifugation tubes with lids and centrifuged at 70 g and 12° C. for 10 min. Following centrifugation, the supernatant was removed and the protoplast pellets were each resuspended in 7 mL wash buffer. The protoplasts were pelleted a second time by centrifugation, as described above. The protoplasts were each resuspended in 1 mL wash buffer and pooled to two centrifugation tubes. The wash buffer volume was adjusted to a final volume of 7 mL in each tube before centrifugation was performed, as described above. Following removal of the supernatant, the protoplast pellets were resuspended in 1 mL wash buffer and pooled to a single tube. The yield of mesophyll protoplasts was estimated using a Neubauer haemocytometer. Evans Blue stain was used to determine the proportion of live cells recovered.

PEG-Mediated Transfection of Mesophyll Protoplasts

About $10^6$ mesophyll protoplasts were added to a 12 mL round bottomed tube and pelleted by centrifugation at 70 g before removing the supernatant. The protoplasts were gently resuspended in 600 µl wash buffer containing 70 µg of plasmid DNA. The plasmid DNA consisted of the Zinc Finger Nuclease constructs described above. Next, an equal volume of 40% PEG solution (40% w/v PEG 4,000, 0.8 M mannitol, 1M $Ca(NO_3)_2$, pH 5.6) was slowly added to the protoplast suspension with simultaneous mixing by gentle rotation of the tube. The protoplast suspension was allowed to incubate for 15 min at room temperature without any agitation.

An additional 6 mL volume of wash buffer was slowly added to the protoplast suspension in sequential aliquots of 1 mL, 2 mL and 3 mL. Simultaneous gentle mixing was used to maintain a homogenous suspension with each sequential aliquot. Half of the protoplast suspension was transferred to a second 12 mL round bottomed tube and an additional 3 mL volume of wash buffer was slowly added to each tube with simultaneous gentle mixing. The protoplasts were pelleted by centrifugation at 70 g for 10 min and the supernatant was removed. The protoplast pellets were each resuspended in 1 mL wash buffer before protoplasts from the paired round bottomed tubes were pooled to a single 12 mL tube. An additional 7 mL wash buffer was added to the pooled protoplasts before centrifugation as described above. The supernatant was completely removed and the protoplast pellet was resuspended in 2 mL Qiao's media (0.44% w/v MS plus vitamins, 3 mM MES, 0.0001% w/v 2,4-D, 0.6 M glucose, pH 5.7). The protoplast suspension was transferred to a sterile 3 cm PETRI™ dish and incubated in the dark for 24° C. for 72 h.

Genomic DNA Isolation from Mesophyll Protoplasts

Transfected protoplasts were transferred from the 3 cm PETRI™ dish to a 2 mL microfuge tube. The cells were pelleted by centrifugation at 70 g and the supernatant was removed. To maximize the recovery of transfected protoplasts, the PETRI™ dish was rinsed three times with 1 mL of wash buffer. Each rinse was performed by swirling the wash buffer in the PETRI™ dish for 1 min, followed by transfer of the liquid to the same 2 ml microfuge tube. At the end of each rinse, the cells were pelleted by centrifugation at 70 g and the supernatant was removed. The pelleted protoplasts were snap frozen in liquid nitrogen before freeze drying for 24 h in a LABCONCO FREEZONE 4.5® (Labconco, Kansas City, Mo.) at −40° C. and $133\times10^{-3}$ mBar pressure. The lyophilized cells were subjected to DNA extraction using the DNEASY® PLANT DNA EXTRACTION MINI kit (Qiagen) following the manufacturer's instructions, with the exception that tissue disruption was not required and the protoplast cells were added directly to the lysis buffer.

PCR Assay of Protoplast Genomic DNA for ZFN Sequence Cleavage

To enable the cleavage efficacy and target site specificity of ZFNs designed for the AHAS gene locus to be investigated, PCR primers were designed to amplify up to a 300-bp fragment within which one or more ZFN target sites were captured. One of the primers was designed to be within a 100-bp window of the captured ZFN target site(s). This design strategy enabled Illumina short read technology to be used to assess the integrity of the target ZFN site in the transfected protoplasts. In addition, the PCR primers were designed to amplify the three homoeologous copies of the AHAS gene and to capture nucleotide sequence variation that differentiated between the homoeologs such that the Illumina sequence reads could be unequivocally attributed to the wheat sub-genome from which they were derived.

A total of four sets of PCR primers were designed to amplify the ZFN target site loci (Table 4). Each primer set was synthesized with the Illumina SP1 and SP2 sequences at the 5' end of the forward and reverse primer, respectively, to provide compatibility with Illumina short read sequencing chemistry. The synthesized primers also contained a phosphorothioate linkage at the penultimate 5' and 3' nucleotides (indicated in Table 4 as an asterisk [*]). The 5' phosphorothioate linkage afforded protection against exonuclease degradation of the Illumina SP1 and SP2 sequences, while the 3' phosphorothioate linkage improved PCR specificity for amplification of the target AHAS sequences using on-off PCR (Yang et al., (2005)). All PCR primers were designed to be between 18 and 27 nucleotides in length and to have a melting temperature of 60 to 65° C., optimal 63° C.

In Table 4, nucleotides specific for the AHAS gene are indicated in uppercase type; nucleotides corresponding to the Illumina SP1 and SP2 sequences are indicated in lowercase type. Each primer set was empirically tested for amplification of the three homoeologous AHAS gene copies through Sanger-based sequencing of the PCR amplification products.

TABLE 4

Primer sequences used to assess AHAS ZFN cleavage efficacy and target site specificity

| Primer Name | AHAS Region | Primer Sequence (5'→3') | SEQ ID NO: |
|---|---|---|---|
| AHAS-500ZFN.F3 | 500-bp upstream of S653 | a*cactctttccctacacgacgctcttccgatct TCCTCTAGGATTCAAGACTTTTG*G | 57 |
| AHAS-500ZFN.R1 | 500-bp upstream of S653 | g*tgactggagttcagacgtgtgctcttccgatc tCGTGGCCGCTTGTAAGTGTA*A | 58 |
| AHASs653Z FN.F1 | Within 30-bp upstream of S653 | a*cactctttccctacacgacgctcttccgatct GAGACCCCAGGGCCATACTT*G | 59 |
| AHASs653Z FN.R3 | Within 30-bp upstream of S653 | g*tgactggagttcagacgtgtgctcttccgatc tCAAGCAAACTAGAAAACGCATG*G | 60 |
| AHASs653Z FN.F5 | Within 80-bp downstream of S653N | a*cactctttccctacacgacgctcttccgatct ATGGAGGGTGATGGCAGGA*C | 61 |

TABLE 4-continued

Primer sequences used to assess AHAS ZFN cleavage efficacy
and target site specificity

| Primer Name | AHAS Region | Primer Sequence (5'→3') | SEQ ID NO: |
|---|---|---|---|
| AHASs653Z FN.R1 | Within 80-bp downstream of S653N | g*tgactggagttcagacgtgtgctcttccgatc tATGACAGCACATCCCTACAAAAG*A | 62 |
| AHAS + 400Z FN.F1 | 400-bp downstream of S653 | a*cactctttccctacacgacgctcttccgatct AACAGTGTGCTGGTTCCTTTCT*G | 63 |
| AHAS + 400Z FN.R3 | 400-bp downstream of S653 | g*tgactggagttcagacgtgtgctcttccgatc tTYTYYCCTCCCAACTGTATTCAG*A | 64 | asterisk (*) is used to indicate a phosphorothioate

PCR amplification of ZFN target site loci from the genomic DNA extracted from transfected wheat mesophyll protoplasts was used to generate the requisite loci specific DNA molecules in the correct format for Illumina-based sequencing-by-synthesis technology. Each PCR assay was optimized to work on 200 ng starting DNA (about 12,500 cell equivalents of the Triticum aestivum genome). Multiple reactions were performed per transfected sample to ensure sufficient copies of the Triticum aestivum genome were assayed for reliable assessment of ZFN efficiency and target site specificity. About sixteen PCR assays, equivalent to 200,000 copies of the Triticum aestivum genome taken from individual protoplasts, were performed per transfected sample. A single PCR master-mix was prepared for each transfected sample. To ensure optimal PCR amplification of the ZFN target site (i.e. to prevent PCR reagents from becoming limiting and to ensure that PCR remained in the exponential amplification stage) an initial assay was performed using a quantitative PCR method to determine the optimal number of cycles to perform on the target tissue. The initial PCR was performed with the necessary negative control reactions on a MX3000P THERMOCYCLER™ (Stratagene). From the data output gathered from the quantitative PCR instrument, the relative increase in fluorescence was plotted from cycle-to-cycle and the cycle number was determined per assay that would deliver sufficient amplification, while not allowing the reaction to become reagent limited, in an attempt to reduce over-cycling and biased amplification of common molecules. The unused master mix remained on ice until the quantitative PCR analysis was concluded and the optimal cycle number determined. The remaining master mix was then aliquoted into the desired number of reaction tubes (about 16 per ZFN assay) and PCR amplification was performed for the optimal cycle number. Following amplification, samples for the same ZFN target site were pooled together and 200 μl of pooled product per ZFN was purified using a QIAQUICK MINIELUTE PCR PURIFICATION KIT™ (Qiagen) following the manufacturer's instructions.

To enable the sample to be sequenced using Illumina short read technology, an additional round of PCR was performed to introduce the Illumina P5 and P7 sequences onto the amplified DNA fragments, as well as a sequence barcode index that could be used to unequivocally attribute sequence reads to the sample from which they originated. This was achieved using primers that were in part complementary to the SP1 and SP2 sequences added in the first round of amplification, but also contained the sample index and P5 and P7 sequences. The optimal number of PCR cycles required to add the additional sequences to the template without over-amplifying common fragments was determined by quantitative PCR cycle analysis, as described above. Following amplification, the generated product was purified using AMPURE MAGNETIC BEADS® (Beckman-Coulter) with a DNA-to-bead ratio of 1:1.7. The purified DNA fragment were titrated for sequencing by Illumina short read technology using a PCR-based library quantification kit (KAPA) according the manufacturer's instructions. The samples were prepared for sequencing using a cBot cluster generation kit (Illumina) and were sequenced on an ILLUMINA GAII$_X$™ or HISEQ2000™ instrument (Illumina) to generate 100-bp paired end sequence reads, according to the manufacturer's instructions.

Data Analysis for Detecting NHEJ at Target ZFN Sites

Following generation of Illumina short read sequence data for sample libraries prepared for transfected mesophyll protoplasts, bioinformatics analysis was performed to identify deleted nucleotides at the target ZFN sites. Such deletions are known to be indicators of in planta ZFN activity that result from non-homologous end joining (NHEJ) DNA repair.

To identify sequence reads with NHEJ deletions, the manufacturer's supplied scripts for processing sequence data generated on the HISEQ2000™ instrument (Illumina) was used to first computationally assign the short sequence reads to the protoplast sample from which they originated. Sample assignment was based on the barcode index sequence that was introduced during library preparation, as described previously. Correct sample assignment was assured as the 6-bp barcode indexes used to prepare the libraries were differentiated from each other by at least a two-step sequence difference.

Following sample assignment, a quality filter was passed across all sequences. The quality filter was implemented in custom developed PERL script. Sequence reads were excluded if there were more than three ambiguous bases, or if the median Phred score was less than 20, or if there were three or more consecutive bases with a Phred score less than 20, or if the sequence read was shorter than 40 nucleotides in length.

Next, the quality trimmed sequences were attributed to the wheat sub-genome from which they originated. This was achieved using a second custom developed PERL script in which sub-genome assignment was determined from the haplotype of the nucleotide sequence variants that were captured by the PCR primers used to amplify the three homoeologous copies of the AHAS gene, as described above.

Finally, the frequency of NHEJ deletions at the ZFN cleavage site in the sub-genome-assigned sequence reads was determined for each sample using a third custom developed PERL script and manual data manipulation in Microsoft Excel 2010 (Microsoft Corporation). This was achieved by counting the frequency of unique NHEJ deletions on each sub-genome within each sample.

Two approaches were used to assess the cleavage efficiency and specificity of the ZFNs tested. Cleavage efficiency was expressed (in parts per million reads) as the proportion of sub-genome assigned sequences that contained a NHEJ deletion at the ZFN target site. Rank ordering of the ZFNs by their observed cleavage efficiency was used to identify ZFNs with the best cleavage activity for each of the four target regions of the AHAS genes in a sub-genome-specific manner.

All of the ZFNs tested showed NHEJ deletion size distributions consistent with that expected for in planta ZFN activity. Cleavage specificity was expressed as the ratio of cleavage efficiencies observed across the three sub-genomes. The inclusion of biological replicates in the data analyses did not substantially affect the rank order for cleavage activity and specificity of the ZFNs tested.

From these results, the ZFNs encoded on plasmid pDAB109350 (i.e. ZFN 29732 and 29730) and pDAB109360 (i.e. ZFN 30012 and 30018) were selected for in planta targeting in subsequent experiments, given their characteristics of significant genomic DNA cleavage activity in each of the three wheat sub-genomes.

Example 4: Evaluation of Donor Designs for ZFN-Mediated AHAS Gene Editing Using Transient Assays To investigate ZFN-mediated genomic editing at the endogenous AHAS gene locus in wheat, a series of experiments were undertaken to assess the effect of donor design on the efficiency of homologous recombination (HR)-directed and non-homologous end joining (NHEJ)-directed DNA repair. These experiments used transient assays to monitor the efficiency for ZFN-mediated addition of the previously described S653N mutation conferring tolerance to imidazolinone class herbicides (Li et al., (2008) Molecular Breeding 22:217-225) at the endogenous AHAS gene locus in wheat, or alternatively for ZFN-mediated introduction of an EcoRI restriction endonuclease sequence site at the double strand DNA break created in the endogenous AHAS genes by targeted ZFN cleavage.

Donor Designs for HR-Directed DNA Repair

Donor DNA designs were based on a plasmid DNA vector containing 750-bp homology arms (i.e. sequence identical to the endogenous AHAS gene) flanking each side of the target cleavage site for ZFNs 29732 and 29730. A plasmid DNA vector was designed for each of the three wheat sub-genomes: pDAS000132 (FIG. 3), pDAS000133 (FIG. 4) and pDAS000134 (FIG. 5) were designed to the A-, B- and D-genome, respectively (SEQ ID NO:65, SEQ ID NO:66, and SEQ ID NO:67). Each plasmid DNA vector was designed to introduce an S653N (AGC→ATT) mutation as a genomic modification conferring tolerance to imidazolinone class herbicides at the target homoeologous copy of the endogenous AHAS gene by ZFN-mediated HR-directed DNA repair. Two additional plasmid DNA constructs were also designed to target the D-genome. The first plasmid DNA, pDAS000135 (SEQ ID NO: 68) (FIG. 6), was identical to pDAS000134 except that it contained two additional (synonymous) single nucleotide point mutations, one each located at 15-bp upstream and downstream of the S653N mutation. The second plasmid DNA, pDAS000131 (SEQ ID: 69) (FIG. 7), did not contain the S653N mutation, but was designed to introduce an EcoRI restriction endonuclease recognition site (i.e., GAATTC) at the double strand DNA break created by target ZFN cleavage in the D-genome copy of the endogenous AHAS gene.

Donor Designs for NHEJ-Directed DNA Repair

Two types of donor DNA designs were used for NHEJ-directed DNA repair.

The first type of donor design was a linear, double stranded DNA molecule comprising 41-bp of sequence that shared no homology with the endogenous AHAS genes in wheat. Two donor DNA molecules were designed, each to target the three homoeologous copies of the AHAS gene. Both donor DNA molecules had protruding 5' and 3' ends to provide ligation overhangs to facilitate ZFN-mediated NHEJ-directed DNA repair. The two donor DNA molecules differed by the sequence at their protruding 3' end. The first donor DNA molecule, pDAS000152 (SEQ ID NO:74 and SEQ ID NO:75), was designed to provide ligation overhangs that were compatible with those generated by cleavage of the endogenous AHAS genes by ZFNs 29732 and 29730 (encoded on plasmid pDAB109350) and to result in the insertion of the 41-bp donor molecule into the endogenous AHAS gene at the site of the double strand DNA break via NHEJ-directed DNA repair. The second donor DNA molecule pDAS000149 (SEQ ID NO: 76 and SEQ ID NO:77) was designed to provide ligation overhangs that were compatible with those generated by the dual cleavage of the endogenous AHAS genes by ZFNs 29732 and 29730 (encoded on plasmid pDAB109350) and ZFNs 30012 and 30018 (encoded on plasmid pDAB109360) and to result in the replacement of the endogenous AHAS sequence contained between the two double strand DNA breaks created by the ZFNs with the 41-bp donor molecule via NHEJ-directed DNA repair.

The second type of donor was a plasmid DNA vector containing 41-bp of sequence that shared no homology with the endogenous AHAS genes in wheat and that was flanked on either side by sequence that was recognized by the ZFN(s) used to create double strand DNA breaks in the endogenous AHAS genes. This donor design allowed in planta release of the unique 41-bp sequence from the plasmid DNA molecule by the same ZFN(s) used to cleave target sites in the endogenous AHAS genes, and simultaneous generation of protruding ends that were suitable for overhang ligation of the released 41-bp sequence into the endogenous AHAS genes via NHEJ-directed DNA repair. Two plasmid donor DNA molecules were designed, each to target the three homoeologous copies of the AHAS gene. The first plasmid donor molecule, pDAS000153 (SED ID NO:78 and SEQ ID NO:79) (FIG. 8), was designed to provide ligation overhangs on the released 41-bp DNA fragment that were compatible with those generated by cleavage of the endogenous AHAS genes by ZFNs 29732 and 29730 (encoded on plasmid pDAB109350). The second plasmid donor molecule, pDAS000150 (SEQ ID NO:80 and SEQ ID NO:81) (FIG. 9), was designed to provide ligation overhangs on the released 41-bp DNA fragment that were at one end compatible with those generated by ZFNs 29732 and 29730 (encoded on plasmid pDAB109350) and at the other end compatible with those generated by ZFNs 30012 and 30018 (encoded on plasmid pDAB109360). This design allowed the replacement of the endogenous AHAS sequence contained between the two double strand DNA breaks created by ZFNs 29732 and 29730 and ZFNs 30012 and 30018 with the 41-bp donor molecule sequence.

Synthesis of Donor DNA for NHEJ-Directed and HDR-Directed DNA Repair

Standard cloning methods commonly known by one skilled in the art were used to build the plasmid vectors. Before delivery to *Triticum aestivum*, plasmid DNA for each donor construct was prepared from cultures of *E. coli* using the PURE YIELD PLASMID MAXIPREP SYSTEM® (Promega Corporation, Madison, Wis.) or PLASMID MAXI KIT® (Qiagen, Valencia, Calif.) following the instructions of the suppliers.

Standard phosphoramidite chemistry was used to synthetically synthesize the double stranded DNA donor molecules (Integrated DNA Technologies, Coralville, Iowa). For each donor molecule, a pair of complementary single stranded DNA oligomers was synthesized, each with two phosphorothioate linkages at their 5' ends to provide protection against in planta endonuclease degradation. The single stranded DNA oligomers were purified by high performance liquid chromatography to enrich for full-length molecules and purified of chemical carryover from the synthesis steps using $Na^+$ exchange. The double stranded donor molecule was formed by annealing equimolar amounts of the two complementary single-stranded DNA oligomers using standard methods commonly known by one skilled in the art. Before delivery to *Triticum aestivum*, the double stranded DNA molecules were diluted to the required concentration in sterile water.

Isolation of Wheat Protoplasts Derived from Somatic Embryogenic Callus

Protoplasts derived from somatic embryogenic callus (SEC) from the donor wheat line cv. Bobwhite MPB26RH were prepared for transfection using polyethylene glycol (PEG)-mediated DNA delivery as follows:

Seedlings of the donor wheat line were grown in an environment controlled growth room maintained at 18/16° C. (day/night) and a 16/8 hour (day/night) photoperiod with lighting provided at 800 mmol $m^2$ per sec. Wheat spikes were collected at 12-14 days post-anthesis and were surface sterilized by soaking for 1 min in 70% (v/v) ethanol. The spikes were threshed and the immature seeds were sterilized for 15 min in 17% (v/v) bleach with gentle shaking, followed by rinsing at least three times with sterile distilled water. The embryos were aseptically isolated from the immature seeds under a dissecting microscope. The embryonic axis was removed using a sharp scalpel and discarded. The scutella were placed into a 9 cm PETRI™ dish containing 2-4 medium without TIMENTIN™, with the uncut scutellum oriented upwards. A total of 25 scutella were plated onto each 9 cm PETRI™ dish. Somatic embryogenic callus (SEC) formation was initiated by incubating in the dark at 24° C. for 3 weeks. After 3 weeks, SEC was separated from non-embryogenic callus, placed onto fresh 2-4 medium without TIMENTIN™ and incubated for a further 3 weeks in the dark at 24° C. Sub-culturing of SEC was repeated for a total of three times before being used for protoplast preparation.

About one gram of SEC was chopped into 1-2 mm pieces using a sharp scalpel blade in a 10 cm PETRI™ dish contained approximately 10 mL of wheat callus digest mix (2.5% w/v Cellulase RS, 0.2% w/v pectolyase Y23, 0.1% w/v DRISELASE®, 14 mM $CaCl_2$), 0.8 mM $MgSO_4$, 0.7 mM $KH_2PO_4$, 0.6 M Mannitol, pH 5.8) to prevent the callus from dehydrating. Additional callus digest mix was added to the PETRI™ dish to a volume of 10 mL per gram fresh weight of callus and subject to vacuum (20" Hg) pressure for 30 min. The PETRI™ dish was sealed with PARAFILM® and incubated at 28° C. with gentle rotational shaking at 30-40 rpm for 4-5 hours.

SEC protoplasts released from the callus were isolated by passing the digestion suspension through a 100 micron mesh and into a 50 mL collection tube. To maximize the yield of protoplasts, the digested callus material was washed three times. Each wash was performed by adding 10 mL SEC wash buffer (0.6 M Mannitol, 0.44% w/v MS, pH 5.8) to the PETRI™ dish, swirling gently for 1 min, followed by passing of the SEC wash buffer through the 100 micron sieve into the same 50 mL collection tube. Next, the filtered protoplast suspension was passed through a 70 micron sieve, followed by a 40 micron sieve. Next, 6 mL aliquots of the filtered protoplast suspension were transferred to 12 mL round bottomed centrifugation tubes with lids and centrifuged in at 70 g and 12° C. for 10 min. Following centrifugation, the supernatant was removed, leaving approximately 0.5 mL supernatant behind, and the protoplast pellets were each resuspended in 7 mL of 22% sucrose solution. The sucrose/protoplast mixture was carefully overlaid with 2 mL SEC wash buffer, ensuring that there was no mixing of the two solutions. The protoplasts were centrifuged a second time by centrifugation, as described above. The band of protoplasts visible between the SEC wash buffer and sucrose solution was collected using a pipette and placed into a clean 12 mL round bottom tube. Seven mL of SEC wash buffer was added to the protoplasts and the tubes were centrifuged, as described above. The supernatant was removed and the SEC protoplasts were combined to a single tube and resuspended in a final volume 1-2 mL of SEC wash buffer. The yield of SEC protoplasts was estimated using a Neubauer haemocytometer. Evans Blue stain was used to determine the proportion of live cells recovered.

PEG-Mediated Transfection of SEC Protoplasts

About two million SEC protoplasts were added to a 12 mL round bottomed tube and pelleted by centrifugation at 70 g before removing the supernatant. The protoplasts were gently resuspended in 480 µl SEC wash buffer containing 70 µg of DNA. The DNA consisted of the Zinc Finger Nuclease and donor DNA constructs described above, with each construct present at the molar ratio required for the experiment being undertaken. Next, 720 µl of 50% PEG solution (50% w/v PEG 4000, 0.8 M mannitol, 1M $Ca(NO_3)_2$, pH 5.6) was slowly added to the protoplast suspension with simultaneous mixing by gentle rotation of the tube. The protoplast suspension was allowed to incubate for 15 min at room temperature without any agitation.

An additional 7 mL volume of SEC wash buffer was slowly added to the protoplast suspension in sequential aliquots of 1 mL, 2 mL and 3 mL. Simultaneous gentle mixing was used to maintain a homogenous suspension with each sequential aliquot. Half of the protoplast suspension was transferred to a second 12 mL round bottomed tube and an additional 3 mL volume of SEC wash buffer was slowly added to each tube with simultaneous gentle mixing. The protoplasts were pelleted by centrifugation at 70 g for 10 min and the supernatant was removed. The protoplast pellets were each resuspended in 1 mL SEC wash buffer before protoplasts from the paired round bottomed tubes were pooled to a single 12 mL tube. An additional 7 mL SEC wash buffer was added to the pooled protoplasts before centrifugation as described above. The supernatant was completely removed and the protoplast pellet was resuspended in 2 mL Qiao's media. The protoplast suspension was transferred to a sterile 3 cm PETRI™ dish and incubated in the dark for 24° C. for 72 h.

Isolation of Scutella from Immature Zygotic Wheat Embryos

Scutella of immature zygotic wheat embryos from the donor wheat line cv. Bobwhite MPB26RH were prepared for transfection using biolistics-mediated DNA delivery as follows.

Seedlings of the donor wheat line were grown in an environment controlled growth room maintained at 18/16° C. (day/night) and a 16/8 hour (day/night) photoperiod with lighting provided at 800 mmol m$^2$ per sec. Wheat spikes were collected at 12-14 days post-anthesis and were surface sterilized by soaking for 1 min in 70% (v/v) ethanol. The spikes were threshed and the immature seeds were sterilized for 15 min in 17% (v/v) bleach with gentle shaking, followed by rinsing at least three times with sterile distilled water. The embryos were aseptically isolated from the immature seeds under a dissecting microscope. The embryonic axis was removed using a sharp scalpel and discarded. The scutella were placed into a 9 cm PETRI™ dish containing osmotic MS (E3 maltose) medium, with the uncut scutellum oriented upwards. A total of 20 scutella were plated onto each 9 cm PETRI™ dish. The prepared embryos were pre-cultured in the dark at 26° C. for a minimum of 4 h before transfection using biolistics-mediated DNA delivery.

Transfection of Scutella of Immature Zygotic Wheat Embryos by Biolistic-Mediated DNA Delivery Gold particles for biolistic-mediated DNA delivery were prepared by adding 40 mg of 0.6 micron colloidal gold particles (BioRad) to 1 mL of sterile water in a 1.5 mL microtube. The gold particles were resuspended by vortexing for 5 min. To prepare sufficient material for 10 bombardments, a 50 µL aliquot of the gold particle suspension was transferred to a 1.5 mL microtube containing 5 µg of DNA resuspended in 5 µL of sterile water. Following thorough mixing by vortexing, 50 µL of 2.5 M CaCl$_2$) and 20 µL of 0.1 M spermidine were added to the microtube, with thorough mixing after the addition of each reagent. The DNA-coated gold particles were pelleted by centrifugation for 1 min at maximum speed in a bench top microfuge. The supernatant was removed and 1 mL of 100% ethanol was added to wash and resuspend the gold particles. The gold particles were pelleted by centrifugation, as described above, and the supernatant discarded. The DNA-coated gold particles were resuspended in 110 µL of 100% ethanol and maintained on ice. Following a brief vortex, 10 µL of the gold particle solution was placed centrally onto a macrocarrier membrane and allowed to air dry.

The PDS-1000/HE PARTICLE GUN DELIVERY SYSTEM™ (BioRad) was used to transfect the scutella of immature zygotic wheat embryos by biolistic-mediated DNA delivery. Delivery of the DNA-coated gold particles was performed using the following settings: gap 2.5 cm, stopping plate aperture 0.8 cm, target distance 6.0 cm, vacuum 91.4-94.8 kPa, vacuum flow rate 5.0 and vent flow rate 4.5. The scutella of immature zygotic wheat embryos were bombarded using a 900 psi rupture disc. Each PETRI™ dish containing 20 scutella was bombarded once. The bombarded scutella were incubated at 26° C. in the dark for 16 h before being transferred onto medium for callus induction. The scutella were cultured on callus induction medium in the dark at 26° C. for 7 d.

Genomic DNA Isolation from SEC Protoplasts

Genomic DNA was extracted from SEC protoplasts using the procedure previously described for mesophyll protoplasts. An additional purification step was performed to reduce the presence of the donor DNA used for transfection. This was achieved using gel electrophoresis to separate the genomic DNA from the SEC protoplasts from the donor DNA used for transfection. The extracted DNA was electrophoresed for 3 h in a 0.5% agarose gel using 0.5×TBE. The DNA was visualized by SYBR® SAFE staining and the band corresponding to genomic DNA from the SEC protoplasts was excised. The genomic DNA was purified from the agarose gel using a QIAQUICK DNA PURIFICATION KIT™ (Qiagen), following the manufacturer's instructions, except that the QIAQUICK™ DNA purification column was replaced with a DNA binding column from the DNEASY PLANT DNA EXTRACTION MINI KIT™ (Qiagen).

Genomic DNA Isolation from Scutella of Immature Zygotic Embryos

The 20 scutella of immature zygotic wheat embryos transfected for each biolistic-mediated DNA delivery were transferred to a 15 ml tube and snap frozen in liquid nitrogen before freeze drying for 24 h in a LABCONCO FREEZONE 4.5® (Labconco, Kansas City, Mo.) at −40° C. and 133×10$^{-3}$ mBar pressure. The lyophilized calli were subjected to DNA extraction using the DNEASY® PLANT DNA EXTRACTION MAXI™ KIT (Qiagen) following the manufacturer's instructions.

An additional purification step was performed to reduce the presence of the donor DNA used for transfection. This was achieved using gel electrophoresis to separate the genomic DNA from the calli from the donor DNA used for transfection. The extracted DNA was electrophoresed for 3 h in a 0.5% agarose gel using 0.5×TBE. The DNA was visualized by SYBR® SAFE staining and the band corresponding to genomic DNA from the calli was excised. The genomic DNA was purified from the agarose gel using a QIAQUICK™ DNA PURIFICATION kit (Qiagen), following the manufacturer's instructions, except that the QIAQUICK™ DNA purification column was replaced with a DNA binding column from the DNEASY® PLANT DNA EXTRACTION MAXI™ KIT (Qiagen).

PCR Assay of Genomic DNA for ZFN-Mediated AHAS Editing

To investigate ZFN-mediated genomic editing at the endogenous AHAS genes in wheat using HR- and NHEJ-directed DNA repair, and assess the effect of donor DNA design on the efficacy of each DNA repair pathway, PCR assays were used to amplify the target AHAS regions from genomic DNA of transfected wheat cells. PCR assays were performed as described previously to generate requisite loci specific DNA molecules in the correct format for Illumina-based sequencing-by-synthesis technology. Each assay was performed using the previously described primer pair (SEQ ID NO: 59 and SEQ ID NO: 60) that were designed to amplify the region targeted by ZFNs 29732 and 29730 (encoded on plasmid pDAB109350) and ZFNs 30012 and 30018 (encoded on plasmid pDAB109360) for each of the three homoeologous copies of the AHAS genes. Multiple reactions were performed per transfected sample to ensure that sufficient copies of the *Triticum aestivum* genome were assayed for reliable assessment of ZFN-mediated gene editing. For transfected SEC protoplasts, up to sixteen PCR assays, equivalent to 200,000 copies of the *Triticum aestivum* genome taken from individual protoplasts, were performed per transfected sample. For transfected scutella of immature zygotic embryos, about forty eight PCR assays, equivalent to 600,000 copies of the *Triticum aestivum* genome taken from individual protoplasts, were performed per transfected sample. Each transfected sample was prepared for sequencing using a CBOT CLUSTER GENERATION KIT™ (Illumina) and was sequenced on an ILLU- MINA GAIIx™ or HISEQ2000™ instrument (Illumina) to generate 100-bp paired end sequence reads, as described previously.

Data Analysis for Detecting ZFN-Mediated HR-Directed Editing at AHAS Gene Locus

Following generation of Illumina short read sequence data for sample libraries prepared for transfected SEC protoplasts and scutella of immature zygotic wheat embryos, analyses were performed to identify molecular evidence for ZFN-mediated HR-directed editing at the target ZFN sites.

To identify sequence reads with molecular evidence for HR-directed gene editing, the short sequence reads were first computationally processed, as previously described, to assign each read to the sample and sub-genome from which they originated, and to perform quality filtering to ensure that only high quality sequences were used for subsequent analyses. Next, custom developed PERL scripts and manual data manipulation in MICROSOFT EXCEL 2010™ (Microsoft Corporation) were used to identify reads that contained sequence for both the donor DNA molecule used for transfection and the endogenous AHAS locus. To ensure unequivocal discernment between sequence reads arising from ZFN-mediated HR-directed gene editing and those resulting from the carryover of (any) donor DNA used for transfection, molecular evidence for gene editing was declared only if the sequence read also contained a NHEJ deletion at the position of the double strand DNA break created by the ZFN; i.e., the sequence read showed evidence for the outcome of imperfect HR-directed DNA repair. The editing frequency (expressed in parts per million reads) was calculated as the proportion of sub-genome-assigned sequence reads that showed evidence for ZFN-mediated HR-directed gene editing.

From the results of three biological replicates performed for each plasmid donor DNA design, molecular evidence was obtained for the enrichment of sequence reads showing ZFN-mediated HR-directed editing at the three homoeologous copies of the endogenous AHAS genes in wheat (Table 5 and Table 6). Strong molecular evidence was obtained for the addition of an EcoRI restriction endonuclease site at the position of the double strand DNA break created by ZFNs 29732 and 29730 in all three homoeologous copies of the endogenous AHAS gene in both samples of SEC protoplasts and scutella of immature zygotic embryos that were transfected with pDAB109350 and pDAS000131. The frequency of ZFN-mediated HR-directed gene editing was highest in the D-genome to which the donor DNA molecule was targeted. Similarly, strong molecular evidence was obtained for the introduction of donor polynucleotide containing the S653N mutation in all three homoeologous copies of the endogenous AHAS genes in samples of scutella of immature zygotic embryos that were transfected with pDAB109350 and either pDAS000132, pDAS000133 or pDAS000134; strong molecular evidence was also observed for samples of SEC protoplasts transfected with pDAB109350 and pDAS000134. The frequency of ZFN-mediated HR-directed gene editing was again highest in the sub-genome for which the donor DNA was designed. Importantly, the editing frequency in samples of SEC protoplasts and scutella of immature zygotic embryos transfected with pDAB109350 and pDAS000135 was lower (about 10-fold) than that observed for samples transfected with pDAB109350 and pDAS000134. This result was expected due to the penalty imposed on the efficiency for HR-directed DNA repair by the presence of the flanking mutations in the pDAS00135 donor design.

TABLE 5

Average HR-directed editing frequency in parts per million (ppm) across three biological replicates of scutella transfected with plasmid donor DNA designs.

| Donor | Sub-genome targeted | ZFN | Donor-to-ZFN molar ratio | Editing Frequency in Wheat Sub-Genome | Editing Frequency (ppm) |
|---|---|---|---|---|---|
| pDAS000131 | D | n/a | n/a | A | 0 |
| pDAS000131 | D | 29732-2A-29730 | 5:1 | A | 251 |
| pDAS000131 | D | 29732-2A-29730 | 10:1 | A | 46 |
| pDAS000131 | D | n/a | n/a | B | 0 |
| pDAS000131 | D | 29732-2A-29730 | 5:1 | B | 106 |
| pDAS000131 | D | 29732-2A-29730 | 10:1 | B | 19 |
| pDAS000131 | D | n/a | n/a | D | 3 |
| pDAS000131 | D | 29732-2A-29730 | 5:1 | D | 2,577 |
| pDAS000131 | D | 29732-2A-29730 | 10:1 | D | 642 |
| pDAS000132 | A | n/a | n/a | A | 5 |
| pDAS000132 | A | 29732-2A-29730 | 5:1 | A | 2,353 |
| pDAS000132 | A | 29732-2A-29730 | 10:1 | A | 1,800 |
| pDAS000132 | A | n/a | n/a | B | 0 |
| pDAS000132 | A | 29732-2A-29730 | 5:1 | B | 42 |
| pDAS000132 | A | 29732-2A-29730 | 10:1 | B | 30 |
| pDAS000132 | A | n/a | n/a | D | 0 |
| pDAS000132 | A | 29732-2A-29730 | 5:1 | D | 110 |
| pDAS000132 | A | 29732-2A-29730 | 10:1 | D | 61 |
| pDAS000133 | B | n/a | n/a | A | 0 |
| pDAS000133 | B | 29732-2A-29730 | 5:1 | A | 230 |
| pDAS000133 | B | 29732-2A-29730 | 10:1 | A | 149 |
| pDAS000133 | B | n/a | n/a | B | 8 |
| pDAS000133 | B | 29732-2A-29730 | 5:1 | B | 5,528 |
| pDAS000133 | B | 29732-2A-29730 | 10:1 | B | 4,472 |
| pDAS000133 | B | n/a | n/a | D | 0 |
| pDAS000133 | B | 29732-2A-29730 | 5:1 | D | 0 |
| pDAS000133 | B | 29732-2A-29730 | 10:1 | D | 0 |
| pDAS000134 | D | n/a | n/a | A | 2 |
| pDAS000134 | D | 29732-2A-29730 | 5:1 | A | 316 |
| pDAS000134 | D | 29732-2A-29730 | 10:1 | A | 959 |
| pDAS000134 | D | n/a | n/a | B | 1 |
| pDAS000134 | D | 29732-2A-29730 | 5:1 | B | 110 |
| pDAS000134 | D | 29732-2A-29730 | 10:1 | B | 318 |
| pDAS000134 | D | n/a | n/a | D | 19 |
| pDAS000134 | D | 29732-2A-29730 | 5:1 | D | 4,662 |
| pDAS000134 | D | 29732-2A-29730 | 10:1 | D | 9,043 |
| pDAS000135 | D | n/a | n/a | A | 0 |
| pDAS000135 | D | 29732-2A-29730 | 5:1 | A | 38 |
| pDAS000135 | D | 29732-2A-29730 | 10:1 | A | 97 |
| pDAS000135 | D | n/a | n/a | B | 0 |
| pDAS000135 | D | 29732-2A-29730 | 5:1 | B | 14 |
| pDAS000135 | D | 29732-2A-29730 | 10:1 | B | 31 |
| pDAS000135 | D | n/a | n/a | D | 1 |

TABLE 5-continued

Average HR-directed editing frequency in parts per million (ppm) across three biological replicates of scutella transfected with plasmid donor DNA designs.

| Donor | Sub-genome targeted | ZFN | Donor-to-ZFN molar ratio | Editing Frequency in Wheat Sub-Genome | Editing Frequency (ppm) |
|---|---|---|---|---|---|
| pDAS000135 | D | 29732-2A-29730 | 5:1 | D | 541 |
| pDAS000135 | D | 29732-2A-29730 | 10:1 | D | 1,191 |

"na" indicates "not applicable."

TABLE 6

Average HR-directed editing frequency in parts per million (ppm) across three biological replicates of SEC protoplasts transfected with plasmid donor DNA designs.

| Donor | Sub-genome targeted | ZFN | Donor-to-ZFN molar ratio | Editing Frequency in Wheat Sub-Genome | Editing Frequency (ppm) |
|---|---|---|---|---|---|
| pDAS000131 | D | n/a | n/a | A | 0 |
| pDAS000131 | D | 29732-2A-29730 | 7:1 | A | 50 |
| pDAS000131 | D | n/a | 7:1 | B | 0 |
| pDAS000131 | D | 29732-2A-29730 | 7:1 | B | 0 |
| pDAS000131 | D | n/a | 7:1 | D | 4 |
| pDAS000131 | D | 29732-2A-29730 | 7:1 | D | 212 |
| pDAS000134 | D | n/a | 7:1 | A | 0 |
| pDAS000134 | D | 29732-2A-29730 | 7:1 | A | 0 |
| pDAS000134 | D | n/a | 7:1 | B | 0 |
| pDAS000134 | D | 29732-2A-29730 | 7:1 | B | 0 |
| pDAS000134 | D | n/a | 7:1 | D | 32 |
| pDAS000134 | D | 29732-2A-29730 | 7:1 | D | 258 |
| pDAS000135 | D | n/a | 7:1 | A | 0 |
| pDAS000135 | D | 29732-2A-29730 | 7:1 | A | 0 |
| pDAS000135 | D | n/a | 7:1 | B | 0 |
| pDAS000135 | D | 29732-2A-29730 | 7:1 | B | 0 |
| pDAS000135 | D | n/a | 7:1 | D | 0 |
| pDAS000135 | D | 29732-2A-29730 | 7:1 | D | 1 |

"na" indicates "not applicable."

Data Analysis for Detecting ZFN-Mediated NHEJ-Directed Editing at AHAS Genes

Following generation of Illumina short read sequence data for sample libraries prepared for transfected SEC protoplasts and scutella of immature zygotic wheat embryos, analyses were performed to identify molecular evidence for ZFN-mediated NHEJ-directed editing at the target ZFN sites.

To identify sequence reads with molecular evidence for NHEJ-directed gene editing, the short sequence reads were first computationally processed, as previously described, to assign each read to the sample and sub-genome from which they originated, and to perform quality filtering to ensure that only high quality sequences were used for subsequent analyses. Next, custom developed PERL scripts and manual data manipulation in Microsoft Excel 2010 (Microsoft Corporation) was used to identify reads that contained sequence for both the donor DNA molecule used for transfection and the endogenous AHAS locus. The editing frequency (expressed in parts per million reads) was calculated as the proportion of sub-genome-assigned sequence reads that showed evidence for ZFN-mediated NHEJ-directed gene editing.

From the results of three biological replicates performed for each linear double stranded DNA donor design, molecular evidence was obtained for the enrichment of sequence reads showing ZFN-mediated NHEJ-directed editing at the three homoeologous copies of the endogenous AHAS genes in wheat (Table 7 and Table 8). Strong molecular evidence was obtained for the integration of the linear, double-stranded 41-bp donor molecule at the position of the double strand DNA break created by cleavage of the homoeologous copies of the AHAS gene by ZFNs 29732 and 29730 in samples of both SEC protoplasts and scutella of immature zygotic embryos that were transfected with pDAB109350 and pDAS000152. Similar editing efficiency was observed across the three wheat sub-genomes in these samples. In contrast, samples of SEC protoplasts and scutella of immature zygotic embryos transfected with pDAB109350 and pDAS000153 showed poor evidence for ZFN-mediated NHEJ-directed gene editing, presumably due to the prerequisite requirement for in planta release of the 41-bp donor sequence from the plasmid backbone. Molecular evidence for the replacement of endogenous AHAS sequence with the 41-bp donor molecule was observed in both SEC protoplasts and scutella of immature zygotic embryos that were transfected with pDAB109350, pDAB109360 and pDAS000149. However, the frequency of editing was significantly lower than that observed for transfections performed using pDAB109350 and pDAS000152, presumably due to the requirement for dual ZFN cleavage of the endogenous AHAS sequence. Limited evidence was obtained for the replacement of endogenous AHAS sequence with the 41-bp donor molecule that required in planta release from plasmid backbone in samples of SEC protoplast and scutella of immature zygotic embryos that were transfected with pDAB109350, pDAB109360 and pDAS000150.

TABLE 7

Average NHEJ editing frequency in parts per million (ppm) across three biological replicates of scutella transfected with linear double-stranded donor DNA designs.

| Donor | ZFN | Donor-to-ZFN molar ratio | Editing Frequency in Wheat Sub-Genome | Editing Frequency (ppm) |
|---|---|---|---|---|
| pDAS000152 | n/a | n/a | A | 0 |
| pDAS000152 | 29732-2A-29730 | 5:1 | A | 0 |
| pDAS000152 | 29732-2A-29730 | 10:1 | A | 131 |
| pDAS000152 | n/a | n/a | B | 0 |
| pDAS000152 | 29732-2A-29730 | 5:1 | B | 0 |
| pDAS000152 | 29732-2A-29730 | 10:1 | B | 47 |
| pDAS000152 | n/a | n/a | D | 0 |
| pDAS000152 | 29732-2A-29730 | 5:1 | D | 0 |
| pDAS000152 | 29732-2A-29730 | 10:1 | D | 75 |
| pDAS000153 | n/a | n/a | A | 0 |
| pDAS000153 | 29732-2A-29730 | 5:1 | A | 4 |
| pDAS000153 | 29732-2A-29730 | 10:1 | A | 0 |

TABLE 7-continued

Average NHEJ editing frequency in parts per million (ppm) across three biological replicates of scutella transfected with linear double-stranded donor DNA designs.

| Donor | ZFN | Donor-to-ZFN molar ratio | Editing Frequency in Wheat Sub-Genome | Editing Frequency (ppm) |
|---|---|---|---|---|
| pDAS000153 | n/a | n/a | B | 0 |
| pDAS000153 | 29732-2A-29730 | 5:1 | B | 0 |
| pDAS000153 | 29732-2A-29730 | 10:1 | B | 0 |
| pDAS000153 | n/a | n/a | D | 0 |
| pDAS000153 | 29732-2A-29730 | 5:1 | D | 0 |
| pDAS000153 | 29732-2A-29730 | 10:1 | D | 0 |
| pDAS000149 | n/a | n/a | A | 0 |
| pDAS000149 | 29732-2A-29730 | 5:1 | A | 23 |
| pDAS000149 | 29732-2A-29730 | 10:1 | A | 9 |
| pDAS000149 | n/a | n/a | B | 0 |
| pDAS000149 | 29732-2A-29730 | 5:1 | B | 7 |
| pDAS000149 | 29732-2A-29730 | 10:1 | B | 3 |
| pDAS000149 | n/a | n/a | D | 0 |
| pDAS000149 | 29732-2A-29730 | 5:1 | D | 7 |
| pDAS000149 | 29732-2A-29730 | 10:1 | D | 0 |
| pDAS000150 | n/a | n/a | A | 0 |
| pDAS000150 | 29732-2A-29730 | 5:1 | A | 1 |
| pDAS000150 | 29732-2A-29730 | 10:1 | A | 0 |
| pDAS000150 | n/a | n/a | B | 0 |
| pDAS000150 | 29732-2A-29730 | 5:1 | B | 0 |
| pDAS000150 | 29732-2A-29730 | 10:1 | B | 0 |
| pDAS000150 | n/a | n/a | D | 0 |
| pDAS000150 | 29732-2A-29730 | 5:1 | D | 4 |
| pDAS000150 | 29732-2A-29730 | 10:1 | D | 0 |
| pDAS000150 | n/a | n/a | A | 0 |

"na" indicates "not applicable."

TABLE 8

Average NHEJ editing frequency in parts per million (ppm) across three biological replicates of SEC protoplast transfected with linear double-stranded donor DNA designs.

| Donor | ZFN | Donor-to-ZFN molar ratio | Editing Frequency in Wheat Sub-Genome | Editing Frequency (ppm) |
|---|---|---|---|---|
| pDAS000152 | n/a | n/a | A | 0 |
| pDAS000152 | 29732-2A-29730 | 5:1 | A | 0 |
| pDAS000152 | 29732-2A-29730 | 10:1 | A | 6717 |
| pDAS000152 | 29732-2A-29730 | 20:1 | A | 5404 |
| pDAS000152 | n/a | n/a | B | 0 |
| pDAS000152 | 29732-2A-29730 | 5:1 | B | 0 |
| pDAS000152 | 29732-2A-29730 | 10:1 | B | 6306 |
| pDAS000152 | 29732-2A-29730 | 20:1 | B | 4106 |
| pDAS000152 | n/a | n/a | D | 0 |
| pDAS000152 | 29732-2A-29730 | 5:1 | D | 0 |
| pDAS000152 | 29732-2A-29730 | 10:1 | D | 7911 |
| pDAS000152 | 29732-2A-29730 | 20:1 | D | 4059 |
| pDAS000153 | n/a | n/a | A | 0 |
| pDAS000153 | 29732-2A-29730 | 5:1 | A | 0 |
| pDAS000153 | 29732-2A-29730 | 10:1 | A | 0 |
| pDAS000153 | 29732-2A-29730 | 20:1 | A | 0 |
| pDAS000153 | n/a | n/a | B | 0 |
| pDAS000153 | 29732-2A-29730 | 5:1 | B | 0 |
| pDAS000153 | 29732-2A-29730 | 10:1 | B | 0 |
| pDAS000153 | 29732-2A-29730 | 20:1 | B | 0 |
| pDAS000153 | n/a | n/a | D | 0 |
| pDAS000153 | 29732-2A-29730 | 5:1 | D | 0 |
| pDAS000153 | 29732-2A-29730 | 10:1 | D | 0 |
| pDAS000153 | 29732-2A-29730 | 20:1 | D | 0 |
| pDAS000153 | n/a | n/a | A | 0 |
| pDAS000153 | 29732-2A-29730 | 5:1 | A | 0 |
| pDAS000149 | n/a | n/a | A | 0 |
| pDAS000149 | 29732-2A-29730 | 5:1 | A | 0 |
| pDAS000149 | 29732-2A-29730 | 10:1 | A | 0 |
| pDAS000149 | 29732-2A-29730 | 20:1 | A | 344 |
| pDAS000149 | n/a | n/a | B | 0 |
| pDAS000149 | 29732-2A-29730 | 5:1 | B | 0 |
| pDAS000149 | 29732-2A-29730 | 10:1 | B | 0 |
| pDAS000149 | 29732-2A-29730 | 20:1 | B | 210 |
| pDAS000149 | n/a | n/a | D | 0 |
| pDAS000149 | 29732-2A-29730 | 5:1 | D | 4 |
| pDAS000149 | 29732-2A-29730 | 10:1 | D | 0 |
| pDAS000149 | 29732-2A-29730 | 20:1 | D | 24 |
| pDAS000150 | n/a | n/a | A | 0 |
| pDAS000150 | 29732-2A-29730 | 5:1 | A | 0 |
| pDAS000150 | 29732-2A-29730 | 10:1 | A | 0 |
| pDAS000150 | 29732-2A-29730 | 20:1 | A | 0 |
| pDAS000150 | n/a | n/a | B | 0 |
| pDAS000150 | 29732-2A-29730 | 5:1 | B | 0 |
| pDAS000150 | 29732-2A-29730 | 10:1 | B | 0 |
| pDAS000150 | 29732-2A-29730 | 20:1 | B | 0 |
| pDAS000150 | n/a | n/a | D | 0 |
| pDAS000150 | 29732-2A-29730 | 5:1 | D | 0 |
| pDAS000150 | 29732-2A-29730 | 10:1 | D | 0 |

TABLE 8-continued

Average NHEJ editing frequency in parts per million (ppm) across three biological replicates of SEC protoplast transfected with linear double-stranded donor DNA designs.

| Donor | ZFN | Donor-to-ZFN molar ratio | Editing Frequency in Wheat Sub-Genome | Editing Frequency (ppm) |
|---|---|---|---|---|
| pDAS000150 | 29732-2A-29730 | 20:1 | D | 0 |

"na" indicates "not applicable."

Collectively, the results provide strong molecular evidence for precise ZFN-mediated NHEJ-directed editing at the endogenous AHAS gene locus in wheat. These results show that all three sub-genomes can be targeted with a single ZFN and donor. The results clearly demonstrate a higher frequency of editing for linear donor DNA designs as compared to plasmid donor DNA designs. Presumably, these results are due to the prerequisite requirement for in planta linearization of the plasmid donor molecules before they can participate in NHEJ-directed DNA repair. The results also indicate that sub-genome-specific mediated NHEJ-directed gene editing is facilitated by a double strand break. The ZFNs that were designed to induce the double strand DNA breaks resulted in a sub-genome-specific mediated NHEJ-directed gene editing when delivered with the donor DNA to the *Triticum aestivum* plant cells.

Example 5: Development of a Transformation System for Producing AHAS Edited Plants The endogenous AHAS gene locus in wheat was selected as a model locus to develop a transformation system for generating plants with precise genome modifications induced by ZFN-mediated gene editing. The endogenous AHAS gene was selected as a model locus due to its ability to produce a selectable phenotype (i.e., tolerance to group B herbicides, or ALS inhibitor herbicides such as imidazolinone or sulfonylurea), knowledge of prerequisite information of sub-genome-specific gene coding sequence, and knowledge of specific mutations conferring tolerance to group B herbicides, or ALS inhibitor herbicides from the characterization of wheat with chemically induced mutations in the AHAS genes. The S653N mutation conferring tolerance to imidazolinone class herbicide was chosen as a target for ZFN-mediated gene editing due to the availability of commercially released wheat varieties carrying the S653N mutation that could be used as positive controls to develop a chemical selection system to enrich for precisely edited events.

Molecular Characterization of *Triticum aestivum* cv. Clearfield Janz

*Triticum aestivum* cv. Clearfield Janz, a commercially released bread wheat variety carrying the S653N mutation in the D-genome, was selected for use as a positive control to develop a chemical selection strategy to enrich for AHAS edited wheat plants produced by ZFN-mediated gene editing. To generate a pure genetic seed stock, 48 seedlings were screened with 96 microsatellite (SSR) markers using Multiplex-Ready PCR technology (Hayden et al., (2008) BMC Genomics 9; 80). Seedlings with identical SSR haplotypes were used to produce seed that was used in subsequent experiments.

To ensure that the wheat plants used to produce seed carried the S653N mutation, a PCR assay was developed to amplify the region of the AHAS gene carrying the mutation from the D-genome of wheat. Sub-genome-specific amplification was achieved using on-off PCR (Yang et al., (2005) Biochemical and Biophysical Research Communications 328:265-72) with primers AHAS-PS-6DF2 and AHAS-PS-6DR2 (SEQ ID NO: 82 and SEQ ID NO: 83) designed to position the penultimate base (which contained a phosphorothioate linkage) over nucleotide sequence variation that distinguished between the homoeologous copies of the AHAS genes. The PCR primers were designed to be between 18 and 27 nucleotides in length and to have a melting temperature of 60 to 65° C., optimal 63° C. The amplified PCR products were purified using a QIAQUICK MINIELUTE PCR PURIFICATION KIT™ (Qiagen) and sequenced using a direct Sanger sequencing method. The sequencing products were purified with ethanol, sodium acetate and EDTA following the BIGDYE® v3.1 protocol (Applied Biosystems) and electrophoresis was performed on an ABI3730XL® automated capillary electrophoresis platform.

Analysis of the amplified AHAS gene sequences using SEQUENCHER v3.7™ (GeneCodes, Ann Arbor, Mich.) revealed segregation for the S653N mutation and enabled the identification of plants that were homozygous (N653/N653) and heterozygous (N653/S653) for the S653N mutation or homozygous (S653/S653) for the herbicide-susceptible allele. The harvest of seed from individual plants provided a seed source having different levels of zygosity for the S653N mutation in the cv. Clearfield Janz genetic background.

Optimization of Chemical Selection Conditions Based on IMAZAMOX™

A series of experiments were performed to determine optimal selection conditions for regenerating AHAS edited wheat plants. These experiments were based on testing the basal tolerance to IMAZAMOX™ of the donor wheat line cv. Bobwhite MPB26RH (S653/S653 genotype) at the callus induction, plant regeneration and rooting stages of an established wheat transformation system. Similar experiments were performed to determine the basal tolerance and resistance of cv. Clearfield Janz genotypes carrying the different doses of the S653N mutation; i.e., plants with N653/N653 and S653/S653 genotypes.

The basal tolerance of the donor wheat line cv. Bobwhite MPB26RH and basal resistance of cv. Clearfield Janz (N653/N653) genotype to IMAZAMOX® at the callus induction stage was determined as follows: Scutella of immature zygotic embryos from each wheat line were isolated as described previously and placed in 10 cm PETRI™ dishes containing CIM medium supplemented with 0, 50, 100, 200, 300, 400 and 500 nM IMAZAMOX® respectively. Twenty scutella were placed in each PETRI™ dish. A total of 60 scutella from each of the donor wheat line cv. Bobwhite MPB26RH and cv. Clearfield Janz genotype were tested for basal tolerance and basal resistance response, respectively, at each IMAZAMOX® concentration. After incubation at 24° C. in the dark for 4 weeks, the amount of somatic embryogenic callus formation (SEC) at each IMAZAMOX® concentration was recorded. The results showed that SEC formation for cv. Bobwhite MPB26RH was reduced by about 70% at 100 nM IMAZAMOX®, compared to untreated samples. Callus formation for the cv. Clearfield Janz genotype was unaffected, relative to the untreated control, at any IMAZAMOX® concentrations tested.

The basal tolerance of the donor wheat line cv. Bobwhite MPB26RH to IMAZAMOX® at the plant regeneration stage was determined as follows: Scutella of immature zygotic embryos from the donor wheat line were isolated as described previously and placed in 10 cm PETRI™ dishes containing CIM medium. Somatic embryogenic callus was allowed to form by incubating at 24° C. in the dark for 4 weeks. The SEC was transferred to 10 cm PETRI™ dishes containing DRM medium supplemented with 0, 100, 200, 300, 400, 500 and 1000 nM IMAZAMOX® respectively. Twenty CIM were placed in each PETRI™ dish. A total of 60 CIM were tested for basal tolerance response at each IMAZAMOX® concentration. After incubation for 2 weeks at 24° C. under a 16/8 (light/dark) hour photoperiod in a growth room, the regeneration response was recorded. The results showed that plant regeneration was reduced by about 80% at 200 nM IMAZAMOX®, compared to untreated samples.

The basal tolerance of the cv. Clearfield Janz (S653/S653) genotype and basal resistance of the cv. Clearfield Janz (N653/N653) genotype to IMAZAMOX® at the plant regeneration stage was determined using a modified approach, as cv. Clearfield Janz was observed to have poor plant regeneration response (i.e., poor embryogenesis) in tissue culture. Seed for each cv. Clearfield Janz genotype was germinated using the aseptic approach described above for producing wheat mesophyll protoplasts. The germinated seedlings were multiplied in vitro by sub-culturing on multiplication medium. Following multiplication, plants for each genotype were transferred to 10 cm PETRI™ dishes containing plant growth medium (MS+10 µM BA+0.8% agar) supplemented with 0, 100, 300, 600, 900, 1200, 1500 and 3000 nM IMAZAMOX®, respectively. Ten plants were placed in each PETRI™ dish. A total of 30 plants per genotype were tested for basal response at each IMAZAMOX® concentration. After incubation for 3 weeks at 24° C. under a 16/8 (light/dark) hour photoperiod in a growth room, the growth response was recorded. The results showed that plant growth for the cv. Clearfield Janz (S653/S653) genotype was severely reduced in medium containing at least 200 nM IMAZAMOX®, compared to untreated samples. This response was similar to that observed for the cv. Bobwhite MPB26RH (S653/S653) genotype. In contrast, plant growth for the cv. Clearfield Janz (N653/N653) genotype was not strongly suppressed, relative to untreated samples, until the IMAZAMOX® concentration exceeded 2,000 nM.

The basal tolerance of the donor wheat line cv. Bobwhite MPB26RH to IMAZAMOX® at the plant rooting stage was determined as follows: Scutella of immature zygotic embryos from the donor wheat line were isolated as described previously and placed in 10 cm PETRI™ dishes containing CIM medium. Somatic embryogenic callus was allowed to form by incubating at 24° C. in the dark for 4 weeks. The SEC was transferred to 10 cm PETRI™ dishes containing DRM medium and incubated for 2 weeks at 24° C. under a 16/8 (light/dark) hour photoperiod to allow plant regeneration to take place. Regenerated plants were transferred to 10 cm PETRI™ dishes containing RM medium supplemented with 0, 100, 200, 300, 400, 500 nM IMAZAMOX®, respectively. Twenty regenerated plants were placed in each PETRI™ dish. A total of 60 regenerated plants were tested for basal tolerance response at each IMAZAMOX® concentration. After incubation for 3 weeks at 24° C. under a 16/8 (light/dark) hour photoperiod in a growth room, the root formation response was recorded. The results showed that root formation was severely restricted at all concentrations of IMAZAMOX® tested, compared to untreated samples.

The basal tolerance of the cv. Clearfield Janz (S653/S653) genotype and basal resistance of the cv. Clearfield Janz (N653/N653) genotype to IMAZAMOX® at the plant rooting stage was determined using a modified approach, as cv. Clearfield Janz was observed to have poor plant regeneration response (i.e., poor embryogenesis) in tissue culture. Seed for each cv. Clearfield Janz genotype was germinated using the aseptic approach described above for producing wheat mesophyll protoplasts. The germinated seedlings were multiplied in vitro by sub-culturing on multiplication medium. Following multiplication, plants for each genotype were transferred to 10 cm PETRI™ dishes containing plant rooting medium (1/2 MS, 0.5 mg/L NAA, 0.8% agar) supplemented with 0, 50, 100, 200 and 250 nM IMAZAMOX®, respectively. Three plants were placed in each PETRI™ dish. A total of 6 plants per genotype were tested for basal response at each IMAZAMOX® concentration. After incubation for 2 weeks at 24° C. under a 16/8 (light/dark) hour photoperiod in a growth room, the root formation response was recorded.

The results showed that root formation for the cv. Clearfield Janz (N653/N653) genotype was restricted, compared to untreated samples, at 250 nM IMAZAMOX®. Root formation was severely restricted in the cv. Clearfield Janz (S653/S653) genotype at all concentrations of IMAZAMOX® tested, compared to untreated samples.

Design and Synthesis of Donor DNA for ZFN-Mediated NHEJ-Directed AHAS Gene Editing Two types of donor DNA molecule were designed to promote precise ZFN-mediated NHEJ-directed gene editing at the endogenous AHAS genes in wheat. Both donor designs allowed for the introduction of the S653N mutation known to confer tolerance to imidazolinone class herbicides (Li et al., (2008) *Molecular Breeding* 22:217-225).

The first design was based on the integration of a 95-bp double stranded donor molecule at the position of the double strand DNA break created by cleavage of a homoeologous copy of the endogenous AHAS gene by ZFNs 29732 and 29730 (encoded on plasmid pDAB109350). The donor DNA molecule, pDAS000267 (SEQ ID NO:84 and SEQ ID NO:85), comprised two portions of the integrating donor polynucleotide. The 5' end contained sequence near identical to the endogenous AHAS gene encoded in the D-genome, starting from the target ZFN cleavage site and finishing at the AHAS stop codon. Six intentional mutations were introduced into this sequence: two mutations encoded the S653N mutation (AGC→AAT), and four mutations were synonymous (in which a silent mutation was incorporated into the donor sequence). The 3' end of the donor molecule contained a unique sequence that could be used for diagnostic PCR to detect ZFN-mediated NHEJ-directed gene editing events. The donor molecule was designed with protruding 5' and 3' ends to provide ligation overhangs to facilitate ZFN-mediated NHEJ-directed DNA repair.

The second design was based on replacement of the endogenous AHAS sequence located between a pair of ZFN target sites with a 79-bp double stranded donor molecule. Specifically, the donor was designed to replace the endogenous AHAS sequence released from chromatin upon dual cleavage of a homoeologous copy of the AHAS gene by ZFNs 29732 and 29730 (encoded on plasmid pDAB109350) and ZFNs 30012 and 30018 (encoded on plasmid pDAB109360). The donor molecule, pDAS000268 (SEQ ID NO:86 and SEQ ID NO:87), comprised sequence near identical to the endogenous AHAS gene encoded in the D-genome, starting from the cleavage site for ZFNs 29732 and 29730, and finishing at the cleavage site for ZFNs 30012 and 30018. Ten deliberate mutations were introduced into this sequence. Six mutations were located at the 5' end of the donor: two mutations encoded the S653N mutation (AGC→AAT) and four mutations were synonymous. Four mutations were located at the 3' end of the donor and were located in non-coding sequence. The donor molecule was designed with protruding 5' and 3' ends to provide ligation overhangs to facilitate ZFN-mediated NHEJ-directed DNA repair.

Standard phosphoramidite chemistry was used to synthetically synthesize the double stranded DNA donor molecules (Integrated DNA Technologies). For each donor molecule, a pair of complementary single stranded DNA oligomers was synthesized, each with two phosphorothioate linkages at their 5' ends to provide protection against in planta endonuclease degradation. The single stranded DNA oligomers were purified by high performance liquid chromatography to enrich for full-length molecules and purified of chemical carryover from the synthesis steps using $Na^+$ exchange. The double stranded donor molecule was formed by annealing equimolar amounts of the two complementary single-stranded DNA oligomers using standard methods commonly known by one skilled in the art. Before delivery to *Triticum aestivum*, the double stranded DNA molecules were diluted to the required concentration in sterile water.

Design and Production of Binary Vector Encoding AHAS (S653N)

Standard cloning methods were used in the construction of binary vector pDAS000143 (SEQ ID: 88) (FIG. 10). The AHAS (S653N) gene expression cassette consists of the promoter, 5' untranslated region and intron from the Ubiquitin (Ubi) gene from *Zea mays* (Toki et al., (1992) Plant Physiology 100; 1503-07) followed by the coding sequence (1935 bp) of the AHAS gene from *T. aestivum* with basepairs 1880 and 1181 mutated from CG to AT in order to induce an amino acid change from serine (S) to aspargine (N) at amino acid residue 653. The AHAS expression cassette included the 3' untranslated region (UTR) of the *nopaline synthase* gene (nos) from *A. tumefaciens* pTi15955 (Fraley et al., (1983) Proceedings of the National Academy of Sciences U.S.A. 80(15); 4803-4807). The selection cassette was comprised of the promoter, 5' untranslated region and intron from the actin 1 (Act1) gene from *Oryza sativa* (McElroy et al., (1990) *The Plant Cell* 2(2); 163-171) followed by a synthetic, plant-optimized version of phosphinothricin acetyl transferase (PAT) gene, isolated from *Streptomyces viridochromogenes*, which encodes a protein that confers resistance to inhibitors of glutamine synthetase comprising phosphinothricin, glufosinate, and bialaphos (Wohlleben et al., (1988) Gene 70(1); 25-37). This cassette was terminated with the 3' UTR from the 35S gene of cauliflower mosaic virus (CaMV) (Chenault et al., (1993) Plant Physiology 101 (4); 1395-1396).

The selection cassette was synthesized by a commercial gene synthesis vendor (GeneArt, Life Technologies) and cloned into a Gateway-enabled binary vector with the RfA Gateway cassette located between the Ubiquitin (Ubi) gene from *Zea mays* and the 3' untranslated region (UTR) comprising the transcriptional terminator and polyadenylation site of the nopaline synthase gene (nos) from *A. tumefaciens* pTi15955. The AHAS(S653N) coding sequence was amplified with flanking attB sites and sub-cloned into pDONR221. The resulting ENTRY clone was used in a LR CLONASE II™ (Invitrogen, Life Technologies) reaction with the Gateway-enabled binary vector encoding the phosphinothricin acetyl transferase (PAT) expression cassette. Colonies of *E. coli* cells transformed with all ligation reactions were initially screened by restriction digestion of miniprep DNA. Restriction endonucleases were obtained from New England BioLabs and Promega. Plasmid preparations were performed using the QIAPREP SPIN MINIPREP KIT™ or the PURE YIELD PLASMID MAXIPREP SYSTEM™ (Promega Corporation, WI) following the manufacturer's instructions. Plasmid DNA of selected clones was sequenced using ABI Sanger Sequencing AND BIG DYE TERMINATOR v3.1™ cycle sequencing protocol (Applied Biosystems, Life Technologies). Sequence data were assembled and analyzed using the SEQUENCHER™ software (Gene Codes Corporation, Ann Arbor, Mich.).

Biolistic-Mediated Transformation System for Generating AHAS Edited Wheat Plants About 23,000 scutella of immature zygotic embryos from the donor wheat line cv. Bobwhite MPB26RH were prepared for biolistics-mediated DNA delivery, as described previously. DNA-coated gold particles were prepared as described above with the following formulations. For transfections performed using pDAS000267, the donor DNA was mixed at a 5:1 molar ratio with plasmid DNA for pDAB109350 (encoding ZFNs 29732 and 29730). For transfections performed using pDAS000268, the donor DNA was mixed at a 10:1:1 molar ratio with plasmid DNA for pDAB109350 (encoding ZFNs 29732 and 29730) and pDAB109360 (encoding ZFNs 30012 and 30018). Transfections performed using pDAS000143 were performed using gold particles that were coated only with plasmid DNA for pDAS000143.

Biolistic-mediated transfections were performed as described previously. A total of 15,620 scutella were bombarded with gold particles coated with DNA containing pDAS000267, a total of 7,310 scutella were bombarded with gold particles coated with DNA containing pDAS000268, and a total of 2,120 scutella were bombarded with gold particles coated with pDAS000143. Following bombardment, the transfected scutella were incubated at 26° C. in the dark for 16 h before being transferred onto medium for callus induction.

Four different chemical selection strategies based on IMAZAMOX® were used to enrich for regenerated wheat plants that had the S653N mutation precisely integrated into one or more homoeologous copies of the endogenous AHAS gene by ZFN-mediated NHEJ-directed gene editing. The four chemical selection strategies are described in Table 9. For each strategy, scutella were cultured in the dark on callus induction medium at 24° C. for 2 weeks. The resultant calli were sub-cultured once onto fresh callus induction medium and kept in the same conditions for a further two weeks. Somatic embryogenic callus (SEC) was transferred onto plant regeneration medium and cultured for 2 weeks at 24° C. under a 16/8 (light/dark) hour photoperiod in a growth room. Regenerated plantlets were transferred onto rooting medium and cultured under the same conditions for 2-3 weeks. To increase stringency for the selection of regenerated plants having the S653N mutation, the roots of regenerated plants were removed and the plants were again sub-cultured on rooting media under the same conditions. Plantlets rooting a second time were transferred to soil and grown under glasshouse containment conditions. $T_1$ seed was harvested from individual plants, following bagging of individual spikes to prevent out-crossing.

The scutella explants bombarded with gold particles coated with pDAS000143 were used to monitor the selection stringency across the four chemical selection strategies for regenerating wheat plants carrying the AHAS S653N mutation. Plants transformed with pDAS000143 were regenerated using process described above.

TABLE 9

Chemical selection strategies used to regenerate wheat plants that had the S653N mutation precisely integrated into one or more homoeologous copies of the endogenous AHAS gene by ZFN-mediated NHEJ-directed gene editing.

| Plant Regeneration Stage | Strategy 1 | Strategy 2 | Strategy 3 | Strategy 4 |
|---|---|---|---|---|
| Callus induction (CIM) | 150 nM IMI | 250 nM IMI | 150 nM IMI | 250 nM IMI |

TABLE 9-continued

Chemical selection strategies used to regenerate wheat plants that had the S653N mutation precisely integrated into one or more homoeologous copies of the endogenous AHAS gene by ZFN-mediated NHEJ-directed gene editing.

| Plant Regeneration Stage | Strategy 1 | Strategy 2 | Strategy 3 | Strategy 4 |
|---|---|---|---|---|
| Plant Regeneration (DRM) | 150 nM IMI | 0 nM IMI | 250 nM IMI | 250 nM IMI |
| Rooting (RM) | 200 nM IMI | 200 nM IMI | 200 nM IMI | 200 nM IMI |

(IMI = IMAZAMOX ™)

Overall, 14 putatively ZFN-mediated NHEJ-directed AHAS edited wheat plants were recovered from the transfection of 22,930 scutella of immature zygotic embryos from the donor wheat line cv. Bobwhite MPB26RH. Putatively edited plants were obtained from all four selection strategies for scutella bombarded with gold particles coated with DNA containing pDAS000267. Two putatively edited plants were obtained from the second selection strategy for scutella bombarded with gold particles coated with DNA containing pDAS000268. A total of 129 putatively transformed wheat plants carrying at least one randomly integrated copy of the AHAS (S653N) donor polynucleotide were recovered across the four chemical selection strategies.

Example 6: Molecular Characterization of Edited Wheat Plants

The wheat plants resulting from bombardments with a donor polynucleotide encoding the S653N mutation were obtained and molecularly characterized to identify the wheat sub-genomes that comprised an integration of the S653N mutation that occurred as a result of the donor integration at a genomic double strand cleavage site. Two series of bombardments were completed. The first set of experiments was completed with pDAS000143, and the second set of experiments was completed with pDAS000267 and pDAS000268. Individual wheat plants were obtained from both sets of experiments and assayed via a molecular method to identify plants which contained an integrated copy of the AHAS donor polynucleotide encoding the S653N mutation.

A hydrolysis probe assay (analogous to the TAQMAN® based assay) for quantitative PCR analysis was used to confirm that recovered wheat plants that had been bombarded with pDAS000143 carried at least one randomly integrated copy of the AHAS donor polynucleotide encoding the S653N mutation. Confirmation via Sanger sequence analysis indicated that wheat plants recovered from bombardments performed with pDAS000267 and pDAS000268 comprised the S653N donor polynucleotide in at least one of the homoeologous copies of the AHAS gene at the position expected for ZFN-mediated NHEJ-directed gene editing.

Genomic DNA Isolation from Regenerated Wheat Plants

Genomic DNA was extracted from freeze-dried leaf tissue harvested from each regenerated wheat plant. Freshly harvested leaf tissue was snap frozen in liquid nitrogen and freeze-dried for 24 h in a LABCONCO FREEZONE 4.5® (Labconco, Kansas City, Mo.) at −40° C. and $133 \times 10^{-3}$ mBar pressure. The lyophilized material was subjected to DNA extraction using the DNEASY® PLANT DNA EXTRACTION MINI KIT™ (Qiagen) following the manufacturer's instructions.

PCR Assay to Confirm Random Integration of AHAS Donor Polynucleotide Encoding S653N Mutation To confirm that the regenerated wheat plants from bombardments performed with pDAS000143 carried at least one randomly integrated copy of the AHAS donor polynucleotide encoding the S653N mutation, a duplex hydrolysis probe qPCR assay (analogous to TAQMAN®) was used to amplify the endogenous single copy gene, puroindoline-b (Pinb), from the D genome of hexaploid wheat (Gautier et al., (2000) Plant Science 153: 81-91; SEQ ID NO: 89, SEQ ID NO: 90 and SEQ ID NO: 91 for forward and reverse primers and probe sequence, respectively) and a region of the Actin (Act1) promoter present on pDAS000143 (SEQ ID NO: 92, SEQ ID NO: 93 and SEQ ID NO: 94 for forward and reverse primers and probe sequence, respectively). Hydrolysis probe qPCR assays were performed on 24 randomly chosen wheat plants that were recovered from each of the four chemical selection strategies. Assessment for the presence, and estimated copy number of pDAS00143 was performed according to the method described in Livak and Schmittgen (2001) Methods 25(4):402-8.

From the results, conclusive evidence was obtained for the integration of at least one copy of the AHAS donor polynucleotide encoding the S653N mutation into the genome of each of the wheat plants tested. These results indicate that the four chemical selection strategies provided stringent selection for the recovery of plants expressing the S653N mutation.

PCR Assay of Genomic DNA for ZFN-Mediated AHAS Editing

To characterize the sub-genomic location and outcome of ZEN-mediated NHEJ-directed gene editing in the recovered wheat plants, PCR with primers AHAS_3F1 and AHAS_3R1 (SEQ ID NO:95 and SEQ ID NO:96) was used to amplify the target region from the homoeologous copies of the AHAS genes. The resulting PCR products were cloned into plasmid vector and Sanger sequenced using BIGDYE® v3.1 chemistry (Applied Biosystems) on an ABI3730XL® automated capillary electrophoresis platform. Sanger sequencing of up to 120 independent plasmid clones was performed to ensure that each allele at the endogenous AHAS homoeologs was sequenced. Sequence analysis performed using SEQUENCHER SOFTWARE™ was used to generate a consensus sequence for each allele of the three homoeologous copies of the AHAS gene in each of the recovered wheat plants, and to determine the sub-genomic origin and sequence for each edited allele.

From the results, conclusive evidence for precise ZFN-mediated NHEJ-directed gene editing at the endogenous AHAS loci was demonstrated for 11 of the 12 recovered wheat plants that were transformed using pDAB109350 and pDAS000267 (Table 10), and both of the recovered wheat plants that were transformed using pDAB109350, pDAB109360 and pDAS000268 (Table 11). Plants with a range of editing outcomes were observed including: (1) independent events with perfect sub-genome-specific allele edits; (2) events with single perfect edits in the A-genome, B-genome and D-genomes; (3) events with simultaneous editing in multiple sub-genomes; and, (4) events demonstrating hemizygous and homozygous sub-genome-specific allele editing. Disclosed for the first time is a method which can be utilized to mutate a gene locus within all three genomes of a wheat plant. Wheat plants comprising an integrated AHAS donor polynucleotide encoding a S653N mutation are exemplified; integration of the polynucleotide sequence provides tolerance to imidazolinone class herbicides. The utilization of ZFN-mediated genomic editing at an endogenous gene locus in wheat allows for the introduction of agronomic traits (via mutation) without time consuming wheat breeding techniques which require backcrossing and introgression steps that can increase the amount of time required for introgressing the trait into all three sub-genomes. Consensus Sanger sequences for the alleles present in each sub-genome for the edited wheat plants are provided as SEQ ID NO:97-180 in Tables 10 and 11.

TABLE 10

ZFN-mediated NHEJ-directed AHAS editing outcomes for wheat plants transformed using pDAB109350 and pDAS000267

| | | A-genome | | B-genome | | D-genome | | |
|---|---|---|---|---|---|---|---|---|
| | | Allele 1 | Allele 2 | Allele 1 | Allele 2 | Allele 1 | Allele 2 | SEQ ID NO: |
| Plant No. 1 | Status | PE | NHEJ | IE | UE | IE | UE | 97-102 |
| | No. clones[1] | 13 | 20 | 12 | 19 | 14 | 22 | |
| Plant No. 2 | Status | NHEJ | UE | UE | nd | IE | UE | 103-108 |
| | No. clones[1] | 9 | 3 | 16 | 0 | 75 | 17 | |
| Plant No. 3 | Status | PE | UE | UE | nd | UE | nd | 109-114 |
| | No. clones[1] | 7 | 11 | 29 | 0 | 35 | 0 | |
| Plant No. 4 | Status | PE | UE | IE | UE | PE | IE | 115-120 |
| | No. clones[1] | 6 | 11 | 44 | 30 | 6 | 11 | |
| Plant No. 5 | Status | PE | UE | NHEJ | UE | UE | nd | 121-126 |
| | No. clones[1] | 10 | 9 | 15 | 26 | 21 | 0 | |
| Plant No. 6 | Status | UE | nd | PE | UE | UE | nd | 127-132 |
| | No. clones[1] | 22 | 0 | 11 | 18 | 43 | 0 | |
| Plant No. 7 | Status | PE | UE | UE | nd | UE | nd | 133-138 |
| | No. clones[1] | 5 | 12 | 26 | 0 | 22 | 0 | |
| Plant No. 8 | Status | UE | nd | UE | nd | UE | nd | 139-144 |
| | No. clones[1] | 32 | 0 | 40 | 0 | 26 | 0 | |
| Plant No. 9 | Status | PE | nd | IE | UE | UE | nd | 145-150 |
| | No. clones[1] | 24 | 0 | 13 | 21 | 33 | 0 | |
| Plant No. 10 | Status | PE | UE | UE | nd | UE | nd | 151-156 |
| | No. clones[1] | 10 | 19 | 37 | 0 | 29 | 0 | |
| Plant No. 11 | Status | UE | nd | UE | nd | PE | UE | 157-162 |
| | No. clones[1] | 35 | 0 | 37 | 0 | 15 | 11 | |
| Plant No. 12 | Status | UE | nd | UE | nd | IE | NHEJ | 163-168 |
| | No. clones[1] | 34 | 0 | 40 | 0 | 14 | 8 | |

[1]Number of independent plasmid clones sequenced.
PE = perfect edit; i.e., ZFN-mediated NHEJ-directed genome editing produced a predicted outcome.
IE = imperfect edit; i.e., ZFN-mediated NHEJ-directed genome editing produced an unpredicted outcome.
UE = unedited allele; i.e., allele had wild-type sequence.
nd = not detected; i.e., sufficient independent plasmid clones were sequenced to conclude that an alternate allele was not present and that the locus was homozygous for a single allele.
NHEJ = Non Homologous End Joining; i.e., evidence for a non-homologous end joining DNA repair outcome that did not result in the integration of a donor molecule at the ZFN cleavage site.

TABLE 11

ZFN-mediated NHEJ-directed AHAS editing outcomes for wheat plants transformed using pDAB109350, pDAB109360 and pDAS000268.

| | | A-genome | | B-genome | | D-genome | | |
|---|---|---|---|---|---|---|---|---|
| | | Allele 1 | Allele 2 | Allele 1 | Allele 2 | Allele 1 | Allele 2 | SEQ ID NO: |
| Plant No. 12a | Status | IE | UE | UE | nd | IE | nd | 169-174 |
| | No. clones[1] | 5 | 14 | 53 | 0 | 1 | 24 | |
| Plant No. 13a | Status | IE | UE | UE | nd | UE | nd | 175-180 |
| | No. clones[1] | 10 | 12 | 49 | 0 | 18 | 0 | |

[1]Number of independent plasmid clones sequenced.
IE = imperfect edit; i.e., ZFN-mediated NHEJ-directed genome editing produced unexpected outcome.
UE = unedited allele; i.e., allele had wild-type sequence.
nd = not detected; i.e., sufficient independent plasmid clones were sequenced to conclude that an alternate allele was not present and that the locus was homozygous for a single allele.

Example 7: Design of Zinc Finger Binding Domains Specific to Region in AHAS Genes Encoding the P197 Amino Acid Residue Zinc finger proteins directed against DNA sequence of the homoeologous copies of the AHAS genes were designed as previously described (see also Example 2). Exemplary target sequence and recognition helices are shown in Table 12 (recognition helix regions designs) and Table 13 (target sites). In Table 13, nucleotides in the target site that are contacted by the ZFP recognition helices are indicated in uppercase letters; non-contacted nucleotides are indicated in lowercase. Zinc Finger Nuclease (ZFN) target sites were upstream (from 2 to 510 nucleotides upstream) of the region in the AHAS gene encoding the proline 197 (P197) amino acid residue.

TABLE 12

| AHAS zinc finger designs (N/A indicates "Not Applicable") | | | | | | |
|---|---|---|---|---|---|---|
| ZFP # | F1 | F2 | F3 | F4 | F5 | F6 |
| 34456 | SEQ ID NO: 227 RSADLTR | SEQ ID NO: 182 RSDDLTR | SEQ ID NO: 182 RSDDLTR | SEQ ID NO: 236 RSDALTQ | SEQ ID NO: 237 ERGTLAR | SEQ ID NO: 182 RSDDLTR |
| 34457 | SEQ ID NO: 184 QSGDLTR | SEQ ID NO: 238 DTGARLK | SEQ ID NO: 182 RSDDLTR | SEQ ID NO: 239 HRRSRDQ | SEQ ID NO: 240 DRSYRNT | N/A |

TABLE 12-continued

AHAS zinc finger designs (N/A indicates "Not Applicable")

| ZFP # | F1 | F2 | F3 | F4 | F5 | F6 |
|---|---|---|---|---|---|---|
| 34470 | SEQ ID NO: 241 RSADLSR | SEQ ID NO: 242 RSDHLSA | SEQ ID NO: 243 QSSDLRR | SEQ ID NO: 233 DRSNLSR | SEQ ID NO: 244 RSDDRKT | N/A |
| 34471 | SEQ ID NO: 184 QSGDLTR | SEQ ID NO: 245 RRADRAK | SEQ ID NO: 182 RSDDLTR | SEQ ID NO: 246 TSSDRKK | SEQ ID NO: 227 RSADLTR | SEQ ID NO: 247 RNDDRKK |
| 34472 | SEQ ID NO: 227 RSADLTR | SEQ ID NO: 198 DRSNLTR | SEQ ID NO: 237 ERGTLAR | SEQ ID NO: 182 RSDDLTR | SEQ ID NO: 218 DRSDLSR | SEQ ID NO: 248 DSSTRRR |
| 34473 | SEQ ID NO: 219 RSDHLSE | SEQ ID NO: 249 HSRTRTK | SEQ ID NO: 210 RSDTLSE | SEQ ID NO: 250 NNRDRTK | SEQ ID NO: 237 ERGTLAR | SEQ ID NO: 224 DRSALAR |
| 34474 | SEQ ID NO: 237 ERGTLAR | SEQ ID NO: 182 RSDDLTR | SEQ ID NO: 218 DRSDLSR | SEQ ID NO: 248 DSSTRRR | SEQ ID NO: 198 DRSNLTR | N/A |
| 34475 | SEQ ID NO: 249 RSDHLSR | SEQ ID NO: 73 QQWDRKQ | SEQ ID NO: 201 DRSHLTR | SEQ ID NO: 216 DSSDRKK | SEQ ID NO: 233 SRSNLSR | SEQ ID NO: 251 VSSNLTS |
| 34476 | SEQ ID NO: 218 DRSDLSR | SEQ ID NO: 248 DSSTRRR | SEQ ID NO: 233 DRSNLSR | SEQ ID NO: 184 QSGDLTR | SEQ ID NO: 198 DRSNLTR | N/A |
| 34477 | SEQ ID NO: 237 ERGTLAR | SEQ ID NO: 249 RSDHLSR | SEQ ID NO: 252 RSDALSV | SEQ ID NO: 253 DSSHRTR | SEQ ID NO: 216 DRRDRKK | N/A |
| 34478 | SEQ ID NO: 254 RSDNLTR | SEQ ID NO: 255 RSDNLAR | SEQ ID NO: 224 DRSALAR | SEQ ID NO: 256 DRSHLSR | SEQ ID NO: 205 TSGNLTR | N/A |
| 34479 | SEQ ID NO: 252 RSDALSV | SEQ ID NO: 253 DSSHRTR | SEQ ID NO: 203 RSDNLSE | SEQ ID NO: 254 ARTGLRQ | SEQ ID NO: 237 ERGTLAR | SEQ ID NO: 224 DRSALAR |
| 34480 | SEQ ID NO: 255 RSDNLAR | SEQ ID NO: 224 DRSALAR | SEQ ID NO: 256 DRSHLSR | SEQ ID NO: 205 TSGNLTR | SEQ ID NO: 249 RSDHLSR | SEQ ID NO: 257 TSSNRKT |
| 34481 | SEQ ID NO: 224 DRSALAR | SEQ ID NO: 252 RSDALSV | SEQ ID NO: 253 DSSHRTR | SEQ ID NO: 203 RSDNLSE | SEQ ID NO: 254 ARTGLRQ | N/A |
| 34482 | SEQ ID NO: 258 RSDDLSK | SEQ ID NO: 254 RSDNLTR | SEQ ID NO: 221 RSDSLSV | SEQ ID NO: 259 RSAHLSR | SEQ ID NO: 260 RSDALST | SEQ ID NO: 261 DRSTRTK |
| 34483 | SEQ ID NO: 216 DSSDRKK | SEQ ID NO: 259 RSAHLSR | SEQ ID NO: 218 DRSDLSR | SEQ ID NO: 219 RSDHLSE | SEQ ID NO: 262 TSSDRTK | N/A |

TABLE 13

Target site of AHAS zinc fingers

| pDAB# | Approximate Cleavage Site Relative to AHAS Pro-197 | ZFP # and Binding Site (5'→3') | SEQ ID NO: |
|---|---|---|---|
| pDAB111850 (34456-2A-34457) | 499-bp upstream | 34456: cnGCGGCCATGGCGGCGGCGagggtttg | 263 |
| | | 34457: acCTCcCCCCGCCGTCGCAttctcnggcg | 264 |
| pDAB111855 (34470-2A-34471) | 109-bp upstream | 34470: ggCCGGACGCGCGGGCGtanccggacgc | 265 |
| | | 34471: cgTCGGCGTCTGCGTCGCCAcctccggc | 266 |
| pDAB111856 (34472-2A-34473) | 99-bp upstream | 34472: acGCCGACGCGGCCgGACGCGcgggcgt | 267 |
| | | 34473: gcGTCGCCaCCTCCGGCCCGGggccac | 268 |
| pDAB111857 (34474-2A-34475) | 96-bp upstream | 34474: caGACGCCGACGCGGCCggacgcgcggg | 269 |
| | | 34475: gtCGCCACcTCCGGCCCGGGGgccacca | 270 |

TABLE 13-continued

Target site of AHAS zinc fingers

| pDAB# | Approximate Cleavage Site Relative to AHAS Pro-197 | ZFP # and Binding Site (5'→3') | SEQ ID NO: |
|---|---|---|---|
| pDAB111858 (34476-2A-34477) | 90-bp upstream | 34476: gcGACGCAGACGCCGACgcggccggacg | 271 |
| | | 34477: ccTCCGGCCCGGGGGCCaccaacctcgt | 272 |
| pDAB111859 (34478-2A-34479) | 24-bp upstream | 34478: ggGATGGAGTCGAGGAGngcgtcngcga | 273 |
| | | 34479: TGGTCGCCATCACGGGCCAGgtcccccg | 274 |
| pDAB111860 (34480-2A-34481) | 18-bp upstream | 34480: acCATGGGGATGGAGTCGAGgagngcgt | 275 |
| | | 34481: ccATCACGGGCCAGGTCccccgccgcat | 276 |
| pDAB111861 (34482-2A-34483) | 16-bp upstream | 34482: cgACCATGGGGATGGAGTCGaggagngc | 277 |
| | | 34483: caTCACGGGCCAGGTCCcccgccgcatg | 278 |

The AHAS zinc finger designs were incorporated into zinc finger expression vectors and verified for cleavage activity using a budding yeast system, as described in Example 2. Of the numerous ZFNs that were designed, produced and tested to bind to the putative AHAS genomic polynucleotide target sites, 14 ZFNs were identified as having in vivo activity at high levels, and selected for further experimentation. All 14 ZFNs were designed to bind to the three homoeologous AHAS and were characterized as being capable of efficiently binding and cleaving the unique AHAS genomic polynucleotide target sites in planta.

Example 8: Evaluation of Zinc Finger Nuclease Cleavage of AHAS Genes Using Transient Assays ZFN Construct Assembly Plasmid vectors containing ZFN expression constructs verified for cleavage activity using the yeast system (as described in Example 7) were designed and completed as previously described in Example 3. The resulting 14 plasmid constructs: pDAB111850 (ZFNs 34456-2A-34457), pDAB111851 (ZFNs 34458-2A-34459), pDAB111852 (ZFNs 34460-2A-34461), pDAB111853 (ZFNs 34462-2A-34463), pDAB111854 (ZFNs 34464-2A-34465), pDAB111855 (ZFNs 34470-2A-34471), pDAB111856 (ZFNs 34472-2A-34473), pDAB111857 (ZFNs 34474-2A-34475), pDAB111858 (ZFNs 34476-2A-34477), pDAB111859 (ZFNs 34478-2A-34479), pDAB111860 (ZFNs 34480-2A-34481), pDAB111861 (ZFNs 34482-2A-34483), pDAB111862 (ZFNs 34484-2A-34485) and pDAB111863 (ZFNs 34486-2A-34487) were confirmed via restriction enzyme digestion and via DNA sequencing.

Preparation of DNA from ZFN Constructs for Transfection

Before delivery to Triticum aestivum protoplasts, plasmid DNA for each ZFN construct was prepared from cultures of E. coli using the PURE YIELD PLASMID MAXIPREP SYSTEM® (Promega Corporation, Madison, Wis.) or PLASMID MAXI KIT® (Qiagen, Valencia, Calif.) following the instructions of the suppliers.

Isolation and Transfection of Wheat Mesophyll Protoplasts

Mesophyll protoplasts from the donor wheat line cv. Bobwhite MPB26RH were prepared and transfected using polyethylene glycol (PEG)-mediated DNA delivery as previously described in Example 3.

PCR Assay of Protoplast Genomic DNA for ZFN Sequence Cleavage

Genomic DNA was isolated from transfected protoplasts and used for PCR assays to assess the cleavage efficiency and target site specificity of ZFNs designed to the region of the AHAS gene encoding P197, as previously described in Example 3. Five sets of PCR primers which contained a phosphorothioate linkage as indicated by the asterisk [*] were used to amplify the ZFN target site loci (Table 14). Each primer set was designed according to criteria previously described in Example 3.

TABLE 14

Primer sequences used to assess AHAS ZFN cleavage efficacy and target site specificity.

| Primer Name | Primer Set | Primer Sequence (5'→3') | SEQ ID NO: |
|---|---|---|---|
| AHAS-P197ZFN.F2 | Set 1 | a*cactattccctacacgacgctatccgatctTCCCCAATTCCAACCCTCT*C | 279 |
| AHAS-P197ZFN.R1 | Set 1 | g*tgactggagttcagacgtgtgctatccgatctCGTCAGCGCCTGGTGGATC*T | 280 |
| AHAS-P197ZFN.F5 | Set 2 | a*cactattccctacacgacgctatccgatctGCCCGTCCGAGCCCCGCA*A | 281 |

TABLE 14-continued

Primer sequences used to assess AHAS ZFN cleavage efficacy and target site specificity.

| Primer Name | Primer Set | Primer Sequence (5'→3') | SEQ ID NO: |
|---|---|---|---|
| AHAS-P197ZFN.R1 | Set 2 | g*tgactggagttcagacgtgtgctatccgatctC GTCAGCGCCTGGTGGATC*T | 282 |
| AHAS-P197ZFN.F7 | Set 3 | a*cactattccctacacgacgctatccgatctGCG CTCGCCCGTCATCA*C | 283 |
| AHAS-P197ZFN.R5 | Set 3 | g*tgactggagttcagacgtgtgctatccgatctA TGGGGATGGAGTCGAGGA*G | 284 |
| AHAS-P197ZFN.F9 | Set 4 | a*cactattccctacacgacgctatccgatctCTT CCGCCACGAGCAGG*G | 285 |
| AHAS-P197ZFN.R5 | Set 4 | g*tgactggagttcagacgtgtgctatccgatctA TGGGGATGGAGTCGAGGA*G | 286 |
| AHAS-P197ZFN.F11 | Set 5 | a*cactattccctacacgacgctatccgatctTCG TCTCCGCGCTCGCTG*A | 287 |
| AHAS-P197ZFN.R6 | Set 5 | g*tgactggagttcagacgtgtgctatccgatctT CCACTATGGGCGTCTCCT*G | 288 |

Data Analysis for Detecting NHEJ at Target ZFN Sites

Following generation of Illumina short read sequence data for sample libraries prepared for transfected mesophyll protoplasts, bioinformatics analysis (as previously described in Example 3) was performed to identify deleted nucleotides at the target ZFN sites. Such deletions are known to be indicators of in planta ZFN activity that result from non-homologous end joining (NHEJ) DNA repair.

Two approaches were used to assess the cleavage efficiency and specificity of the ZFNs tested. Cleavage efficiency was expressed (in parts per million reads) as the proportion of sub-genome assigned sequences that contained a NHEJ deletion at the ZFN target site (Table 15). Rank ordering of the ZFNs by their observed cleavage efficiency was used to identify ZFNs with the best cleavage activity for the target region of the AHAS genes in a sub-genome-specific manner. All of the ZFNs tested showed NHEJ deletion size distributions consistent with that expected for in planta ZFN activity. Cleavage specificity was expressed as the ratio of cleavage efficiencies observed across the three sub-genomes.

TABLE 15

ZFN cleavage efficacy (expressed as number of NHEJ events per million reads) and target site specificity.

| ZFN | A-genome | B-genome | D-genome |
|---|---|---|---|
| pDAB111850 (34456-2A-34457) | 12,567 | 1,716 | 10,399 |
| pDAB111851 (34458-2A-34459) | 2,088 | 995 | 874 |
| pDAB111852 (34460-2A-34461) | 2 | 2 | 3 |
| pDAB111853 (34462-2A-34463) | 3 | 0 | 3 |
| pDAB111854 (34464-2A-34465) | 47 | 92 | 308 |
| pDAB111855 (34470-2A-34471) | 177,866 | 156,139 | 134,694 |
| pDAB111856 (34472-2A-34473) | 119,857 | 100,300 | 87,770 |
| pDAB111857 (34474-2A-34475) | 248,115 | 251,142 | 202,711 |
| pDAB111858 (34476-2A-34477) | 48,339 | 56,001 | 44,459 |
| pDAB111859 (34478-2A-34479) | 3,069 | 2,731 | 3,069 |
| pDAB111860 (34480-2A-34481) | 11,790 | 11,946 | 11,790 |
| pDAB111861 (34482-2A-34483) | 28,719 | 33,888 | 28,719 |
| pDAB111862 (34484-2A-34485) | 216 | 111 | 216 |
| pDAB111863 (34486-2A-34487) | 54 | 28 | 54 |

From these results, the ZFNs encoded on plasmids pDAB111855 (34470-2A-34471), pDAB111856 (34472-2A-34473) and pDAB111857 (34474-2A-34475) were selected for in planta targeting in subsequent experiments, given their characteristics of significant genomic DNA cleavage activity in each of the three wheat sub-genomes.

Example 9: Artificial Crossing and Molecular Analysis to Recover Plants with Specific Combinations of Precise Genome Modifications Wheat events that are produced via transformation with donor DNA and zinc finger nuclease constructs result in the integration of donor molecule sequence at one or more copies of the target endogenous locus. As shown previously in Example 6, ZFN-mediated genome modification effectuates simultaneous editing of multiple alleles across multiple sub-genomes. Artificial crossing of transformation events can be subsequently used to select for specific combinations of precise genome modifications. For example, artificial crossing of transformation events produced in Example 5 that have precisely modified AHAS genes with the S653N mutation can be used to produce wheat plants that have the S653N mutation in either a specific sub-genome, in any combination of multiple sub-genomes, or in all three sub-genomes.

Similarly, self-pollination of transformation events having genome modifications at multiple copies of the target endogenous locus can be subsequently used to produce wheat events that have the S653N mutation at only a specific sub-genome. Subsequent self-pollination of transformation events is especially useful for removing undesirable genome modifications from an event, such as imperfect editing at one or more copies of the target endogenous locus.

Molecular and phenotypic assays, such as those previously described, can be used to track the inheritance of specific genome modifications in the progeny derived from artificial crossing and self-pollination of transformed events.

Inheritance and Expression of Precision Genome Modifications in Wheat

To verify stable expression and inheritance of the AHAS herbicide tolerance phenotype conferred by the S653N mutation carried by the wheat transformation events generated in Example 5, T1 seed from three wheat events were subjected to molecular and phenotypic analysis. The three independent wheat events each carried the integrated S653N mutation in the AHAS gene located within the A-genome.

T1 seed were derived from self-pollination of each T0 event. The seeds were surface sterilized and germinated in vitro by sub-culturing the sterilized seeds on multiplication medium, as described previously. After 10 days of growth at 24° C. under a 16/8 (light/dark) hour photoperiod, the roots of the germinated seedlings were removed and the seedlings were transferred onto rooting medium containing 200 nM IMAZAMOX® (imidazolinone). The seedlings were incubated for 2-3 weeks under the same conditions and the presence or absence of root re-growth was recorded. Leaf tissue harvested from each seedling was used for DNA extraction, and a PCR assay to test for the presence of the modified AHAS gene using primers AHAS_3F1 and AHAS_3R1 (SEQ ID NO:95 and SEQ ID NO:96) was completed, as described previously. Electrophoretic separation of the resulting PCR products on agarose gel was used to detect the presence of the modified AHAS gene. The amplification of only a 750-bp fragment PCR product indicated the absence of the modified AHAS gene. Comparatively, the amplification of only a 850-bp fragment indicated the presence of the modified AHAS gene in the homozygous state. Furthermore, the amplification of both a 750-bp and 850-bp fragment indicated the presence of the modified AHAS gene in the hemizygous state.

Next, a chi-square test was used to confirm the inheritance of the modified AHAS gene as a single genetic unit. Expected Mendelian inheritance was observed in the T1 generation for each of the three wheat transformation events. The modified AHAS gene segregated at the 3:1 ratio expected for a PCR test producing a dominant marker (Table 16) in the T1 seedlings. Similarly, IMAZAMOX® tolerance showed 3:1 segregation, as expected for the dominant AHAS herbicide tolerance phenotype conferred by the S653N mutation (Table 17) in the T1 seedlings.

TABLE 16

Segregation of modified AHAS gene in T1 seedlings derived from self-pollination of transformed wheat plants from Example 5.

| Event | No. of T1 plants | No. of T1 plants with exogenous sequence | No. of T1 plants without exogenous sequence | Segregation ratio tested | P-value |
|---|---|---|---|---|---|
| mb1k-7783-1-1 | 25 | 19 | 6 | 3:1 | p < 0.05 |
| yr00-7794-1-1 | 54 | 44 | 10 | 3:1 | p < 0.05 |
| yt02-7786-1-1 | 33 | 27 | 6 | 3:1 | p < 0.05 |

TABLE 17

Segregation of IMAZAMOX ® tolerance phenotype in T1 seedlings derived from self-pollination of transformed wheat plants from Example 5.

| Event | No. of T1 plants | No. of T1 plants IMI tolerance | No. of T1 plants without IMI tolerance | Segregation ratio tested | P-value |
|---|---|---|---|---|---|
| mb1k-7783-1-1 | 25 | 19 | 6 | 3:1 | p < 0.05 |
| yr00-7794-1-1 | 54 | 44 | 10 | 3:1 | p < 0.05 |
| yt02-7786-1-1 | 33 | 27 | 6 | 3:1 | p < 0.05 |

The stability of expression of the modified AHAS gene was verified by its correspondence with the AHAS herbicide tolerance phenotype. Complete concordance was observed between the presence of one or more copies of the modified AHAS gene and IMAZAMOX® tolerance.

Self-Pollination and Artificial Crossing to Recover Plants with Specific Combinations of Precise Genome Modifications Artificial crossing between wheat transformation events produced in Example 5 can be used to generate wheat plants that have the S653N mutation on a specific sub-genome, on multiple sub-genomes, or on all three sub-genomes.

To generate homozygous wheat plants having the S653N mutation on a specific sub-genome, three wheat events from Example 5 were allowed to self-pollinate and produce T1 seed. The three events; mblk-7783-1-1, yw06-7762-2-1 and yw06-7834-1-1 were selected to have hemizygous AHAS genome modifications on the A-genome, B-genome and D-genome, respectively. About 15 T1 seed from each event were germinated and grown under glasshouse containment conditions to produce T2 seed. Leaf material harvested from each T1 plant was used for DNA extraction and PCR assays were completed to determine the zygosity of the modified AHAS gene. This PCR zygosity test was designed to amplify a fragment from each of the three homoeologous copies of the endogenous AHAS gene within a region containing the binding site for ZFNs 29732 and 29730 (encoded on plasmid pDAB190350), and to include genomic nucleotide sequence variation. Enough genomic nucleotide sequence variation was included to differentiate between the AHAS homoeologs, such that the resulting amplicons could be unequivocally attributed (at the sequence level) to the wheat sub-genome from which they were derived. The primer pairs were synthesized with the Illumina™ SP1 and SP2 sequences at the 5' end to provide compatibility with Illumina™ sequencing-by-synthesis chemistry. The synthesized primers also contained a phosphorothioate linkage at the penultimate 5' and 3' nucleotides. The 5' phosphorothioate linkage afforded protection against exonuclease degradation of the Illumina™ SP1 and SP2 sequences. Likewise, the 3' phosphorothioate linkage improved PCR specificity for amplification of the target AHAS sequences using on-off PCR (Yang et al., (2005) Biochem. Biophys. Res. Commun., March 4:328(1):265-72). The sequences of the primer pairs are provided in Table 18.

TABLE 18

Primer sequences used to assess the zygosity of the modified AHAS gene in transgenic wheat events from Example 5.

| Primer Name | Primer Sequence (5'→3') | SEQ ID NO: |
|---|---|---|
| AHASs653ZFN.F2 | a*cactctttccctacacgacgctcttccgatctGCAATCAAGAAGAT GCTTGAGAC*C | 297 |
| AHASs653ZFN.R1 | g*tgactggagttcagacgtgtgctcttccgatctTCTTTTGTAGGGA TGTGCTGTCA*T | 298 |

The asterisk(*) indicates a phosphorothioate; lowercase font indicates SP1 and SP2 sequences, and uppercase font indicates the genomic DNA sequence.

The resulting PCR amplicons were prepared for deep sequencing as described previously, and sequenced on an Illumina MiSEQ™ instrument to generate 250-bp paired-end sequence reads, according to the manufacturer's instructions. The resultant sequence reads were computationally processed, as described previously, to assign each read to sample (based on the barcode index) and the sub-genome from which they were derived (based on nucleotide variation that distinguished between homoeologous copies of the AHAS gene), and to perform quality filtering to ensure that only high quality sequences were used for subsequent analyses. Custom developed PERL scripts and manual data manipulation in MICROSOFT EXCEL 2010™ (Microsoft Corporation) were used to process the data and determine the zygosity of the modified AHAS gene in each T1 wheat event.

As the integration of pDAS000267 into the endogenous AHAS locus resulted in only a 95-bp size difference between the wild-type (unmodified) and resulting transgenic (modified) allele, the PCR zygosity assay was expected to amplify both the wild-type and modified AHAS gene. Consequently, T1 plants, homozygous for the target genome modification, were expected to produce only sequence reads that originate from the amplification of the transgenic allele at the modified AHAS locus. These alleles were distinguishable at the sequence level by the six mutations deliberately introduced into the AHAS exon in pDAS000267 (e.g., the two mutations encoding the S653N mutation, and the four codon-optimized, synonymous mutations positioned across the binding site of ZFN 29732 prevented re-cleavage of the integrated donor). The T1 plants hemizygous for the target genome modification were expected to produce sequence reads originating from both the wild-type and transgenic allele at the modified AHAS locus. Whereas, T1 plants without the modified AHAS gene were expected to only produce sequence reads originating from the wild-type allele at the modified AHAS locus. Based on the PCR zygosity test, T1 plants homozygous for the S653N mutation in only the A-genome, B-genome, or D-genome were identified (Table 19).

TABLE 19

PCR zygosity assay results for T1 plants derived from self-pollination of transgenic wheat events from Example 5.

| | | A-genome | | B-genome | | D-genome | | |
|---|---|---|---|---|---|---|---|---|
| Event | T1 plant | No. of WT reads[1] | No. of ED reads[2] | No. of WT reads | No. of ED reads | No. of WT reads | No. of ED reads | Genotype[3] |
| mb1k-7783-1 | mb1k-7783-1-29 | 39,305 | 46,481 | 92,167 | 2,011 | 85,048 | 2,222 | AaBBDD |
| mb1k-7783-1 | mb1k-7783-1-31 | 95,696 | 61,451 | 203,228 | 3,913 | 200,232 | 4,087 | AaBBDD |
| mb1k-7783-1 | mb1k-7783-1-33 | 32,608 | 27,270 | 67,551 | 1,440 | 70,588 | 1,632 | AaBBDD |
| mb1k-7783-1 | mb1k-7783-1-39 | 37,172 | 56,416 | 76,005 | 1,693 | 77,899 | 1,787 | AaBBDD |
| mb1k-7783-1 | mb1k-7783-1-41 | 31,782 | 37,945 | 74,540 | 1,478 | 76,916 | 1,892 | AaBBDD |
| mb1k-7783-1 | mb1k-7783-1-43 | 3,784 | 93,125 | 189,570 | 4,164 | 160,769 | 3,931 | aaBBDD |
| mb1k-7783-1 | mb1k-7783-1-46 | 208,627 | 4,902 | 241,948 | 4,567 | 247,912 | 5,094 | AABBDD |
| mb1k-7783-1 | mb1k-7783-1-47 | 66,472 | 39,215 | 134,076 | 2,464 | 126,823 | 2,613 | AaBBDD |
| mb1k-7783-1 | mb1k-7783-1-49 | 83,048 | 1,906 | 85,267 | 1,586 | 87,773 | 1,794 | AABBDD |
| mb1k-7783-1 | mb1k-7783-1-53 | 41,810 | 34,455 | 81,446 | 1,603 | 82,871 | 1,776 | AaBBDD |
| mb1k-7783-1 | mb1k-7783-1-55 | 73,129 | 48,692 | 164,791 | 3,233 | 155,375 | 3,205 | AaBBDD |
| mb1k-7783-1 | mb1k-7783-1-57 | 2,971 | 119,900 | 97,509 | 2,161 | 96,476 | 2,563 | aaBBDD |
| mb1k-7783-1 | mb1k-7783-1-58 | 2,076 | 60,517 | 62,638 | 1,444 | 59,721 | 1,827 | aaBBDD |
| mb1k-7783-1 | mb1k-7783-1-59 | 1,777 | 78,101 | 56,566 | 1,239 | 55,302 | 1,326 | aaBBDD |
| mb1k-7783-1 | mb1k-7783-1-61 | 64,093 | 57,599 | 135,703 | 2,713 | 132,205 | 2,863 | AaBBDD |
| yw06-7762-2 | yw06-7762-2-23 | 13,123 | 374 | 21,286 | 532 | 21,471 | 560 | AABBDD |
| yw06-7762-2 | yw06-7762-2-24 | 56,120 | 1,382 | 87,745 | 1,635 | 82,753 | 2,170 | AABBDD |
| yw06-7762-2 | yw06-7762-2-25 | 39,091 | 1,053 | 1,525 | 38,594 | 61,284 | 1,578 | AAbbDD |
| yw06-7762-2 | yw06-7762-2-27 | 24,551 | 804 | 1,428 | 19,364 | 37,500 | 1,184 | AAbbDD |
| yw06-7762-2 | yw06-7762-2-28 | 44,494 | 1,234 | 32,935 | 18,811 | 64,736 | 1,733 | AABbDD |
| yw06-7762-2 | yw06-7762-2-29 | 33,554 | 964 | 22,898 | 11,718 | 45,887 | 1,221 | AABbDD |
| yw06-7762-2 | yw06-7762-2-30 | 33,410 | 1,011 | 1,481 | 26,659 | 46,214 | 1,430 | AAbbDD |
| yw06-7762-2 | yw06-7762-2-31 | 56,639 | 1,516 | 44,649 | 17,155 | 85,830 | 2,116 | AABbDD |
| yw06-7762-2 | yw06-7762-2-32 | 45,753 | 1,223 | 35,723 | 13,649 | 69,858 | 1,781 | AABbDD |
| yw06-7762-2 | yw06-7762-2-33 | 12,239 | 306 | 17,611 | 333 | 18,324 | 498 | AABBDD |
| yw06-7762-2 | yw06-7762-2-34 | 38,709 | 1,001 | 32,109 | 14,549 | 61,150 | 1,620 | AABbDD |
| yw06-7762-2 | yw06-7762-2-35 | 48,185 | 1,329 | 40,719 | 16,138 | 75,876 | 1,953 | AABbDD |
| yw06-7762-2 | yw06-7762-2-36 | 44,420 | 1,096 | 71,463 | 1,374 | 72,604 | 1,721 | AABBDD |
| yw06-7762-2 | yw06-7762-2-37 | 23,752 | 685 | 37,126 | 796 | 36,283 | 941 | AABBDD |
| yw06-7834-1 | yw06-7834-1-28 | 43,467 | 1,092 | 68,043 | 1,317 | 65,748 | 1,677 | AABBDD |

TABLE 19-continued

PCR zygosity assay results for T1 plants derived from self-pollination of transgenic wheat events from Example 5.

| | | A-genome | | B-genome | | D-genome | | |
|---|---|---|---|---|---|---|---|---|
| Event | T1 plant | No. of WT reads[1] | No. of ED reads[2] | No. of WT reads | No. of ED reads | No. of WT reads | No. of ED reads | Genotype[3] |
| yw06-7834-1 | yw06-7834-1-29 | 47,463 | 1,177 | 72,531 | 1,390 | 38,007 | 14,387 | AABBDd |
| yw06-7834-1 | yw06-7834-1-31 | 51,138 | 1,484 | 77,266 | 1,797 | 1,770 | 27,955 | AABBdd |
| yw06-7834-1 | yw06-7834-1-32 | 42,666 | 1,336 | 70,422 | 1,578 | 38,234 | 17,932 | AABBDd |
| yw06-7834-1 | yw06-7834-1-33 | 33,075 | 907 | 55,545 | 1,331 | 28,610 | 10,916 | AABBDd |
| yw06-7834-1 | yw06-7834-1-34 | 47,971 | 1,277 | 78,765 | 1,671 | 1,536 | 29,627 | AABBdd |
| yw06-7834-1 | yw06-7834-1-35 | 44,355 | 1,043 | 74,365 | 1,347 | 68,161 | 1,634 | AABBDD |
| yw06-7834-1 | yw06-7834-1-36 | 67,661 | 1,788 | 93,068 | 2,329 | 2,214 | 31,935 | AABBdd |
| yw06-7834-1 | yw06-7834-1-37 | 33,663 | 826 | 49,051 | 973 | 52,989 | 1,274 | AABBDD |
| yw06-7834-1 | yw06-7834-1-38 | 45,974 | 1,080 | 67,706 | 1,258 | 67,774 | 1,619 | AABBDD |
| yw06-7834-1 | yw06-7834-1-39 | 2,687 | 27,436 | 88,976 | 2,084 | 92,612 | 2,892 | AABBDD |
| yw06-7834-1 | yw06-7834-1-40 | 62,142 | 1,713 | 93,532 | 2,233 | 49,886 | 21,129 | AABBDd |
| yw06-7834-1 | yw06-7834-1-41 | 50,781 | 1,381 | 77,168 | 1,696 | 37,412 | 14,167 | AABBDd |
| yw06-7834-1 | yw06-7834-1-42 | 44,020 | 1,233 | 61,262 | 1,517 | 1,374 | 27,505 | AABBdd |
| yw06-7834-1 | yw06-7834-1-43 | 68,958 | 1,456 | 48,972 | 1,009 | 91,624 | 2,062 | AABBDD |

[1]Number of sequence reads originating from the specified sub-genome and having the sequence haplotype corresponding to the wild-type (unmodified) AHAS locus. The usage of "WT" indicates wild-type.
[2]Number of sequence reads originating from the specified sub-genome and having the sequence haplotype corresponding to the transgenic (modified) AHAS locus. The usage of "ED" indicates edited.
[3]Genotype for the T1 plant, where uppercase and lowercase letters indicate the presence of the wild-type and transgenic AHAS loci on the specified sub-genome, respectively. For example, AaBBDD indicates the T1 plant has a hemizygous AHAS genome modification on the A-genome and homozygous wild-type AHAS loci on the B- and D-genomes. The zygosity at each of the three endogenous AHAS loci is determined from the frequency of the sequence reads corresponding to the wild-type and modified alleles originating from each sub-genome. Hemizygous genotypes have a similar frequency of wild-type and modified alleles originating from an endogenous AHAS locus, where homozygous genotypes reveal predominantly wild-type or modified alleles. The low frequency of alternate alleles originating from homozygous AHAS loci is due to PCR chimerism between reads originating from different sub-genomes.

One skilled in the art can deploy subsequent rounds of artificial crossing between different wheat transformation events, in combination with the described PCR zygosity test, to produce homozygous wheat plants having the S653N mutation on any combination of multiple sub-genomes (e.g., the A-genome and B-genome, the A-genome and D-genome, or the B-genome and D-genome), or on all three sub-genomes. For example, artificial crossing of T1 plant mblk-7783-1-43 (i.e., aaBBDD genotype) with T1 plant yw06-7762-2-25 (i.e., AAbbDD genotype) would produce T2 seed that are hemizygous for modified AHAS genes in the A-genome and B-genomes; i.e., with the AaBbDD genotype. Subsequent, growth and self-pollination of T2 plants would produce T3 seed segregating for homozygous genotypes for the modified AHAS genes on the A- and B-genomes (i.e., aabbDD genotype), which can be identified using the described PCR zygosity assay.

Example 10: Development of a Transformation System for Sequential, Exogenous Transgene Stacking at the Endogenous AHAS Loci in Wheat The endogenous AHAS gene locus in wheat was selected as a model locus to develop a ZFN-mediated, exogenous transformation system for generating plants with one or more transgenes precisely positioned at the same genomic location. The transformation system enables parallel (simultaneous integration of one or more transgenes) or sequential stacking (consecutive integration of one or more transgenes) at precisely the same genomic location. In addition, the transformation system includes simultaneous parallel or sequential stacking at multiple alleles across multiple sub-genomes. The strategies exploit incorporating mutations in the AHAS gene that confer tolerance to Group B herbicides (e.g., ALS inhibitors such as imidazolinone or sulfonylurea). ZFN-mediated integration of a donor DNA into the wild-type (herbicide susceptible) AHAS locus was used to introduce transgene(s) and a mutation to the endogenous AHAS gene that conferred tolerance to imidazolinones, thus allowing the regeneration of correctly targeted plants that possess tolerance to an imidazolinone selection agent.

Stacking of a second transgene(s) at the AHAS locus is achieved by integration of a donor DNA that introduces one or more additional transgenes and confers susceptibility to imidazolinones, but tolerance to sulfonylureas, thus allowing the regeneration of correctly targeted plants using a sulfonylurea selection agent.

Stacking of a third transgene is achieved by integration of a donor molecule that introduces further transgene(s) and confers susceptibility to sulfonylurea and tolerance to imidazolinones, thus allowing the regeneration of correctly targeted plants using an imidazolinone selection agent.

As such, continued rounds of sequential transgene stacking are possible by the use of donor DNA that introduce transgene(s) and mutations at the endogenous AHAS gene for differential cycling between imidazolinone and sulfonylurea selection agents. The transgenes can be integrated within the AHAS gene and stacked via an NHEJ and/or HDR pathway. The desired repair and recombination pathway can be determined by the design of the donor transgene. In an embodiment, exogenous sequences that are integrated and stacked within the AHAS gene would be designed to contain a 5' and 3' region of homology to the genomic integration site; i.e. the AHAS gene. The 5' and 3' region of homology would flank the payload (e.g., AHAS mutation and gene of interest). Accordingly, such a design would utilize an HDR pathway for the integration and stacking of the donor polynucleotide within the chromosome. In a subsequent embodiment, transgenes that are integrated and stacked within the AHAS gene would be designed to contain single or double cut ZFN sites that flank the payload (e.g., AHAS mutation and gene of interest). Accordingly, such a design would utilize an NHEJ pathway for the integration and stacking of the donor polynucleotide within the chromosome.

Design and Production of Donor DNA for First Sequential Transgene Stacking at an Endogenous AHAS Locus Using NHEJ-Directed DNA Repair The donor DNA for the first round of transgene stacking was designed to promote precise donor integration at an endogenous AHAS locus via ZFN-mediated, NHEJ-directed repair. The design was based on the integration of a double stranded donor molecule at the position of the double strand DNA break created by cleavage of a homoeologous copy of the endogenous AHAS gene by ZFNs 29732 and 29730 (encoded on plasmid pDAB109350, FIG. 1).

The donor molecule backbone of pDAS000433 (SEQ ID NO:71; FIG. 12) comprised several polynucleotide sequence features. The 5' end contained sequence that was nearly identical to the endogenous AHAS gene encoded in the D-genome. This sequence was made up of a fragment that spanned from the target ZFN cleavage site and finished at the AHAS stop codon. In addition, seven deliberate mutations were introduced into the sequence: the two mutations that encoded the S653N mutation and the five codon-optimized, synonymous mutations positioned across the binding site of ZFN 29732. The five codon-optimised, synonymous mutations were included to prevent re-cleavage of the integrated donor. Next, the stop codon was followed by 316-bp of non-coding sequence corresponding to the conserved 3'untranslated region (3'UTR) across the AHAS homoeologs. In addition, the 3'UTR sequence was followed by Zinc Finger binding sites for ZFNs 34480 and 34481 (encoded on plasmid pDAB111860) and ZFNs 34482 and 34483 (encoded on plasmid pDAB111861). These Zinc Finger binding sites allow for self-excision of donor-derived AHAS (coding and 3'UTR) sequence integrated at the endogenous locus during the second round of transgene stacking. The self-excision Zinc Finger binding sites were followed by two additional Zinc Finger binding sites, which were flanked by 100-bp of random sequence. These two additional Zinc-Finger binding sites were immediately followed by a pair of unique restriction endonuclease cleavage sites that were used to insert the transgene expression cassette (i.e., the PAT expression cassette, as described below). Following the two unique restriction endonuclease sites were two more Zinc Finger binding sites, which were again flanked by 100-bp of random sequence. The inclusion of the four additional Zinc Finger binding sites enable future excision of transgenes integrated at an AHAS locus by sequential marker-free transgene stacking, or continued sequential transgene stacking at the same genomic location using an alternate stacking method.

The donor backbone cassette was synthesized by a commercial gene service vendor (GeneArt, Life Technologies) with a short stretch of additional flanking sequence at the 5' and 3' ends to enable generation of a donor molecule with protruding 5' and 3' ends that were compatible with the ligation overhangs generated by ZFNs 29732 and 29730 (encoded on plasmid pDAB109350) upon cleavage of an endogenous AHAS locus.

The PAT expression cassette was inserted, using standard methods known to a person skilled in the art, into the donor backbone cassette of pDAS000433 between the two unique restriction endonuclease sites to produce the donor molecule cassette "QA_pDAS000434" (SEQ ID NO:314; FIG. 19). The PAT selection cassette was comprised of the promoter, 5' untranslated region, and intron from the Actin (Act1) gene from *Oryza sativa* (McElroy et al., (1990) *The Plant Cell*, 2(2): 163-171) followed by a synthetic, plant-optimized version of phosphinothricin acetyl transferase (PAT) gene, isolated from *Streptomyces viridochromogenes*, which encodes a protein that confers resistance to inhibitors of glutamine synthetase comprising phosphinothricin, glufosinate, and bialaphos (Wohlleben et al., (1988) *Gene*, 70(1): 25-37). This cassette was terminated with the 3' UTR comprising the transcriptional terminator and polyadenylation sites from the 35s gene of cauliflower mosaic virus (CaMV) (Chenault et al., (1993) *Plant Physiology* 101 (4): 1395-1396). Plasmid DNA for "QA_pDAS000434" was prepared using the PURE YIELD PLASMID MAXIPREP SYSTEM™ (Promega Corporation, WI) following the manufacturer's instructions.

PCR amplification of "QA_pDAS000434" followed by digestion with restriction endonuclease BbsI was used to produce linear double-stranded DNA donor molecules with protruding 5' and 3' ends that were compatible with the ligation overhangs generated by ZFNs 29732 and 29730 (encoded on plasmid pDAB109350) upon cleavage of an endogenous AHAS locus. PCR amplification was performed with primers AHAS_TSdnr1_F1 and AHAS_TSdnr1_R1 (SEQ ID NO: 297 and 298, respectively), which were designed to the short stretch of additional sequence added to the 5' and 3' ends of the donor backbone cassette "QA_pDAS000434". The resulting amplicons were purified using the Agencourt AMPure™ XP-PCR purification kit (Beckman Coulter) and digested with BbsI (New England Biolabs). The amplicons were purified a second time using the Agencourt AMPure™ XP-PCR purification kit (Beckman Coulter), followed by ethanol precipitation and resuspension in sterile water at a DNA concentration appropriate for wheat transformation. Standard methods known to a person skilled in the art were used to prepare the linear double-stranded DNA donor molecule.

Production of Control Binary Vector Encoding AHAS (S653N)

A binary vector pDAS000143 (SEQ ID NO:88, FIG. 10) containing AHAS(S653N) expression and PAT selection cassettes was designed and assembled using skills and techniques commonly known in the art as previously described. Plasmid DNA for the binary was prepared using the PURE YIELD PLASMID MAXIPREP SYSTEM™ (Promega Corporation, WI) following the manufacturer's instructions. The binary vector pDAS000143 was transformed into wheat cells as a control.

Biolistics-Mediated Transformation for Generating Wheat Events with First Sequential Transgene Stack at an Endogenous AHAS Locus Using NHEJ-Directed DNA Repair A total of 55,468 scutella of immature zygotic embryos from the donor wheat line cv. Bobwhite MPB26RH were prepared for biolistics-mediated DNA delivery, as described previously. DNA-coated gold particles were prepared with the formulations as described above. For transfections performed using the linear double-stranded donor DNA derived from "QA_pDAS000434" or pDAS000433, the donor DNA was mixed at a 5:1 molar ratio with plasmid DNA for pDAB109350 (encoding ZFNs 29732 and 29730). Transfections performed using pDAS000143 were performed using gold particles that were coated only with plasmid DNA for pDAS000143.

Biolistic-mediated transfections were performed as described previously. Following bombardment, the transfected scutella were incubated at 26° C. in the dark for 16 h before being transferred onto medium for callus induction.

Two different chemical selection strategies were used to enrich for regenerated wheat plants with an integrated linear double-stranded donor molecule. The first strategy based on IMAZAMOX® was used to recover wheat events that had the donor molecule precisely integrated into one or more homoeologous copies of the endogenous AHAS gene by ZFN-mediated NHEJ-directed gene editing. Such events are expected to have the AHAS herbicide tolerance phenotype conferred by the S653N mutation. The second strategy based on BASTA® (DL-Phosphinothricin) was used to recover events that had the donor molecule integrated at either a random (non-targeted) position in the wheat genome, or imperfectly integrated into one or more homoeologous copies of the endogenous AHAS gene by ZFN-mediated NHEJ-directed gene editing. These events are expected to exhibit the BASTA® herbicide tolerance phenotype conferred by the PAT gene, but not necessarily the AHAS herbicide tolerance phenotype conferred by the S653N mutation. The purpose of the second chemical selection strategy was to allow the frequency of precise (on-target) versus random (off-target) donor integration to be quantified, as well as the frequency of perfect and imperfect integration at the endogenous AHAS loci. The two chemical selection strategies are described in Table 20.

TABLE 20

Chemical selection strategies used to regenerate wheat plants that had an integrated donor molecule

| Plant Regeneration Stage | IMI Selection | PPT Selection |
| --- | --- | --- |
| Callus Induction (CIM) | 150 nM | None |
| Plant Regeneration (DRM) | 150 nM | 5 mg/ml PPT |
| Rooting (RM) | 200 nM | 5 mg/ml PPT |

("IMI" indicates IMAZAMOX® and "PPT" indicates BASTA® selection).

A total of 34,546 and 23,550 transfected scutella were subject to IMAZAMOX® and BASTA® selection, respectively. For each strategy, scutella were cultured in the dark on callus induction medium at 24° C. for 2 weeks. The resultant calli were sub-cultured once onto fresh callus induction medium and kept in the same conditions for a further two weeks. Somatic embryogenic callus (SEC) were transferred onto plant regeneration medium and cultured for 2 weeks at 24° C. under a 16/8 (light/dark) hour photoperiod in a growth room. Regenerated plantlets were transferred onto rooting medium and cultured under the same conditions for 2-3 weeks. For IMAZAMOX® selection, the regenerated plants were sub-cultured for a total of three times on rooting media. At the end of each round, the roots of regenerated plants were removed and the plants were again sub-cultured on rooting media under the same conditions. Plantlets with roots were transferred to soil and grown under glasshouse containment conditions. $T_1$ seed was harvested from individual plants, following bagging of individual spikes to prevent out-crossing.

The scutella explants bombarded with gold particles coated with pDAS000143 were used to monitor the selection stringency across both the IMAZAMOX® and BASTA® chemical selection strategies. Plants transformed with pDAS000143 were regenerated using the process described above.

A total of 36 wheat plants were recovered from each chemical selection strategy for scutella explants transfected with pDAS000143. Molecular testing of these events using the hydrolysis probe assay described in Example 6 confirmed that all of the recovered wheat plants carried at least one randomly integrated copy of the pDAS000143 insert. These results indicated that the IMAZAMOX® and BASTA® selection conditions were sufficiently stringent to ensure a low escape rate (i.e., recovery of wheat plants that were not transformed), whilst allowing the recovery of events carrying one or more integrated copies of the AHAS (S653N) and PAT donor polynucleotides, respectively.

No wheat plants having the AHAS herbicide tolerance phenotype conferred by the S653N mutation were recovered from IMAZAMOX® selection under the specific selection conditions described above. As IMAZAMOX® selection is expected only to recover wheat plants that have precise integration of the donor molecule into one or more copies of the homoeologous AHAS gene, these results suggest that the chemical selection regime was sub-optimal, and that the conditions should be modified for precise ZFN-mediated NHEJ-directed integration of pDAS000433 donor at an endogenous AHAS locus, or that the scale of transformation was not appropriate for the chemical selection conditions used in the current work. In contrast, 1,652 wheat plants were recovered from BASTA® selection. As BASTA® is expected to recover wheat plants that have both targeted and non-targeted (random) donor integration, molecular characterization of these events can distinguish between targeted and non-targeted donor integration, which can provide guidance for refining IMAZAMOX® selection conditions.

Molecular Characterisation of BASTA®-Selected Wheat Plants for Evidence of First Transgene Stacking at an Endogenous AHAS Locus A total of 1,162 wheat plants recovered from BASTA®-selection were molecularly characterized to assess the frequency of targeted and off-target (random) donor integration, as well as the frequency of targeted perfect and imperfect donor integration at the endogenous AHAS loci.

Three molecular assays were performed for each wheat plant using genomic DNA extracted with the DNEASY® PLANT DNA EXTRACTION MINI KIT™ (Qiagen) from freeze-dried leaf tissue, as described previously.

The first molecular test was used to confirm that the regenerated wheat plants carried at least one integrated copy of the linear double-strand DNA derived from "QA_pDAS000434". This test involved a PCR assay to amplify a region of the Actin (Act1) promoter present in "QA_pDAS000434" (SEQ ID NOs: 92 and 93 for forward and reverse primers, respectively), followed by electrophoretic separation of the resulting amplicon on an agarose gel. The presence of a PCR fragment of expected size (218-bp) indicated integration of at least one copy of the donor molecule. Of the 1,162 wheat events, 1,065 (92%) produced a PCR fragment of the expected size.

The second molecular test was used to identify wheat plants having the donor molecule putatively integrated into one or more copies of the endogenous AHAS locus. This test comprised an on-off PCR assay using a primer designed to hybridize to a region upstream of the binding site for ZFNs 29732 and 29730 (encoded on plasmid pDAB190350) in each of the homoeologous copies of the endogenous AHAS gene, and a primer designed to hybridize to a region within the 100-bp of random sequence flanking the binding site for ZFNs 34480 and 34481 (encoded on plasmid pDAB111860) in "QA_pDAS000434" (SEQ ID NO: 299 and 300 for forward and reverse primers, respectively). Each primer was designed with a phosphorothioate linkage positioned at the penultimate base to maximize specificity for primer extension during PCR amplification. Amplification of a PCR fragment with size greater than 300-bp when separated by electrophoresis on agarose gel was considered as suggestive evidence for targeted integration (of least a portion) of the donor molecule into one or more copies of the endogenous AHAS gene. Of the 1,065 wheat events tested, 543 (51%) amplified a PCR fragment of greater than 300-bp in size.

The third molecular assay was used to further characterize wheat plants showing suggestive evidence for targeted integration of the donor molecule in one or more copies of the endogenous AHAS gene. This test involved a PCR assay using a pair of primers designed to amplify a 256-bp region from the three homoeologous copies of the endogenous AHAS gene. This region contained the binding site for ZFNs 29732 and 29730 (encoded on plasmid pDAB190350), and to include genomic nucleotide sequence variation. Enough genomic nucleotide sequence variation was included to differentiate between the AHAS homoeologs, such that the resulting amplicons could be unequivocally attributed (at the sequence level) to the wheat sub-genome from which they were derived. The primer pairs were synthesized with the Illumina™ SP1 and SP2 sequences at the 5' end, respectively, to provide compatibility with Illumina™ sequencing-by-synthesis chemistry. The synthesized primers also contained a phosphorothioate linkage at the penultimate 5' and 3' nucleotides. The 5' phosphorothioate linkage afforded protection against exonuclease degradation of the Illumina™ SP1 and SP2 sequences, while the 3' phosphorothioate linkage improved PCR specificity for amplification of the target AHAS sequences using on-off PCR. These sequences of the primer pair are given in Table 21.

As the hybridization site for primer AHASs653ZFN.R3 (Table 21) was also present in the AHAS_3' untranslated region (UTR) in "QA_pDAS000434", the third molecular assay allowed for differentiation between targeted and random donor integration, as well as between perfect and imperfect donor integration at one or more copies of the endogenous AHAS locus. Wheat plants having perfect hemizygous on-target editing are expected to produce sequence reads that originate from amplification of both the wild-type (unedited) and edited alleles at each modified AHAS locus. These alleles are distinguishable at the sequence level by the seven deliberate mutations introduced into the AHAS exon in "QA_pDAS000434" (i.e., the two mutations encoding the S653N mutation and the five codon-optimized, synonymous mutations positioned across the binding site of ZFN 29732, which were incorporated to prevent re-cleavage of the integrated donor). Theoretically, the frequency of reads corresponding to the wild-type and edited alleles should occur at a ratio of 1:1 for each endogenous AHAS locus with perfect hemizygous editing. In contrast, wheat plants having perfect homozygous on-target editing are expected to only generate sequence reads that originate from the pair of edited alleles at each modified endogenous AHAS locus. As the primer pair used in the

TABLE 21

Primer sequences used to further characterize wheat plants having suggestive evidence for targeted integration of the donor molecule in one or more copies of the endogenous AHAS gene.

| Primer Name | Primer Sequence (5'→3') | SEQ ID NO: |
|---|---|---|
| AHASs653ZFN.F2 | a*cactctttccctacacgacgctcttccgatctGCAATCAAGAAGATGCTTGAGAC*C | 301 |
| AHASs653ZFN.R3 | g*tgactggagttcagacgtgtgctcttccgatctCAAGCAAACTAGAAAACGCATG*G | 302 |

The asterisk(*) indicates a phosphorothioate; lowercase font indicates SP1 and SP2 sequences, and upper case font indicates the genomic DNA sequence.

PCR amplicons produced by the third molecular assay were prepared for deep sequencing by performing an additional round of PCR to introduce the Illumina™ P5 and P7 sequences onto the amplified DNA fragments, as well as a sequence barcode index that could be used to unequivocally attribute sequence reads to the sample from which they originated. This was achieved using primers that were in part complementary to the SP1 and SP2 sequences added in the first round of amplification, but also contained the sample index and P5 and P7 sequences. Following amplification, the generated products were sequenced on an Illumina MiSEQ™ instrument to generate 250-bp paired-end sequence reads, according to the manufacturer's instructions.

The resultant paired-end 250-bp sequence reads were computationally processed, as described previously, to assign each read to sample (based on the barcode index) and the sub-genome from which they were derived (based on nucleotide variation that distinguished between homoeologous copies of the AHAS gene), and to perform quality filtering to ensure that only high quality sequences were used for subsequent analyses. Custom developed PERL scripts and manual data manipulation in MICROSOFT EXCEL 2010™ (Microsoft Corporation) were used, as described below, to identify reads that contained evidence for targeted integration of the donor into one or more copies of the endogenous AHAS gene.

third molecular assay were designed to amplify all three homoeologous copies of the AHAS gene, the expected generation of reads originating from all three wheat sub-genomes can also be used to detect on-target imperfect donor integration (e.g., integration of a partial donor fragment, or integration of the donor fragment in the wrong orientation). Imperfect on-target donor integration is expected to result in amplification of only the wild-type (unedited) allele from each modified endogenous AHAS locus due to PCR competition favoring the amplification of the shorter wild-type fragment. Consequently, hemizygous on-target imperfect donor integration is expected to generate about half as many reads originating from the sub-genome into which integration occurred, compared to unedited sub-genomes. For homozygous on-target imperfect donor integration, no reads are expected to originate from the sub-genome into which integration occurred. Conversely, off-target (random) donor integration is expected to generate an equal proportion of sequence reads originating from all three homoeologous copies of the AHAS gene.

Sequence analysis of the 543 wheat plants tested revealed 38 events with molecular evidence for on-target donor integration in one or more copies of the endogenous AHAS gene. Event di01-9632-1-1 had perfect hemizygous donor integration in the AHAS locus situated in the B-genome. These results were indicated by the presence of both wild-type and perfectly edited reads originating from the B-genome, and only wild-type alleles originating from the A- and D-genome (Table 22). Two events had imperfect hemizygous donor integration in the AHAS loci on the A- and D-genomes, respectively. Event y102-9453-1-2 had both wild-type and imperfectly edited reads originating from the D-genome, and only wild-type alleles originating from the A- and B-genomes. Comparatively, event y102-9552-21-1 had both wild-type and imperfectly edited reads originating from the A-genome, and only wild-type alleles originating from the other sub-genomes.

The remaining 35 events showed molecular evidence for imperfect donor integration into at least one copy of the endogenous AHAS gene, where the donor molecule was likely to be truncated or integrated in the wrong orientation (Table 22). These events were characterized by a lower than expected frequency of reads originating from one or more of the wheat sub-genomes. For example, event y102-9552-7-1 had a statistically significant lower frequency of wild-type AHAS reads originating from the B-genome than expected for an unedited locus. The remaining 453 events showed only evidence for random integration of the donor elsewhere in the wheat genome, indicating that the amplified product from the second molecular assay most likely arose from PCR chimerism. The consensus sequences for the edited alleles present in the B, D and A sub-genome of wheat events di01-9632-1-1, y102-9453-1-2 and y102-9552-21-1 are provided as SEQ ID NOs:303, 304 and 305, respectively.

TABLE 22

Molecular evidence for integration of QA_pDAS000434 into one or more homoeologous copies of the endogenous AHAS locus.

| | A-genome | | | | |
|---|---|---|---|---|---|
| Event | No. of reads | % Reads | % WT | % PE | % IE |
| di01-9632-1-1 | 17,312 | 9 | 99 | 0 | 1 |
| yl02-9453-1-2 | 8,548 | 20 | 97 | 3 | 0 |
| yl02-9552-21-1 | 3,049 | 10 | 47 | 0 | 53 |
| yl02-9552-7-1 | 43,845 | 66 | 100 | 0 | 0 |
| gt19-9595-10-1 | 48,681 | 62 | 100 | 0 | 0 |
| yr00-9553-3-1 | 16,212 | 16 | 98 | 1 | 0 |
| yr00-9580-9-1 | 69,153 | 35 | 97 | 2 | 1 |
| yl02-9532-1-1 | 85,431 | 43 | 100 | 0 | 0 |
| yl02-9532-16-1 | 14,318 | 29 | 100 | 0 | 0 |
| di01-9603-10-1 | 825 | 1* | 100 | 0 | 0 |
| yl02-9578-1-1 | 1,662 | 1* | 100 | 0 | 0 |
| di01-9603-2-1 | 833 | 5* | 100 | 0 | 0 |
| yc06-9547-1-1 | 831 | 1* | 100 | 0 | 0 |
| yl02-9532-9-1 | 2,168 | 1* | 100 | 0 | 0 |
| yc06-9522-1-1 | 4,233 | 2* | 100 | 0 | 0 |
| mb1k-9539-31-1 | 2,355 | 2* | 100 | 0 | 0 |
| yl02-9503-1-1 | 1,381 | 1* | 100 | 0 | 0 |
| mb1k-9546-4-1 | 1,971 | 2* | 100 | 0 | 0 |
| di01-9603-18-1 | 1,436 | 1* | 100 | 0 | 0 |
| di01-9603-25-1 | 819 | 1* | 100 | 0 | 0 |
| yl02-9503-2-1 | 1,241 | 1* | 100 | 0 | 0 |
| di01-9550-14-1 | 2,846 | 2* | 100 | 0 | 0 |
| yr00-9580-28-1 | 708 | 0* | 100 | 0 | 0 |
| yl02-9552-19-1 | 4,127 | 2* | 100 | 0 | 0 |
| hw12-9569-5-1 | 1,959 | 1* | 100 | 0 | 0 |
| gt19-9582-2-1 | 244 | 0* | 99 | 0 | 1 |
| gt19-9593-6-1 | 9,426 | 7* | 100 | 0 | 0 |
| mb1k-9539-25-1 | 982 | 1* | 100 | 0 | 0 |
| yl02-9457-7-1 | 467 | 0* | 100 | 0 | 0 |
| yr00-9553-16-1 | 433 | 0* | 100 | 0 | 0 |
| yw06-9345-15-1 | 146 | 4* | 100 | 0 | 0 |
| mb1k-9546-2-1 | 93,058 | 97 | 99 | 0 | 1 |
| yr00-9541-5-1 | 131,675 | 93 | 100 | 0 | 0 |
| yl02-9552-47-1 | 180,989 | 97 | 100 | 0 | 0 |
| gt19-9551-4-1 | 144,978 | 99 | 100 | 0 | 0 |
| yc06-9340-5-1 | 96,105 | 98 | 100 | 0 | 0 |
| yc06-9584-2-1 | 98,385 | 98 | 100 | 0 | 0 |
| yr00-9541-1-1 | 115,671 | 98 | 100 | 0 | 0 |

| | B-genome | | | | |
|---|---|---|---|---|---|
| Event | No. of reads | % Reads | % WT | % PE | % IE |
| di01-9632-1-1 | 9,498 | 5 | 70 | 29 | 1 |
| yl02-9453-1-2 | 13,374 | 32 | 97 | 3 | 0 |
| yl02-9552-21-1 | 16,817 | 55 | 100 | 0 | 0 |
| yl02-9552-7-1 | 6,254 | 9* | 100 | 0 | 0 |
| gt19-9595-10-1 | 5,146 | 7* | 100 | 0 | 0 |
| yr00-9553-3-1 | 8,683 | 8* | 100 | 0 | 0 |
| yr00-9580-9-1 | 1,768 | 1* | 98 | 1 | 1 |
| yl02-9532-1-1 | 6,644 | 3* | 100 | 0 | 0 |
| yl02-9532-16-1 | 34,310 | 70 | 100 | 0 | 0 |
| di01-9603-10-1 | 3,228 | 4* | 100 | 0 | 0 |
| yl02-9578-1-1 | 2,176 | 1* | 100 | 0 | 0 |
| di01-9603-2-1 | 1,225 | 7* | 100 | 0 | 0 |
| yc06-9547-1-1 | 723 | 1* | 100 | 0 | 0 |
| yl02-9532-9-1 | 1,012 | 0* | 100 | 0 | 0 |
| yc06-9522-1-1 | 3,979 | 2* | 100 | 0 | 0 |
| mb1k-9539-31-1 | 2,359 | 2* | 100 | 0 | 0 |
| yl02-9503-1-1 | 601 | 0* | 100 | 0 | 0 |
| mb1k-9546-4-1 | 364 | 0* | 100 | 0 | 0 |
| di01-9603-18-1 | 106,322 | 96 | 100 | 0 | 0 |
| di01-9603-25-1 | 101,834 | 98 | 100 | 0 | 0 |
| yl02-9503-2-1 | 221,040 | 99 | 100 | 0 | 0 |
| di01-9550-14-1 | 130,434 | 96 | 100 | 0 | 0 |
| yr00-9580-28-1 | 174,074 | 99 | 100 | 0 | 0 |
| yl02-9552-19-1 | 174,186 | 95 | 100 | 0 | 0 |
| hw12-9569-5-1 | 260,971 | 98 | 100 | 0 | 0 |
| gt19-9582-2-1 | 67,764 | 99 | 100 | 0 | 0 |
| gt19-9593-6-1 | 110,669 | 84 | 100 | 0 | 0 |
| mb1k-9539-25-1 | 75,915 | 96 | 100 | 0 | 0 |
| yl02-9457-7-1 | 125,465 | 99 | 100 | 0 | 0 |
| yr00-9553-16-1 | 111,825 | 99 | 100 | 0 | 0 |
| yw06-9345-15-1 | 3,655 | 93 | 100 | 0 | 0 |
| mb1k-9546-2-1 | 1,448 | 2* | 100 | 0 | 0 |
| yr00-9541-5-1 | 4,403 | 3* | 100 | 0 | 0 |
| yl02-9552-47-1 | 2,236 | 1* | 100 | 0 | 0 |
| gt19-9551-4-1 | 740 | 1* | 100 | 0 | 0 |
| yc06-9340-5-1 | 620 | 1* | 100 | 0 | 0 |
| yc06-9584-2-1 | 617 | 1* | 100 | 0 | 0 |
| yr00-9541-1-1 | 781 | 1* | 100 | 0 | 0 |

| | D-genome | | | | |
|---|---|---|---|---|---|
| Event | No. of reads | % Reads | % WT | % PE | % IE |
| di01-9632-1-1 | 170,321 | 86 | 99 | 0 | 1 |
| yl02-9453-1-2 | 19,841 | 48 | 68 | 32 | 0 |
| yl02-9552-21-1 | 10,665 | 35 | 100 | 0 | 0 |
| yl02-9552-7-1 | 15,936 | 24 | 100 | 0 | 0 |
| gt19-9595-10-1 | 24,091 | 31 | 100 | 0 | 0 |
| yr00-9553-3-1 | 79,529 | 76 | 98 | 1 | 0 |
| yr00-9580-9-1 | 128,317 | 64 | 97 | 2 | 1 |
| yl02-9532-1-1 | 105,821 | 53 | 100 | 0 | 0 |
| yl02-9532-16-1 | 434 | 1* | 99 | 1 | 0 |
| di01-9603-10-1 | 84,718 | 95 | 100 | 0 | 0 |
| yl02-9578-1-1 | 152,767 | 98 | 100 | 0 | 0 |
| di01-9603-2-1 | 14,671 | 88 | 100 | 0 | 0 |
| yc06-9547-1-1 | 71,423 | 98 | 100 | 0 | 0 |
| yl02-9532-9-1 | 230,632 | 99 | 100 | 0 | 0 |
| yc06-9522-1-1 | 167,492 | 95 | 100 | 0 | 0 |
| mb1k-9539-31-1 | 142,061 | 97 | 100 | 0 | 0 |
| yl02-9503-1-1 | 199,717 | 99 | 100 | 0 | 0 |
| mb1k-9546-4-1 | 89,309 | 97 | 100 | 0 | 0 |
| di01-9603-18-1 | 2,921 | 3* | 100 | 0 | 0 |
| di01-9603-25-1 | 1,715 | 2* | 96 | 0 | 4 |
| yl02-9503-2-1 | 1,741 | 1* | 100 | 0 | 0 |
| di01-9550-14-1 | 3,140 | 2* | 100 | 0 | 0 |
| yr00-9580-28-1 | 1,012 | 1* | 100 | 0 | 0 |
| yl02-9552-19-1 | 5,470 | 3* | 100 | 0 | 0 |
| hw12-9569-5-1 | 2,479 | 1* | 100 | 0 | 0 |
| gt19-9582-2-1 | 496 | 1* | 99 | 0 | 1 |

TABLE 22-continued

Molecular evidence for integration of QA_pDAS000434 into one or more homoeologous copies of the endogenous AHAS locus.

| | | | | | |
|---|---|---|---|---|---|
| gt19-9593-6-1 | 11,821 | 9* | 100 | 0 | 0 |
| mb1k-9539-25-1 | 1,898 | 2* | 100 | 0 | 0 |
| yl02-9457-7-1 | 555 | 0* | 100 | 0 | 0 |
| yr00-9553-16-1 | 604 | 1* | 100 | 0 | 0 |
| yw06-9345-15-1 | 150 | 4* | 100 | 0 | 0 |
| mb1k-9546-2-1 | 1,191 | 1* | 100 | 0 | 0 |
| yr00-9541-5-1 | 4,766 | 3* | 100 | 0 | 0 |
| yl02-9552-47-1 | 3,537 | 2* | 100 | 0 | 0 |
| gt19-9551-4-1 | 1,171 | 1* | 99 | 0 | 0 |
| yc06-9340-5-1 | 1,186 | 1* | 100 | 0 | 0 |
| yc06-9584-2-1 | 1,234 | 1* | 100 | 0 | 0 |
| yr00-9541-1-1 | 1,566 | 1* | 100 | 0 | 0 |

"No. of reads" indicates the number of sequence reads assigned to the wheat sub-genome;
"% Reads" indicates the percentage of sequence reads assigned to the wheat sub-genome as a proportion of all assigned reads;
"% WT" indicates the percentage of sequence reads identified as wild type (unedited) alleles;
"% PE" indicates the percentage of sequence reads indicating precise donor integration into the wheat sub-genome;
"% IE" indicates the percentage of sequence reads indicating imperfect donor integration into the wheat sub-genome;
Asterisks* indicate occurrence of statistically significant fewer sequence reads than expected for an unedited endogenous AHAS locus Overall, 3% (38/1,162) of the BASTA®-selected wheat events showed molecular evidence for targeted donor integration into one or more of the homoeologous copies of the endogenous AHAS gene.

Example 11: Development of a Transformation System for Sequential, Exogenous Marker-Free Transgene Stacking at the Endogenous AHAS Loci in Wheat Wheat plants containing a donor integrated polynucleotide within the AHAS locus to introduce the S653N mutation are produced via the previously described methods. For example, the regeneration of event di01-9632-1-1 (Table 23) showing molecular evidence of perfect hemizygous integration of "QA_pDAS000434" in the B-genome of wheat indicates that donor DNA and zinc finger nuclease constructs can be utilized for the integration of donor molecule sequences at one or more copies of the target endogenous AHAS locus within wheat. Producing such an event, that is free of any additional transgenic selectable markers, is the initiating act for sequential, exogenous transgenic selectable marker-free stacking of a donor polynucleotide at an endogenous AHAS locus in the genome of wheat. The edited plant events are obtained via alternative selection conditions as previously described in Example 10.

The previously described selection conditions can be modified by a number of methodologies. Other approaches can be implemented to enhance the recovery of wheat plants with precise integration of the S653N mutation (as encoded on "QA_pDAS000434" or pDAS000433) into one or more copies of the endogenous AHAS locus, without using a transgenic selectable marker.

Two additional approaches can be implemented to enhance the recovery of wheat plants with precise integration of the S653N mutation into one or more copies of the endogenous AHAS locus, without the usage of a transgenic selectable marker.

For example, IMAZAMOX® selection conditions are modified, to include selection at differing stages of culturing and/or lower concentrations of the herbicide. Accordingly, selection at the plant regeneration stage is reduced by lowering the concentration of IMAZAMOX® added to the plant regeneration media or as another alternative the usage of herbicide at this plant regeneration stage is completely eliminated. As such, stronger growth of regenerated plantlets is observed, thereby ensuring larger plantlets that are less susceptible to tissue damage when sub-cultured to rooting media. Furthermore, the plantlets may be required to be dissected from the embryogenic callus from which they originate. Smaller plantlets are more susceptible to tissue damage, which can result in tissue necrosis and potential loss of transformed plantlets during sub-culturing. Maintenance of IMAZAMOX® selection at the callus induction stage helps to restrict embryogenesis from untransformed cells, while its maintenance at the rooting stage would provide strong selection for plantlets with precise integration of pDAS000433 at one or more copies of the endogenous AHAS locus, which is required to produce the AHAS herbicide tolerance phenotypes conferred by the S653N mutation. The success of such IMAZAMOX® selection strategies for generating precisely edited wheat plants was demonstrated in Example 5.

In another example, a different transformation system is used to generate wheat plants with precisely integrated donor DNA. For example, protoplast-based transformation could be used to produce individual calli, where each callus is derived from a single cell. Protoplast-derived calli provide several advantages over callus derived from biolistic-bombarded scutella of immature zygotic embryos. Unlike callus derived from biolistics-bombardment, and which is chimeric for both transformed and untransformed cells, protoplast-derived callus is clonal. Hence, cell survival in callus derived from a transformed protoplast in which precise pDAS000433 integration has occurred cannot be compromised by the presence of neighboring untransformed cells when subject to IMAZAMOX® selection. In the case of callus derived from biolistics-bombardment, the chimeric composition of the callus means that the survival of a precisely transformed can be compromised by the death of surrounding untransformed cells when subjected to IMAZAMOX® selection. Protoplast-based transformation systems also provide the advantage of scalability, compared to biolistics bombardment, since many more cells can be transformed for an given amount of effort, thereby providing for higher probability for recovering wheat plants with precise integration of pDAS000433 in one or more copies of the endogenous AHAS gene. Several protoplast-based transformation systems for wheat have been described in published scientific literature (Qiao et al. (1992) *Plant Cell Reports* 11:262-265; Ahmed and Sagi (1993) *Plant Cell Reports* 12:175-179; Pauk et al. (1994) *Plant Cell, Tissue and Organ Culture* 38: 1-10; He et al. (1994) *Plant Cell Reports* 14: 92-196; Gu and Lang (1997) *Plant Cell, Tissue and Organ Culture* 50: 139-145; and Li et al. (1999) *Plant Cell, Tissue and Organ Culture* 58: 119-125).

A series of experiments are performed to determine optimal selection conditions for regenerating wheat plants expressing the AHAS(S653N) mutation conferring tolerance to IMAZAMOX® from a protoplast-based transformation system such as those described above.

IMAZAMOX® selection conditions are optimized using protoplasts derived from somatic embryogenic callus (SEC)-derived cell suspension culture of the wheat line cv. Bobwhite MPB26RH. While protoplasts derived from Bobwhite MPB26RH are non-totipotent (i.e., cannot be used to regenerate entire plants), the selection conditions established for enriching for events expressing the AHAS(653N) mutation are expected to be transferrable to any protoplast-based transformation system based on a totipotent wheat genotype, which those in the art would recognize. The experiments conducted establish the basal tolerance of the wild-type donor wheat line cv. Bobwhite MPB26RH (S653/S653 genotype, which confers susceptibility to imidazolinones) to IMAZAMOX®. The use of IMAZAMOX® selection conditions stronger than basal tolerance will strongly enrich for transformed cells expressing the AHAS(S653N) mutation.

Further transformation methods are applicable. For example a cell suspension culture for wheat line cv. Bobwhite MPB26RH can be established. Somatic embryogenic callus (SEC) is induced from immature zygotic embryos of wheat line cv. Bobwhite MPB26RH as described previously. A fast growing callus line is selected after six cycles of sub-culturing on callus induction media. For each cycle of sub-culturing, the fast-growing calli are transferred onto new callus induction media and cultured in the dark at 26° C. for 14 d.

A cell suspension culture is initiated by transferring 1gram calli of the fast-growing callus line to a flask containing 20 ml liquid growth medium and culturing at 25° C. in the dark on a gyratory shaker at 90 rpm. Every seven days the cell suspension culture is sub-cultured by passing the culture through a fine gauze to remove cell clumps greater than 2 mm in diameter, and replacing two thirds of the culture media with fresh medium. After 3 months of repeated filtration and sub-culturing a fast-growing SEC-derived cell suspension culture is established.

Next protoplasts are isolated from the SEC-derived cell suspension culture. About 4 grams fresh weight of cell clumps are obtained by passing 7 day old SEC-derived cell suspension culture through a fine-mesh. The cell clumps are digested in wheat callus digest mix, as described previously, to release the protoplasts. The yield of SEC-derived cell suspension culture protoplasts is estimated using a Neubauer™ haemocytometer. Evans Blue stain is used to determine the proportion of live cells recovered.

The protoplast culture selection conditions with the herbicide IMAZAMOX® are selected. An agarose bead-type culture system is used for protoplast culture. About $1 \times 10^6$ protoplasts are precipitated by gentle centrifugation and the supernatant is removed. The protoplasts are resuspended by gentle agitation in 1 ml of melted 1.2% Sea-Plaque™ agarose cooled to 40° C. and transferred to a 3.5 cm petri dish. Following agarose solidification, 1 ml culture medium is added to the petri dish and the plate is incubated at 25° C. in the dark for 1 week. The agarose plug is transferred into a 20 cm petri dish containing 10 ml culture medium and incubated at 25° C. in the dark on a gyratory shaker at 90 rpm. Every 14 days the culture medium is replaced with fresh media. Protoplast cell division is typically observed 3 days after embedding in agarose, with clumps of multiple cells visible after 7 days.

The basal tolerance of wheat line cv. Bobwhite MPB26RH to IMAZAMOX® is determined by incubating the agarose bead-type cultures in media supplemented with 0, 50, 100, 200, 400 and 600 nM IMAZAMOX® and assessing the rate of calli growth after 2 weeks. IMAZAMOX® concentrations higher than 200 nM impede calli development, indicating that concentrations of 200 nM and higher are optimal for enriching and selecting wheat cells having the AHAS (S653N) mutation.

Establishment of tissue culture selection conditions for obtaining transgenic plants with a donor integrated fragment resulting in the S653N mutation within the AHAS locus are obtained. The edited plant events are used to generate explant material (e.g., protoplasts or scutella of immature zygotic embryos) for a second round of transfection. As described in the next example, the explant material is subsequently co-transfected with a donor DNA molecule and a plasmid encoding a ZFN that is designed to target a Zinc Finger binding site located in the AHAS genes upstream of the region encoding the P197 amino acid residue.

Example 12: Alternate Transformation Systems for Sequential, Exogenous Marker-Free Transgene Stacking at the Endogenous AHAS Loci in Wheat Molecular evidence provided in Example 10 for the regenerated wheat plant event di01-9632-1-1 demonstrates the technical feasibility for sequential, exogenous marker-free transgene stacking at the endogenous AHAS loci in wheat. Refinement of IMAZAMOX® selection conditions or use of a different transformation system permit the production of wheat plants with sequentially stacked transgenes at an endogenous AHAS locus. This example describes approaches for achieving exogenous marker-free sequential transgene stacking at an endogenous AHAS locus by alternating between different selective agents (e.g., imidazolinone and sulfonylurea) and corresponding AHAS mutations (e.g., S653N and P197S). First, the selection conditions for sulfonylurea were determined.

Optimization of Chemical Selection Conditions; Generation of Low-Copy, Randomly Integrated T-DNA Wheat Plants with AHAS(P197S) Expression Constructs A binary vector pDAS000164 (SEQ ID NO:289, FIG. 11) containing AHAS(P197S) expression and PAT selection cassettes was designed and assembled using skills and techniques commonly known in the art. The AHAS (P197S) expression cassette consisted of the promoter, 5' untranslated region, and intron from the Ubiquitin (Ubi) gene from *Zea mays* (Toki et al., (1992) *Plant Physiology*, 100: 1503-07) followed by the coding sequence (1,935 bp) of the AHAS gene from *T. aestivum* cv. Bobwhite MPB26RH with nucleotide 511 mutated from C to T in order to induce an amino acid change from proline (P) to serine (S). The AHAS expression cassette included the 3' untranslated region (UTR) comprising the transcriptional terminator and polyadenylation site of the nopaline synthase gene (nos) from *A. tumefaciens* pTi15955 (Fraley et al., (1983) *Proceedings of the National Academy of Sciences U.S.A.*, 80(15): 4803-4807). The selection cassette was comprised of the promoter, 5' untranslated region, and intron from the Actin (Act1) gene from *Oryza sativa* (McElroy et al., (1990) *The Plant Cell* 2(2): 163-171) followed by a synthetic, plant-optimized version of phosphinothricin acetyl transferase (PAT) gene, isolated from *Streptomyces viridochromogenes*, which encodes a protein that confers resistance to inhibitors of glutamine synthetase comprising phosphinothricin, glufosinate, and bialaphos (Wohlleben et al., (1988) *Gene*, 70(1): 25-37). This cassette was terminated with the 3' UTR comprising the transcriptional terminator and polyadenylation sites from the 35s gene of the cauliflower mosaic virus (CaMV) (Chenault et al., (1993) *Plant Physiology*, 101 (4): 1395-1396).

The selection cassette was synthesized by a commercial gene synthesis vendor (e.g., GeneArt, Life Technologies, etc.) and cloned into a GATEWAY®-enabled binary vector with the RfA Gateway cassette located between the Ubiquitin (Ubi) gene from *Zea mays* and the 3' untranslated region (UTR) comprising the transcriptional terminator and polyadenylation site of the nopaline synthase gene (nos) from *A. tumefaciens* pTi15955. The AHAS (P197S) coding sequence was amplified with flanking attB sites and sub-cloned into pDONR221. The resulting ENTRY clone was used in a LR CLONASE II® (Invitrogen, Life Technologies) reaction with the Gateway-enabled binary vector encoding the phosphinothricin acetyl transferase (PAT) expression cassette. Colonies of all assembled plasmids were initially screened by restriction digestion of miniprep DNA. Restriction endonucleases were obtained from New England BioLabs (NEB; Ipswich, Mass.) and Promega (Promega Corporation, WI). Plasmid preparations were performed using the QIAPREP SPIN MINIPREP KIT® (Qiagen, Hilden) or the PURE YIELD PLASMID MAXIPREP SYSTEM® (Promega Corporation, WI) following the instructions of the suppliers. Plasmid DNA of selected clones was sequenced using ABI Sanger Sequencing and BIG DYE TERMINATOR V3.1® cycle sequencing protocol (Applied Biosystems, Life Technologies). Sequence data were assembled and analyzed using the SEQUENCHER™ software (Gene Codes Corporation, Ann Arbor, Mich.).

The resulting binary expression clone pDAS000164 was transformed into *Agrobacterium tumefaciens* strain EHA105. Transgenic wheat plants with randomly integrated T-DNA were generated by *Agrobacterium*-mediated transformation using the donor wheat line cv. Bobwhite MPB26RH, following a protocol similar to Wu et al. (2008) *Transgenic Research* 17:425-436. Putative $T_0$ transgenic events expressing the AHAS (P197) expression constructs were selected for phosphinothricin (PPT) tolerance, the phenotype conferred by the PAT transgenic selectable marker, and transferred to soil. The $T_0$ plants were grown under glasshouse containment conditions and $T_1$ seed was produced.

Genomic DNA from each $T_0$ plant was extracted from leaf tissue, using the protocols as previously described in Example 6, and tested for the presence or absence of carryover *Agrobacterium tumefaciens* strain and for the number of integrated copies of the T-DNA encoding AHAS (P197S). The presence or absence of the *A. tumefaciens* strain was performed using a duplex hydrolysis probe qPCR assay (analogous to TAQMAN') to amplify the endogenous ubiquitin gene (SEQ ID NO:290, SEQ ID NO:291, and SEQ ID NO:292 for forward and reverse primers and probe sequence, respectively) from the wheat genome, and virC from pTiBo542 (SEQ ID NO: 293, SEQ ID NO:294, and SEQ ID NO:70 for forward and reverse primers and probe sequence, respectively). The number of integrated T-DNA copies was estimated using a duplex hydrolysis probe qPCR assay, as previously described in Example 6, based on the puroindoline-b gene (Pinb) from the D genome of hexaploid wheat and a region of the Actin (Act1) promoter present on pDAS000164. Overall, 35 independent $T_0$ events with fewer than three randomly integrated copies of T-DNA were generated.

Optimization of Chemical Selection Conditions; Conditions for Regenerating Wheat Plants on Sulfometuron Methyl A series of experiments were performed to determine optimal selection conditions for regenerating wheat plants expressing the AHAS (P197S) mutation conferring tolerance to sulfonylurea class herbicides. These experiments were based on testing the basal tolerance of the wild-type donor wheat line cv. Bobwhite MPB26RH (P197/P197genotype, which confers susceptibility to sulfonylureas) at the callus induction, plant regeneration and rooting stages of an established wheat transformation system. Similar experiments were performed to determine the basal tolerance of transgenic cv. Bobwhite MPB26RH events that had randomly integrated T-DNA expressing the AHAS (P197S) mutation, which confers tolerance to sulfonylurea selection agents.

The basal tolerance of the wild-type donor wheat line to sulfometuron methyl at the callus induction stage was determined as follows: scutella of immature zygotic embryos were isolated, as previously described in Example 4, and placed in 10 cm petri dishes containing CIM medium supplemented with 0, 100, 500, 1000, 1500 and 2000 nM sulfometuron methyl, respectively. Twenty scutella were placed in each petri dish. A total of 60 scutella were tested at each sulfometuron methyl concentration. After incubation at 24° C. in the dark for 4 weeks, the amount of somatic embryogenic callus formation (SEC) at each sulfometuron methyl concentration was recorded. The results showed that SEC formation for cv. Bobwhite MPB26RH was reduced by about 70% at 100 nM sulfometuron methyl, compared to untreated samples.

The basal tolerance of the wild-type donor wheat line to sulfometuron methyl at the plant regeneration stage was determined as follows: scutella of immature zygotic embryos from the donor wheat line were isolated and placed in 10 cm petri dishes containing CIM medium. Then SEC was allowed to form by incubating at 24° C. in the dark for 4 weeks. The SEC was transferred to 10 cm petri dishes containing DRM medium supplemented with 0, 100, 500, 1000, 1500, 2000, 2500 and 3000 nM sulfometuron methyl, respectively. Twenty CIM were placed in each petri dish. A total of 60 CIM were tested for basal tolerance response at each sulfometuron methyl concentration. After incubation for 2 weeks at 24° C. under a 16/8 (light/dark) hour photoperiod in a growth room, the regeneration response was recorded. The results showed that plant regeneration was reduced by about 80% at 2000 nM sulfometuron methyl, compared to untreated samples.

The basal tolerance of the wild-type donor wheat line to sulfometuron methyl at the plant rooting stage was determined as follows: scutella of immature zygotic embryos were isolated and placed in 10 cm petri dishes containing CIM medium. Then SEC was allowed to form by incubating at 24° C. in the dark for 4 weeks. The SEC was transferred to 10 cm petri dishes containing DRM medium and incubated for 2 weeks at 24° C. under a 16/8 (light/dark) hour photoperiod to allow plant regeneration to take place. Regenerated plants were transferred to 10 cm petri dishes containing RM medium supplemented with 0, 100, 200, 250, 300, 400, 500, 1000 and 2000 nM sulfometuron methyl, respectively. Ten regenerated plants were placed in each petri dish. A total of 30 regenerated plants were tested for basal tolerance response at each sulfometuron methyl concentration. After incubation for 3 weeks at 24° C. under a 16/8 (light/dark) hour photoperiod in a growth room, the root formation response was recorded. The results showed that root formation was severely inhibited when concentrations of sulfometuron methyl higher than 400 nM, compared to untreated samples.

The basal tolerance of transgenic wheat events with randomly integrated, low-copy (≤3) T-DNA expressing the AHAS (P197S) mutation to sulfometuron methyl from pDAS000164 at the plant rooting stage was determined as follows: four independent transgenic events were randomly selected and multiplied in vitro by sub-culturing on multiplication medium. Following multiplication, plants for each event were transferred to 10 cm petri dishes containing RM medium supplemented with 0, 400, 450, 500, 550 and 600 nM sulfometuron methyl, respectively. Four plants (one from each of the four events) were placed in each petri dish. A total of 3 plants per event were tested for basal tolerance at each sulfometuron methyl concentration. After incubation for 2 weeks at 24° C. under a 16/8 (light/dark) hour photoperiod in a growth room, the root formation response was recorded. The results showed that root formation was not restricted, compared to untreated controls, at any of the concentrations tested, indicating that the AHAS(P197S) mutation conferred high tolerance to sulfometuron methyl.

Design and Synthesis of Donor DNA for First Sequential Transgene Stacking at an Endogenous AHAS Locus Using NHEJ-Directed DNA Repair The donor DNA of the pDAS000433 construct (FIG. 12) for the first round of transgene stacking is designed and synthesized as described in Examples 10 and 11 to promote precise donor integration (containing the S653N mutation) at an endogenous AHAS locus via ZFN-mediated, NHEJ-directed repair. Whole plants that are resistant to IMAZAMOX® are obtained and prepared for a second round of targeting to introduce the Design and Synthesis of Donor DNA for Second Sequential Transgene Stack at an Endogenous AHAS Locus Using NHEJ-Directed DNA Repair The donor DNA (pDAS000434; FIG. 13; SEQ ID NO:72) containing a P197S mutation for the second round of transgene stacking is designed to promote precise donor integration at the same AHAS locus targeted in the first transgene stack via ZFN-mediated, NHEJ-directed repair. The design is based on the integration of a double stranded donor molecule at the double strand DNA break created by cleavage of the AHAS gene copy containing the first stacked transgene by ZFNs 34480 and 34481 (encoded on plasmid pDAB111860) or ZFNs 34482 and 34483 (encoded on plasmid pDAB111861). The pDAS000434 donor molecule comprises several portions of polynucleotide sequences. The 5' end contains sequence nearly identical to the endogenous AHAS gene encoded in the D-genome, starting from the target ZFN cleavage site and finishing at the AHAS stop codon. Several deliberate mutations are introduced into this sequence: mutations encoding the P197S mutation and codon-optimized, synonymous mutations positioned across the binding site of ZFNs 34481 and 34483 to prevent re-cleavage of the integrated donor. Following the stop codon is 316-bp of non-coding sequence corresponding to the conserved 3'untranslated region (3'UTR) in the AHAS homoeologs. The 3'UTR sequence is followed by Zinc Finger binding sites for ZFNs 34474 and 34475 (encoded on plasmid pDAB111857) and ZFNs 34476 and 34477 (encoded on plasmid pDAB111858). These Zinc Finger binding sites allow for self-excision of donor-derived AHAS (coding and 3'UTR) sequence integrated at an endogenous locus in the next round of transgene stacking. The self-excision Zinc Finger binding sites are followed by several additional Zinc Finger binding sites (each of which is separated by 100-bp of random sequence) that flank unique restriction endonuclease cleavage sites, and which enable insertion of a transgene expression cassette (e.g., the DGT-28 expression cassette, as described in U.S. Pat. Pub. No. 20130205440). The additional Zinc Finger binding sites enable future excision of transgenes that can be integrated at an AHAS locus by sequential marker-free transgene stacking, or continued sequential transgene stacking at the same genomic location using an alternate stacking method. The donor cassette is synthesized by a commercial gene service vendor (e.g., GeneArt, Life Sciences) with a short stretch of additional flanking sequence at the 5' and 3' ends to enable generation of a donor molecule with protruding 5' and 3' ends that are compatible with the ligation overhangs generated by ZFNs 34474 and 34475 (encoded on plasmid pDAB111857) or ZFNs 34476 and 34477 (encoded on plasmid pDAB111858), upon cleavage of an endogenous AHAS locus.

The donor molecule with protruding 5' and 3' ends is generated by digesting plasmid DNA containing the donor molecule, or following PCR amplification as described for "QA_pDAS000434" and/or pDAS000433, with the restriction endonuclease BbsI using standard methods known to one in the art.

Figure 14B:
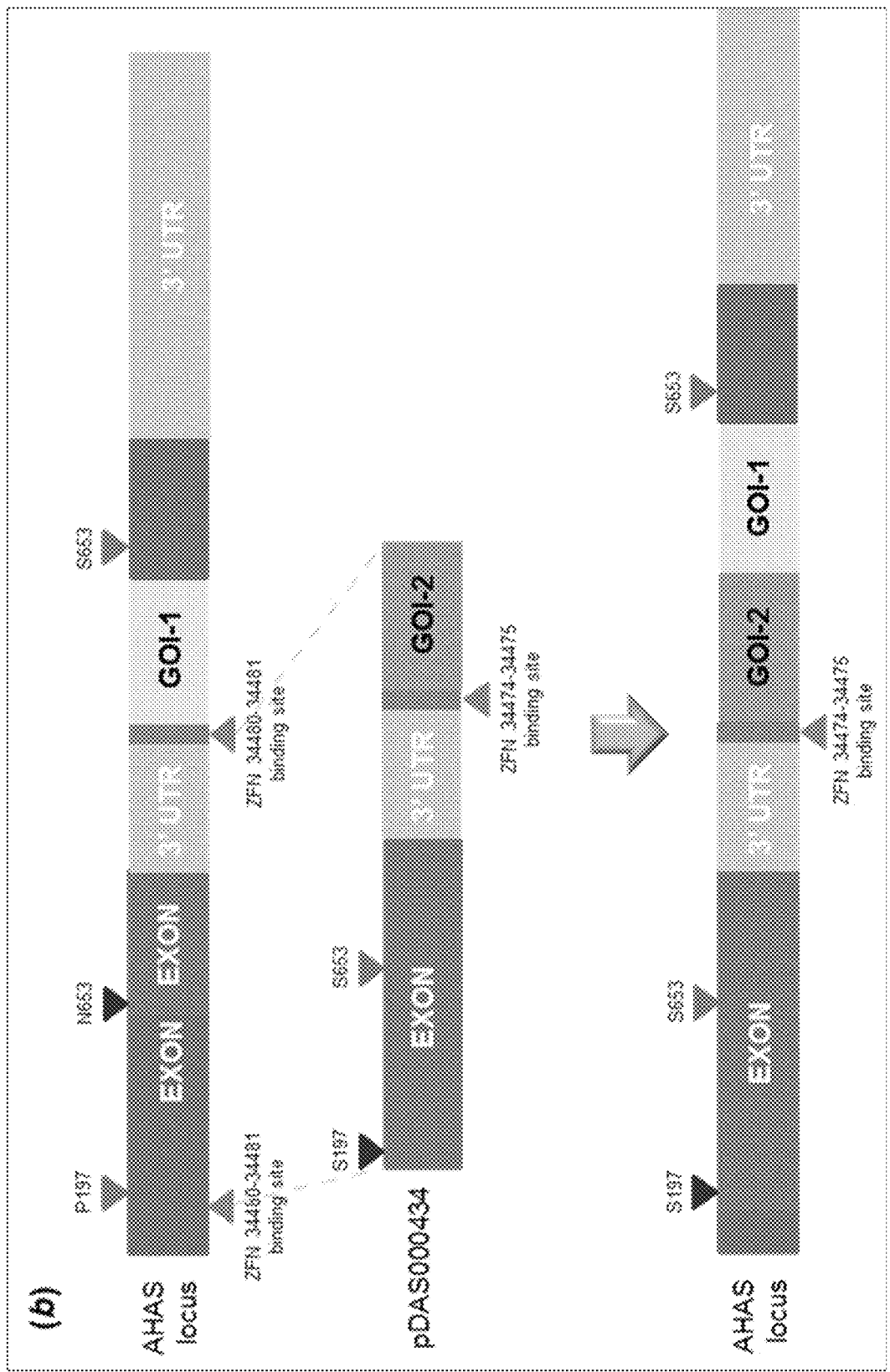

Transformation System for Exogenous Marker-Free, Sequential Transgene Stacking at an Endogenous AHAS Locus in Wheat Using NHEJ-Directed DNA Repair Transgenic wheat events with multiple transgenes stacked at the same endogenous AHAS locus are produced by exogenous marker-free, sequential transgene stacking via transformation with donor pDAS000433 and ZFNs 29732 and 29730 (encoded on plasmid pDAB109350). Precise ZFN-mediated, NHEJ-directed donor integration introduces the first transgene and S653N mutation conferring tolerance to imidazolinones at an AHAS locus, thus allowing for the regeneration of correctly targeted plants using IMAZAMOX® as a selection agent, as previously described in Example 5. FIG. 14a depicts the integration. Subsequent transformation of wheat cells, derived from first transgene stacked events, with donor pDAS000434 and ZFNs 34480 and 34481 (encoded on plasmid pDAB111860) results in the replacement of the endogenous chromatin located between the ZFN binding sites positioned upstream of P197 and at the self-excision site integrated during the first transgene stack with the donor molecule. This results in integration of the second transgene and a P197S mutation conferring tolerance to sulfonylurea, thus allowing for the regeneration of correctly targeted plants using sulfometuron methyl as a selection agent. At the same time, integration of the second donor removes the S653N mutation, thus restoring susceptibility to imidazolinones (FIG. 14b). One skilled in the art will appreciate that stacking of a third transgene can be achieved by transformation with appropriate zinc finger nucleases and a donor that contains an additional transgene and confers susceptibility to sulfonylurea and tolerance to imidazolinones, thus allowing the regeneration of correctly targeted plants using IMAZAMOX® as a selection agent. As such, continued rounds of sequential transgene stacking are possible via transformation with donors that introduce transgenes and mutations in the endogenous AHAS genes for differential cycling between imidazolinone and sulfonylurea selection agents.

The transformation system used to regenerate wheat plants with sequentially stacked transgenes at an endogenous AHAS locus is based on the previously described approach for biolistics-mediated DNA delivery to scutella of immature zygotic wheat embryos, or direct DNA delivery to wheat protoplasts using approaches known to one skilled in the art; for example, using the method of He et al. (1994) *Plant Cell Reports* 14: 92-196, or any of the methods described in Example 11.

Figure 16:
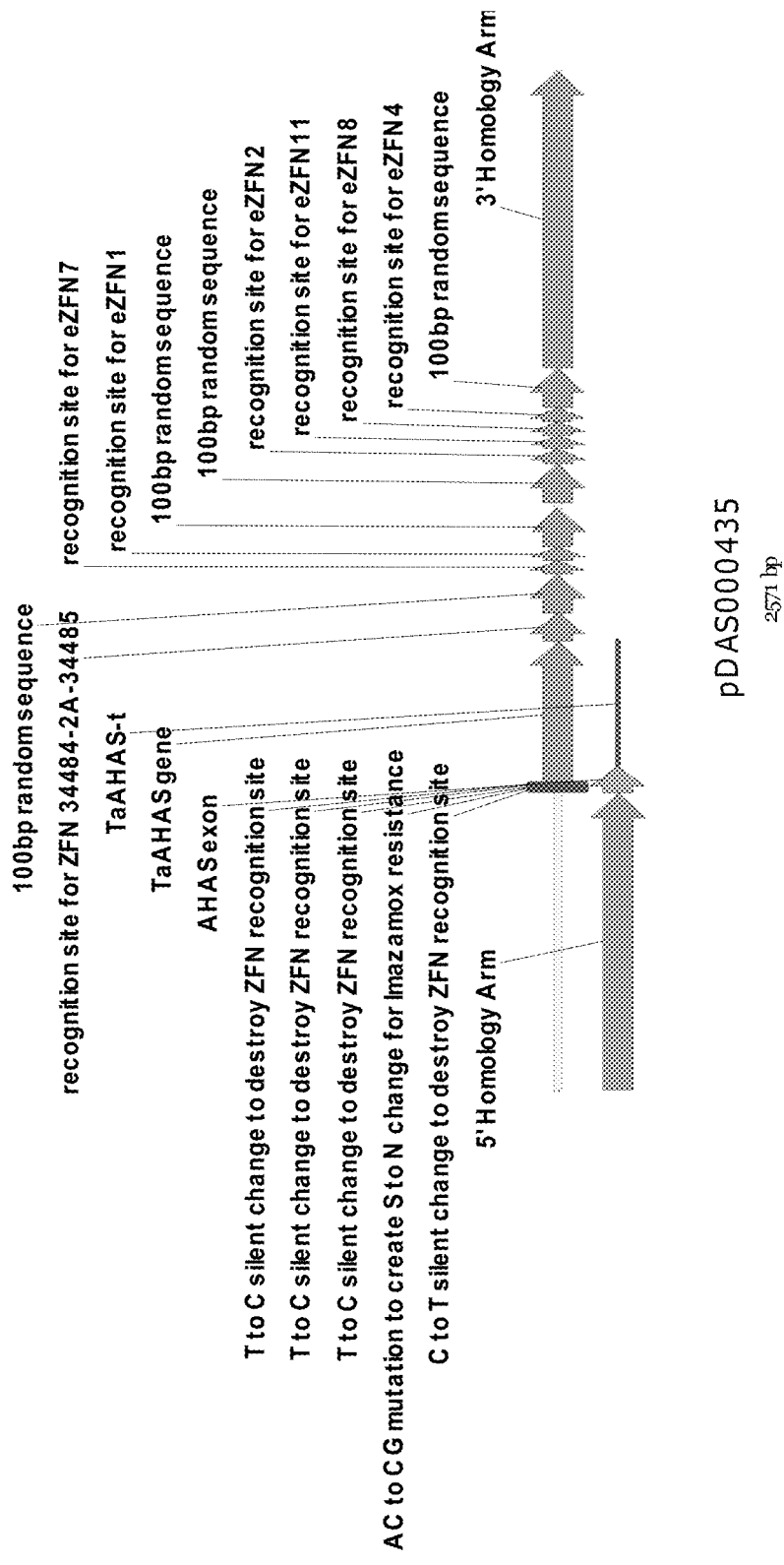
FIG. 16 is a schematic showing a linear map of pDAS000435.

Design and Synthesis of Donor DNA for First Sequential Transgene Stacking at an Endogenous AHAS Locus Using HDR-Directed DNA Repair The donor DNA for the first round of transgene stacking is designed to promote precise donor integration at an endogenous AHAS locus via ZFN-mediated, HDR-directed homology repair. The design is based on the integration of a double stranded donor molecule at the position of the double strand DNA break created by cleavage of a homoeologous copy of the endogenous AHAS gene by ZFNs 29732 and 29730 (encoded on plasmid pDAB109350). The donor molecule (pDAS000435; FIG. 16; SEQ ID NO:295) is identical in sequence to pDAS000433 (FIG. 12).

The donor cassette is synthesized by a commercial gene service vendor (e.g., GeneArt, Life Sciences, etc.) with 750-bp homology arms at each end. The homology arms at the 5' and 3' ends of the donor correspond to endogenous AHAS sequence immediately upstream and downstream of the double strand DNA break created by ZFNs 29732 and 29730 (encoded on plasmid pDAB109350).

Figure 17:
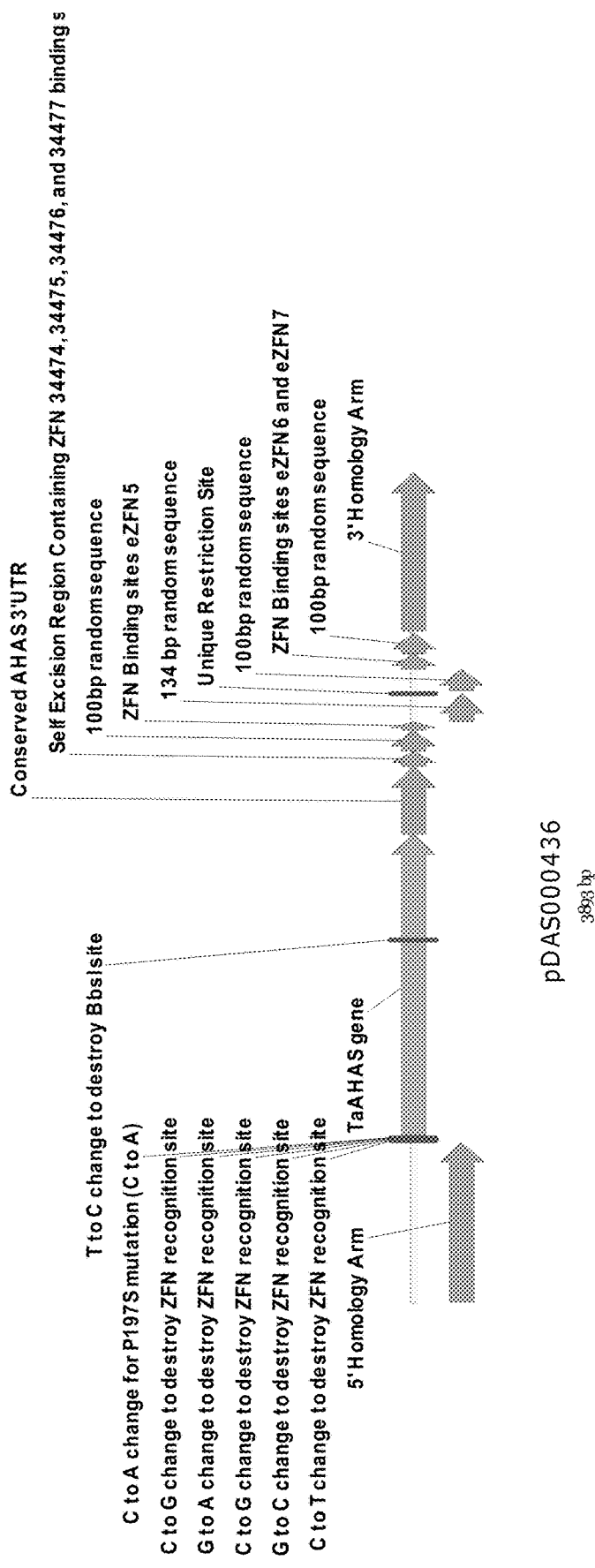
FIG. 17 is a schematic showing a linear map of pDAS000436.

Design and Synthesis of Donor DNA for Second Sequential Transgene Stacking at an Endogenous AHAS Locus Using HDR-Directed DNA Repair The donor DNA for the second round of transgene stacking is designed to promote precise donor integration at the same AHAS locus targeted in the first transgene stack via ZFN-mediated, HDR-directed homology repair. The design is based on the integration of a double stranded donor molecule at the double strand DNA break created by cleavage of the AHAS gene copy containing the first stacked transgene by ZFNs 34480 and 34481 (encoded on plasmid pDAB111860) or ZFNs 34482 and 34483 (encoded on plasmid pDAB111861). The donor molecule (pDAS000436; FIG. 17; SEQ ID NO:296) is identical in sequence to pDAS000434 (FIG. 13).

The donor cassette is synthesized by a commercial gene service vendor (e.g., GeneArt, Life Sciences, etc.) with 750-bp homology arms at each end. The homology arm at the 5' end of the donor corresponds to endogenous AHAS sequence immediately upstream of the double strand DNA break created by ZFNs 34480 and 34481 (encoded on plasmid pDAB111860). The homology arm at the 3' end of the donor corresponds to GOI-1 sequence adjacent to the double stand DNA break created by ZFNs 34480 and 34481 in the donor DNA integrated in the first transgene stack.

Figure 15A:
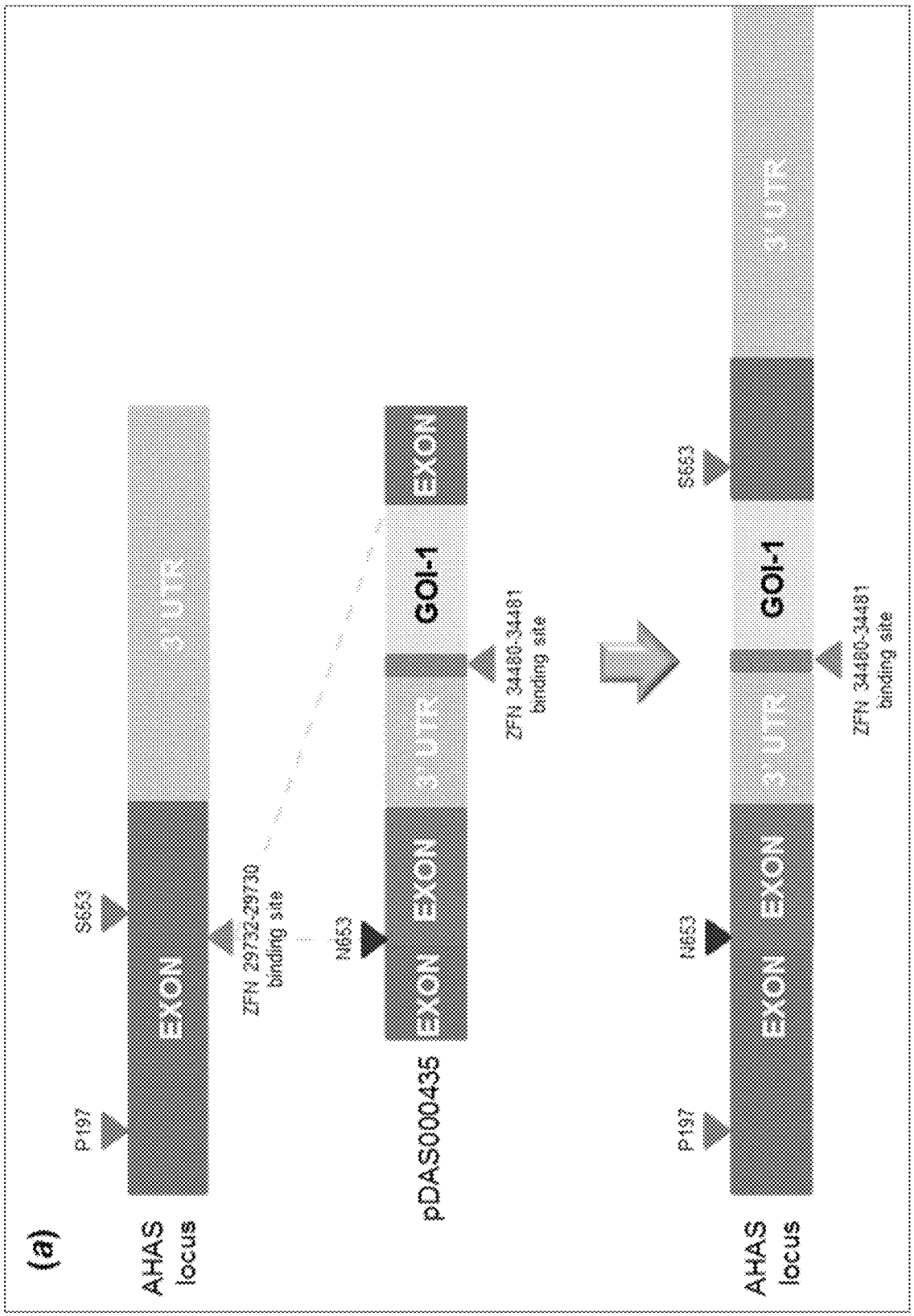
FIGS. 15A and 15B are schematics depicting exogenous marker-free, sequential transgene stacking at an endogenous AHAS locus in the wheat genome of *Triticum aestivum* using ZFN-mediated, HDR-directed DNA repair.
Figure 15B:
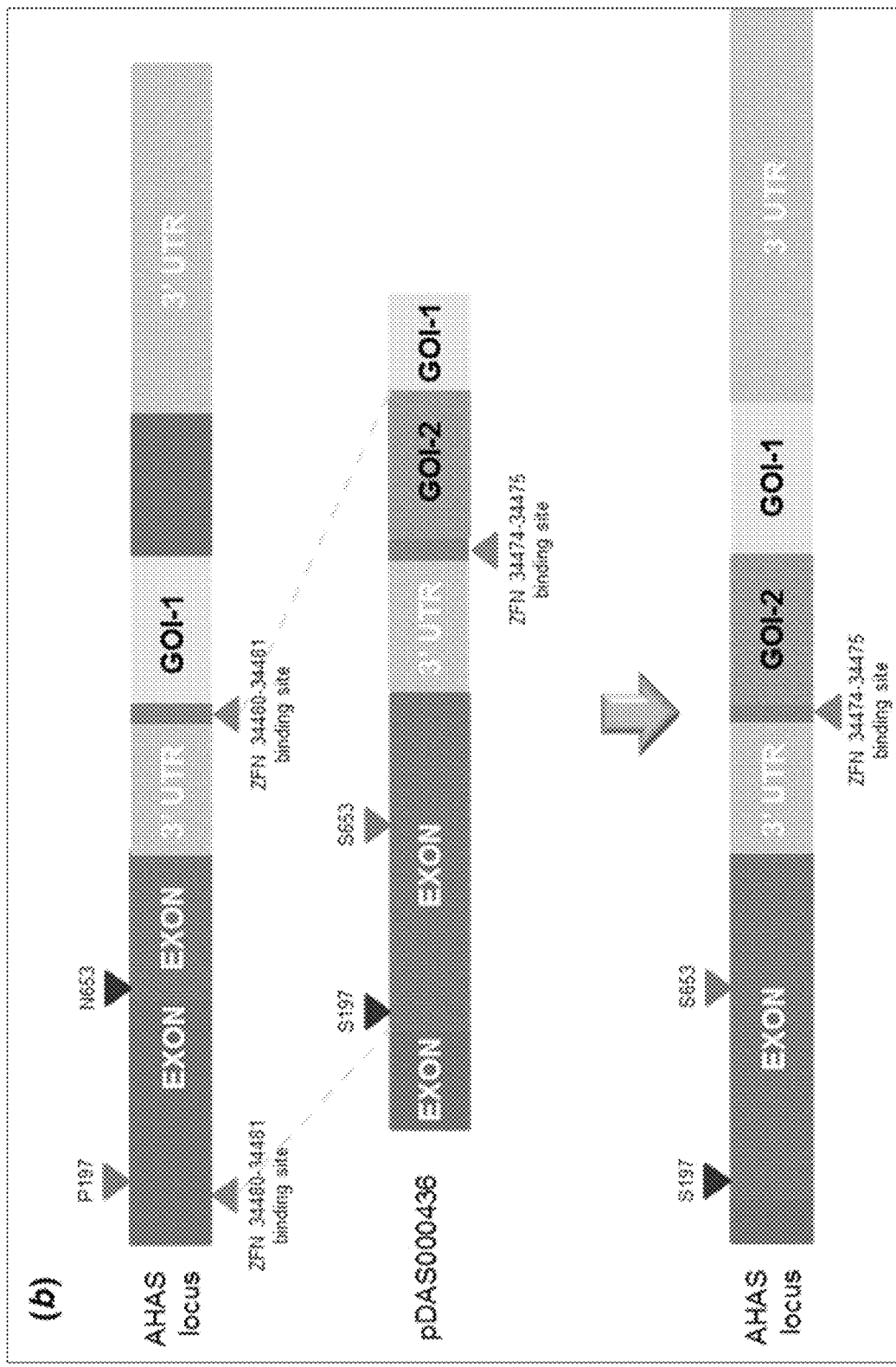

Transformation System for Exogenous Marker-Free, Sequential Transgene Stacking at an Endogenous AHAS Locus in Wheat Using HDR-Directed DNA Repair Transgenic wheat events with multiple transgenes stacked at the same endogenous AHAS locus are produced by exogenous transgenic marker-free, sequential stacking of transgenes encoding traits (without use of a transgenic marker) via transformation with donor pDAS000435 and ZFNs 29732 and 29730 (encoded on plasmid pDAB109350). Precise ZFN-mediated, HDR-directed donor integration introduces the first transgene and S653N mutation conferring tolerance to imidazolinones at an AHAS locus, thus allowing for the regeneration of correctly targeted plants using IMAZAMOX® as a selection agent, as previously described in Example 5. FIG. 15a depicts the integration. Subsequent transformation of wheat cells, derived from first transgene stacked events, with donor pDAS000436 and ZFNs 34480 and 34481 (encoded on plasmid pDAB111860) results in the replacement of the endogenous chromatin located between the ZFN binding sites positioned upstream of P197 and at the self-excision site integrated during the first transgene stack with the donor molecule. This results in integration of the second transgene, and a P197S mutation conferring tolerance to sulfonylurea. Subsequently, the integration of the second transgene allows for the regeneration of correctly targeted plants using sulfometuron methyl as a selection agent. At the same time, integration of the second donor removes the S653N mutation, thus restoring susceptibility to imidazolinones (FIG. 15b). As will be obvious to one skilled in the art, stacking of a third transgene can be achieved by transformation with appropriate zinc finger nucleases and a donor that contains an additional transgene and confers susceptibility to sulfonylurea and tolerance to imidazoliones, thus allowing the regeneration of correctly targeted plants using IMAZAMOX® as a selection agent. As such, continued rounds of sequential transgene stacking are possible via transformation with donors that introduce transgenes and mutations in the endogenous AHAS genes for differential cycling between imidiazolinone and sulfonylurea selection agents.

The transformation system used to regenerate wheat plants with sequentially stacked transgenes at an endogenous AHAS locus is based on the previously described approach for biolistics-mediated DNA delivery to scutella of immature zygotic wheat embryos, or direct DNA delivery to wheat protoplasts using approaches known to one skilled in the art; for example, using the of He et al. (1994) Plant Cell Reports 14: 92-196, or any of the methods described in Example 11.

Example 13: Development of a Transformation System for Exogenous Marker-Free Genome Editing at a Non-Selectable Trait Locus in Wheat Precision genome modification of endogenous loci provides an effectual approach to modify trait expression. The generation of exogenous marker-free transformation events with precise genome modifications at one or more non-selectable endogenous trait loci provides opportunities to create new and novel high-value alleles for crop improvement. Here, we describe the development of a transformation system for ZFN-mediated, exogenous marker-free, precision genome editing at non-selectable trait loci in wheat that can be adapted for both integrative and non-integrative trait modification.

The transformation system is based on a two-step process. In the first step, ZFN-mediated precision genome modification is used to simultaneously modify two independent loci in the plant genome; one locus is modified to confer tolerance to a selectable marker, the other is modified to alter expression for a non-selectable trait of interest. Transformation T0 events co-edited at both loci are generated by selecting for the introduced exogenous selectable marker. In the second step, marker-free events with only the modified trait locus are recovered by PCR screening of segregating T1 plants. The approach can be adapted for non-integrative precision genome modification that results in either the ablation of the non-selectable endogenous gene, or re-writing (editing) of the nucleotide sequence of the non-selectable endogenous gene. Alternatively, the approach can be adapted for integrative precision genome modification in which the function of the non-selectable endogenous gene is altered. More broadly, the approach could be adapted for non-integrative precision genome modification in which previously integrated exogenous DNA, for example a transgene, is excised.

The endogenous AHAS gene in wheat was selected as a model locus to establish and validate the transformation system for exogenous marker-free precision genome editing at a non-selectable trait locus in wheat.

Preparation of Donor DNA for ZFN-Mediated NHEJ-Directed AHAS Gene Editing

The donor DNA molecule, pDAS000267 (SEQ ID NO:84 and SEQ ID NO:85) was designed and synthesized as described in Example 6. Briefly, the donor DNA consisted a 95-bp double stranded molecule that was designed to integrate at the position of the double strand DNA break created by cleavage of a homoeologous copy of the endogenous AHAS gene by ZFNs 29732 and 29730 (encoded on plasmid pDAB109350). The pDAS000267 construct consisted of two parts. The 5' end contained sequence nearly identical to the endogenous AHAS gene encoded in the D-genome, starting from the target ZFN cleavage site and finishing at the AHAS stop codon. Six intentional mutations were introduced into this sequence: two mutations encoded the S653N mutation (AGC→AAT), and four synonymous mutations (in which a silent mutation was incorporated into the donor sequence). The 3' end of the donor molecule contained a unique sequence that could be used for diagnostic PCR to detect ZFN-mediated NHEJ-directed gene editing events. The donor molecule was designed with protruding 5' and 3' ends to provide ligation overhangs to facilitate ZFN-mediated NHEJ-directed DNA repair.

Preparation of ZFN Construct DNA

Plasmid DNA for pDAB109350 (FIG. 1) encoding ZFNs 29732 and 29730 was prepared from cultures of E. coli using the PURE YIELD PLASMID MAXIPREP SYSTEM® (Promega Corporation, Madison, Wis.) following the manufacturer's instructions.

Design and Production of Binary Vector Encoding PAT Selection Cassette

Standard cloning methods were used to construct the binary vector pDAS000004 (SEQ ID: 303; FIG. 18). The PAT selection cassette consisted of the promoter, 5' untranslated region and intron from the Actin (Act1) gene from Oryza sativa (McElroy et al., (1990) The Plant Cell 2(2): 163-171) followed by a synthetic, plant-optimized version of phosphinothricin acetyl transferase (PAT) gene, isolated from Streptomyces viridochromogenes, which encodes a protein that confers resistance to inhibitors of glutamine synthetase comprising phosphinothricin, glufosinate, and bialaphos (Wohlleben et al., (1988) Gene, 70(1): 25-37). This cassette was terminated with the 3' UTR comprising the transcriptional terminator and polyadenylation sites from the 35s gene of cauliflower mosaic virus (CaMV) (Chenault et al., (1993) Plant Physiology 101 (4): 1395-1396).

The selection cassette was synthesized by a commercial gene synthesis vendor (GeneArt, Life Technologies, etc.) and cloned into Gateway-enabled binary vector. Colonies of the assembled plasmid were screened by restriction digestion of miniprep DNA using restriction endonucleases obtained from New England BioLabs and Promega. Plasmid preparations were performed using the QIAPREP SPIN MINIPREP KIT™ following the manufacturer's instructions. Plasmid DNA of selected clones was sequenced using ABI Sanger Sequencing and BIG DYE TERMINATOR v3.1™ cycle sequencing protocol (Applied Biosystems, Life Technologies). Sequence data were assembled and analyzed using the SEQUENCHER™ software (Gene Codes Corporation, Ann Arbor, Mich.). Plasmid DNA used for transfection was prepared from cultures of E. coli using the PURE YIELD PLASMID MAXIPREP SYSTEM® (Promega Corporation, Madison, Wis.) following the manufacturer's instructions.

Biolistic-Mediated Transformation System for Generating Exogenous Marker-Free Wheat Plants with Precise Genome Modifications at Non-Selectable Endogenous Trait Loci A total of 2,320 scutella of immature zygotic embryos from the donor wheat line cv. Bobwhite MPB26RH were prepared for biolistics-mediated DNA delivery, as described previously. DNA-coated gold particles were prepared as described above using a DNA mixture comprising 2.5 µg of donor pDAS000267 and plasmid pDAB109350 (at a molar ratio of 7:1, respectively) and 2.5 µg of plasmid pDAS000004.

Following bombardment, the transfected scutella were incubated at 26° C. in the dark for 16 h before being transferred onto medium for callus induction. The scutella were cultured in the dark on callus induction medium at 24° C. for 2 weeks. The resultant calli were sub-cultured once onto fresh callus induction medium, and kept in the same conditions for a further two weeks. The SEC was transferred onto plant regeneration medium containing 5 mg/ml BASTA® and cultured for 2 weeks at 24° C. under a 16/8 (light/dark) hour photoperiod in a growth room. Regenerated plantlets were transferred onto rooting medium containing 5 mg/ml BASTA® and cultured under the same conditions for 2-3 weeks. Regenerated plantlets producing roots were expected have one or more copies of the PAT selection cassette randomly inserted into the plant genome. The roots of these plantlets were removed and the plants were again sub-cultured on rooting media containing 200 nM IMAZAMOX® under the same conditions for 2-3 weeks. Plants with regrown roots were expected to have the S653N mutation (resulting from precise integration of pDAS000267) in one or more copies of endogenous AHAS gene.

A total of 170 wheat plants producing strong root growth on rooting medium containing BASTA® were obtained from the transfection of the 2,320 scutella of immature zygotic embryos from the donor wheat line cv. Bobwhite MPB26RH. Of these, two wheat plants produced roots when transferred to rooting medium containing IMAZAMOX®. These plants were transferred to soil and grown under glasshouse containment conditions to produce T1 seed.

Optimization of BASTA® Chemical Selection for Enrichment of Transformed Events in a Wheat Protoplast-Based Transformation System A series of experiments are performed to determine optimal selection conditions for regenerating wheat plants expressing the PAT gene conferring tolerance to BASTA® from a protoplast-based transformation system such as those described by Qiao et al. (1992) Plant Cell Reports 11:262-265; Ahmed and Sagi (1993) Plant Cell Reports 12:175-179; Pauk et al. (1994) Plant Cell, Tissue and Organ Culture 38: 1-10; He et al. (1994) Plant Cell Reports 14: 92-196; Gu and Lang (1997) Plant Cell, Tissue and Organ Culture 50: 139-145; and Li et al. (1999) Plant Cell, Tissue and Organ Culture 58: 119-125.

BASTA® selection conditions are optimized using protoplasts derived from somatic embryogenic callus (SEC)-derived cell suspension culture of the wheat line cv. Bobwhite MPB26RH. While protoplasts derived from Bobwhite MPB26RH are non-totipotent (i.e., cannot be used to regenerate entire plants), the selection conditions established for enriching the events that express the PAT gene are expected to be transferrable to any protoplast-based transformation system based on a totipotent wheat genotype. The experiments are conducted, and the basal tolerance of the wild-type donor wheat line cv. Bobwhite MPB26RH to BASTA® is established. The use of BASTA® selection conditions stronger than basal tolerance are identified and used to select for transformed cells expressing the PAT gene.

Establishment of Agarose Bead-Type Cultures and BASTA® Selection Conditions

Protoplasts are isolated from an established SEC-derived cell suspension culture and used to establish agarose bead-types cultures, as described previously. The basal tolerance of wheat line cv. Bobwhite MPB26RH to BASTA® is determined by incubating the agarose bead-type cultures in media supplemented with 0, 0.5, 2.5, 5, 7.5, 10, 20, 30, 40 and 50 mg/L BASTA® and assessing the rate of calli growth after 2 weeks. The BASTA® concentrations (e.g., higher than 20 mg/L) that severely impeded calli development are optimal for enriching and selecting wheat cells having the PAT gene.

Molecular Characterization of the Transformed Wheat Plants with BASTA® and IMAZAMOX® Tolerant Phenotypes The two wheat plants having both the BASTA® and IMAZAMOX® herbicide tolerant phenotypes were molecularly characterized to identify the endogenous AHAS gene that contained the S653N mutation resulting from integration of pDAS000267 donor at a genomic double cleavage site created by ZFNs 29732 and 29730 encoded on pDAB109350.

Two molecular assays were performed for each wheat plant using genomic DNA extracted with the DNEASY® PLANT DNA EXTRACTION MINI KIT™ (Qiagen) from freeze-dried leaf tissue, as described previously.

The first molecular test was used to confirm that the regenerated wheat plants had at least one randomly integrated copy of the PAT gene. A duplex hydrolysis probe qPCR assay (analogous to TAQMAN®) was used to amplify the endogenous single copy gene, puroindoline-b (Pinb) gene, from the D genome of hexaploid wheat (Gautier et al., (2000) Plant Science 153, 81-91; SEQ ID NO: 89, SEQ ID NO: 90 and SEQ ID NO: 91 for forward primer, reverse primer, and probe sequence, respectively) and a region of the Actin (Act1) promoter present on pDAS000004 (SEQ ID NO: 92, SEQ ID NO: 93 and SEQ ID NO: 94 for forward primer, reverse primer, and probe sequence, respectively). Assessment for the presence, and estimated copy number of pDAS000004 was performed according to the method described in Livak and Schmittgen (2001) Methods 25(4): 402-8. From the results, evidence was obtained for the integration of the PAT polynucleotide sequence into the genome of wheat plant events yc06-9110-1 and yr00-9311-1, respectively.

The second molecular test was used to characterize the sub-genomic location and outcome for ZFN-mediated NHEJ-directed donor integration at the endogenous AHAS genes. PCR with primers AHASs653ZFN.F2 and AHASs653ZFN.R1 (SEQ ID NO: 301 and 302; Table 18) was used to amplify the DNA fragment from each of the three homoeologous copies of the endogenous AHAS gene. The amplified fragment contained a region containing the binding site for ZFNs 29732 and 29730 (encoded on plasmid pDAB190350), and to include genomic nucleotide sequence variation. Enough genomic nucleotide sequence variation was included to differentiate between the AHAS homoeologs, such that the resulting amplicons could be unequivocally attributed (at the sequence level) to the wheat sub-genome from which they were derived. The resulting amplicons were prepared for deep sequencing as described in Example 12 and sequenced on an Illumina MiSEQ™ instrument to generate 250-bp paired-end sequence reads, according to the manufacturer's instructions. The resultant sequence reads were computationally processed, as described previously, to assign each read to sample (based on the barcode index) and the sub-genome from which they were derived (based on nucleotide variation that distinguished between homoeologous copies of the AHAS gene). As described in Example 9, the integration of pDAS000267 into an endogenous AHAS locus results in a 95-bp size difference between the wild-type (unmodified) and resulting transgenic (modified) allele. Hence, PCR amplification of both the wild-type and modified AHAS gene loci is expected. Custom developed PERL scripts and manual data manipulation in MICROSOFT EXCEL 2010™ (Microsoft Corporation) were used to characterize the sub-genomic location and outcome for donor integration into the endogenous AHAS genes.

From the results of the second molecular assay, conclusive evidence for precise ZFN-mediated NHEJ-directed gene editing at an endogenous AHAS locus was demonstrated for both wheat plants. Event yc06-9110-1 had perfect hemizygous donor integration in the B-genome (Table 24). Event yr00-9311-1 had simultaneous donor integration into multiple sub-genomes. In the A-genome, independent editing of both endogenous AHAS loci was observed. One allele had partial donor integration that resulted in the expected integration of the S653N mutation for expression of the AHAS herbicide tolerance phenotype. However, a fragment spanning 24-bp nucleotides were deleted from the 3' end of the donor molecule. The other allele had integration of a 51-bp polynucleotide sequence of unknown origin. No sequence reads originating from the B-genome were obtained, suggesting independent integration of a large polynucleotide sequence into each of the endogenous AHAS loci (Table 24). Consensus sequences for the alleles present in each sub-genome for two regenerated wheat plants are provided as SEQ ID NOs: 304-313. The absence of evidence of sequence originating from pDAS0000004 in both wheat plant events indicates that the PAT gene conferring tolerance to BASTA® was randomly integrated into a different locus in the plant genome.

TABLE 24

ZFN-mediated NHEJ-directed AHAS editing outcomes for wheat plants yc06-9110-1 and yr00-9311-1

| | | A-genome | | B-genome | | D-genome | | |
| --- | --- | --- | --- | --- | --- | --- | --- | --- |
| | | Allele 1 | Allele 2 | Allele 1 | Allele 2 | Allele 1 | Allele 2 | SEQ ID NO: |
| yc06-9110-1 | Status | UE | UE | PE | UE | UE | UE | 304-309 |
| | No. Reads [1] | 143,159 | | 76,903 | 110,846 | 219,858 | | |
| yr00-9311-1 | Status | IE | IE | nd | nd | UE | UE | 310-313 |
| | No. Reads [1] | 164,038 | 138,539 | 0 | | 556,123 | | |

[1] Number of sequence reads originating from the specified sub-genome and having the sequence haplotype corresponding to wild-type (unmodified) or transgenic (modified) AHAS loci.
"PE" indicates perfect edit; i.e., ZFN-mediated NHEJ-directed genome editing produced a predicted outcome.
"IE" indicates imperfect edit; i.e., ZFN-mediated NHEJ-directed genome editing produced an unpredicted outcome.
"UE" indicates unedited allele; i.e., allele had wild-type sequence.
"nd" indicates not detected.

These results disclose for the first time a transformation method which can be utilized to generate exogenous marker-free wheat plants having precise genome modifications at one or more non-selectable trait loci. Wheat plants comprising an integrated AHAS donor polynucleotide encoding a S653N mutation conferring tolerance to imidazolinone class herbicides are exemplified. As will be appreciated by one skilled in the art, wheat plants without the exogenous transgenic selectable marker (e.g., PAT) can be recovered by screening T1 plants derived from these events using PCR assays specific for either the PAT or the modified AHAS genes.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method of integrating one or more exogenous sequences into the genome of a plant cell, the method comprising:
   a) expressing one or more site-specific nucleases that cleave an acetohydroxyacid synthase (AHAS) locus in the plant cell, wherein the one or more site-specific nucleases bind to a target site comprising a sequence within any one of SEQ ID NO:35-37 or 263-278, and further wherein the AHAS locus comprises any of SEQ ID NO:35-56 or 263-278; and
   b) integrating one or more exogenous sequences into the cleaved AHAS locus within any of SEQ ID NO:37-56 or 263-278; between SEQ ID NO:35 and 36; between SEQ ID NO:37 and 39; between SEQ ID NO:38 and 39 or 40; between SEQ ID NO:41 and 42; between SEQ ID NO:43 and 45; between SEQ ID NO:44 and 45; between SEQ ID NO:46 and 47; between SEQ ID NO:48 and 29; between SEQ ID NO:50 and 51; between SEQ ID NO:52 or 53 and 54; between SEQ ID NO:55 and 56; between SEQ ID NO:263 and 264; between SEQ ID NO:265 and 266; between SEQ ID NO:267 and 268; between SEQ ID NO:269 and 270; between SEQ ID NO:271 and 272; between SEQ ID NO:273 and 274; between SEQ ID NO:275 and 276; or between SEQ ID NO:277 and 278 of the AHAS locus following cleavage of the AHAS locus by the site-specific nuclease;
   thereby integrating the one or more exogenous sequences into the genome of the plant cell.

2. The method of claim 1, wherein the one or more exogenous sequences are selected from the group consisting of a donor polynucleotide, a transgene, or any combination thereof.

3. The method of claim 1, wherein integrating the one or more exogenous sequences occurs by homologous recombination or non-homologous end joining.

4. The method of claim 1, wherein the one or more exogenous sequences are incorporated simultaneously or sequentially into the AHAS locus.

5. The method of claim 4, wherein the AHAS gene is located on an A, B, or D genome of a polyploidy genome.

6. The method of claim 1, wherein the one or more exogenous sequences encode a S653N AHAS mutation.

7. The method of claim 1, wherein the one or more exogenous sequences encode a P197S AHAS mutation.

8. The method of any of claim 1, wherein the site-specific nuclease is selected from the group consisting of a zinc finger nuclease, a TAL effector domain nuclease, a homing endonuclease, and a single guide RNA of a CRISPR/Cas nuclease.

9. The method of claim 8, wherein the site-specific nuclease comprises a zinc finger DNA-binding domain and a FokI cleavage domain.

10. The method of any claim 1, wherein the one or more exogenous sequences encode a transgene or produce an RNA molecule.

11. The method of claim 10, wherein the transgene encodes a protein selected from the group consisting of a protein that increases crop yield, a protein conferring disease resistance, a protein that increases growth, a protein conferring insect resistance, a protein conferring herbicide tolerance, and combinations thereof.

12. The method of claim 10, wherein the integration of the transgene further comprises introduction of one or more indels that disrupt expression from the AHAS locus and produce the selectable phenotype.

13. The method of claim 1, the method further comprising the steps of;
   c) selecting plant cells comprising the one or more exogenous sequences integrated within the AHAS locus;
   d) culturing the selected plant cells comprising the one or more exogenous sequences; and e) obtaining a whole plant comprising the one or more exogenous sequences integrated within the AHAS locus.

14. The method of claim 1, wherein at least one of the exogenous sequences confer herbicide tolerance and a selection agent comprising an imidazolinone, or a sulfonylurea selection agent is used to select the plant cells.

15. The method of claim 13, wherein the whole plant comprising the one or more exogenous sequences integrated within the AHAS locus of the plant genome is further modified to incorporate an additional exogenous sequence.

16. The method of claim 13, wherein the one or more exogenous sequence does not encode a transgenic selectable marker.

* * * * *